US011098035B2

(12) United States Patent
Bastos et al.

(10) Patent No.: US 11,098,035 B2
(45) Date of Patent: *Aug. 24, 2021

(54) COMPOUNDS, COMPOSITIONS, AND METHODS FOR INCREASING CFTR ACTIVITY

(71) Applicant: Proteostasis Therapeutics, Inc., Boston, MA (US)

(72) Inventors: Cecilia M. Bastos, South Grafton, MA (US); Benito Munoz, Newtonville, MA (US); Bradley Tait, Malden, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,406

(22) Filed: Jul. 12, 2019

(65) Prior Publication Data
US 2020/0190072 A1 Jun. 18, 2020

Related U.S. Application Data

(63) Continuation of application No. 15/539,392, filed as application No. PCT/US2015/000212 on Dec. 23, 2015, now Pat. No. 10,392,372.

(60) Provisional application No. 62/199,661, filed on Jul. 31, 2015, provisional application No. 62/196,839, filed on Jul. 24, 2015, provisional application No. 62/102,244, filed on Jan. 12, 2015, provisional application No. 62/096,374, filed on Dec. 23, 2014.

(51) Int. Cl.
| | |
|---|---|
| C07D 413/12 | (2006.01) |
| A61K 31/42 | (2006.01) |
| A61K 31/4245 | (2006.01) |
| C07D 413/14 | (2006.01) |
| C07D 409/14 | (2006.01) |
| C07D 417/12 | (2006.01) |
| C07D 261/18 | (2006.01) |
| C07D 307/54 | (2006.01) |
| C07D 405/12 | (2006.01) |
| C07D 407/12 | (2006.01) |
| A61K 31/422 | (2006.01) |
| A61K 31/433 | (2006.01) |
| A61K 31/5377 | (2006.01) |
| A61K 45/06 | (2006.01) |
| C07D 307/68 | (2006.01) |
| G01N 33/50 | (2006.01) |

(52) U.S. Cl.
CPC .......... *C07D 413/12* (2013.01); *A61K 31/42* (2013.01); *A61K 31/422* (2013.01); *A61K 31/4245* (2013.01); *A61K 31/433* (2013.01); *A61K 31/5377* (2013.01); *A61K 45/06* (2013.01); *C07D 261/18* (2013.01); *C07D 307/54* (2013.01); *C07D 307/68* (2013.01); *C07D 405/12* (2013.01); *C07D 407/12* (2013.01); *C07D 409/14* (2013.01); *C07D 413/14* (2013.01); *C07D 417/12* (2013.01); *G01N 33/502* (2013.01); *G01N 33/5044* (2013.01)

(58) Field of Classification Search
None
See application file for complete search history.

(56) References Cited

U.S. PATENT DOCUMENTS

| | | | |
|---|---|---|---|
| 5,780,393 A | 7/1998 | Newton | |
| 5,888,941 A | 3/1999 | Bartroli et al. | |
| 7,846,951 B2 | 12/2010 | Miller et al. | |
| 7,915,297 B2 | 3/2011 | Cho et al. | |
| 7,981,935 B2 | 7/2011 | Olson et al. | |
| 8,193,225 B2 | 6/2012 | Schneider et al. | |
| 8,236,838 B2 | 8/2012 | Jones et al. | |
| 8,623,860 B2 | 1/2014 | Fleck et al. | |
| 8,815,924 B2 | 8/2014 | Dorsch et al. | |
| 9,745,292 B2 | 8/2017 | Bastos et al. | |
| 9,790,219 B2 | 10/2017 | Bastos et al. | |
| 10,017,503 B2 | 7/2018 | Bastos et al. | |
| 10,174,014 B2 | 1/2019 | Bastos et al. | |
| 10,344,023 B2 | 7/2019 | Bastos et al. | |
| 10,392,372 B2 | 8/2019 | Bastos et al. | |
| 10,392,378 B2 | 8/2019 | Bastos et al. | |
| 10,548,878 B2 | 2/2020 | Munoz et al. | |
| 10,550,106 B2 | 2/2020 | Munoz et al. | |
| 2004/0072871 A1* | 4/2004 | Dublanchet | A61P 19/10 514/336 |
| 2006/0041006 A1 | 2/2006 | Ibrahim et al. | |
| 2006/0100226 A1 | 5/2006 | Sikorski et al. | |
| 2008/0090882 A1 | 4/2008 | Dorsch et al. | |
| 2009/0069288 A1 | 3/2009 | Breinlinger et al. | |
| 2009/0163545 A1 | 6/2009 | Goldfarb | |
| 2009/0264486 A1 | 10/2009 | Jones et al. | |

(Continued)

FOREIGN PATENT DOCUMENTS

| | | |
|---|---|---|
| CA | 2736441 A1 | 10/2012 |
| EP | 0337263 A2 | 10/1989 |

(Continued)

OTHER PUBLICATIONS

U.S. Appl. No. 14/900,345, published as US 2016-0151335 A1 on Jun. 2, 2016, Methods of Modulating CFTR Activity, filed Dec. 21, 2015.

(Continued)

*Primary Examiner* — Zinna Northington Davis
(74) *Attorney, Agent, or Firm* — Goodwin Procter LLP

(57) ABSTRACT

The present disclosure is directed to disclosed compounds that increase cystic fibrosis transmembrane conductance regulator (CFTR) activity as measured in human bronchial epithelial (hBE) cells.

2 Claims, No Drawings

(56) References Cited

U.S. PATENT DOCUMENTS

| | | |
|---|---|---|
| 2009/0318429 A1 | 12/2009 | Doyle et al. |
| 2010/0234367 A1 | 9/2010 | Nomura et al. |
| 2011/0003784 A1 | 1/2011 | Garvey et al. |
| 2011/0082181 A1 | 4/2011 | Seiders et al. |
| 2011/0212975 A1 | 9/2011 | Kao et al. |
| 2012/0095002 A1 | 4/2012 | Ratcliffe et al. |
| 2012/0264738 A1 | 10/2012 | Sugimoto et al. |
| 2013/0217883 A1 | 8/2013 | Adaway |
| 2013/0237502 A1 | 9/2013 | Curtis et al. |
| 2014/0364467 A1 | 12/2014 | Schneider et al. |
| 2016/0151335 A1 | 6/2016 | Tait et al. |
| 2017/0001991 A1 | 1/2017 | Bastos et al. |
| 2017/0001993 A1 | 1/2017 | Bastos et al. |
| 2017/0233379 A1 | 8/2017 | Bastos et al. |
| 2017/0362214 A1 | 12/2017 | Bastos et al. |
| 2017/0369480 A1 | 12/2017 | Bastos et al. |
| 2017/0369482 A1 | 12/2017 | Bastos et al. |
| 2018/0127400 A1 | 5/2018 | Bastos et al. |
| 2018/0147187 A1 | 5/2018 | Bastos et al. |
| 2018/0214419 A1 | 8/2018 | Munoz et al. |
| 2018/0327363 A1 | 11/2018 | Bastos et al. |
| 2019/0022071 A1 | 1/2019 | Lee |
| 2019/0308960 A1 | 10/2019 | Bastos et al. |
| 2020/0010461 A1 | 1/2020 | Parks et al. |

FOREIGN PATENT DOCUMENTS

| | | |
|---|---|---|
| EP | 0957099 A2 | 11/1999 |
| JP | 2006176443 A | 7/2006 |
| JP | 2007/086584 A | 4/2007 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |
| WO | WO-2017112853 A1 | 6/2017 |

OTHER PUBLICATIONS

U.S. Pat. No. 9,790,219, issued on Oct. 17, 2017, U.S. Appl. No. 15/125,827; published as US 2017-0001993 A1 on Jan. 5, 2017, Compounds, Compositions and Methods for Increasing CFTR Activity, filed Sep. 13, 2016.

U.S. Pat. No. 9,745,292, issued on Aug. 29, 2017, U.S. Appl. No. 15/125,830; published as US 2017-0001991 A1 on Jan. 5, 2017, Compounds, Compositions and Methods for Increasing CFTR Activity, filed Sep. 13, 2016.

U.S. Pat. No. 10,017,503, issued on Jul. 10, 2018; U.S. Appl. No. 15/653,934, published as US 2018-0127400 A1 on May 10, 2018, Compounds, Compositions and Methods for Increasing CFTR Activity, filed Jul. 19, 2017.

U.S. Pat. No. 10,174,014, issued on Jan. 8, 2019; U.S. Appl. No. 15/320,172, published as US 2017-0233379 A1 on Aug. 17, 2017, Compounds, Compositions and Methods for Increasing CFTR Activity, filed Dec. 19, 2016.

U.S. Appl. No. 16/190,964 published as US-2019-0308960-A1 on Oct. 10, 2019, Compounds, Compositions and Methods for Increasing CFTR Activity, filed Nov. 14, 2018.

U.S. Pat. No. 10,392,372, issued on Aug. 27, 2019; U.S. Appl. No. 15/539,392, published as US 2017-0369480 A1 on Dec. 28, 2017, Compounds, Compositions and Methods for Increasing CFTR Activity, filed Jun. 23, 2017.

U.S. Pat. No. 10,392,378; issued on Aug. 27, 2019; U.S. Appl. No. 15/539,397, published as US 2017-0369482 A1 on Dec. 28, 2017, Derivatives of 5-Phenyl- or 5-Heteroarylathiazol-2-Carboxylic Amide Useful for the Treatment of Infer Alia Cystic Fibrosis, filed Jun. 23, 2017.

U.S. Appl. No. 15/539,401, published as US 2018-0327363 A1 on Nov. 15, 2018 Derivatives of 5-(Hetero)Arylpyrazol-3-Carboxylic Amide or 1-(Hetero)Aryltriazol-4-Carboxylic Amide Useful for the Treatment of Infer Alia Cystic Fibrosis, filed Jun. 23, 2017.

U.S. Pat. No. 10,344,023; issued on Jul. 9, 2019; U.S. Appl. No. 15/539,405, published as US 2017-0362214 A1 on Dec. 21, 2017, Derivatives of 3-Heteroarylisoxazol-5-Carboxylic Amide Useful for the Treatment of Infer Alia Cystic Fibrosis, filed Jun. 23, 2017.

U.S. Appl. No. 15/542,997, published as US 2018-0147187 A1on May 31, 2018, Compounds, Compositions, and Methods of Increasing CFTR Activity, filed Jul. 12, 2017.

U.S. Pat. No. 10,548,878; issued on Feb. 4, 2020; U.S. Appl. No. 15/747,290, published as US 2018-0214419 A1 on Aug. 2, 2018, Compounds, Compositions, and Methods of Increasing CFTR Activity, filed Jan. 24, 2018.

U.S. Appl. No. 16/710,688, Compounds, Compositions, and Methods of Increasing CFTR Activity, filed Dec. 11, 2019.

U.S. Appl. No. 15/755,738, published as US 2019-0022071 A1 on Jan. 24, 2019, Methods of Treating Pulmonary Diseases and Disorders, filed Feb. 27, 2018.

U.S. Pat. No. 10,550,106; issued on Feb. 4, 2020; U.S. Appl. No. 15/766,667, published as US 2018-0291006 A1 on Oct. 11, 2018, Compounds, Compositions, and Methods for Modulating CFTR, filed Apr. 6, 2018.

U.S. Appl. No. 16/716,765, Compounds, Compositions, and Methods for Modulating CFTR, filed Dec. 17, 2019.

U.S. Appl. No. 16/065,384, published as US 2018-0369209 A1 on Dec. 27, 2018, Methods of Treating Pulmonary Diseases and Disorders, filed Jun. 22, 2018.

U.S. Appl. No. 16/311,397; published as US 2020-0010461 A1 on Jan. 9, 2020, Compounds, Compositions, and Methods for Modulating CFTR, filed Dec. 19, 2018.

"Aid 775-Screen for Chemicals that Extend Yeast Lifespan," PubChem, 1-11 (Jul. 12, 2007), XP055331102.

Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.

CAS Registry No. 797781-85-2 (available Dec. 15, 2004).

Chang, X., "3-(2-chlorophenyl)-N-methylisoxazole-5-Carboxamide," ACTA Crystallographica, Section E: Structure Reports Online, vol. E63(7), pp. o3074-sup-7 (2007).

Compound Summary for CID 70741394, Pubchem: Create Date: Mar. 4, 2013 [retrieved on May 12, 2015].

(56) References Cited

OTHER PUBLICATIONS

Compound Summary for CID 70756362, Pubchem: Create Date: Mar. 4, 2013 [retrieved on May 12, 2015].
Compound Summary for: CID 36257620, Pubchem: Create Date: May 29, 2009 [retrieved on May 12, 2015].
Compound Summary for: CID 55795703, Pubchem: Create Date: Jan. 25, 2012 [retrieved on May 12, 2015].
Demina et al., "5-substituted Pyridylisoxazoles as Effective Inhibitors of Platelet Aggregation," Russian Chemical Bulletin, International Edition, vol. 63(2) 2095-2113 (2014).
International Search Report and Written Opinion for International Application No. PCT/US2014/044100, dated Oct. 10, 2014, 8 pages.
International Search Report and Written Opinion for International Application No. PCT/US2015/000189, dated Mar. 18, 2016, 10 pages.
International Search Report and Written Opinion for International Application No. PCT/US2015/000202, dated Mar. 22, 2016, 8 pages.
International Search Report and Written Opinion for International Application No. PCT/US2015/000211, dated Mar. 29, 2016, 10 pages.
International Search Report and Written Opinion for International Application No. PCT/US2015/000212, dated Jul. 1, 2016, 22 pages.
International Search Report and Written Opinion for International Application No. PCT/US2015/020460, dated Jun. 9, 2015, 7 pages.
International Search Report and Written Opinion for International Application No. PCT/US2015/020499, dated Jun. 9, 2015, 8 pages.
International Search Report and Written Opinion for International Application No. PCT/US2015/036691, dated Aug. 20, 2015, 12 pages.
International Search Report and Written Opinion for International Application No. PCT/US2016/012982, dated Mar. 7, 2016, 12 pages.
International Search Report and Written Opinion for International Application No. PCT/US2016/043835, dated Oct. 10, 2016, 8 pages.
International Search Report and Written Opinion for International Application No. PCT/US2016/068266, dated Feb. 27, 2017, 11 pages.
International Search Report and Written Opinion for International Application No. PCT/US2017/040606, dated Nov. 30, 2016, 10 pages.
Kalid et al., "Small Molecule Correctors of F508del-CFTR Discovered by Structure-based Virtual Screening," Journal of Computer-Aided Molecular Design, vol. 24:971-991 (2010).
Lack et al., "Targeting the Binding Function 3 (BF3) Site of the Human Androgen Receptor through Virtual Screening," Journal of Medicinal Chemistry, vol. 54(24) 8563-8573 (2011).
Liedtke, W., "Role of TRPV ion Channels in Sensory Transduction of Osmotic Stimuli in Mammals," Experimental Physiology, 92:3 507-512 (2007) XP055252392.
Lukevics et al.,"Synthesis and Cytotoxicity of Silyl- and Carbonyl-substituted Isoxazoles,"Chemistry of Heterocyclic Compounds, Springer New York LLC, vol. 36(10); 1226-1231 (1995).
Munchhof et al., "Discovery of PF-04449913, a Potent and Orally Bioavailable Inhibitor of Smoothened," ACS Medicinal Chemistry Letters, vol. 3(2) 106-111 (2012).
Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.
Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].
Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Serial No. 14816975.8 (19 pages).
U.S. Appl. No. 15/542,997, "Compounds, Compositions, and Methods for Increasing CFTR Activity," filed Jul. 12, 2017 (175 pages).
U.S. Appl. No. 15/653,934, "Compounds, Compositions, and Methods for Increasing CFTR Activity," filed Jul. 19, 2017 (76 pages).
U.S. Appl. No. 15/697,901, "Compounds, Compositions, and Methods for Increasing CFTR Activity," filed Sep. 7, 2017 (112 pages).
U.S. Appl. No. 16/716,765, "Compounds, Compositions, and Methods for Modulating CFTR," filed Dec. 17, 2019 (310 pages).

\* cited by examiner

COMPOUNDS, COMPOSITIONS, AND METHODS FOR INCREASING CFTR ACTIVITY

CROSS REFERENCE TO RELATED APPLICATIONS

This application is a continuation of U.S. application Ser. No. 15/539,392, filed Jun. 23, 2017, which is a national stage filing under 35 U.S.C. § 371 of PCT/US2015/000212, filed Dec. 23, 2015, which claims the benefit of, and priority to, U.S. provisional application Ser. Nos. 62/199,661, filed Jul. 31, 2015, 62/196,839, filed Jul. 24, 2015, 62/102,244, filed Jan. 12, 2015, and 62/096,374, filed Dec. 23, 2014, the contents of each of which are hereby incorporated by reference herein in their entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis (Cl⁻, Na⁺, HCO₃⁻) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7(6): e39809.doi:10.1371/journal.pone.0039809; Bombieri et al. (2011), J Cyst Fibros. 2011 June; 10 Suppl 2:S86-102; (Albert et al. (2008), Clinical Respiratory Medicine, Third Ed., Mosby Inc.; Levin et al. (2005), Invest Ophthalmol Vis Sci., 46(4):1428-34; Froussard (2007), Pancreas 35(1): 94-5).

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds such as those having disclosed formulas) can increase cystic fibrosis transmembrane conductance regulator (CFTR) activity as measured in human bronchial epithelial (hBE) cells.

For example, disclosed herein are compounds having formulas:

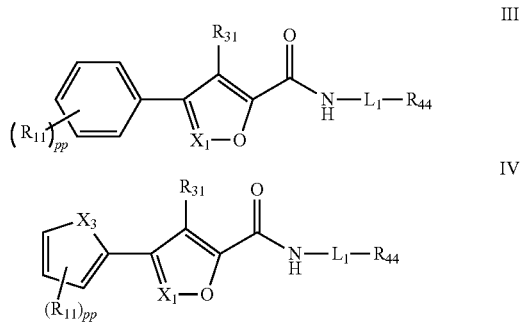

and pharmaceutically acceptable salts, stereoisomers, and prodrugs thereof, wherein:

$X_1$ is $CR_{33}$ or N;

$X_3$ is selected from the group consisting of O, S, and $NR_{hh}$;

pp is 1, 2, or 3;

$R_{11}$ is independently selected for each occurrence from the group consisting of hydrogen, halogen, $C_{1-4}$ alkyl (optionally substituted by one, two or three halogens);

$R_{31}$ is selected from the group consisting of hydrogen, halogen, and $C_{1-4}$ alkyl;

$R_{33}$ is selected from the group consisting of H, halogen, $C_{1-4}$ alkyl, and —NR'R"

$L_1$ is selected from the group consisting of $C_{1-6}$ alkylene, $C_{3-6}$ cycloalkylene, $C_{3-6}$ cycloalkylene-$C_{1-4}$ alkylene, $C_{1-3}$ alkylene-$NR_{hh}$—$S(O)_w$—, —$C_{1-3}$ alkylene-$S(O)_w$—$NR_{hh}$—, $C_{3-6}$ cycloalkylene-$C_{0-2}$ alkylene-$S(O)_w$—$NR_{hh}$ and $C_{3-6}$ cycloalkylene-$C_{0-2}$ alkylene $NR_{hh}$—$S(O)_w$—, wherein $L_1$ may be optionally substituted by one, two or three substituents selected from the group consisting of halogen, hydroxyl, and $C_{1-3}$ alkyl (optionally substituted by one, two or three substituents each selected independently from $R_{ff}$);

$R_{44}$ is selected from the group consisting of H, halogen, hydroxyl, $C_{1-3}$ alkoxy, heterocycle, and a 5-6 membered monocyclic or 8-10 membered bicyclic heteroaryl having one, two or three heteroatoms each selected from O, N, and S; wherein the heterocycle and the heteroaryl may be optionally substituted by one or two substituents each selected independently from $R_{gg}$;

$R_{ff}$ is selected for each occurrence from group consisting of halogen, hydroxyl, $C_{1-4}$ alkyl, $C_{1-4}$ alkyoxy, $C_{2-4}$ alkenyl, $C_{3-6}$ cycloalkyl, —NR'R", —NR'—S(O)$_w$—$C_{1-3}$ alkyl, S(O)$_w$—NR'R", and —S(O)$_w$—$C_{1-3}$ alkyl, where w is 0, 1, or 2, wherein $C_{1-4}$ alkyl, $C_{1-4}$ alkyoxy, $C_{2-4}$ alkenyl and $C_{3-6}$ cycloalkyl may be optionally substituted by one, two or three substituents each independently selected from the group consisting of halogen, hydroxyl, —NR'R", —NR'—S(O)$_w$—$C_{1-3}$ alkyl, S(O)$_w$—NR'R", and —S(O)$_w$—$C_{1-3}$ alkyl$R_{gg}$ is selected for each occurrence from the group consisting of: halogen, hydroxyl, —NR'R", —NR'R", —NR'—S(O)$_w$—$C_{1-3}$ alkyl, —S(O)$_w$—NR'R", and —S(O)$_w$—$C_{1-3}$ alkyl, where w is 0, 1, or 2; $C_{1-6}$ alkyl, $C_{3-6}$ cycloalkyl, and $C_{1-6}$ alkenyl, wherein $C_{1-6}$ alkyl, $C_{3-6}$ cycloalkyl, and $C_{1-6}$ alkenyl are optionally substituted by one, two, or three substituents each independently selected from $R_{jj}$; and heterocycle, optionally substituted by one, two, or three substituents each independently selected from $R_{ll}$;

$R_{jj}$ is selected for each occurrence from the group consisting of halogen, hydroxyl, $C_{3-6}$ cycloalkyl, $C_{1-6}$ alkoxy (optionally substituted by one, two, or three substituents each independently selected from $R_{kk}$), heterocycle, C(O)OH, —C(O)O$C_{1-6}$ alkyl, —NR'R", —NR'—S(O)$_w$—$C_{1-3}$ alkyl, —S(O)$_w$—NR'R", and —S(O)$_w$—$C_{1-3}$ alkyl, where w is 0, 1, or 2;

$R_{kk}$ is selected for each occurrence from the group consisting of halogen, hydroxyl, $C_{1-6}$ alkyl (optionally substituted by one, two, or three substituents each independently selected from halogen, hydroxyl, $C_{3-6}$ cycloalkyl, and heterocycle (optionally substituted by $C_{1-6}$ alkyl)), $C_{3-6}$ cycloalkyl (optionally substituted by one, two, or three substituents each independently selected from halogen, hydroxyl, and $C_{1-6}$ alkyl), phenyl, heterocycle (optionally substituted by one, two or three substituents independently selected from halogen, hydroxyl, and $C_{1-6}$ alkyl), and heteroaryl;

$R_{ll}$ is selected for each occurrence from the group consisting of halogen, hydroxyl, $C_{1-6}$ alkyl (optionally substituted by one, two, or three substituents each independently selected from halogen, hydroxyl, and $C_{3-6}$ cycloalkyl) and heterocycle (optionally substituted by one, two or three substituents independently selected from halogen, hydroxyl, and $C_{1-6}$ alkyl);

R' and R" are each independently selected for each occurrence from H and $C_{1-4}$ alkyl or taken together with the nitrogen to which they are attached form a heterocyclic ring;

w is 0, 1 or 2; and $R_{hh}$ is selected for each occurrence from the group consisting of H, $C_{1-6}$ alkyl and $C_{3-6}$ cycloalkyl.

Also contemplated herein are pharmaceutical compositions that include a disclosed compound (such as those compounds having disclosed formulas such as Formula (Ia), (IIa), (Ib), (IIb), (III), or (IV)) and a pharmaceutically acceptable carrier or excipient. In certain embodiments, the compositions can include at least one additional CFTR modulator as described anywhere herein or at least two additional CFTR modulators, each independently as described anywhere herein.

In additional embodiments, a method of enhancing (e.g., increasing) cystic fibrosis transmembrane conductance regulator (CFTR) activity in a subject in need thereof is provided comprising administering to said subject an effective amount of a disclosed compound of e.g., Formula (Ia), (IIa), (Ib), (IIb), (III), or (IV).

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, 1507del, R1162X, 1898+1G>A, 3659delC, G85E, D1152H, R560T, R347P, 2184insA, A455E, R334W, Q493X, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X; Δ508F) are enhanced (e.g., increased).

In certain of these embodiments, the subject (e.g., a human patient) is suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najj ar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, and Straussler-Scheinker syndrome). In certain embodiments, the disease is cystic fibrosis.

Also contemplated herein is a method for treating a patient suffering from cystic fibrosis comprising administering to said patient an effective amount of a disclosed compound.

In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, GLPG2222 and GLPG2665) or potentiator (e.g., ivacaftor and genistein). In certain of these embodiments, one of the at least two additional therapeutic agents is a CFTR corrector (e.g., VX-809, VX-661, VX-983, VX-152, VX-440, GLPG2222 and GLPG2665) and the other is a CFTR potentiator (e.g., ivacaftor and genistein).

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii)

comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein or a pharmaceutically acceptable salt, prodrug or solvate thereof, pharmaceutical compositions, methods of increasing CFTR activity and methods of treating cystic fibrosis.

For example, disclosed herein are compounds having formulas:

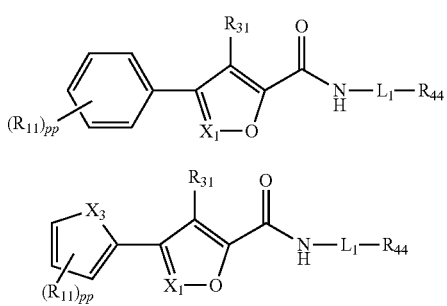

and pharmaceutically acceptable salts, stereoisomers, and prodrugs thereof, wherein:

$X_1$ is $CR_{33}$ or N;

$X_3$ is selected from the group consisting of O, S, and $NR_{hh}$;

pp is 1, 2, or 3;

$R_{11}$ is independently selected for each occurrence from the group consisting of hydrogen, halogen, $C_{1-4}$ alkyl (optionally substituted by one, two or three halogens);

$R_{31}$ is selected from the group consisting of hydrogen, halogen, and $C_{1-4}$ alkyl;

$R_{33}$ is selected from the group consisting of H, halogen, $C_{1-4}$ alkyl, and —NR'R" wherein R' and R" are each independently selected for each occurrence from H and $C_{1-4}$ alkyl or taken together with the nitrogen to which they are attached form a heterocyclic ring;

$L_1$ is selected from the group consisting of $C_{1-6}$ alkylene, $C_{3-6}$ cycloalkylene, $C_{3-6}$ cycloalkylene-$C_{1-4}$ alkylene, $C_{1-3}$ alkylene-$NR_{hh}$—S(O)$_w$—, —$C_{1-3}$ alkylene-S(O)$_w$—$NR_{hh}$—, $C_{3-6}$ cycloalkylene-$C_{0-2}$ alkylene-S(O)$_w$—$NR_{hh}$, and $C_{3-6}$ cycloalkylene-$C_{0-2}$ alkylene $NR_{hh}$—S(O)$_w$—, wherein $L_1$ may be optionally substituted by one, two or three substituents selected from the group consisting of halogen, hydroxyl, and $C_{1-3}$ alkyl (optionally substituted by one, two or three substituents each selected independently from $R_{ff}$);

$R_{44}$ is selected from the group consisting of H, halogen, hydroxyl, $C_{1-3}$ alkoxy, phenyl, —O-phenyl, —NR'-phenyl, heterocycle, and a 5-6 membered monocyclic or 8-10 membered bicyclic heteroaryl having one, two or three heteroatoms each selected from O, N, and S; wherein phenyl, —O-phenyl, —NR'-phenyl, heterocycle and heteroaryl may be optionally substituted by one or two substituents each selected independently from $R_{gg}$;

$R_{ff}$ is selected for each occurrence from group consisting of halogen, hydroxyl, $C_{1-4}$ alkyl, $C_{1-4}$ alkyoxy, $C_{2-4}$ alkenyl, $C_{3-6}$ cycloalkyl, —NR'R", —NR'—S(O)$_w$—$C_{1-3}$ alkyl, S(O)$_w$—NR'R", and —S(O)$_w$—$C_{1-3}$ alkyl, where w is 0, 1, or 2, wherein $C_{1-4}$ alkyl, $C_{1-4}$ alkyoxy, $C_{2-4}$ alkenyl and $C_{3-6}$ cycloalkyl may be optionally substituted by one, two or three substituents each independently selected from the group consisting of halogen, hydroxyl, —NR'R", —NR'—S(O)$_w$—$C_{1-3}$ alkyl, S(O)$_w$—NR'R", and —S(O)$_w$—$C_{1-3}$ alkyl;

$R_{gg}$ is selected for each occurrence from the group consisting of:

a) halogen, hydroxyl, cyano, —NR'R", —NR'—S(O)$_w$—$C_{1-3}$ alkyl, —S(O)$_w$—NR'R", and —S(O)$_w$—$C_{1-3}$ alkyl, where w is 0, 1, or 2;

b) $C_{1-6}$ alkyl, $C_{3-6}$ cycloalkyl, and $C_{1-6}$ alkenyl, wherein $C_{1-6}$ alkyl, $C_{3-6}$ cycloalkyl, and $C_{1-6}$ alkenyl are optionally substituted by one, two, or three substituents each independently selected from $R_{jj}$; and c) heterocycle, optionally substituted by one, two, or three substituents each independently selected from $R_{ll}$;

$R_{jj}$ is selected for each occurrence from the group consisting of halogen, hydroxyl, $C_{3-6}$ cycloalkyl, $C_{3-6}$ cycloalkoxy, $C_{1-6}$ alkoxy (optionally substituted by one, two, or three substituents each independently selected from $R_{kk}$), heterocycle, C(O)OH, —C(O)O$C_{1-6}$ alkyl, —NR'R", —NR'—S(O)$_w$—$C_{1-3}$ alkyl, —S(O)$_w$—NR'R", and —S(O)$_w$—$C_{1-3}$ alkyl, where w is 0, 1, or 2;

$R_{kk}$ is selected for each occurrence from the group consisting of halogen, hydroxyl, $C_{1-6}$ alkyl (optionally substituted by one, two, or three substituents each independently selected from halogen, hydroxyl, $C_{3-6}$ cycloalkyl, and heterocycle (optionally substituted by $C_{1-6}$ alkyl)), $C_{3-6}$ cycloalkyl (optionally substituted by one, two, or three substituents each independently selected from halogen, hydroxyl, and $C_{1-6}$ alkyl), phenyl, heterocycle (optionally substituted by one, two or three substituents independently selected from halogen, hydroxyl, and $C_{1-6}$ alkyl), and heteroaryl;

$R_{ll}$ is selected for each occurrence from the group consisting of halogen, hydroxyl, $C_{1-6}$ alkyl (optionally substituted by one, two, or three substituents each independently selected from halogen, hydroxyl, and $C_{3-6}$ cycloalkyl) and heterocycle (optionally substituted by one, two or three substituents independently selected from halogen, hydroxyl, and $C_{1-6}$ alkyl);

R' and R" are each independently selected for each occurrence from H and $C_{1-4}$ alkyl;

w is 0, 1 or 2; and $R_{hh}$ is selected for each occurrence from the group consisting of H, $C_{1-6}$ alkyl and $C_{3-6}$ cycloalkyl.

For example, in certain of these embodiments, $L_1$ of one or more of the above formulas is $C_{1-3}$ alkylene, $C_{3-5}$ cycloalkylene, or $C_{3-6}$ cycloalkylene-$C_{1-4}$ alkylene and/or $R_{31}$ is H or F.

In certain embodiments, $R_{gg}$ is selected from the group consisting of:

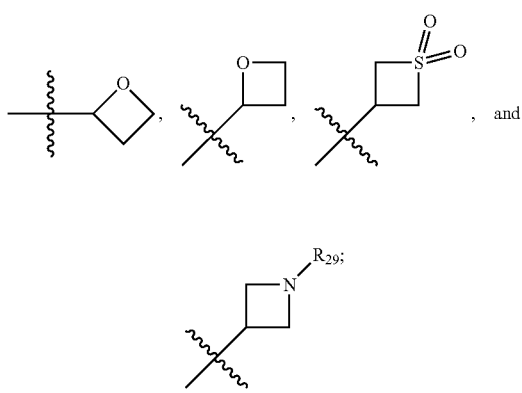

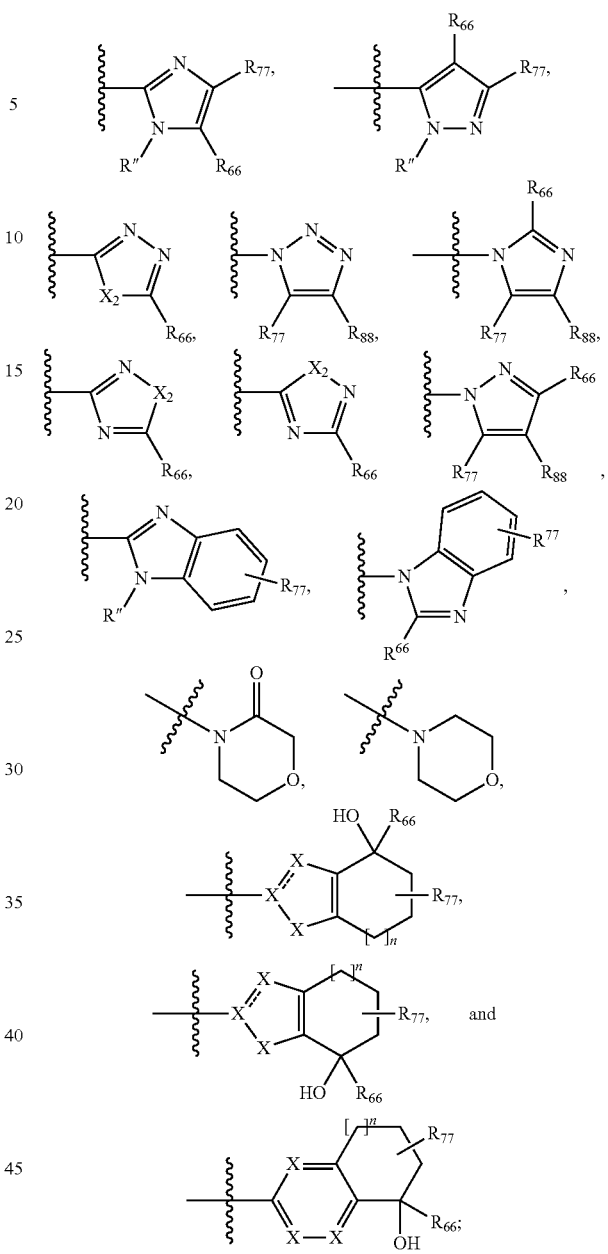

wherein $R_{29}$ is selected from $C_{1-6}$ alkyl (optionally substituted by one, two or three substituents each independently selected from the group consisting of halogen, hydroxyl, $C_{1-6}$ alkoxy, and cycloalkyl) and heterocycle (optionally substituted by one, two or three substituents each independently selected from the group consisting of halogen, hydroxyl, $C_{1-6}$ alkyl and $C_{1-6}$ alkoxy). For example, $R_{29}$ may be selected from the group consisting of:

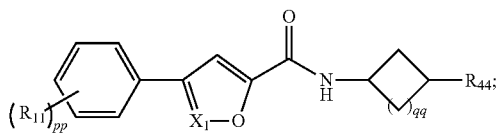

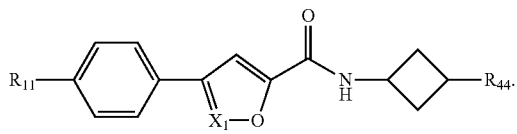

In an embodiment, a disclosed compound has the formula:

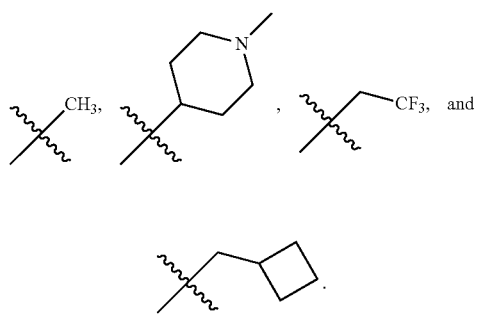

wherein qq is 0 or 1. For example, a disclosed compound may have, in certain embodiments the following formula:

For example, $R_{44}$ as in the above formulas may be selected from the group consisting of: pyrrolidinyl, piperidinyl, tetrahydropyranyl, and tetrahydofuranyl. In other embodiments, $R_{44}$ is selected from the group consisting of:

wherein X independently for each occurrence is selected from the group consisting of O, S, $NR_{hh}$, C, $C(R_{88})$, and $C(R_{88})(R_{99})$; $X_2$ independently for each occurrence is selected from the group consisting of O, S and $NR_{hh}$; R" is H or $C_{1-4}$alkyl, each $R_{66}$, $R_{77}$, $R_{88}$ and $R_{99}$ is independently selected for each occurrence from H and $R_{gg}$, and n is 0, 1, 2, or 3.

In certain embodiments, each of $R_{66}$, $R_{77}$, $R_{88}$ and $R_{99}$ is independently selected for each occurrence from the group consisting of hydrogen, halogen, hydroxyl, $C_{1-6}$ alkyl, $C_{3-6}$ cycloalkyl, and heterocycle, wherein $C_{1-6}$ alkyl, $C_{3-6}$ cycloalkyl, and heterocycle are optionally substituted by one, two or three substituents each independently selected from the group consisting of hydroxyl, $C_{1-6}$ alkyl, $C_{1-6}$ alkoxy, —S(O)$_w$—$C_{1-3}$ alkyl (w is 0, 1, or 2) and —NR'S(O)$_2C_{1-6}$ alkyl. In some embodiments, R' is H or $C_{1-4}$ alkyl. In certain embodiments, $R_{66}$, $R_{77}$ and $R_{88}$ may be selected from the group consisting of H, halogen, methyl (optionally substituted by one, two or three substituents each selected from halogen, hydroxyl, methoxy and ethoxy), ethyl (optionally substituted by one, two or three substituents each selected from halogen, hydroxyl, methoxy and ethoxy), propyl ((optionally substituted by one, two or three substituents each selected from halogen, hydroxyl, methoxy and ethoxy), isopropyl ((optionally substituted by one, two or three substituents each selected from halogen, hydroxyl, methoxy and ethoxy), n-butyl (optionally substituted by one, two or three substituents each selected from halogen, hydroxyl, methoxy and ethoxy), t-butyl (optionally substituted by one, two or three substituents each selected from halogen, hydroxyl, methoxy and ethoxy), s-butyl (optionally substituted by one, two or three substituents each selected from halogen, hydroxyl, methoxy and ethoxy) and isobutyl (optionally substituted by one, two or three substituents each selected from halogen, hydroxyl, methoxy and ethoxy).

In certain embodiments, pp is 0, 1 or 2, and $R_{11}$ is selected from H, F, or methyl.

For example, provided herein is a compound represented by:

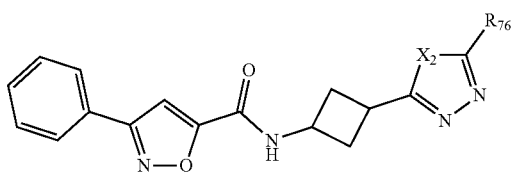

wherein $X_2$ is selected from the group consisting of O, S or $NR_{hh}$ (defined above);

$R_{76}$ is selected from the group consisting of $C_{1-6}$alkyl (optionally interrupted by one or more oxygen atoms or NR", and optionally substituted by one or more substituents selected from the group consisting of halogen, hydroxyl, $S(O)_w$—$C_{1-3}$ alkyl (w is 0, 1, or 2), $C_{3-6}$cycloalkyl (optionally substituted by one or more substituents selected from heterocycle, $C_{1-6}$alkyl, and halogen) and heterocycle (optionally substituted by one or more substituents selected from heterocycle, $C_{1-6}$alkyl, and halogen)); and heterocycle (optionally substituted by one or more substituents selected from the group consisting of halogen, hydroxyl, $S(O)_w$—$C_{1-3}$ alkyl (w is 0, 1, or 2), $C_{3-6}$cycloalkyl (optionally substituted by one or more substituents selected from heterocycle, $C_{1-6}$alkyl, and halogen) and heterocycle (optionally substituted by one or more substituents selected from heterocycle, $C_{1-6}$alkyl, and halogen).

Also disclosed herein are compounds having the Formula (Ia) or the Formula (IIa):

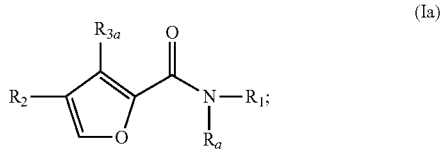

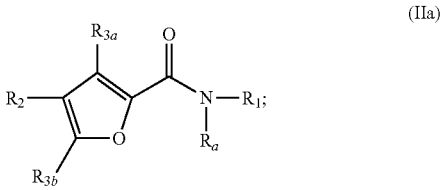

or a pharmaceutically acceptable salt, prodrug or solvate thereof, wherein:

$R_1$ is selected from the group consisting of:

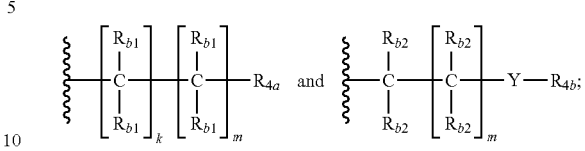

$R_2$ is selected from the group consisting of optionally substituted aryl and optionally substituted heteroaryl;

$R_{3a}$ and $R_{3b}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, (C=$NR_d$)$R_c$, optionally substituted heterocyclic and optionally substituted heteroaryl;

$R_{4a}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $S(O)_nR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)R_c$, $N(R_d)(CO-OR_c)$, $NR_dC(O)C(O)R_c$, $NR_dC(O)NR_dR_d$, $NR_dS(O)_nR_dR_d$, $NR_dS(O)_nR_c$, $S(O)NR_dR_d$, $OC(O)OR_c$, (C=$NR_d$)$R_c$, optionally substituted heterocyclic and optionally substituted heteroaryl;

$R_{4b}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, optionally substituted heterocyclic and optionally substituted heteroaryl;

$R_a$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $C(O)OR_c$, $C(O)R_c$, $C(O)C(O)R_c$ and $S(O)_nR_c$;

or alternatively, $R_a$ and the nitrogen atom to which it is attached is taken together with an adjacent $C(R_{b1})(R_{b1})$ or $C(R_{b2})(R_{b2})$ to form an optionally substituted, 4- to 12-membered heterocyclic ring containing one or more ring nitrogen atoms, wherein said heterocyclic ring optionally contains one or more ring heteroatoms selected from oxygen and sulfur;

each $R_{b1}$ and $R_{b2}$ is independently selected for each occurrence from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_n$ $R_c$, $S(O)_nR_c$, $S(O)_nNR_dR_d$, $OC(O)OR_c$ and $(C=NR_d)R_c$; or alternatively, two geminal $R_{b1}$ groups or two geminal $R_{b2}$ groups and the carbon to which they are attached are taken together to form a C(O) group, or yet alternatively, two geminal $R_{b1}$ groups or two geminal $R_{b2}$ groups are taken together with the carbon atom to which they are attached to form a spiro $C_3$-$C_{12}$ cycloalkyl, a spiro $C_3$-$C_{12}$ cycloalkenyl, a spiro heterocyclic, a spiro aryl or spiro heteroaryl, each optionally substituted;

Y is selected from the group consisting of $S(O)_n$, $NR_d$, $NR_dS(O)_n$, $NR_dS(O)_nNR_d$, $NR_dC(O)$, $NR_dC(O)O$, $NR_dC(O)C(O)$, $NR_dC(O)NR_d$, $S(O)_nNR_d$, and O;

each $R_c$ is independently selected for each occurrence from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected for each occurrence from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

k is 0 or 1;

m is 0, 1, 2, 3, 4, or 5;

each n is independently 0, 1 or 2.

In some embodiments, m is 0, 1 or 2. In some embodiments, k is 0. In some embodiments, m is 0, 1 or 2, k is 0.

In some embodiments, each of $R_{3a}$ and $R_{3b}$ is hydrogen.

In some embodiments, $R_a$ is hydrogen or $C_1$-$C_4$ alkyl (optionally substituted by 1, 2 or 3 halogens).

In some embodiments, $R_{b1}$ and $R_{b2}$ are each independently selected from the group consisting of hydrogen, hydroxyl, $C_{1-4}$ alkoxy (optionally substituted by one, two or three substituents independently selected from halogen and hydroxyl) and $C_1$-$C_4$ alkyl (optionally substituted by one, two or three substituents independently selected from halogen and hydroxyl). In certain embodiments, $R_{b1}$ and $R_{b2}$ for each occurrence are hydrogen.

In some embodiments, $R_2$ is selected from the group consisting of phenyl and a 5-6 membered heteroaryl having one or two heteroatoms each selected from N, S, and O, wherein $R_2$ is optionally substituted by one or two substituents each independently selected from the group consisting of halogen, and $C_1$-$C_4$ alkyl (optionally substituted by one, two or three halogens).

In certain embodiments, $R_2$ is phenyl.

In other embodiments, $R_2$ is selected from the group consisting of: optionally substituted thienyl, optionally substituted furanyl and optionally substituted pyridinyl.

In some embodiments, $R_{4a}$ is selected from the group consisting of optionally substituted $C_1$-$C_6$ alkyl, optionally substituted $C_3$-$C_7$ cycloalkyl, phenyl, $OR_c$, $C(O)OR_c$, $C(O)R_c$, optionally substituted heterocycle and optionally substituted heteroaryl, wherein $R_c$ is selected, independently for each occurrence, from the group consisting of H and $C_{1-6}$ alkyl.

In certain embodiments, $R_{4a}$ is heterocycle, or a 5-6 membered monocyclic or a 8-10 membered bicyclic heteroaryl having one, two or three heteroatoms selected from N, S or O, wherein the heterocycle or heteroaryl are optionally substituted by one, two or three substituents independently selected for each occurrence from the group consisting of halogen, $C_{1-6}$ alkyl (optionally substituted by one, two or three substituents each independently selected from halogen and hydroxyl), $C_{1-6}$ alkoxy (optionally substituted by one, two or three halogens), hydroxyl, and $NR_dR_d$ wherein $R_d$ is independently for each occurrence selected from H and $C_{1-4}$ alkyl, or the two $R_d$s taken together with the N to which they are attached form a heterocyclic ring). For example, $R_{4a}$ can be selected from the group consisting of tetrahydropyranyl, thiadiazolyl, tetrahydrofuranyl, and morpholinyl. As another example, $R_{4a}$ can be a monocyclic heteroaryl containing one, two or three ring nitrogen atoms. As a further example, $R_{4a}$ can be selected from the group consisting of furanyl, pyridinyl, pyrazinyl, pyrazolyl, imidazolyl, isoxazolyl, triazolyl, thiazolyl, oxadiazolyl, thiadiazolyl, thienyl, piperazinyl, and benzimidazolyl, each optionally substituted.

In certain embodiments, $R_{4a}$ is selected from the group consisting of:

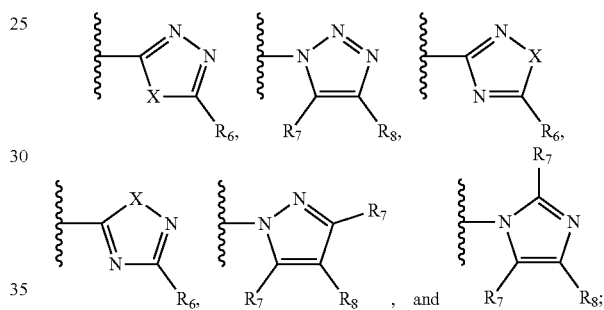

wherein each X is independently O, S or $NR_g$;

each $R_g$ is independently selected from the group consisting of hydrogen, $C_1$-$C_4$ alkyl, $C_3$-$C_6$ cycloalkyl, and each $R_6$, $R_7$ and $R_8$ is independently selected for each occurrence from the group consisting of hydrogen, $C_1$-$C_6$ alkyl, $C_2$-$C_6$ alkenyl, $C_2$-$C_{16}$ alkynyl, $C_3$-$C_7$ cycloalkyl, $C_3$-$C_7$ cycloalkenyl, phenyl, heterocycle, heteroaryl, halo, hydroxyl, carboxyl, $OR_c$, $NR_dR_d$, $C(O)OR_c$, CN, $C(O)R_c$, wherein the $C_{1-6}$ alkyl, $C_2$-$C_6$ alkenyl, $C_2$-$C_{16}$ alkynyl, $C_3$-$C_7$ cycloalkyl, $C_3$-$C_7$ cycloalkenyl, phenyl, heterocycle, and heteroaryl of $R_6$, $R_7$ and $R_8$ may each be optionally substituted by one, two or three substituents selected from halo, hydroxyl, $C_{1-6}$ alkyl and $C_{1-6}$ alkoxy;

$R_c$ is $C_{1-4}$ alkyl; and $R_d$ is independently for each occurrence selected from the group consisting of H and $C_{1-4}$ alkyl, or the two $R_d$s taken together with the N to which they are attached form a heterocyclic ring.

In some embodiments, a disclosed compound has the Formula (Ib) or the Formula (IIb):

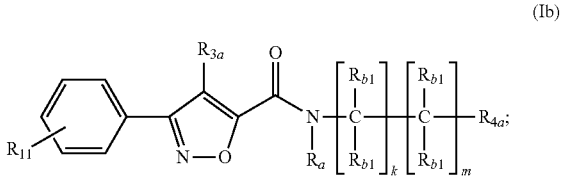

-continued

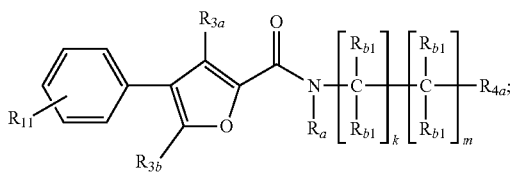

(IIb)

wherein, $R_{11}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, and halo. In certain embodiments, $R_{4a}$ is an optionally substituted $C_3$-$C_7$ cycloalkyl (e.g., optionally substituted cyclopropyl or an optionally substituted cyclobutyl).

In certain of these embodiments, $R_{4a}$ is substituted with a substituent having the formula:

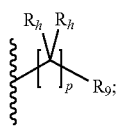

wherein each $R_h$ is independently selected for each occurrence from the group consisting of hydrogen, halo, hydroxyl, $C_1$-$C_6$ alkyl, and $C_3$-$C_6$ cycloalkyl, or two geminal $R_h$ groups are independently taken together with the carbon atom to which they are attached to form an optionally substituted carbocyclic or heterocycle;

$R_9$ is selected from the group consisting of hydrogen, halo, CN, hydroxyl, methyl (optionally substituted by one, two or three substituents selected from halogen and hydroxyl), $C_2$-$C_4$ alkenyl, $C_2$-$C_4$ alkynyl, $C_3$-$C_6$ cycloalkyl, $C_{1-6}$ alkoxy, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$;

$R_c$ is independently selected for each occurrence from the group consisting of H, $C_1$-$C_6$ alkyl, $C_{3-6}$ cycloalkyl, heterocycle, and heteroaryl;

$R_d$ is independently selected for each occurrence from H and $C_{1-4}$ alkyl, or the two $R_d$s taken together with the N to which they are attached form a heterocyclic ring; and p is 0, 1, or 2.

For example, $R_{4a}$ can be selected from the group consisting of:

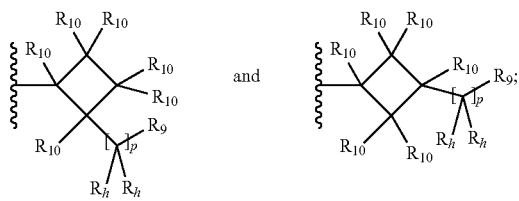

wherein each $R_{10}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, optionally substituted $C_3$-$C_6$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl; alternatively, two geminal $R_{10}$ groups are taken together with the carbon atom to which they are attached to form a spiro $C_3$-$C_7$ cycloalkyl, a spiro $C_3$-$C_7$ cycloalkenyl, a spiro heterocyclic, a spiro aryl or spiro heteroaryl, each optionally substituted; or yet alternatively, two vicinal $R_{10}$ groups are taken together with the carbon atoms to which they are attached to form a fused, optionally substituted cyclic group selected from the group consisting of $C_4$-$C_8$ cycloalkyl, $C_4$-$C_8$ cycloalkenyl, 4- to 8-membered heterocyclic, aryl and heteroaryl, each optionally substituted; or further alternatively, two $R_{10}$ groups attached to non-adjacent carbon atoms are taken together with the carbon atoms to which they are attached to form a bridged cyclic group selected from the group consisting of $C_3$-$C_8$ cycloalkyl, $C_3$-$C_8$ cycloalkenyl, and 4- to 8-membered heterocyclic, each optionally substituted;

each $R_h$ is independently selected from the group consisting of hydrogen, halo, optionally substituted $C_1$-$C_{10}$ alkyl, and optionally substituted $C_3$-$C_6$ cycloalkyl, or two geminal $R_h$ groups are independently taken together with the carbon atom to which they are attached to form an optionally substituted heterocyclic or an optionally substituted heteroaryl;

$R_9$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl; and p is 0, 1, or 2.

In some embodiments, Y is S, $S(O)_2$ or $S(O)_2NR_d$.

In some embodiments, $R_{4b}$ is heterocycle or a 5-6 membered monocyclic or a 8-10 membered bicyclic heteroaryl having one, two or three heteroatoms selected from N, S or O, wherein the heterocycle or heteroaryl are optionally substituted by one, two or three substituents independently selected for each occurrence from the group consisting of halogen, $C_{1-6}$ alkyl (optionally substituted by one, two or three substituents each independently selected from halogen and hydroxyl), $C_{1-6}$ alkoxy (optionally substituted by one, two or three halogens), hydroxyl, and $NR_dR_d$ wherein $R_d$ is independently for each occurrence selected from H and $C_{1-4}$ alkyl, or the two $R_d$s taken together with the N to which they are attached form a heterocyclic ring). For example, $R_{4b}$ can be selected from the group consisting of furanyl, pyridinyl, pyrazinyl, pyrazolyl, imidazolyl, isoxazolyl, triazolyl, thiazolyl, oxadiazolyl, thiadiazolyl, thienyl, piperazinyl, and benzimidazolyl, each optionally substituted.

Exemplary compounds are shown below in Table 1:
TABLE 1
| # | Structure |
|---|---|
| 1 | 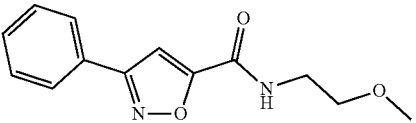 [SMILES: COCCNC(=O)c1cc(-c2ccccc2)no1] |
| 2 | 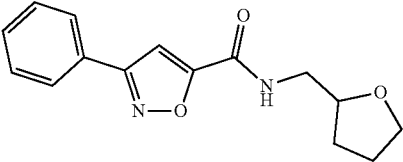 [SMILES: O=C(NCC1CCCO1)c1cc(-c2ccccc2)no1] |
| 3 | 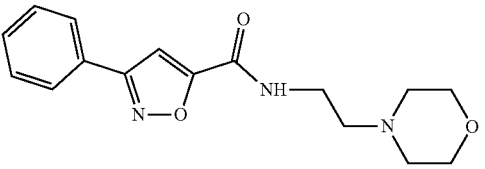 |
| 4 | 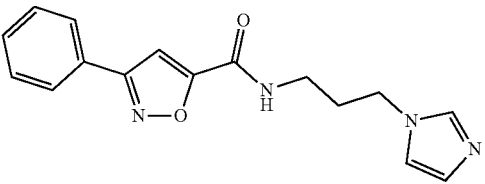 [SMILES: O=C(NCCCn1ccnc1)c1cc(-c2ccccc2)no1] |
| 5 | 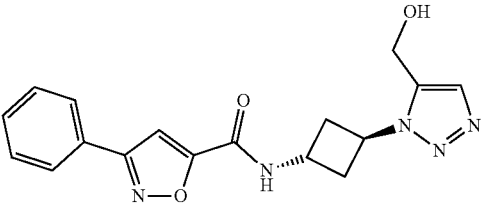 |
| 6 | 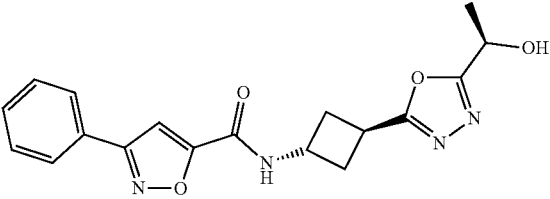 |
| 7 | 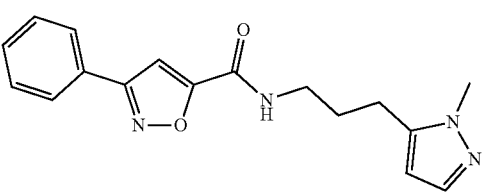 [SMILES: Cn1nccc1CCCNC(=O)c1cc(-c2ccccc2)no1] |
| 8 | 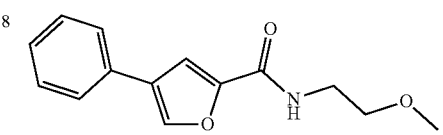 |

TABLE 1-continued

| # | Structure |
|---|-----------|
| 9 | N-((tetrahydrofuran-2-yl)methyl)-4-phenylfuran-2-carboxamide |
| 10 | N-(2-morpholinoethyl)-4-phenylfuran-2-carboxamide |
| 11 | N-(3-(1H-imidazol-1-yl)propyl)-4-phenylfuran-2-carboxamide |
| 12 | N-cyclopropyl-4-phenylfuran-2-carboxamide |
| 13 | N-(3-(5-(1-(methylsulfonyl)ethyl)-1,3,4-oxadiazol-2-yl)cyclobutyl)-3-phenylisoxazole-5-carboxamide |
| 14 | N-(3-(5-(1-methoxyethyl)-1,3,4-oxadiazol-2-yl)cyclobutyl)-3-phenylisoxazole-5-carboxamide |
| 15 | N-(3-(5-(2,2,2-trifluoroethoxymethyl)-1,3,4-oxadiazol-2-yl)cyclobutyl)-3-phenylisoxazole-5-carboxamide |
| 16 | N-(3-(5-(2,2,2-trifluoroethoxymethyl)-1,3,4-oxadiazol-2-yl)cyclobutyl)-3-phenylisoxazole-5-carboxamide |

TABLE 1-continued
| # | Structure |
|---|---|
| 17 | 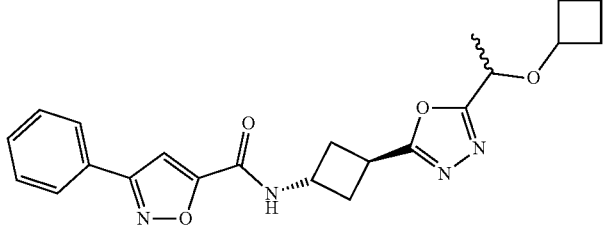 |
| 18 | 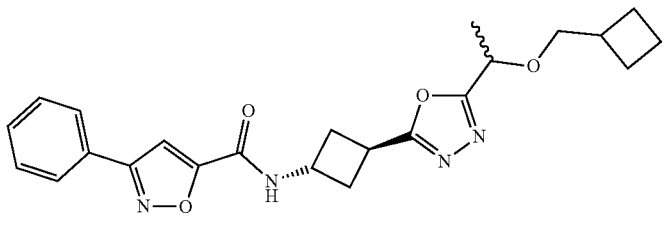 |
| 19 | 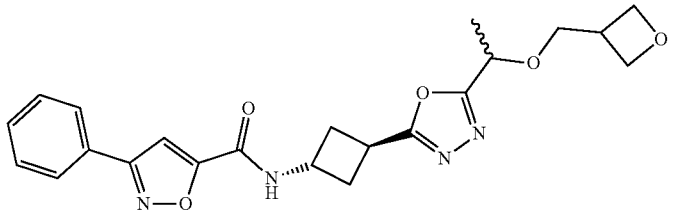 |
| 20 | 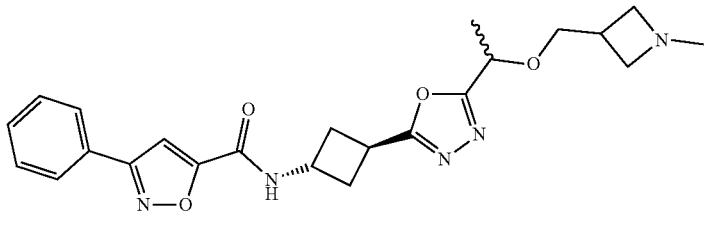 |
| 21 | 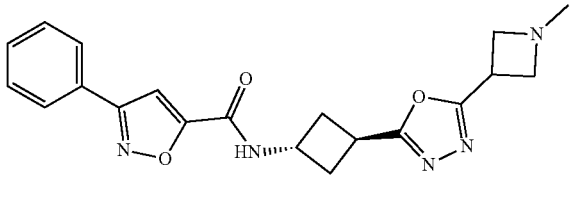 [SMILES: CN1CC(c2nnc([C@H]3C[C@H](NC(=O)c4cc(-c5ccccc5)no4)C3)o2)C1] |
| 22 | 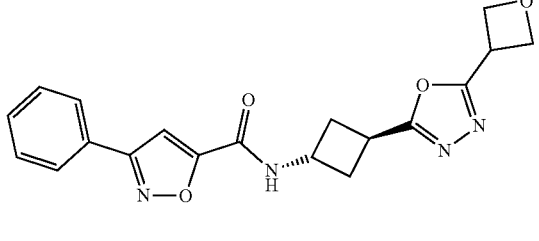 |
| 23 | 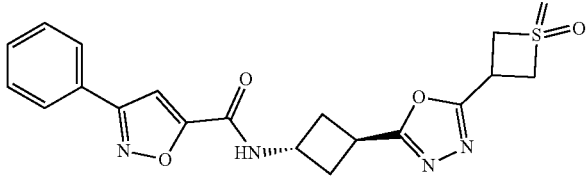 |

TABLE 1-continued
| # | Structure |
|---|---|
| 24 | 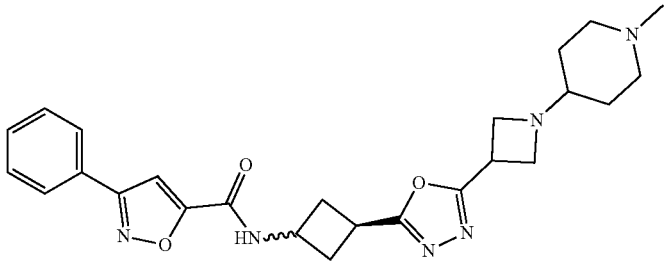 |
| 25 | 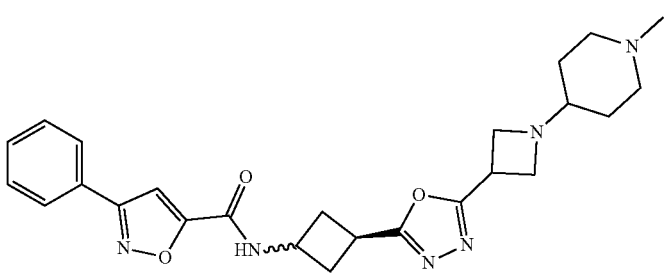 |
| 26 | 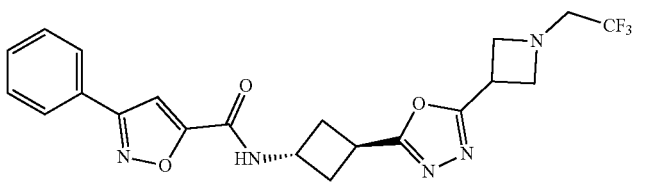 [SMILES: O=C(N[C@H]1C[C@H](c2nnc(C3CN(CC(F)(F)F)C3)o2)C1)c1cc(-c2ccccc2)no1] |
| 27 | 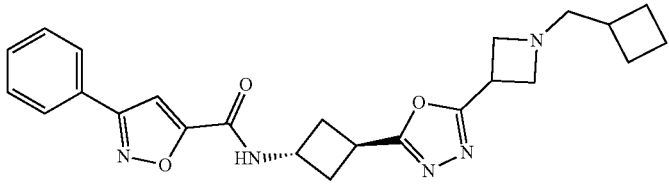 [SMILES: O=C(N[C@H]1C[C@H](c2nnc(C3CN(CC4CCC4)C3)o2)C1)c1cc(-c2ccccc2)no1] |
| 28 | 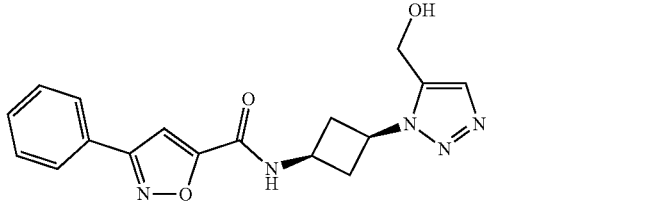 [SMILES: O=C(N[C@H]1C[C@@H](n2nncc2CO)C1)c1cc(-c2ccccc2)no1] |
| 29 | 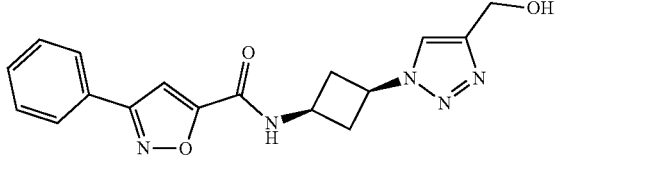 [SMILES: O=C(N[C@H]1C[C@@H](n2cc(CO)nn2)C1)c1cc(-c2ccccc2)no1] |
| 30 | 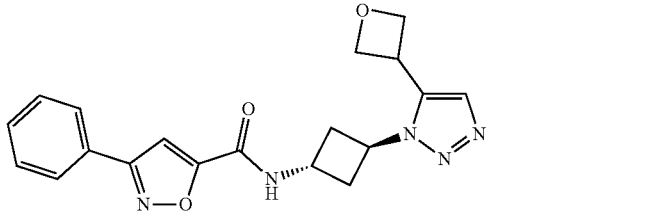 [SMILES: O=C(N[C@H]1C[C@H](n2nncc2C2COC2)C1)c1cc(-c2ccccc2)no1] |

TABLE 1-continued
| # | Structure |
|---|---|
| 31 | 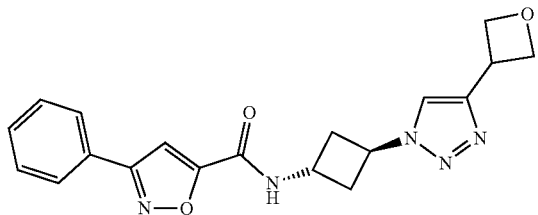 |
| 32 | 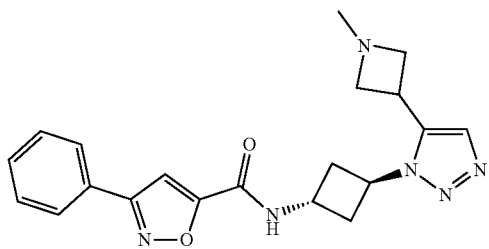 [SMILES: CN1CC(c2cnnn2[C@H]2C[C@H](NC(=O)c3cc(-c4ccccc4)no3)C2)C1] |
| 33 | 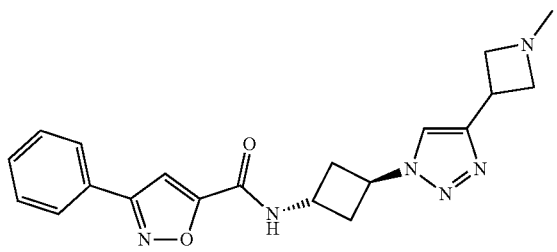 |
| 34 | 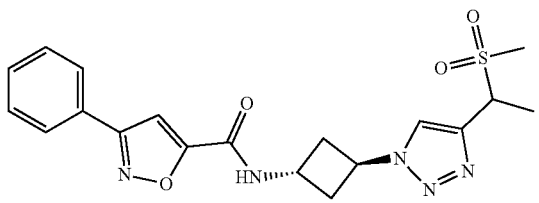 [SMILES: CC(c1cn([C@H]2C[C@H](NC(=O)c3cc(-c4ccccc4)no3)C2)nn1)S(C)(=O)=O] |
| 35 | 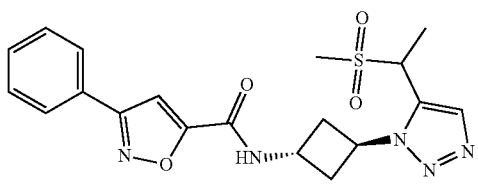 [SMILES: CC(c1cnnn1[C@H]1C[C@H](NC(=O)c2cc(-c3ccccc3)no2)C1)S(C)(=O)=O] |
| 36 | 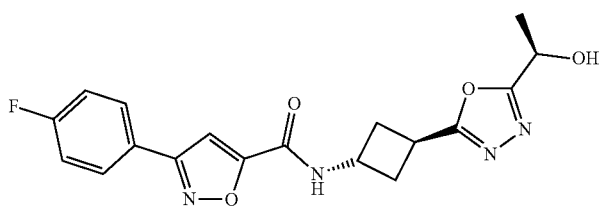 |
| 37 | 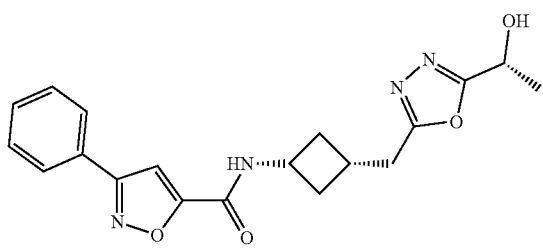 |

TABLE 1-continued

| # | Structure |
|---|---|
| 38 | 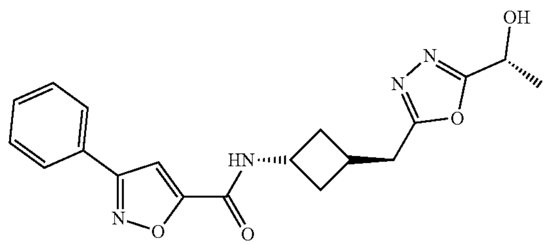 |
| 39 | 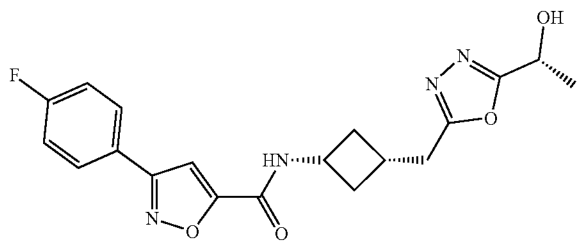 |
| 40 | 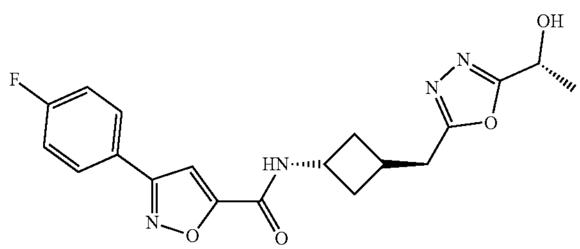 |
| 41 | 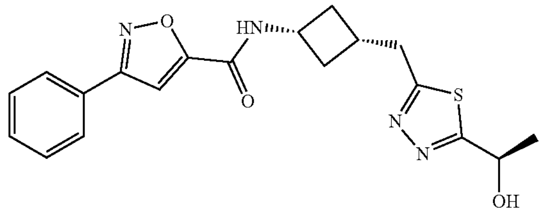 [SMILES: C[C@@H](O)c1nnc(C[C@H]2C[C@@H](NC(=O)c3cc(-c4ccccc4)no3)C2)s1] |
| 42 | 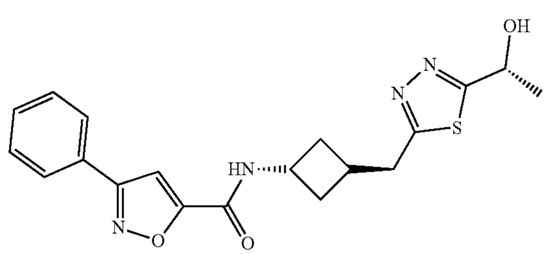 |
| 43 | 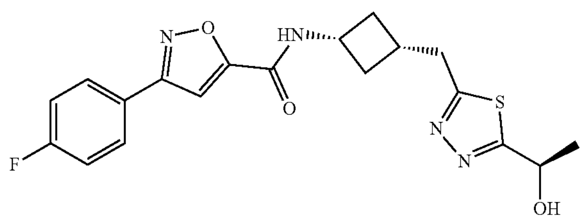 [SMILES: C[C@@H](O)c1nnc(C[C@H]2C[C@@H](NC(=O)c3cc(-c4ccc(F)cc4)no3)C2)s1] |

TABLE 1-continued

| # | Structure |
|---|-----------|
| 44 | 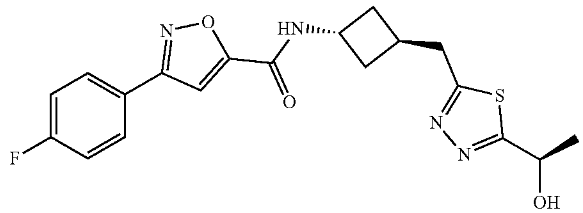 [SMILES: C[C@@H](O)c1nnc(C[C@H]2C[C@H](NC(=O)c3cc(-c4ccc(F)cc4)no3)C2)s1] |
| 45 | 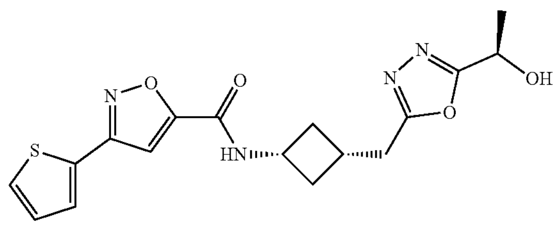 [SMILES: C[C@@H](O)c1nnc(C[C@H]2C[C@@H](NC(=O)c3cc(-c4cccs4)no3)C2)o1] |
| 46 | 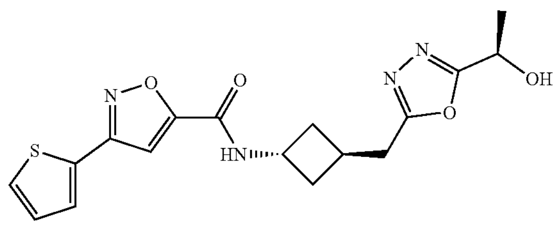 [SMILES: C[C@@H](O)c1nnc(C[C@H]2C[C@H](NC(=O)c3cc(-c4cccs4)no3)C2)o1] |
| 47 | 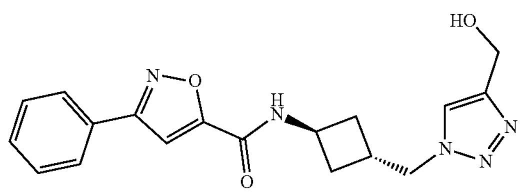 [SMILES: O=C(N[C@H]1C[C@H](Cn2cc(CO)nn2)C1)c1cc(-c2ccccc2)no1] |
| 48 | 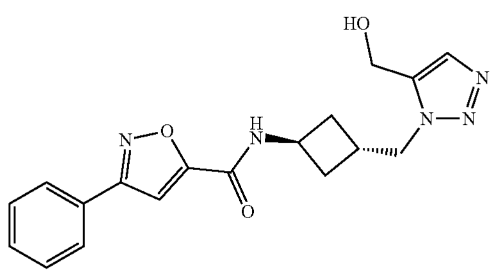 [SMILES: O=C(N[C@H]1C[C@H](Cn2nncc2CO)C1)c1cc(-c2ccccc2)no1] |
| 49 | 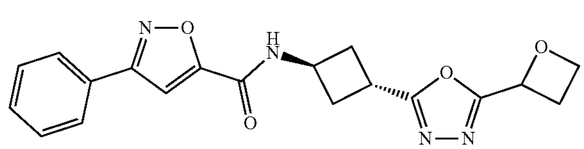 [SMILES: O=C(N[C@H]1C[C@H](c2nnc(C3CCO3)o2)C1)c1cc(-c2ccccc2)no1] |
| 50 | 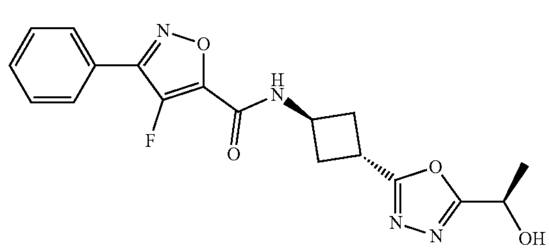 [SMILES: C[C@@H](O)c1nnc([C@H]2C[C@H](NC(=O)c3onc(-c4ccccc4)c3F)C2)o1] |

TABLE 1-continued

| # | Structure |
|---|---|
| 51 | [structure: 3-phenylisoxazole-5-carboxamide linked to cyclobutyl-1,2,3-triazole bearing a 1-hydroxyethyl group] |
| 52 | [structure: 3-phenylisoxazole-5-carboxamide linked to cyclobutyl-1,2,3-triazole bearing (R)-1-hydroxyethyl group] |
| 53 | [structure: 3-phenylisoxazole-5-carboxamide linked to cyclobutyl-1,2,3-triazole bearing a 1-hydroxyethyl group] |
| 54 | [structure: 3-phenylisoxazole-5-carboxamide linked to cyclobutyl-1,2,3-triazole bearing a 1-hydroxyethyl group] |
| 55 | [structure: 3-phenylisoxazole-5-carboxamide linked to cyclobutyl-methylene-1,2,3-triazole bearing a 1-hydroxyethyl group] |
| 56 | [structure: 3-phenylisoxazole-5-carboxamide linked to cyclobutyl-methylene-1,2,3-triazole bearing a 1-hydroxyethyl group] |

TABLE 1-continued
| # | Structure |
|---|---|
| 57 | 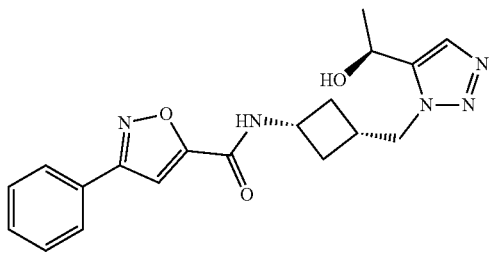 [SMILES: C[C@H](O)c1cnnn1C[C@H]1C[C@@H](NC(=O)c2cc(-c3ccccc3)no2)C1] |
| 58 | 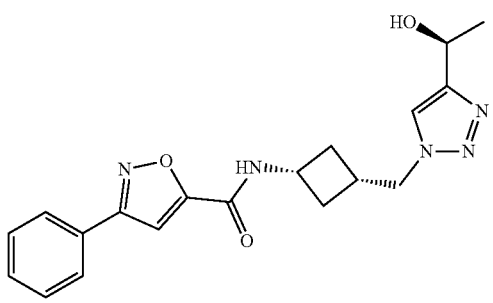 [SMILES: C[C@H](O)c1cn(C[C@H]2C[C@@H](NC(=O)c3cc(-c4ccccc4)no3)C2)nn1] |
| 59 | 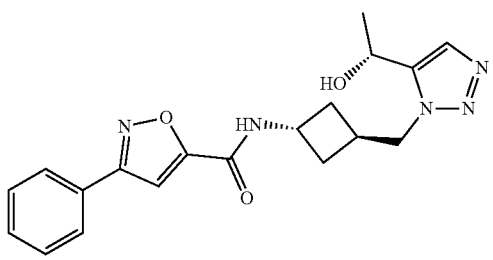 [SMILES: C[C@@H](O)c1cnnn1C[C@H]1C[C@H](NC(=O)c2cc(-c3ccccc3)no2)C1] |
| 60 | 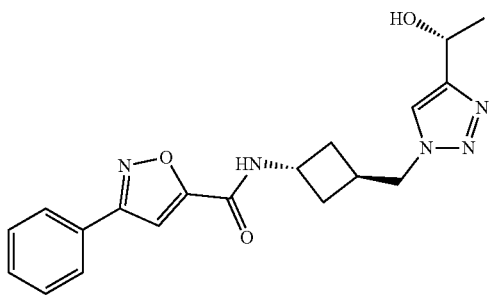 [SMILES: C[C@@H](O)c1cn(C[C@H]2C[C@H](NC(=O)c3cc(-c4ccccc4)no3)C2)nn1] |
| 61 | 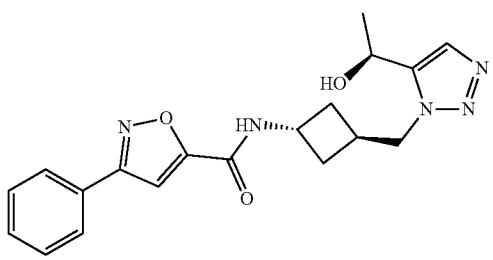 [SMILES: C[C@H](O)c1cnnn1C[C@H]1C[C@H](NC(=O)c2cc(-c3ccccc3)no2)C1] |

TABLE 1-continued

| # | Structure |
|---|-----------|
| 62 | 3-phenyl-N-(cis-3-((4-((R)-1-hydroxyethyl)-1H-1,2,3-triazol-1-yl)methyl)cyclobutyl)isoxazole-5-carboxamide |
| 63 | 3-phenyl-N-((1R,3r)-3-((3-((R)-1-hydroxyethyl)-1H-pyrazol-1-yl)methyl)cyclobutyl)isoxazole-5-carboxamide |
| 64 | 3-phenyl-N-((1S,3r)-3-((3-((S)-1-hydroxyethyl)-1H-pyrazol-1-yl)methyl)cyclobutyl)isoxazole-5-carboxamide |
| 65 | 3-phenyl-N-((1R,3s)-3-((3-((S)-1-hydroxyethyl)-1H-pyrazol-1-yl)methyl)cyclobutyl)isoxazole-5-carboxamide |
| 66 | 3-phenyl-N-((1S,3s)-3-((3-((R)-1-hydroxyethyl)-1H-pyrazol-1-yl)methyl)cyclobutyl)isoxazole-5-carboxamide |
| 67 | 3-phenyl-N-((1S,3r)-3-((4-((S)-1-hydroxyethyl)-1H-pyrazol-1-yl)methyl)cyclobutyl)isoxazole-5-carboxamide |
| 68 | 3-phenyl-N-((1R,3r)-3-((4-((R)-1-hydroxyethyl)-1H-pyrazol-1-yl)methyl)cyclobutyl)isoxazole-5-carboxamide |

TABLE 1-continued

| # | Structure |
|---|---|
| 69 | (structure: 3-phenyl-isoxazole-5-carboxamide linked to (1S,3s)-cyclobutyl-CH2-pyrazole bearing (R)-1-hydroxyethyl) |
| 70 | (structure: 3-phenyl-isoxazole-5-carboxamide linked to (1R,3s)-cyclobutyl-CH2-pyrazole bearing (S)-1-hydroxyethyl) |
| 71 | (structure: 3-phenyl-isoxazole-5-carboxamide linked to (1r,3r)-cyclobutyl-CH2-O-(4-fluorophenyl)) |
| 72 | (structure: 3-phenyl-isoxazole-5-carboxamide linked to (1s,3s)-cyclobutyl-CH2-O-(4-fluorophenyl)) |
| 73 | (structure: 3-phenyl-isoxazole-5-carboxamide linked to (1r,3r)-cyclobutyl-CH2-O-(4-cyanophenyl)) |
| 74 | (structure: 3-phenyl-isoxazole-5-carboxamide linked to (1s,3s)-cyclobutyl-CH2-O-(4-cyanophenyl)) |
| 75 | (structure: 3-(5-fluorothiophen-2-yl)-isoxazole-5-carboxamide linked to cyclobutyl-CH2-1,3,4-oxadiazole bearing 1-hydroxyethyl) |

TABLE 1-continued

| # | Structure |
|---|---|
| 76 | (structure: 5-fluorothiophene-isoxazole-C(O)NH-cyclobutyl-1,3,4-oxadiazole-CH(OH)) |

Also contemplated herein are pharmaceutical compositions that include a disclosed compound such as those compounds having Formula (Ia), (IIa), (Ib), (IIb), (III), or (IV) and a pharmaceutically acceptable carrier or excipient. In certain embodiments, the compositions can include at least one additional CFTR modulator as described anywhere herein or at least two additional CFTR modulators, each independently as described anywhere herein.

It is to be understood that the specific embodiments described herein can be taken in combination with other specific embodiments delineated herein. For example, as discussed above, in some embodiments, $R_{2a}$ is fluoro, and in some embodiments described above, A is an optionally substituted imidazolyl or pyrazolyl. For example, disclosed compounds of Formula (Ia), (IIa), (Ib), (IIb), (III), or (IV) wherein $R_{2a}$ is fluoro and A is an optionally substituted imidazolyl or pyrazolyl are contemplated.

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the present invention herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$ alkenyl, and $C_{3-4}$ alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively for example. Examples of cycloalkyl include, but are not limited to, cyclopropyl, cyclobutyl, cyclopentyl, cyclohexyl, cycloheptyl and adamantyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$ alkoxy, and $C_{2-6}$ alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring, a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

Cycloalkyl, cycloalkenyl, and heterocyclic groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, naphthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "substituted" refers to substitution by independent replacement of one, two, or three or more of the hydrogen atoms with substituents including, but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —$C(O)R_y$, —$C(O)C(O)R_y$, —$OCO_2R_y$, —$OC(O)R_y$, $OC(O)C(O)R_y$, —$NHC(O)R_y$, —$NHCO_2R_y$, —$NHC(O)C(O)R_y$, $NHC(S)NH_2$, —NHC(S)$NHR_x$, —$NHC(NH)NH_2$, —$NHC(NH)NHR_x$, —NHC(NH)$R_x$, —C(NH)$NHR_x$, and (C=$NR_x$)$R_x$; —$NR_xC(O)R_x$, —$NR_xC(O)N(R_x)_2$, —$NR_xCO_2R_y$, —$NR_xC(O)C(O)R_y$, —$NR_xC(S)NH_2$, —$NR_xC(S)NHR_x$, —$NR_xC(NH)NH_2$, —$NR_xC(NH)NHR_x$, —$NR_xC(NH)R_x$, —C($NR_x$)$NHR_x$—S (O)$R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of disclosed compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasterisomers of disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that disclosed compounds include both solvated and unsolvated forms. In one embodiment, a disclosed compound is amorphous or, in another embodiment, a single polymorph. In another embodiment, a disclosed compound is a mixture of polymorphs. In another embodiment, a disclosed compound is in a crystalline form.

Isotopically labeled compounds are also contemplated herein, which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a disclosed compound may have one or more H atom replaced with deuterium.

Certain isotopically labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the examples herein by substituting an isotopically labeled reagent for a non-isotopically labeled reagent.

In some embodiments one or more of the nitrogen atoms of a disclosed compound if present are oxidized to N-oxide.

Representative synthetic routes for the preparation of the compounds disclosed herein are provided throughout the Examples section. As will be understood by the skilled artisan, diastereomers can be separated from the reaction mixture using column chromatography.

Disclosed compounds may be also be prepared using methods described in the literature, including, but not limited to, *J. Med. Chem.* 2011, 54(13), 4350-64; *Russian Journal of Organic Chemistry*, 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, contemplated herein in an embodiment is a method of increasing CFTR activity in a subject comprising administering an effective amount of a disclosed compound. Also contemplated herein is a method of treating a patient suffering from a condition associated with CFTR activity comprising administering to said patient an effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+ 10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10kbC>T; Δ303K/384; and DF508/G178R).

In certain embodiments, the mutation is a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, the invention also encompasses a method of treating cystic fibrosis. Methods of treating other conditions associated with CFTR activity, including conditions associated with deficient CFTR activity, comprising administering an effective amount of a disclosed compound, are also provided herein.

For example, provided herein is a method of treating a condition associated with deficient or decreased CFTR activity comprising administering an effective amount of a disclosed compound that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, a disclosed method of treatment comprises administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), VX-809 (3-(6-(1-(2,2-difluorobenzo[d][1,3]dioxol-5-yl)cyclopropanecarboxamido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, VX-152, VX-440, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG 2665, GLPG2222 (for example, a CFTR corrector); and compounds described in, e.g., WO2014/144860 and 2014/176553, hereby incorporated by reference. Non-limiting examples of modulators include QBW-251, QR-010, NB-124, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agent and incorporated by reference. Non-limiting examples of anti-inflammatory agents include N6022 (3-(5-(4-(1H-imidazol-1-yl) phenyl)-1-(4-carbamoyl-2-methylphenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, GLPG2222 and GLPG2665) or potentiator (e.g., ivacaftor, genistein and GLPG1837). In certain of these embodiments, one of the at least two additional therapeutic agents is a CFTR corrector (e.g., VX-809, VX-661, VX-983, VX-152, and VX-440) and the other is a CFTR potentiator (e.g., ivacaftor and genistein). In certain of these embodiments, one of the at least two additional therapeutic agents is a CFTR corrector (e.g., GLPG2222 or GLPG2665) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances readthrough of stop codons (e.g., NB 124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, VX-152, VX-440, GLPG2222, GLPG2665, NB 124, ataluren) and/or the other is a CFTR potentiator (e.g., ivacaftor, genistein, and GLPG1837); e.g., one of the at least two additional therapeutic agents is GLPG2222 or GLPG2665, and the other is GLPG1837; or one of the at least two additional therapeutic agents is VX-809 or VX-661, and the other is a ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1 G > A Splice-site mutation in gene intron 16 |
| VI | Reduced due to protein instability | N287Y a A -> T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120 + 1 G > A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E. G1349D, G178R, G551S, S1251N, S1255P, S549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g, ΔF508 mutation, as compared to administration of ivacaftor alone. Another combination therapy that includes a disclosed compound may also include an effective amount of a read-through agent (e.g., ataluren, NB124) and an effect amount of disclosed compound that may act as an amplifier.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g, VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

In an embodiment, contemplated methods may include for example, administering prodrugs of the compounds described herein, for example, prodrugs of a compound of Formula (Ia), (IIa), (Ib), (IIb), (III), or (IV) or a pharmaceutical composition thereof.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., *Nature Reviews Drug Discovery* 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di $(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-(($C_{1-6}$) alkylcarbonyloxy)ethyl, 1-methyl-1-(($C_{1-6}$)alkylcarbonyloxy)ethyl ($C_{1-6}$)alkoxycarbonyloxy)methyl, N—($C_{1-6}$)

alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Also contemplated in certain embodiments is the use of clathrates of the compounds described herein, pharmaceutical compositions comprising the clathrates, and methods of use of the clathrates. Clathrates of a disclosed compound or a pharmaceutical composition thereof are also contemplated herein.

As discussed above, the disclosure also contemplates administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

Disclosed compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the disclosure contemplates s administering a disclosed compound e.g., Formula (Ia), (IIa), (Ib), (IIb), (III), or (IV) that corrects protein misfolding, reduces protein aggregation, corrects or restores protein trafficking and/or affects protein degradation for the treatment of a condition associated with a dysfunction in proteostasis. In some aspects, a disclosed compound e.g., Formula (Ia), (IIa), (Ib), (IIb), (III), or (IV) that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucosaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. The compounds of Formula (Ia), (IIa), (Ib), (IIb), (III), or (IV) can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, a disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, a treatment of a disease associated with a dysfunction in proteostasis is diabetes and/or complications of diabetes, including, but not limited to, diabetic retinopathy, cardiomyopathy, neuropathy, nephropathy, and impaired wound healing is contemplated.

In a further embodiment, a treatment of a disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration is contemplated.

In yet additional embodiments, a disclosed method is directed to treating a disease associated with a dysfunction in proteostasis, wherein the disease affects the respiratory system or the pancreas. In certain additional embodiments, a contemplated method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. For example, provided herein are methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). In another embodiment, methods for treating hearing loss, such as noise-induced hearing loss, aminoglycoside-induced hearing loss, and cisplatin-induced hearing loss comprising administering a disclosed compound are provided.

Additional conditions include those associated with a defect in protein trafficking and that can be treated according to a disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The invention is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Preparation of tert-butyl (trans-3-azidocyclobutyl) carbamate

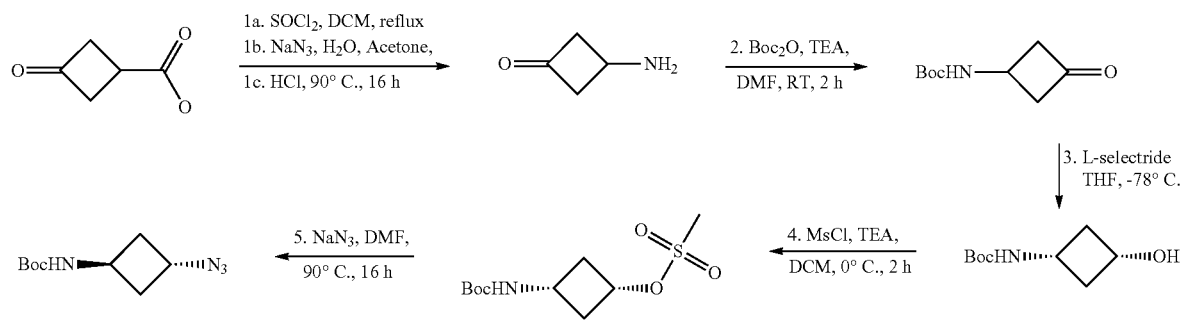

Step 1: 3-Amino-cyclobutan-1-one

SOCl$_2$ (15.6 g, 131.46 mmol) was added dropwise to an ice-cooled solution of 3-oxocyclobutane carboxylic acid (5.0 g, 43.82 mmol) in dry DCM (30 mL) and the reaction mixture was refluxed for 3 h. The reaction mixture was cooled to room temperature and the volatiles were removed under reduced pressure to get the crude compound which was azeotropically distilled with toluene (20 mL×2) to remove acidic traces. The crude compound was dissolved in dry acetone (15 mL) and to the resulting solution was added a solution of NaN$_3$ (5.69 g, 87.64 mmol) in water (20 mL) at 0° C. over 30 min. The reaction mixture was stirred for 1 h at 0° C. and crushed ice was added to the reaction mixture. The aq. phase was extracted with ether (3×50 mL), dried over sodium sulfate and concentrated to ~¼th volume. Then the reaction mixture was added to toluene (70 mL) and heated to 90° C., until evolution of N$_2$ ceased (~30 min). To the resulting reaction mixture was added 20% HCl (50 mL) at 0° C. and the reaction mixture was gently heated to 90° C. for 16 h. The organic layer was separated and washed with water (50 mL). The aqueous layer was concentrated under vacuum to afford the product (5 g, crude) as a brown solid. $^1$H-NMR (400 MHz, CDCl$_3$) δ 8.75 (br, 3H), 3.92-3.86 (m obscured by solvent signal, 2H), 3.38-3.31 (m, 3H).

Step 2: tert-butyl (3-oxocyclobutyl) carbamate

TEA (29.72 g, 293.73 mmol) was added dropwise to a solution of 3-aminocyclobutan-1-one (5.0 g, 58.74 mmol) and Boc$_2$O (25.64 g, 117.49 mmol) in DMF (80 mL) and the reaction mixture was stirred at room temperature for 2 h. After complete consumption of starting material as indicated by TLC, the reaction mixture was diluted with water (100 mL) and extracted with diethyl ether (6×70 mL). The combined organic layer was washed with brine (2×100 mL) and dried over Na$_2$SO$_4$. The solvent was removed under reduced pressure to get the crude compound which was purified by silica gel (100-200) column chromatography using 30% ethyl acetate in n-hexane to afford the product (5.3 g, 65% after two steps) as an off-white solid. $^1$H-NMR (400 MHz, CDCl$_3$) δ 4.91 (br, 1H), 4.25 (br, 1H), 3.41-3.34 (m, 2H), 3.07-3.00 (m, 2H), 1.44 (s, 9H).

Step 3: tert-butyl cis-3-hydroxycyclobutyl)carbamate

A solution of L-Selectride (1M solution in THF) (8.053 mL, 8.05 mmol) was added dropwise over a period of 20 min to a solution of tert-butyl (3-oxocyclobutyl)carbamate (1.0 g, 5.40 mmol) in THF (25 mL) under N2 atmosphere at −78° C. and the reaction mixture was stirred for 1 h at −78° C. To the resulting reaction mixture was added a solution of NaOH (3.25 g) in water (4 mL) over a period of 10 min followed by 30% aqueous H$_2$O$_2$ (3 mL) over a period of 20 min. The reaction mixture was allowed to warm to room temperature and diluted with ethyl acetate (100 mL). The organic layer was separated off and washed with 10% aq. Na$_2$SO$_3$ (40 mL) followed by brine (40 mL). The organic layer dried over Na$_2$SO$_4$ and concentrated under reduced pressure to get the crude compound which was further purified by neutral alumina column chromatography using 50% ethyl acetate in n-hexane as eluent to afford the desired compound. The compound was washed with n-hexane to afford the product (0.750 g, 74%) as white solid. m. p. 119° C. (lit. value 117° C.); $^1$H NMR (400 MHz, CDCl$_3$) δ 4.63 (br, 1H), 4.03-3.96 (m, 1H), 3.66-3.64 (m, 1H), 2.76-2.72 (m, 2H), 1.91 (br, 1H), 1.79-1.76 (m, 2H), 1.42 (s, 9H).

Step 4: cis-3-((tert-butoxycarbonyl)amino)cyclobutyl methanesulfonate

Triethylamine (1.0 g, 9.93 mmol) was added to a cold (~10° C.) solution of tert-butyl (cis-3-hydroxycyclobutyl) carbamate (0.62 g, 3.31 mmol) in DCM (30 mL) followed by dropwise addition of methanesulfonyl chloride (0.45 g, 3.97 mmol) and the reaction mixture was stirred at −10° C. for 2 h. The reaction mixture was diluted with DCM (100 mL) and washed with water (5 mL) followed by dilute citric acid (30 mL) and brine (30 mL). The organic layer was dried over Na$_2$SO$_4$, concentrated under reduced pressure to afford the product (0.800 g, crude) as white solid which was used as such in next step without further purification. $^1$H NMR (400 MHz, CDCl$_3$) δ 4.73-4.66 (m, 2H), 3.85-3.80 (m, 1H), 2.98 (s, 3H), 2.93-2.86 (m, 2H), 2.20-2.13 (m, 2H), 1.42 (s, 9H).

Step 5: tert-butyl (trans-3-azidocyclobutyl) carbamate

NaN$_3$ (0.49 g, 7.54 mmol) was added to a solution of cis-3-((tert-butoxycarbonyl) amino)cyclobutyl methanesulfonate (0.8 g, 3.01 mmol) in dry DMF (20 mL) and the mixture was heated at 85° C. for 16 h. The reaction mixture was diluted with water (40 mL) and the aqueous phase was extracted with ethyl acetate (50 mL×3). The combined organic layer was washed with brine (50 mL×4) and dried over Na$_2$SO$_4$. The solvent was removed under reduced pressure to get the crude product (0.73 g) as an off-white solid.

Preparation of tert-butyl (cis-3-azidocyclobutyl) carbamate

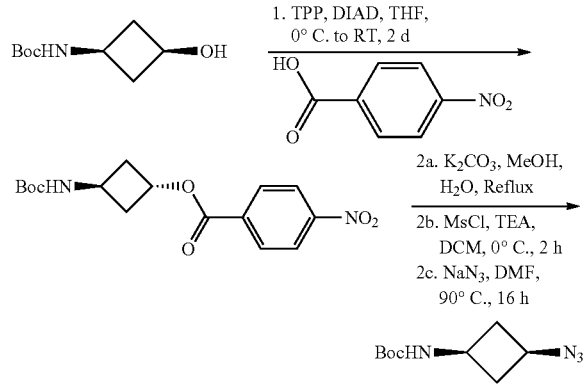

Step 1: trans-3-((tert-butoxycarbonyl)amino)cyclobutyl 4-nitrobenzoate

To an ice-cooled solution of tert-butyl (cis-3-hydroxycyclobutyl)carbamate (1.5 g, 80.11 mmol) and 4-nitrobenzoic acid (1.47 g, 88.12 mmol) in dry THF (60 mL) was added triphenylphosphine (3.15 g, 12.01 mmol) followed by dropwise addition of DIAD (8.09 g, 40.05 mmol) and the reaction mixture was stirred at room temperature for 2 days. The solvent was removed under reduced pressure to afford the crude compound which was purified by silica gel (100-200 mesh) column chromatography. Elution with 50% ethyl acetate in n-hexane followed by washing with diethyl ether (4 mL×2) gave the product (2.3 g, 85%) as a white solid. $^1$H-NMR (400 MHz, CDCl$_3$) δ 8.29-8.27 (q, 2H, J=8.92 Hz), 8.21-8.19 (q, 2H, J=8.92 Hz), 5.37-5.32 (m, 1H), 4.77 (br, 1H), 4.41-4.38 (m, 1H), 2.64-2.58 (m, 2H), 2.47-2.40 (m, 2H), 1.44 (s, 9H); LC-MS (ES, M/Z): [M+H]$^+$=336.8.

Step 2a: Trans-tert-butyl-3-hydroxycyclobutyl carbamate

Trans-3-((tert-butoxycarbonyl) amino) cyclobutyl 4-nitrobenzoate was added (2.3 g, 68.38 mmol) to a suspension of K$_2$CO$_3$ (1.41 g, 10.25 mmol) in MeOH (50 mL) and water (10 mL) and the reaction mixture was heated at reflux for 2 h. The reaction mixture was cooled and filtered through celite bed. The filtrate was concentrated under reduced pressure to afford the crude product (4.2 g, crude) as an off-white solid which was used as such without further purification.

Step 2b: trans-3-((tert-butoxycarbonyl)amino)cyclobutyl methanesulfonate

Triethylamine (6.8 g, 67.29 mmol) was added to a suspension of trans-tert-butyl-3-hydroxycyclobutyl carbamate (4.2 g, 22.43 mmol) in DCM (100 mL) followed by dropwise addition of methanesulfonyl chloride (3.08 g, 26.91 mmol) at −10° C. and the reaction mixture was stirred at −10° C. for 2 h. The reaction mixture was diluted with DCM (100 mL) and washed with water (50 mL) followed by brine (30 mL). The organic layer was dried over sodium sulfate and concentrated under reduced pressure to obtain the crude product (3.4 g, crude) as a yellow solid which was used as such in next step without purification.

Step 2c: cis-tert-butyl (3-azidocyclobutyl)carbamate

Sodium azide (2.08 g, 32.035 mmol) was added to a solution of trans-3-((tert-butoxycarbonyl)amino)cyclobutyl methanesulfonate (3.4 g, 12.81 mmol) in dry DMF (20 mL) at room temperature and the reaction mixture was heated at 85° C. for 16 h. The crude reaction mixture was diluted with water (50 mL) and the aqueous phase was extracted with ethyl acetate (50 mL×3). The combined organic layer was washed with brine (50 mL×4) and dried over Na$_2$SO$_4$. The solvent was removed under reduced pressure to give the crude compound which was purified by neutral alumina column chromatography using 10% MeOH in DCM as eluent to afford the product (1.0 g, 68% after two steps) as a white solid. $^1$H NMR (400 MHz, CDCl$_3$) δ 4.66 (br, 1H), 3.86-3.84 (m, 1H), 3.57-3.53 (m, 1H), 2.76-2.69 (m, 2H), 1.92-1.85 (m, 2H), 1.42 (s, 9H).

Preparation of trans-3-(3-phenylisoxazole-5-carboxamido)cyclobutane-1-carboxylic acid

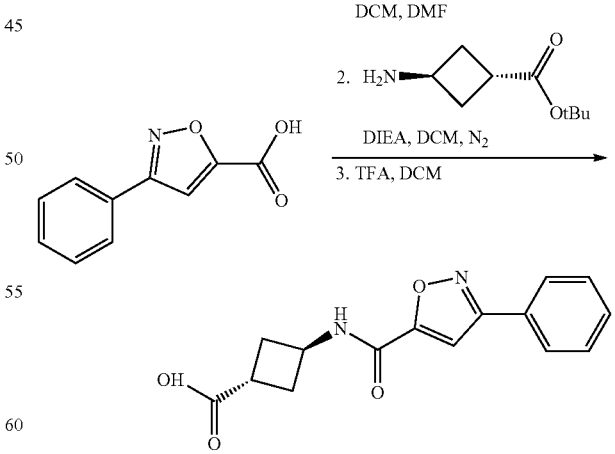

Step 1: 3-phenylisoxazole-5-carbonyl chloride

DMF (0.5 mL) was added to a solution of 3-phenylisoxazole-5-carboxylic acid (10 g, 52.86 mmol, 1.00 eq.) and oxalyl chloride (8.74 g, 68.86 mmol, 1.30 eq.) in dichloromethane (200 mL) and the solution was stirred for 1 h at 0° C. The resulting mixture was concentrated under vacuum to give 11.265 g (crude) of 3-phenylisoxazole-5-carbonyl chloride as a yellow solid.

Step 2: tert-butyl 3-trans-(3-phenylisoxazole-5-amido)cyclobutane-1-carboxylate

A solution of 3-phenylisoxazole-5-carbonyl chloride (8.21 g, 39.54 mmol, 1.50 eq.) in dichloromethane (60 mL) was added dropwise to a solution of tert-butyl 3-trans-aminocyclobutane-1-carboxylate (4.5 g, 26.28 mmol, 1.00 eq.) and DIEA (6.79 g, 52.54 mmol, 2.00 eq.) in dichloromethane (30 mL) under N2. The resulting solution was stirred for 2 h at 0° C. and then quenched with 100 mL of 5% K$_2$CO$_3$ aqueous. The resulting solution was extracted with dichloromethane and the organic layers combined, dried and concentrated under vacuum to give 9.7 g (crude) of tert-butyl 3-(3-phenylisoxazole-5-amido)cyclobutane-1-carboxylate as a light yellow solid. LC-MS (ES, m/z): [M+1]$^+$=343.1.

Step 3: -3-trans-(3-phenylisoxazole-5-amido)cyclobutane-1-carboxylic acid

A solution of tert-butyl 3-trans-(3-phenylisoxazole-5-amido)cyclobutane-1-carboxylate (9.7 g, 28.33 mmol, 1.00 eq.) and trifluoroacetic acid (30 mL) in dichloromethane (100 mL) was stirred for 6 h at room temperature. The resulting mixture was concentrated under vacuum, dissolved in 20 mL of toluene and the solids were collected by filtration to obtain 5.116 g (63%) of 3-trans-(3-phenylisoxazole-5-amido)cyclobutane-1-carboxylic acid as a light yellow solid. LC-MS (ES, m/z): [M+1]$^+$=287.0.

Preparation of (R)-2-methoxypropanehydrazide

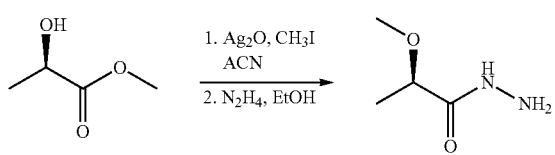

Step 1: methyl (2R)-2-methoxypropanoate

Ag$_2$O (6.1 g, 26.4 mmol, 1.10 eq.) was added to a solution of iodomethane (27.3 g, 192 mmol, 8.00 eq.) and methyl (2R)-2-hydroxypropanoate (2.5 g, 24 mmol, 1.00 eq.) in acetonitrile (30 mL) and the solution was stirred for 16 h at 85° C. in an oil bath. The solids were filtered and the mixture was diluted with DCM (100 mL). The resulting mixture was washed with water (3×50 mL), dried over anhydrous sodium sulfate and concentrated under vacuum to obtain 2 g (70%) of methyl (2R)-2-methoxypropanoate as colorless oil. $^1$H NMR (400 MHz, CDCl$_3$): δ 3.92-3.87 (m, 1H), 3.76 (s, 3H), 3.40 (s, 3H), 1.42-1.40 (d, J=6.8 Hz, 3H).

Step 2: (2R)-2-methoxypropanehydrazide

A solution of methyl (2R)-2-methoxypropanoate (2 g, 16.93 mmol, 1.00 eq.) and hydrazine hydrate (5.3 g, 84.70 mmol, 5.00 eq.) in ethanol (50 mL) was stirred for 16 h at 70° C. in an oil bath. The resulting mixture was concentrated under vacuum to obtain 2 g (crude) of (2R)-2-methoxypropanehydrazide as light yellow oil. LC-MS (ES, m/z): [M+1]$^+$=119.

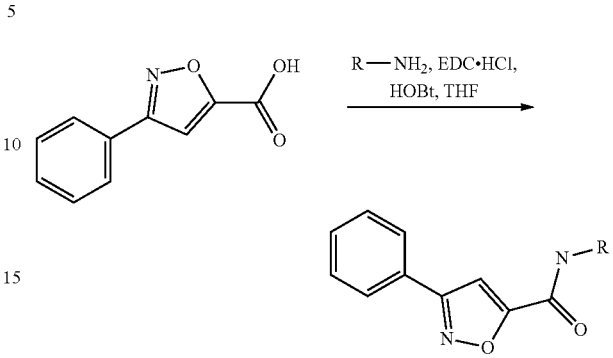

General Procedure (1) for Amide Coupling:

EDC.HCl (1.98 mmol), HOBt.H$_2$O (1.32 mmol) and the appropriate amine (1.45 mmol) were added to a solution of 3-phenylisoxazole-5-carboxylic acid (1.32 mmol) in THF (10 mL) at room temperature. Reaction mixture was stirred for 15 h at room temperature and the reaction mixture was concentrated to dryness. The crude solid was extracted with EtOAc (3×10 mL) and washed with water. The combined organic layers were dried over Na$_2$SO$_4$ and concentrated. The crude compound was purified by Combiflash chromatography to give the corresponding amide.

Example 1: N-(2-methoxyethyl)-3-phenylisoxazole-5-carboxamide

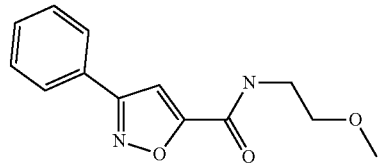 [SMILES: COCCNC(=O)c1cc(-c2ccccc2)no1]

Compound 1 was obtained as an off white solid using the general procedure 1 (0.120 g, 37.0%); $^1$H-NMR (400 MHz, CDCl$_3$) δ 7.82-7.79 (m, 2H), 7.50-7.45 (m, 3H), 7.21 (s, 1H), 6.98-6.97 (br, 1H), 3.68-3.64 (m, 2H), 3.57-3.55 (t, 2H), 3.40 (s, 3H); LC-MS (ES, m/z): [M+H]$^+$=247.2; HPLC purity: 99.76% at 220 nm and 99.64% at 254 nm.

Example 2: 3-phenyl-N-((tetrahydrofuran-2-yl)methyl)isoxazole-5-carboxamide

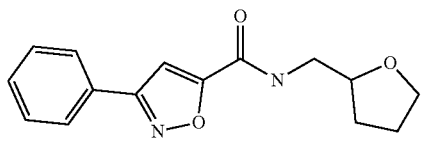 [SMILES: O=C(NCC1CCCO1)c1cc(-c2ccccc2)no1]

Compound 2 was obtained as a white solid using the general procedure 1 (0.110 g, 30.6%); $^1$H NMR (400 MHz, CDCl$_3$) δ 7.82-7.80 (m, 2H), 7.49-7.45 (m, 3H), 7.25-7.21 (d, J=14.9 Hz, 1H), 6.95 (br, 1H), 4.08-4.06 (m, 1H), 3.92-3.89 (m, 1H), 3.81-3.71 (m, 2H), 3.44-3.39 (m, 1H), 2.06-1.99 (m, 1H), 1.96-1.91 (m, 2H), 1.63-1.58 (m, 1H); LC-MS (ES, m/z): [M+H]⁺=273.2; HPLC purity: 99.78% at 220 nm and 99.79% at 254 nm.

Example 3: N-(2-morpholinoethyl)-3-phenylisoxazole-5-carboxamide

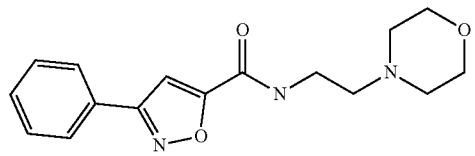 [SMILES: O=C(NCCN1CCOCC1)c1cc(-c2ccccc2)no1]

Compound 3 was obtained as a white solid using the general procedure 1 (0.125 g, 31.5%); $^1$H NMR (400 MHz, CDCl$_3$) δ 7.82-7.80 (m, 2H), 7.49-7.46 (m, 3H), 7.21 (s, 2H), 3.75-3.72 (t, 4H), 3.58-3.53 (q, 2H), 2.61-2.58 (t, 2H), 2.51-2.50 (m, 4H); LC-MS (ES, m/z): [M+H]⁺=302.1; HPLC purity: 99.81% at 220 nm and 99.87% at 254 nm.

Example 4: N-(3-(1H-imidazol-1-yl)propyl)-3-phenylisoxazole-5-carboxamide

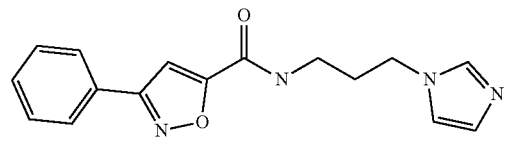 [SMILES: O=C(NCCCn1ccnc1)c1cc(-c2ccccc2)no1]

Compound 4 was obtained as a white solid using the general procedure 1 (0.127 g, 32.6%); $^1$H NMR (400 MHz, CDCl$_3$) δ 7.82-7.79 (m, 2H), 7.52 (s, 1H), 7.50-7.46 (m, 3H), 7.22 (s, 1H), 7.08 (s, 1H), 6.98-6.97 (m, 1H), 6.79-6.76 (m, 1H), 4.08-4.04 (t, 2H), 3.52-3.47 (m, 2H), 2.18-2.11 (m, 2H); LC-MS (ES, m/z): [M+H]⁺=297.2; HPLC purity: 98.05% at 220 nm and 97.78% at 254 nm.

Example 5: N-trans-3-(5-(hydroxymethyl)-1H-1,2,3-triazol-1-yl)cyclobutyl)-3-phenylisoxazole-5-carboxamide

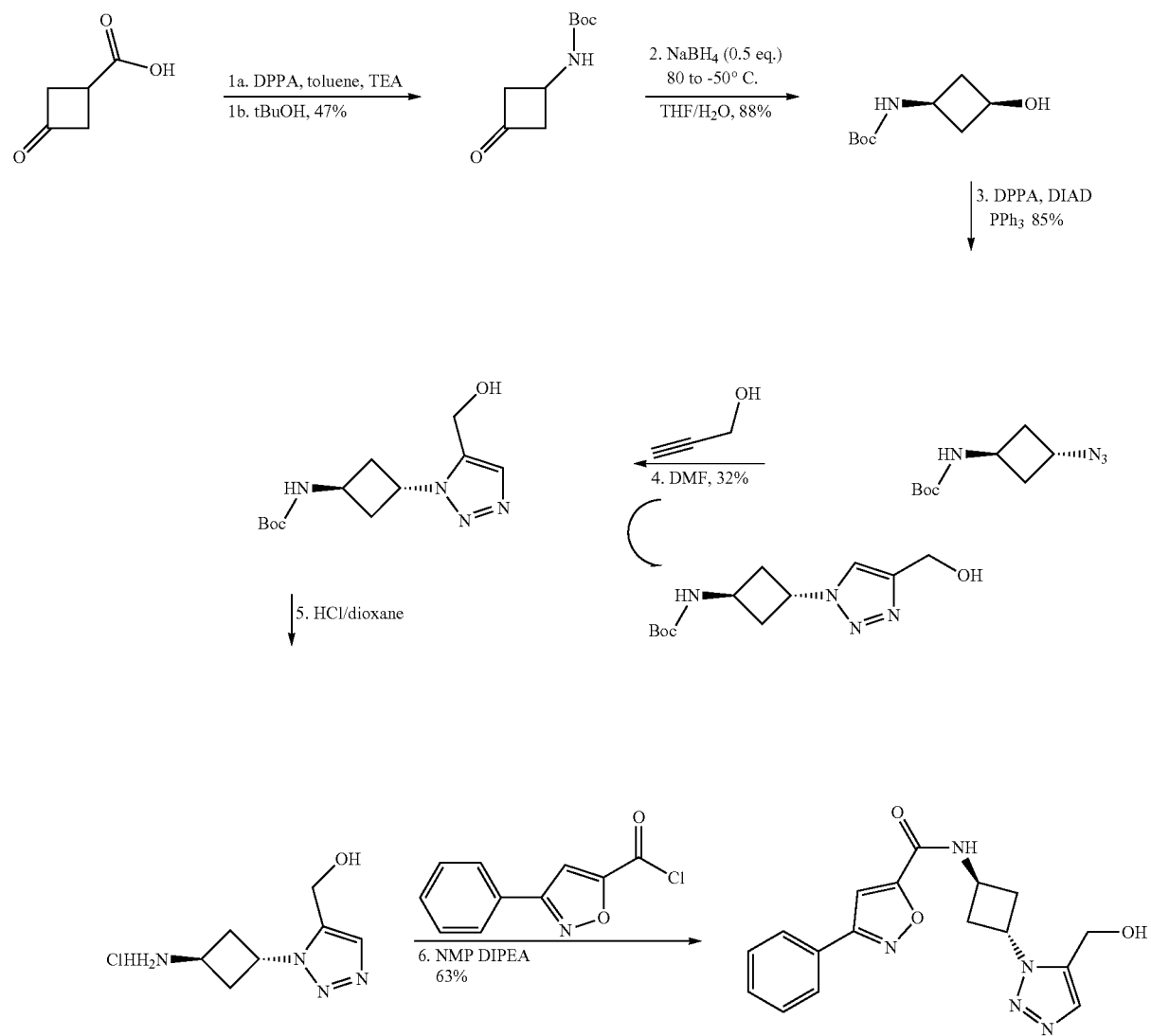

Step 1: tert-butyl (3-oxocyclobutyl)carbamate

DPPA (4.0 g, 1.1 eq.) was added dropwise to a cold (−5~5° C.) solution of 3-oxocyclobutanecarboxylic acid (1.5 g, 1.0 eq.) and TEA (1.5 g, 1.1 eq.) in toluene (30 mL), and the mixture was stirred at −5~0° C. for 16 h. The reaction mixture was washed with NaHCO$_3$ (2×9 mL), water (1×9 mL) and NaCl aq. (1×4.5 mL) at 0~10° C. The combined organic layer was dried over Na$_2$SO$_4$, filtered, and t-BuOH (7.5 mL) added to the filtrate. The reaction mixture was heated at 90~100° C. for 16 h. The mixture was concentrated under vacuum at 60~70° C., suspended in TBME (4.5 mL), filtered, and the solid dried over air to give 1.15 g (purity: 98.5%, yield: 47.2%) of product as a white solid.

Step 2: tert-butyl (cis-3-hydroxycyclobutyl)carbamate

A solution of tert-butyl (3-oxocyclobutyl)carbamate (200 mg, 1.0 eq.) in THF (1 mL) was added dropwise to a cold (below −70° C.) solution of NaBH$_4$ (20.4 mg, 0.5 eq.) in THF (1.8 mL) and water (2 mL), maintaining the temperature at −80~−70° C. (ca. for 2 h for completion of addition). The mixture was stirred at −60~−50° C. for 3 h, water (2 mL) was added to the reaction mixture and allowed to warm up to 15° C. The reaction mixture was then extracted with ethyl acetate (2 mL, 2×1 mL) and the combined organic layers were washed with brine (1 mL). The organic layer was concentrated under vacuum at 35~40° C., the solid dissolved in toluene (1 mL, 80~90° C.) and gradually cooled to 25-30° C. for 2.5 h. The mixture was stirred for 2 h at 25-30° C., filtered, and the solid dried in the air to give the product (177 mg with ratio of cis:trans (96.4:3.6), yield: 87.6%) as an off-white solid.

Step 3: tert-butyl (trans-3-azidocyclobutyl)carbamate

A solution of PPh$_3$ (315 mg) and DIAD (243 mg) in THF (3 mL) was stirred for 20 min at 0-10° C. A solution of tert-butyl (cis-3-hydroxycyclobutyl)carbamate (150 mg, 1.0 eq.) and DPPA (265 mg, 1.2 eq.) in THF (1 ml) was added dropwise and mixture was then warmed to 25-30° C. and stirred for 2 h. Brine (3 mL) was added to the reaction mixture, extracted with ethyl acetate (3 mL) and then concentrated under vacuum to give the crude oil. The mixture was purified by SiO$_2$ column chromatography and eluted with ethyl acetate/petroleum ether (0%~10%) gradually. The product was suspended in n-heptane (0.3 mL) and stirred for 0.5 h at 20~25° C. The mixture was filtered and the solid dried in air to give the product in 85% yield and ratio of cis/trans=4:96 checked by $^1$H NMR.

Step 4: tert-butyl (trans-3-(5-(hydroxymethyl)-1H-1,2,3-triazol-1-yl)cyclobutyl)carbamate A solution of tert-butyl (trans-3-azidocyclobutyl)carbamate (246 mg, 1.0 eq.) and prop-2-yn-1-ol (326 mg, 5.0 eq.) in DMF (1.2 mL) was heated at 90~95° C. for 20 h. The mixture was concentrated under vacuum at 65° C. to give a ~1:1 mixture of 4 and 5 regioisomers (353 mg). The mixture was purified by SFC to give tert-butyl (trans-3-(5-(hydroxymethyl)-1H-1,2,3-triazol-1-yl)cyclobutyl)carbamate (101 mg 32% yield, purity: 99.9% (205 nm)) as a solid.

Step 5: (1-(trans-3-aminocyclobutyl)-1H-1,2,3-triazol-5-yl)methanol hydrochloride Tert-butyl (trans-3-(5-(hydroxymethyl)-1H-1,2,3-triazol-1-yl)cyclobutyl)carbamate (101 mg, 1.0 eq.) was added slowly (5 portions) to a solution of HCl/dioxane (3.5 mol/L, 2 mL) at 20~30° C., and then stirred for 18 h at 20~30° C. The reaction mixture was concentrated under vacuum at 55° C. to give the product (93.4 mg, assay 67% based on free base, Y: 100%) as a solid.

Step 6: N-(trans-3-(5-(hydroxymethyl)-1H-1,2,3-triazol-1-yl)cyclobutyl)-3-phenylisoxazole-5-carboxamide DIPEA (388 mg, 3.00 mmol, 3.00 eq.) was added dropwise to a 0° C. solution of lithio 3-phenylisoxazole-5-carboxylate (190 mg, 0.97 mmol, 1.00 eq.), [1-[trans-3-aminocyclobutyl]-1H-1,2,3-triazol-5-yl]methanol hydrochloride (204 mg, 1.00 mmol, 1.00 eq.) and HATU (684 mg, 1.80 mmol, 1.80 eq.) in DMF (5 mL). The resulting solution was stirred for 1 hour at room temperature and then diluted with 50 mL of water/ice. The resulting solution was extracted with ethyl acetate (3×50 mL) and the organic layers combined. The resulting mixture was washed with brine (2×30 mL), dried over anhydrous sodium sulfate and concentrated under vacuum. The crude product was purified by Flash-Prep-HPLC with the following conditions (IntelFlash-1): Column, C18; mobile phase, H$_2$O/CH$_3$CN=100:1 increasing to H$_2$O/CH$_3$CN=1:100 within 30 min; Detector, UV 254 nm to afford 100 mg (30%) of 3-phenyl-N-[trans-3-[5-(hydroxymethyl)-1H-1,2,3-triazol-1-yl]cyclobutyl]isoxazole-5-carboxamide as a white solid. LC-MS (ES, m/z): [M+1]$^+$=340; $^1$H NMR (400 MHz, DMSO-d$_6$): δ 9.54-9.52 (d, J=7.2 Hz, 1H), 7.96-7.94 (m, 2H), 7.69-7.63 (m, 2H), 7.56-7.54 (m, 3H), 5.45-5.42 (t, J=5.6 Hz, 1H), 5.27-5.20 (m, 1H), 4.80-4.71 (m, 1H), 4.56-4.55 (d, J=5.6 Hz, 2H), 2.93-2.87 (m, 2H), 2.81-2.75 (m, 2H).

Example 6: N-trans-3-(5-((R)-1-hydroxyethyl)-1,3,4-oxadiazol-2-yl)cyclobutyl)-3-phenylisoxazole-5-carboxamide

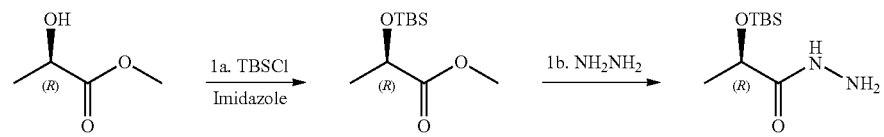

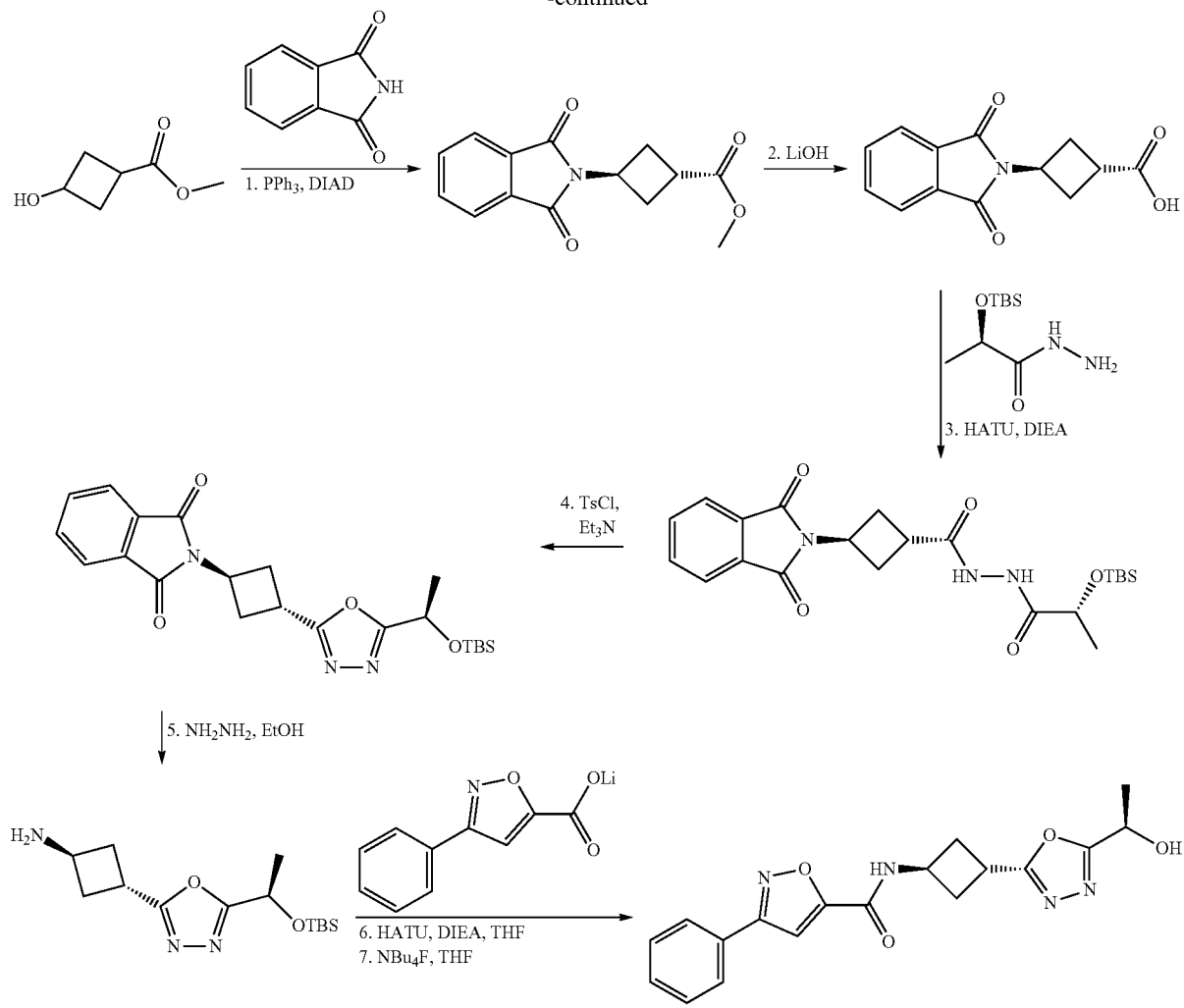

Step 1a: methyl (2R)-2-[(tert-butyldimethylsilyl)oxy]propanoate

Into a 250-mL round-bottom flask was placed a solution of methyl (2R)-2-hydroxypropanoate (5 g, 48.03 mmol, 1.00 eq.) and imidazole (6.5 g, 95.59 mmol, 2.00 eq.) in dichloromethane (100 mL), followed by the dropwise addition of a solution of tert-butyl(chloro)dimethylsilane (8.7 g, 57.72 mmol, 1.20 eq.) in dichloromethane (50 mL) at 0° C. The resulting solution was stirred for 2 h at room temperature. The reaction was quenched by the addition of 100 mL of water/ice. The resulting solution was extracted with dichloromethane (3×100 mL) and the organic layers combined. The resulting mixture was washed with brine (3×50 mL), dried over anhydrous sodium sulfate and concentrated under vacuum to afford 7 g (67%) of methyl (2R)-2-[(tert-butyldimethylsilyl)oxy]propanoate as a colorless oil.

Step 1b: (2R)-2-[(tert-butyldimethylsilyl)oxy]propanehydrazide

Into a 250-mL round-bottom flask was placed a solution of methyl (2R)-2-[(tert-butyldimethylsilyl)oxy]propanoate (7 g, 32.06 mmol, 1.00 eq.) in ethanol (100 mL). To the solution was added hydrazine (10 g, 159.81 mmol, 5.00 eq., 80%). The resulting solution was stirred for 15 h at 90° C. in an oil bath. The resulting solution was quenched by the addition of water/ice. The resulting solution was extracted with ethyl acetate (3×100 mL) and the organic layers combined. The resulting mixture was washed with brine (2×100 mL), dried over anhydrous sodium sulfate and concentrated under vacuum to afford 6.5 g (93%) of (2R)-2-[(tert-butyldimethylsilyl)oxy]propanehydrazide as a colorless oil. LC-MS (ES, m/z): [M+1]$^+$=219.

Step 1: methyl (trans-3-(1,3-dioxo-2,3-dihydro-1H-isoindol-2-yl)cyclobutane-1-carboxylate Into a 250-mL round-bottom flask, under nitrogen was placed a solution of methyl 3-cis-hydroxycyclobutane-1-carboxylate (8 g, 61.47 mmol, 1.00 eq.), 2,3-dihydro-1H-isoindole-1,3-dione (18.1 g, 123.02 mmol, 2.00 eq.) and triphenylphosphine (32.3 g, 123.15 mmol, 2.00 eq.) in THF (100 mL), followed by addition of DIAD (24.9 g, 123.14 mmol, 2.00 eq.) dropwise with stirring at 0° C. The resulting solution was stirred for 2.5 hours at room temperature. The resulting mixture was concentrated under vacuum. The residue was applied onto a silica gel column with ethyl acetate/petroleum ether (1:5). The crude product was re-crystallized from petroleum ether/ethyl acetate in the ratio of 10:1 to afford 7.2 g (45%) of methyl trans-3-(1,3-dioxo-2,3-dihydro-1H-isoindol-2-yl)cyclobutane-1-carboxylate as a white solid. LC-MS (ES, m/z): [M+1]$^+$=260. $^1$H-NMR (400 MHz, CDCl$_3$): δ 7.85-7.82 (m, 2H), 7.74-7.71 (m, 2H), 5.08-5.04 (m, 1H), 3.75 (s, 3H), 3.34-3.32 (m, 1H), 3.20-3.12 (m, 2H), 2.66-2.60 (m, 2H).

Step 2: trans-3-(1,3-dioxo-2,3-dihydro-1H-isoindol-2-yl)cyclobutane-1-carboxylic acid Into a 100-mL round-bottom flask, was placed a solution of methyl trans-3-(1,3-dioxo-2,3-dihydro-1H-isoindol-2-yl)cyclobutane-1-carboxylate (7.2 g, 27.77 mmol, 1.00 eq.) in 1,4-dioxane (100 mL). To the solution was added 5M hydrogen chloride aqueous (10 mL). The resulting solution was stirred for 4 hours at 80° C. in an oil bath. The resulting mixture was concentrated under vacuum to afford 6.2 g (91%) of trans-3-(1,3-dioxo-2,3-dihydro-1H-isoindol-2-yl)cyclobutane-1-carboxylic acid as a white solid. LC-MS (ES, m/z): [M−1]$^−$=244.

Step 3: (2R)-2-[(tert-butyldimethylsilyl)oxy]-N-[trans-3-(1,3-dioxo-2,3-dihydro-1H-isoindol-2-yl)cyclobutyl]carbonyl]propanehydrazide Into a 250-mL round-bottom flask, was placed a solution of trans-3-(1,3-dioxo-2,3-dihydro-1H-isoindol-2-yl)cyclobutane-1-carboxylic acid (6.2 g, 25.28 mmol, 1.00 eq.), (2R)-2-[(tert-butyldimethylsilyl)oxy]propanehydrazide (6.61 g, 30.27 mmol, 1.20 eq.) and HATU (14.4 g, 37.89 mmol, 1.50 eq.) in THF (100 mL), followed by the addition of DIEA (9.81 g, 75.91 mmol, 3.00 eq.) dropwise with stirring at 0° C. The resulting solution was stirred for 1 hour at room temperature. The reaction was then quenched by the addition of 100 mL of water/ice. The resulting solution was extracted with ethyl acetate (3×50 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:4) to afford 7 g (62%) of (2R)-2-[(tert-butyldimethylsilyl)oxy]-N-[trans-3-(1,3-dioxo-2,3-dihydro-1H-isoindol-2-yl)cyclobutyl]carbonyl]propanehydrazide as colorless oil. LC-MS (ES, m/z): [M+1]$^+$=446.

Step 4: 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione Into a 250-mL round-bottom flask was placed a solution of (2R)-2-[(tert-butyldimethylsilyl)oxy]-N-[[trans-3-(1,3-dioxo-2,3-dihydro-1H-isoindol-2-yl)cyclobutyl]carbonyl]propanehydrazide (6.95 g, 15.60 mmol, 1.00 eq.) and TEA (7.89 g, 77.97 mmol, 5.00 eq.) in dichloromethane (100 mL), followed by addition of a solution of 4-methylbenzene-1-sulfonyl chloride (8.92 g, 46.79 mmol, 3.00 eq.) in dichloromethane (50 mL) dropwise with stirring at 0° C. The resulting solution was stirred for 15 hours at room temperature. The reaction was then quenched by the addition of 100 mL of water/ice. The resulting solution was extracted with dichloromethane (2×50 mL) and the organic layers combined. The resulting mixture was washed with brine (2×50 mL), dried over anhydrous sodium sulfate and concentrated under vacuum. The crude product was purified by Flash-Prep-HPLC with the following conditions (IntelFlash-1): Column, C18; mobile phase, H$_2$O/CH$_3$CN=100:1 increasing to H$_2$O/CH$_3$CN=1:100 within 30 min; Detector, UV 254 nm to afford 3.28 g (49%) of 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione as colorless oil. LC-MS (ES, m/z): [M+1]$^+$=428. $^1$H-NMR (400 MHz, CDCl$_3$): δ 7.72-7.70 (m, 2H), 7.60-7.58 (m, 2H), 5.04-4.96 (m, 2H), 3.83-3.78 (m, 1H), 3.26-3.24 (m, 2H), 2.67-2.62 (m, 2H), 1.49-1.48 (d, J=6.8 Hz, 3H), 0.76 (s, 9H), 0.01 (s, 3H), 0.00 (s, 3H).

Step 5: trans-3-[5-[(1R)-1-[(tert-butyldimethylsilyl)oxy]ethyl]-1,3,4-oxadiazol-2-yl]cyclobutan-1-amine Into a 250-mL round-bottom flask, was placed a solution of 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione (1.18 g, 2.76 mmol, 1.00 eq.) in ethanol (100 mL). To the solution was added hydrazine hydrate (3.45 g, 55.13 mmol, 20.00 eq., 80%). The resulting solution was stirred for 3 hours at room temperature. The solids were filtered. The resulting mixture was concentrated under vacuum to afford 760 mg (crude) of trans-3-[5-[(1R)-1-[(tert-butyldimethylsilyl)oxy]ethyl]-1,3,4-oxadiazol-2-yl]cyclobutan-1-amine as colorless oil. LC-MS (ES, m/z): [M+1]$^+$=298.

Step 6: N-(trans-3-[5-[(1R)-1-[(tert-butyldimethylsilyl)oxy]ethyl]-1,3,4-oxadiazol-2-yl]cyclobutyl)-3-phenylisoxazole-5-carboxamide Into a 100-mL round-bottom flask, was placed a solution of lithio 3-phenylisoxazole-5-carboxylate (300 mg, 1.54 mmol, 1.20 eq.), 3-[5-[(1R)-1-[(tert-butyldimethylsilyl)oxy]ethyl]-1,3,4-oxadiazol-2-yl]cyclobutan-1-amine (380 mg, 1.28 mmol, 1.00 eq.) and HATU (728 mg, 1.92 mmol, 1.50 eq.) in THF (50 mL). This was followed by the addition of DIEA (500 mg, 3.87 mmol, 3.00 eq.) dropwise with stirring at 0° C. The resulting solution was stirred for 1 hour at room temperature. The resulting solution was diluted with 50 mL of water/ice. The resulting solution was extracted with ethyl acetate (3×50 mL) and the organic layers combined. The resulting mixture was washed with brine (2×30 mL), dried over anhydrous sodium sulfate and concentrated under vacuum to afford 300 mg (50%) of N-(trans-3-[5-[(1R)-1-[(tert-butyldimethylsilyl)oxy]ethyl]-1,3,4-oxadiazol-2-yl]cyclobutyl)-3-phenylisoxazole-5-carboxamide as an off-white crude solid. LC-MS (ES, m/z): [M+1]$^+$=469.

Step 7: N-(trans-3-[5-[(1R)-1-hydroxyethyl]-1,3,4-oxadiazol-2-yl]cyclobutyl)-3-phenylisoxazole-5-carboxamide Into a 50-mL round-bottom flask, was placed a solution of N-(3-[trans-5-[(1R)-1-[(tert-butyldimethylsilyl)oxy]ethyl]-1,3,4-oxadiazol-2-yl]cyclobutyl)-3-phenylisoxazole-5-carboxamide (300 mg, 0.64 mmol, 1.00 eq.) and TBAF (1 mol/L in tetrahydrofuran, 1 mL) in THF (5 mL). The resulting solution was stirred for 3 hours at room temperature and diluted with 20 mL of water. The resulting solution was extracted with ethyl acetate (3×30 mL) and the organic layers combined. The resulting mixture was washed with brine (2×10 mL), dried over anhydrous sodium sulfate and concentrated under vacuum. The residue was applied onto a silica gel column with dichloromethane/methanol (20:1). The crude product was purified by Flash-Prep-HPLC with the following conditions (IntelFlash-1): Column, C18; mobile phase, H$_2$O/CH$_3$CN=100:1 increasing to H$_2$O/CH$_3$CN=1:100 within 30 min; Detector, UV 254 nm to afford 149.2 mg (66%) of N-(trans-3-[5-[(1R)-1-hydroxy-ethyl]-1,3,4-oxadiazol-2-yl]cyclobutyl)-3-phenylisoxazole-5-carboxamide as a white solid. LC-MS (ES, m/z): [M+1]$^+$= 355; $^1$H NMR (400 MHz, DMSO-d$_6$): δ 9.48-9.46 (d, J=7.6 Hz, 1H), 7.96-7.93 (m, 2H), 7.67 (s, 1H), 7.56-7.54 (m, 3H), 5.95-5.94 (d, J=5.6 Hz, 1H), 4.95-4.89 (m, 1H), 4.73-4.63 (m, 1H), 3.77-3.71 (m, 1H), 2.73-2.50 (m, 4H), 1.50-1.48 (d, J=6.8 Hz, 3H).

Example 7: N-(3-(1-methyl-1H-pyrazol-5-yl)propyl)-3-phenylisoxazole-5-carboxamide

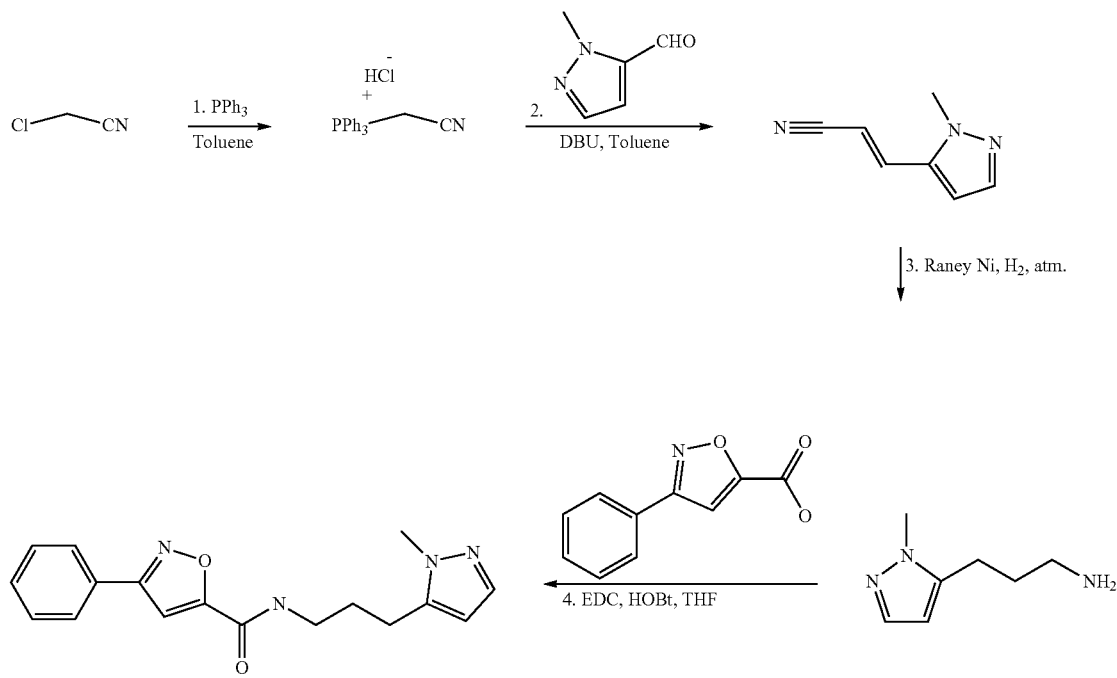

Step 1: Cyanomethyl triphenylphosphonium chloride

Chloroacetonitrile (10 g, 0.132 mol) was added dropwise to a solution of triphenylphosphine (23.5 g, 0.0895 mol) in (120 mL) toluene and heated at reflux for 6 h. The reaction mixture was cooled to room temperature, the solids filtered and washed with (2×20 mL) diethyl ether. Compound (15 g, 49.58%) was obtained as a white solid. $^1$H-NMR (400 MHz, DMSO) δ 8.02-7.97 (m, 3H), 7.90-7.79 (m, 12H), 5.94 (s, 1H), 5.90 (s, 1H); LC-MS (ES, m/z): [M+H]$^+$=301.7

Step 2: 3-(2-Methyl-2H-pyrazol-3-yl)-acrylonitrile (4)

To a stirred solution of 2-methyl-2H-pyrazole-3-carbaldehyde 3 (3.8 g, 0.0345 mol) in toluene (50 mL) was added cyanomethyl triphenylphosphonium chloride (12.8 g, 0.0389 mol) at room temperature. DBU (1.52 mL, 0.0099 mol) was then added dropwise and heated to reflux for 3 h. After completion of the reaction, the toluene was distilled off completely under vacuum. The resultant crude product was purified on combi flash, with the desired product eluted in 15% EtOAc:Hexane to afford the product (1.1 g, 24.01% yield) as a white solid. $^1$H NMR (400 MHz, CDCl$_3$) δ 7.46-7.45 (d, J=176 Hz, 1H), 7.3-7.25 (m, 1H), 6.56 (s, 1H), 5.79-5.75 (d, J=16.34 Hz, 1H), 3.93 (s, 3H). LC-MS (ES, m/z): [M+H]$^+$=134.1.

Step 3: 3-(1-methyl-1H-pyrazol-5-yl)propan-1-amine

Raney Ni (1 g, 50% in water suspension) was added to a solution of 3-(2-methyl-2H-pyrazol-3-yl)-acrylonitrile (1.0 g, 0.0075 mol) in ethanol (10 mL) at room temperature. The reaction mixture was then stirred under a hydrogen atmosphere for 16 h, filtered through a celite bed and washed with ethanol (2×10 mL). The filtrate was evaporated under vacuum to afford the compound (0.9 g, 86.53% yield) as a yellow oil. The crude product was used directly for amide coupling.

Step 4: N-(3-(1-methyl-1H-pyrazol-5-yl)propyl)-3-phenylisoxazole-5-carboxamide EDC.HCl (0.220 g, 0.00115 mole) and HOBt.H$_2$O (0.129 g, 0.00084 mole) were added to a solution of 3-phenylisoxazole-5-carboxylic acid (0.150 g, 0.00076 mol) in THF (5 mL) and stirred at room temperature for 20 minutes. To this reaction mixture was added 3-(1-methyl-1H-pyrazol-5-yl)propan-1-amine (0.16 g, 0.00115 mol) and DIPEA (0.590 mL, 0.0023 mole) and stirred for 16 h. The reaction mixture was concentrated on a rotary evaporator and the mixture was purified using combiflash, desired product eluted in 35% EtOAc:hexane (0.115 g, 47.23%) as an off white solid. $^1$H NMR (400 MHz, CDCl$_3$) δ 7.54-7.53 (m, 1H), 7.50-7.48 (m, 1H), 7.38-7.37 (d, J 1.84 Hz, 1H), 7.15-7.14 (m, 1H), 6.88 (br, 1H), 6.81 (s, 1H), 3.79 (s, 3H), 3.56-3.51 (q, 2H), 2.71-2.67 (t, 2H), 2.02-1.95 (m, 2H); LC-MS (ES, m/z): [M+H]$^+$=316.9; HPLC purity: 95.83% at 220 nm and 98.85% at 254 nm.

Example 8: N-(2-methoxyethyl)-4-phenylfuran-2-carboxamide

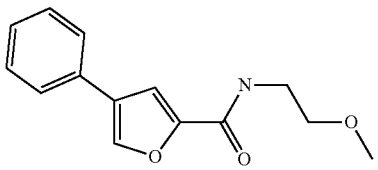 [SMILES: COCCNC(=O)c1cc(-c2ccccc2)co1]

Compound 8 was obtained as an off white solid using the general procedure 1. Yield: 57%; $^1$H-NMR (400 MHz, DMSO-$d_6$) δ 8.42 (br, 1H), 8.35 (s, 1H), 7.66 (d, J=7.6 Hz, 2H), 7.57 (s, 1H), 7.42 (t, J=7.6 Hz, 2H), 7.31 (t, J=7.3 Hz, 1H), 3.44-3.39 (m, 4H), 3.26 (s, 3H); LC-MS (ES, m/z): [M+H]$^+$=246.0; HPLC purity 99.32% at 220 nm and 99.35% at 254 nm.

Example 9: 4-phenyl-N-((tetrahydrofuran-2-yl)methyl)furan-2-carboxamide

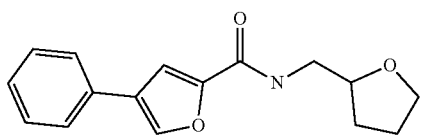 [SMILES: O=C(NCC1CCCO1)c1cc(-c2ccccc2)co1]

Compound 9 was obtained as an off white solid using the general procedure 1. Yield: 46%; $^1$H-NMR (400 MHz, DMSO-$d_6$) δ 8.42 (br, 1H), 8.35 (s, 1H), 7.66 (d, J=7.6 Hz, 2H), 7.59 (s, 1H), 7.42 (t, J=7.2 Hz, 2H), 7.31 (t, J=7.2 Hz, 1H), 3.97 (m, 1H), 3.79 (m, 1H), 3.64 (m, 1H), 3.27 (s, 2H), 1.90-1.78 (m, 3H), 1.61 (m, 1H); LC-MS (ES, m/z): [M+H]$^+$=271.9; HPLC purity 98.21% at 220 nm and 98.35% at 254 nm.

Example 10: N-(2-morpholinoethyl)-4-phenylfuran-2-carboxamide

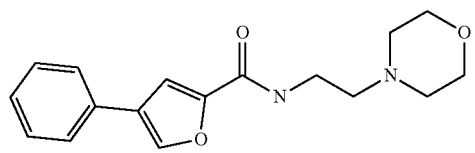 [SMILES: O=C(NCCN1CCOCC1)c1cc(-c2ccccc2)co1]

Compound 10 was obtained as an off white solid using the general procedure 1. Yield: 42%; $^1$H-NMR (400 MHz, DMSO-$d_6$) δ 8.35 (m, 2H), 7.67 (d, J=7.6 Hz, 2H), 7.54 (s, 1H), 7.42 (t, J=7.2 Hz, 2H), 7.31 (t, J=7.2 Hz, 1H), 3.56 (s, 4H), 3.36 (s, 2H), 2.46-2.40 (m, 6H); LC-MS (ES, m/z): [M+H]$^+$=300.7; HPLC purity 99.42% at 220 nm and 99.36% at 254 nm.

Example 11: N-(3-(1H-imidazol-1-yl)propyl)-4-phenylfuran-2-carboxamide

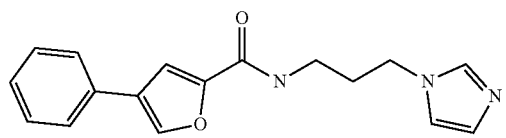 [SMILES: O=C(NCCCn1ccnc1)c1cc(-c2ccccc2)co1]

Compound 11 was obtained as an off white solid using the general procedure 1. Yield: 33%; $^1$H-NMR (400 MHz, DMSO-$d_6$) δ 8.54 (t, J=5.6 Hz, 1H), 8.36 (s, 1H), 7.67 (d, J=7.2 Hz, 2H), 7.56 (s, 1H), 7.43 (t, J=7.2 Hz, 2H), 7.31 (t, J=7.2 Hz, 1H), 7.21 (s, 1H), 6.89 (s, 1H), 4.02 (t, J=6.8 Hz, 2H), 3.23 (q, J=6.8 Hz, 2H), 1.97 (quintet, J=6.8 Hz, 2H); LC-MS (ES, m/z): [M+H]$^+$=296.1; HPLC purity 99.51% at 220 nm and 99.21% at 254 nm.

Example 12: N-cyclopropyl-4-phenylfuran-2-carboxamide

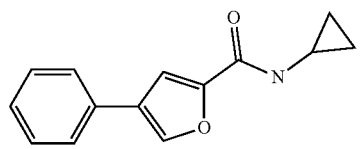 [SMILES: O=C(NC1CC1)c1cc(-c2ccccc2)co1]

Compound 12 was obtained as an off white solid using the general procedure 1 (0.032 g, 19.04%); $^1$H NMR (400 MHz, CDCl$_3$) δ 7.66 (s, 1H), 7.48-7.46 (m, 2H), 7.41-7.36 (m, 3H), 7.31-7.24 (m, 1H), 6.44 (s, 1H), 2.89-2.85 (m, 1H), 0.89-0.84 (m, 2H), 0.65-0.61 (m, 2H); LC-MS (ES, m/z): [M+H]$^+$=228.1; HPLC purity: 99.57% at 220 nm and 99.02% at 254 nm.

Example 13: N-(trans-3-(5-(1-(methylsulfonyl)ethyl)-1,3,4-oxadiazol-2-yl)cyclobutyl)-3-phenylisoxazole-5-carboxamide

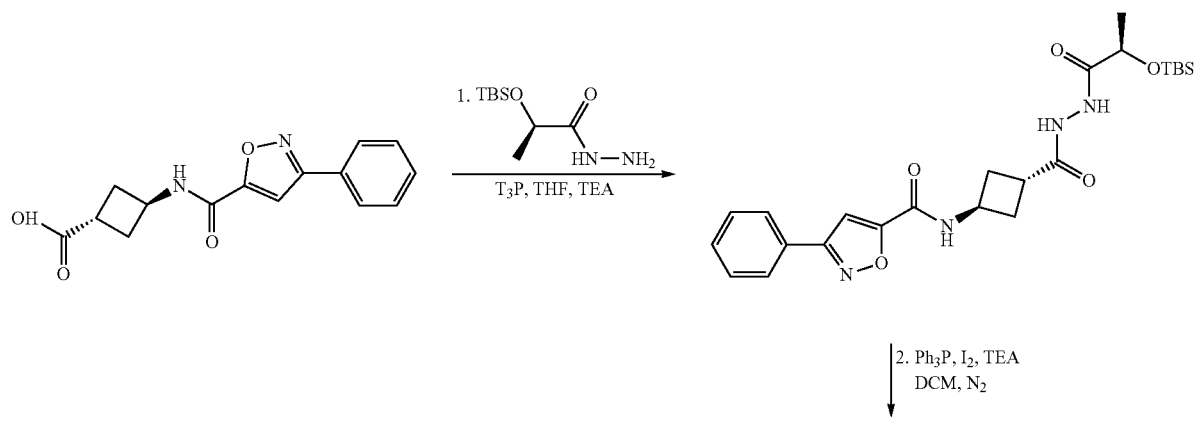

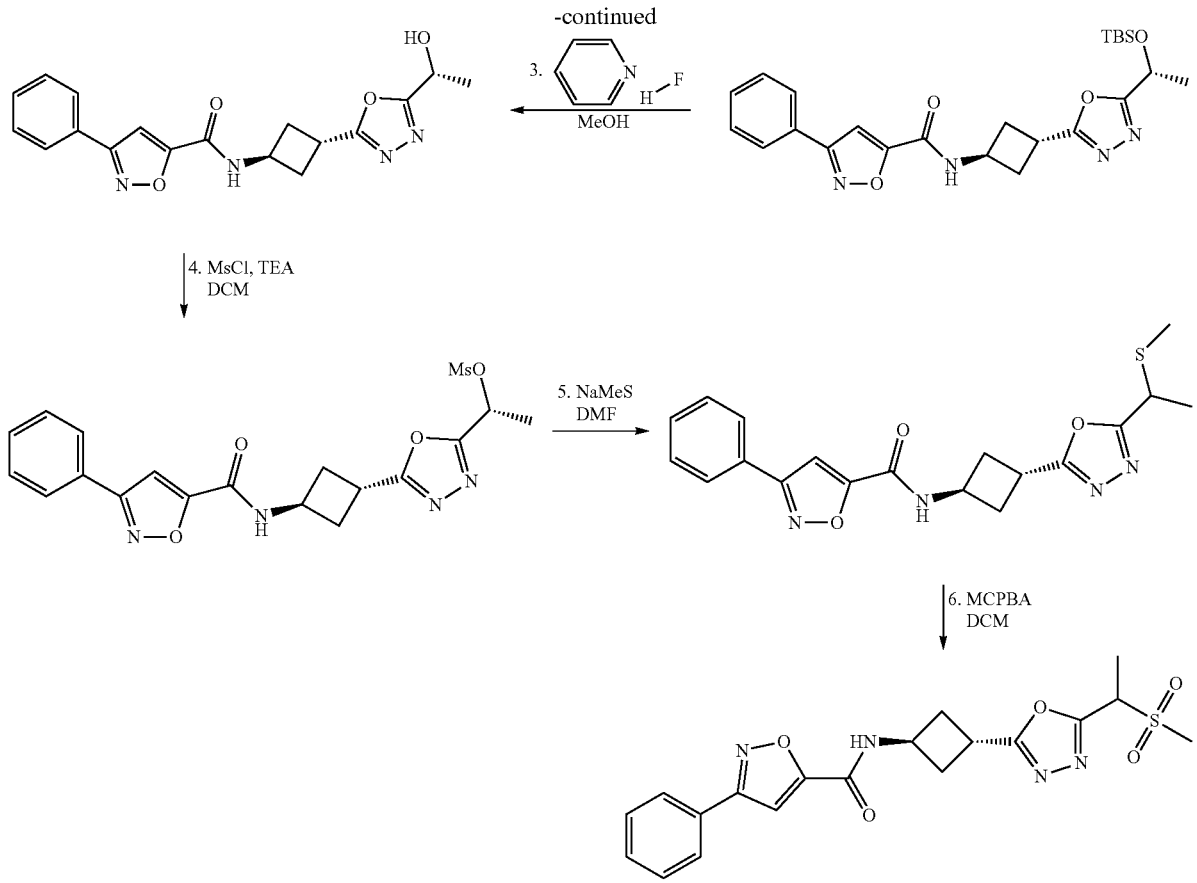

Step 1: N-trans-(3-[[(2R)-2-[(tert-butyldimethylsilyl)oxy]propanehydrazido]carbonyl]cyclobutyl)-3-phenylisoxazole-5-carboxamide T₃P (50%) (55.6 g, 5.00 eq.), TEA (8.83 g, 87.26 mmol, 5.00 eq.) and (2R)-2-[(tert-butyldimethylsilyl)oxy]propanehydrazide (4.95 g, 22.67 mmol, 1.30 eq.) were added to a solution of 3-(3-phenylisoxazole-5-amido)cyclobutane-1-carboxylic acid (5 g, 17.47 mmol, 1.00 eq.) in tetrahydrofuran (50 mL) and the solution was stirred for 1.5 hours at 30° C. The reaction was then quenched by the addition of water, extracted with dichloromethane and the organic layers combined, dried and concentrated under vacuum. The residue was applied onto a silica gel column with ethyl acetate/petroleum ether (1:1) to give 8.45 g (crude) of N-trans-(3-[[(2R)-2-[(tert-butyldimethylsilyl)oxy]propanehydrazido]carbonyl]cyclobutyl)-3-phenylisoxazole-5-carboxamide as a light yellow solid; LC-MS (ES, m/z): [M+1]⁺= 487.1.

Step 2: N-trans-(3-[5-[(R)-1-[(tert-butyldimethylsilyl)oxy]ethyl]-1,3,4-oxadiazol-2-yl]cyclobutyl)-3-phenylisoxazole-5-carboxamide I₂ (20.74 g, 5.00 eq.) and TEA (9.98 g, 98.63 mmol, 6.00 eq.) were added to a solution of Ph₃P (21.56 g, 5.00 eq.) in dichloromethane (50 mL), followed by the dropwise addition of a solution of N-trans-(3-[[(2R)-2-[(tert-butyldimethylsilyl)oxy]propanehydrazido]carbonyl]cyclobutyl)-3-phenylisoxazole-5-carboxamide (8 g, 16.44 mmol, 1.00 eq.) in dichloromethane (50 mL). The resulting solution was stirred for 2.5 hours at 0° C., then quenched by the addition of water, and the solution was extracted with dichloromethane and the organic layers combined, dried and concentrated under vacuum to afford 3.19 g (41%) of N-trans-(3-[5-[(R)-1-[(tert-butyldimethylsilyl)oxy]ethyl]-1,3,4-oxadiazol-2-yl]cyclobutyl)-3-phenylisoxazole-5-carboxamide as a brown solid; LC-MS (ES, m/z): [M+1]⁺=469.1.

Step 3: N-trans-(3-[5-[(1R)-1-hydroxyethyl]-1,3,4-oxadiazol-2-yl]cyclobutyl)-3-phenylisoxazole-5-carboxamide A solution of N-trans-(3-[5-[(1R)-1-[(tert-butyldimethylsilyl)oxy]ethyl]-1,3,4-oxadiazol-2-yl]cyclobutyl)-3-phenylisoxazole-5-carboxamide (25.3 g, 53.99 mmol, 1.00 eq.) and pyridine hydrofluoride (15 g, 151.35 mmol, 2.80 eq.) in methanol (50 mL) was stirred for 5 hours at room temperature. The reaction was then quenched by the addition of water, extracted with dichloromethane and the organic layers combined, dried and concentrated under vacuum. The residue was dissolved in 50 mL of toluene and the solids were collected by filtration to give 1.85 g (10%) of N-trans-(3-[5-[(1R)-1-hydroxyethyl]-1,3,4-oxadiazol-2-yl]cyclobutyl)-3-phenylisoxazole-5-carboxamide as a yellow solid; LC-MS (ES, m/z): [M+1]⁺=355.0.

Step 4: (R)-1-[5-trans-[3-(3-phenylisoxazole-5-amido)cyclobutyl]-1,3,4-oxadiazol-2-yl]ethyl methanesulfonate TEA (1.28 g, 12.65 mmol, 3.00 eq.) and MsCl (0.725 g, 1.50 eq.) were added to a solution of N-trans-(3-[5-[(R)-1- hydroxyethyl]-1,3,4-oxadiazol-2-yl]cyclobutyl)-3-phenylisoxazole-5-carboxamide (1.5 g, 4.23 mmol, 1.00 eq.) in dichloromethane (50 mL) and the solution was stirred for 3 hours at 0° C. The reaction was then quenched by the addition of 200 mL of saturation $NH_4Cl$, extracted with dichloromethane and the organic layers combined, dried and concentrated under vacuum to give 1.72 g (94%) of (R)-1-[5-trans-[3-(3-phenylisoxazole-5-amido)cyclobutyl]-1,3,4-oxadiazol-2-yl]ethyl methanesulfonate as a yellow solid; LC-MS (ES, m/z): $[M+1]^+=433.0$.

Step 5: N-trans-(3-[5-[1-(methylsulfanyl)ethyl]-1,3,4-oxadiazol-2-yl]cyclobutyl)-3-phenylisoxazole-5-carboxamide A solution of (R)-1-[5-trans-[3-(3-phenylisoxazole-5-amido)cyclobutyl]-1,3,4-oxadiazol-2-yl]ethyl methanesulfonate (400 mg, 0.92 mmol, 1.00 eq.) and NaMeS (132 mg, 2.00 eq.) in DMF (3 mL) was stirred for 5 hours at 100° C. The resulting mixture was concentrated under vacuum and the residue was applied onto a silica gel column with ethyl acetate/petroleum ether (4:5) to give 254 mg (71%) of N-trans-(3-[5-[1-(methylsulfanyl)ethyl]-1,3,4-oxadiazol-2-yl]cyclobutyl)-3-phenylisoxazole-5-carboxamide as a yellow solid; LC-MS (ES, m/z): $[M+1]^+=385.0$.

Step 6: N-(3-[5-trans-[1-methanesulfonylethyl]-1,3,4-oxadiazol-2-yl]cyclobutyl)-3-phenylisoxazole-5-carboxamide A solution of N-(3-[5-trans-[1-(methylsulfanyl)ethyl]-1,3,4-oxadiazol-2-yl]cyclobutyl)-3-phenylisoxazole-5-carboxamide (230 mg, 0.60 mmol, 1.00 eq.) and MCPBA (0.42 g, 4.00 eq.) in dichloromethane (5 mL) was stirred for 2 hours at room temperature. The resulting mixture was concentrated under vacuum and the residue was applied onto a silica gel column with dichloromethane/methanol (25:1) to give 80 mg (32%) of a racemic mixture of N-(3-[5-trans-[1-methanesulfonylethyl]-1,3,4-oxadiazol-2-yl]cyclobutyl)-3-phenylisoxazole-5-carboxamide as a yellow solid; LC-MS (ES, m/z): $[M+1]^+=417.0$. $^1H$ NMR (DMSO-$d_6$, 400 MHz, ppm): δ 9.44 (s, 1H), 7.93-7.91 (m, 2H), 7.65 (s, 1H), 7.54-7.52 (m, 3H), 5.16-5.11 (m, 1H), 4.69-4.63 (m, 1H), 3.78-3.75 (m, 1H), 3.14 (s, 3H), 2.72-2.65 (m, 4H), 1.74-1.70 (m, 3H); HPLC purity: 97.1% at 254 nm.

Example 14: N-(trans-3-(5-((R)-1-methoxyethyl)-1,3,4-oxadiazol-2-yl)cyclobutyl)-3-phenylisoxazole-5-carboxamide

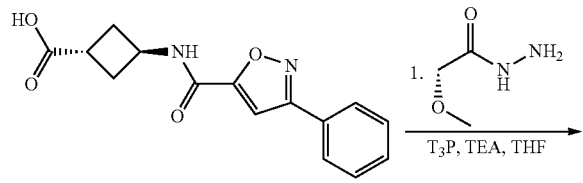

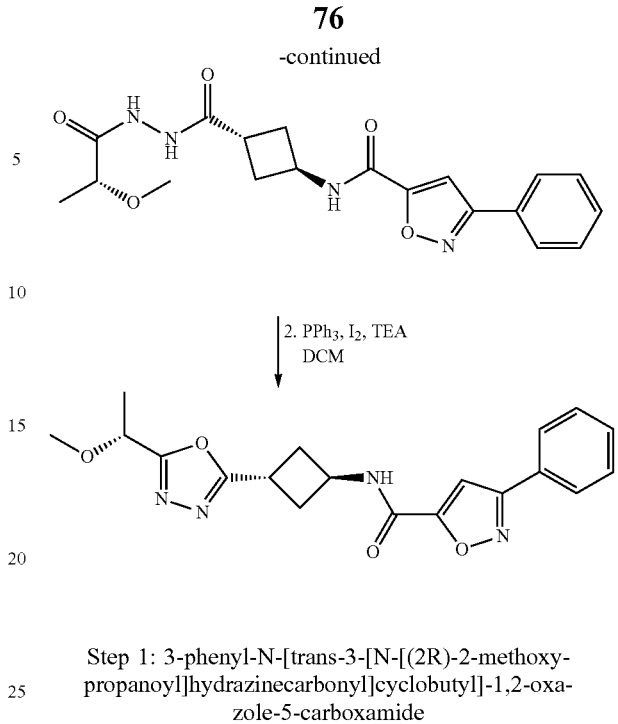

Step 1: 3-phenyl-N-[trans-3-[N-[(2R)-2-methoxypropanoyl]hydrazinecarbonyl]cyclobutyl]-1,2-oxazole-5-carboxamide TEA (315 mg, 3.11 mmol, 2.97 eq.) and $T_3P$ (667 mg) were added to a solution of trans-3-(3-phenylisoxazole-5-amido)cyclobutane-1-carboxylic acid (300 mg, 1.05 mmol, 1.00 eq.) and (2R)-2-methoxypropanehydrazide (185 mg, 1.57 mmol, 1.49 eq.) in tetrahydrofuran (5 mL) and the mixture was stirred for 2 hours at room temperature. The resulting mixture was concentrated under vacuum, diluted with 5 mL of methanol. The solids were collected by filtration and dried in an oven under reduced pressure to give 200 mg (49%) of 3-phenyl-N-[trans-3-[N-[(2R)-2-methoxypropanoyl]hydrazinecarbonyl]cyclobutyl]-1,2-oxazole-5-carboxamide as a white solid. LC-MS (ES, m/z): $[M+1]^+=387.2$.

Step 2: 3-phenyl-N-[trans-3-[5-[(1S)-1-methoxyethyl]-1,3,4-oxadiazol-2-yl]cyclobutyl]-1,2-oxazole-5-carboxamide 3-phenyl-N-[trans-3-[N-[(2R)-2-methoxypropanoyl]hydrazinecarbonyl]cyclobutyl]-1,2-oxazole-5-carboxamide (150 mg, 0.39 mmol, 1.00 eq.) was added to a solution of $PPh_3$ (150 mg, 0.57 mmol, 1.47 eq.), $I_2$ (150 mg) and TEA (120 mg, 1.19 mmol, 3.05 eq.) in dichloromethane (5 mL) and the mixture was stirred for 2 hours at 0° C. The resulting mixture was washed with water (2×5 mL) and concentrated under vacuum. The crude product was purified by Prep-HPLC with the following conditions: (Waters): Column: XBridge C18 OBD Prep Column 10 μm, 19 mm×250 mm; mobile phase, water (0.5% $NH_4HCO_3$) and $CH_3CN$; Gradient; 40% of $CH_3CN$ to 45% of $CH_3CN$ in 10 min; Detector, UV 254 nm to give 101.8 mg (71%) of 3-phenyl-N-[trans-3-[5-[(1S)-1-methoxyethyl]-1,3,4-oxadiazol-2-yl]cyclobutyl]-1,2-oxazole-5-carboxamide as a light yellow solid. LC-MS (ES, m/z): $[M+1]^+=369.0$; $^1H$ NMR (DMSO-$d_6$, 300 MHz, ppm): δ 9.46-9.44 (d, J=7.2 Hz, 1H), 7.94-7.93 (m, 2H), 7.66 (s, 1H), 7.55-7.54 (m, 3H), 4.72-4.64 (m, 2H), 3.78-3.73 (m, 1H), 3.29 (s, 3H), 2.73-2.61 (m, 4H), 1.51-1.49 (d, J=6.8 Hz, 3H); HPLC purity: 99.1% at 254 nm.

Example 15 and 16: 3-phenyl-N-(trans-3-(5-((S)-1-(2,2,2-trifluoroethoxy)ethyl)-1,3,4-oxadiazol-2-yl)cyclobutyl)isoxazole-5-carboxamide and 3-phenyl-N-(trans-3-(5-((R)-1-(2,2,2-trifluoroethoxy)ethyl)-1,3,4-oxadiazol-2-yl)cyclobutyl)isoxazole-5-carboxamide

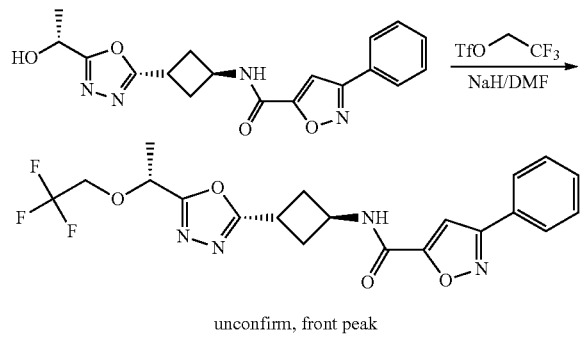

unconfirm, front peak

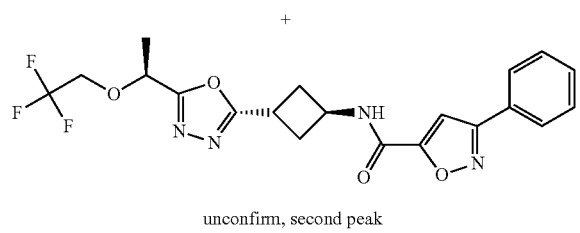

unconfirm, second peak 2,2,2-trifluoroethyl trifluoromethanesulfonate (491 mg, 2.12 mmol, 1.50 eq.) was added to a solution of 3-phenyl-N-[trans-3-[5-[(1R)-1-hydroxyethyl]-1,3,4-oxadiazol-2-yl]cyclobutyl]-isoxazole-5-carboxamide (500 mg, 1.41 mmol, 1.00 eq.) and sodium hydride (85 mg, 2.12 mmol, 1.50 eq.) in DMF (10 mL) and the solution was stirred for 2 hours at room temperature. The reaction mixture was diluted with water (30 mL), extracted with ethyl acetate (3×30 mL) and the organic layers were combined, dried over anhydrous sodium sulfate and concentrated under vacuum. The crude product was purified by Prep-HPLC with the following conditions (Waters): Column: XBridge C18 OBD Prep Column 10 μm, 19 mm×250 mm; Mobile Phase A: water (10 mmol/L NH$_4$HCO$_3$), Mobile Phase B: ACN; Flow rate: 25 mL/min; Gradient: 15% B to 65% B in 8 min; 254/220 nm. The isomers were purified by Chiral-Prep-HPLC with the following conditions: Column: Chiralpak IA 2*25 cm, 5 um; Mobile Phase A: Hexane; HPLC, Mobile Phase B: EtOH; HPLC Flow rate: 18 mL/min; Gradient: 40 B to 40 B in 15 min; 254/220 nm; RT1: 9.505; RT2: 11.208. This resulted in 19.1 mg (3%) of front peak as a white solid and 16.8 mg of second peak as a white solid.

Front Peak

LC-MS (ES, m/z): [M+1]$^+$=437.1. $^1$H-NMR (DMSO-d$_6$, 300 MHz, ppm): δ 7.87-7.86 (m, 2H), 7.49-7.47 (m, 3H), 7.37 (s, 1H), 5.00-4.94 (m, 1H), 4.11-4.02 (m, 2H), 3.81-3.74 (m, 1H), 2.78-2.68 (m, 4H), 1.64-1.62 (d, J=6.6 Hz, 3H); HPLC purity: 98.6% at 254 nm.

Second Peak

LC-MS (ES, m/z): [M+1]$^+$=437.1; $^1$H NMR (DMSO-d$_6$, 300 MHz, ppm): δ 7.86 (br, 2H), 7.48 (br, 3H), 7.37 (s, 1H), 5.00-4.94 (m, 1H), 4.10-4.02 (m, 2H), 3.79-3.77 (m, 1H), 2.78-2.69 (m, 4H), 1.64-1.62 (d, J=6.6 Hz, 3H); HPLC purity: 98.9% at 254 nm.

Example 17: N-(trans-3-(5-(1-cyclobutoxyethyl)-1,3,4-oxadiazol-2-yl)cyclobutyl)-3-phenylisoxazole-5-carboxamide

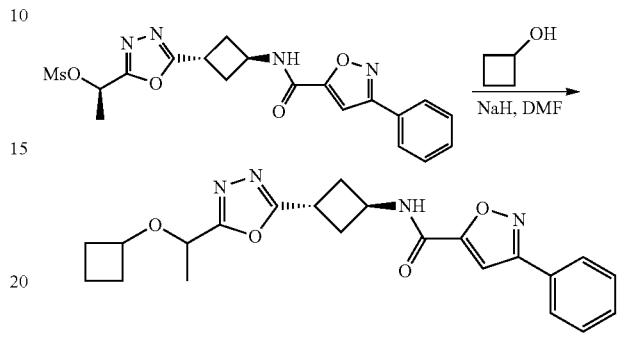

Sodium hydride (84 mg, 2.10 mmol, 3.00 eq.) was added in portions to a cold (0° C.) solution of cyclobutanol (150 mg, 2.08 mmol, 3.00 eq.) in DMF (10 mL) and the resulting solution was stirred for 30 min at 0° C. (R)-1-[5-trans-[3-(3-phenylisoxazole-5-amido)cyclobutyl]-1,3,4-oxadiazol-2-yl]ethyl methanesulfonate (300 mg, 0.69 mmol, 1.00 eq.) was added to the mixture and stirred for an additional 2 hours at 25° C. The reaction was then quenched by the addition of 100 mL of water, extracted with ethyl acetate (2×100 mL) and the organic layers combined. The resulting mixture was washed with brine (2×100 mL), dried over anhydrous sodium sulfate and concentrated under vacuum. The crude product was purified by Prep-TLC (petroleum ether:ethyl acetate=1:1) to give 50.2 mg (18%) of 3-phenyl-N-[trans-3-[5-(1-cyclobutoxyethyl)-1,3,4-oxadiazol-2-yl]cyclobutyl]isoxazole-5-carboxamide as a white solid; LC-MS (ES, m/z): [M+H]$^+$=409.4; $^1$H NMR (300 MHz, DMSO-d$_6$) δ 9.46-9.43 (d, J=7.2 Hz, 1H), 7.95-7.92 (m, 2H), 7.65 (s, 1H), 7.56-7.54 (m, 3H), 4.78-4.64 (m, 2H), 4.04-3.99 (m, 1H), 3.77-3.74 (m, 1H), 2.71-2.50 (m, 4H), 2.18-2.14 (m, 1H), 1.97-1.85 (m, 2H), 1.75-1.57 (m, 2H), 1.49-1.47 (d, J=6.6 Hz, 3H), 1.47-1.40 (m, 1H); HPLC purity: 98.0% at 254 nm.

Example 18: N-(trans-3-(5-(1-(cyclobutylmethoxy)ethyl)-1,3,4-oxadiazol-2-yl)cyclobutyl)-3-phenylisoxazole-5-carboxamide

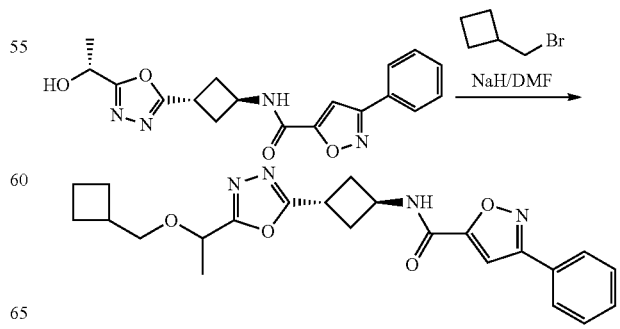

(Bromomethyl)cyclobutane (83 mg, 0.56 mmol, 2.00 eq.) was added to a solution of 3-phenyl-N-[trans-3-[5-(1-hydroxyethyl)-1,3,4-oxadiazol-2-yl]cyclobutyl]isoxazole-5-carboxamide (100 mg, 0.28 mmol, 1.00 eq.) and sodium hydride (17 mg, 0.42 mmol, 1.50 eq.) in DMF (2 mL). The resulting solution was stirred for 2 hours at room temperature, the reaction mixture was quenched by the addition of water (20 mL) and the solution was extracted with ethyl acetate (3×10 mL). The organic layers were combined and dried over anhydrous sodium sulfate and concentrated under vacuum. The crude product was purified by Prep-HPLC with the following conditions (Waters): Column: XBridge Prep C18 OBD Column 19×150 mm, 5 um; Mobile Phase A: water (10 mmol/L NH$_4$HCO$_3$), Mobile Phase B: ACN; Flow rate: 20 mL/min; Gradient: 40% B to 80% B in 8 min; 254 nm to give 21.2 mg (18%) of 3-phenyl-N-[trans-3-[5-[1-(cyclobutylmethoxy)ethyl]-1,3,4-oxadiazol-2-yl]cyclobutyl]isoxazole-5-carboxamide as a white solid; LC-MS (ES, m/z): [M+1]$^+$=421.0; $^1$H NMR (DMSO-d$_6$, 300 MHz, ppm): δ 9.46-9.43 (d, J=7.2 Hz, 1H), 7.94-7.93 (m, 2H), 7.66 (s, 1H), 7.57-7.54 (m, 3H), 4.81-4.74 (m, 1H), 4.72-4.64 (m, 1H), 3.77-3.74 (m, 1H), 3.49-3.36 (m, 2H), 2.70-2.65 (m, 4H), 1.96-1.91 (m, 2H), 1.88-1.80 (m, 2H), 1.75-1.67 (m, 2H), 1.50-1.48 (d, J=6.6 Hz, 3H); HPLC purity: 99.8% at 254 nm.

Example 19: N-(trans-3-(5-(1-(oxetan-3-ylmethoxy)ethyl)-1,3,4-oxadiazol-2-yl)cyclobutyl)-3-phenylisoxazole-5-carboxamide

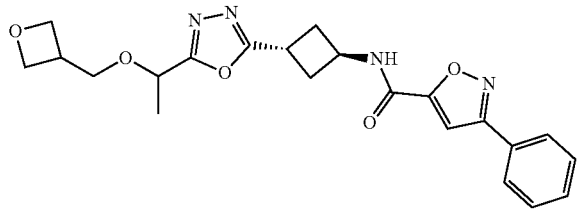 [SMILES: CC(OCC1COC1)c1nnc([C@H]2C[C@H](NC(=O)c3cc(-c4ccccc4)no3)C2)o1]

The title compound was prepared using the method shown in example 18.

Example 20: N-(trans-3-(5-((R)-1-((1-methylazetidin-3-yl)methoxy)ethyl)-1,3,4-oxadiazol-2-yl)cyclobutyl)-3-phenylisoxazole-5-carboxamide Step 1: tert-butyl 3-[(methanesulfonyloxy)methyl]azetidine-1-carboxylate MsCl (549 mg, 4.82 mmol, 1.20 eq.) and TEA (606 mg, 6.00 mmol, 1.50 eq.) were added to a solution of tert-butyl 3-(hydroxymethyl)azetidine-1-carboxylate (750 mg, 4.01 mmol, 1.00 eq.) in dichloromethane (20 mL) and the solution was stirred for 3 hours at room temperature. The resulting solution was diluted with ethyl acetate (50 mL), washed with saturated sodium carbonate aq. (1×30 mL), water (1×30 mL), dried over anhydrous sodium sulfate and concentrated under vacuum to give 980 mg (92%) of tert-butyl 3-[(methanesulfonyloxy)methyl]azetidine-1-carboxylate as colorless oil.

Step 2: tert-butyl 3-[(1-[5-[trans-3-(3-phenylisoxazole-5-amido)cyclobutyl]-1,3,4-oxadiazol-2-yl]ethoxy)methyl]azetidine-1-carboxylate Tert-butyl 3-[(methanesulfonyloxy)methyl]azetidine-1-carboxylate (670 mg, 2.53 mmol, 1.50 eq.) was added to a solution of 3-phenyl-N-[trans-3-[5-[(1R)-1-hydroxyethyl]-1,3,4-oxadiazol-2-yl]cyclobutyl]-isoxazole-5-carboxamide (600 mg, 1.69 mmol, 1.00 eq.) and t-BuOK (570 mg, 5.08 mmol, 3.00 eq.) in THF (15 mL). The reaction was stirred for 16 hours at 80° C. in an oil bath then diluted with ethyl acetate (100 mL). The resulting solution was washed with water (2×30 mL), brine (1×30 mL), dried over anhydrous sodium sulfate and concentrated under vacuum. The residue was applied onto a silica gel column with ethyl acetate/petroleum ether (1:10 up to 1:2) to give 287 mg (32%) of tert-butyl 3-[(1-[5-[trans-3-(3-phenylisoxazole-5-amido)cyclobutyl]-1,3,4-oxadiazol-2-yl]ethoxy)methyl]azetidine-1-carboxylate as a light yellow solid; LC-MS (ES, m/z): [M+H]$^+$=524.2.

Step 3: 3-phenyl-N-[trans-3-[5-[1-(azetidin-3-ylmethoxy)ethyl]-1,3,4-oxadiazol-2-yl]cyclobutyl]isoxazole-5-carboxamide A solution of tert-butyl 3-[(1-[5-[trans-3-(3-phenylisoxazole-5-amido)cyclobutyl]-1,3,4-oxadiazol-2-yl]ethoxy)methyl]azetidine-1-carboxylate (237 mg, 0.45 mmol, 1.00 eq.) and TFA (1.5 mL) in DCM (4 mL) was stirred for 2 hours at room temperature. The reaction was quenched by

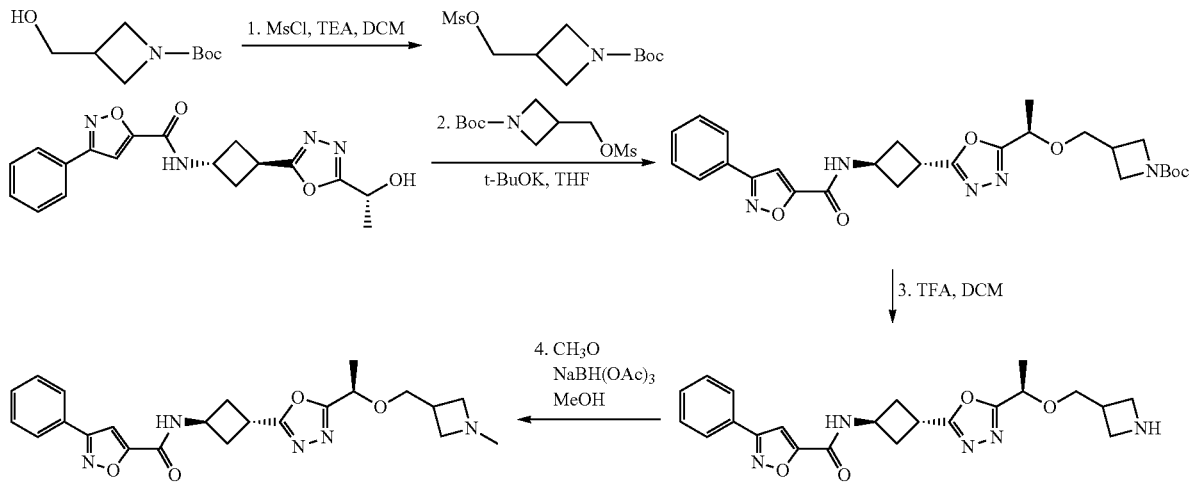

addition of 20 mL of saturated sodium carbonate aqueous and extracted with ethyl acetate (2×50 mL). The combined organic layer was washed with water (1×10 mL), brine (1×10 mL), dried over anhydrous sodium sulfate and concentrated under vacuum to give 150 mg (78%) of 3-phenyl-N-[trans-3-[5-[1-(azetidin-3-ylmethoxy)ethyl]-1,3,4-oxadiazol-2-yl]cyclobutyl]isoxazole-5-carboxamide as a yellow solid; LC-MS (ES, m/z): [M+H]⁺=424.2.

Step 4: 3-phenyl-N-[trans3-(5-[1-[(1-methylazetidin-3-yl)methoxy]ethyl]-1,3,4-oxadiazol-2-yl)cyclobutyl]-isoxazole-5-carboxamide HCHO (57 mg, 0.70 mmol, 1.50 eq.) was added to a solution of 3-phenyl-N-[trans-3-[5-[1-(azetidin-3-ylmethoxy)ethyl]-1,3,4-oxadiazol-2-yl]cyclobutyl]isoxazole-5-carboxamide (150 mg, 0.35 mmol, 1.00 eq.) in methanol (3 mL) and stirred for 30 min. NaBH(OAc)₃ (150 mg, 0.71 mmol, 2.00 eq.) was added to the reaction mixture and stirred 16 hours at room temperature. After removing the solid by filtration, the crude product (3 mL) was purified by Prep-HPLC with the following conditions (Waters): Column: XBridge C18 OBD Prep Column 10 m, 19 mm×250 mm; Mobile Phase A: water (10 mmol/L NH₄HCO₃), Mobile Phase B: ACN; Flow rate: 20 mL/min; Gradient: 15% B to 45% B in 8 min; 220/254 nm to give 68.6 mg (44%) of 3-phenyl-N-[trans3-(5-[1-[(1-methylazetidin-3-yl)methoxy]ethyl]-1,3,4-oxadiazol-2-yl)cyclobutyl]-isoxazole-5-carboxamide as a white solid; LC-MS (ES, m/z): [M+H]⁺= 438.2; ¹H NMR (CDOD, 400 MHz): δ 7.89-7.87 (m, 2H), 7.51-7.50 (m, 3H), 7.39 (s, 1H), 4.85-4.78 (m, 2H), 3.85-3.59 (m, 3H), 3.48-3.43 (m, 2H), 3.16-3.11 (m, 2H), 2.87-2.73 (m, 4H), 2.60-2.57 (m, 1H), 2.35-2.33 (m, 3H), 1.61-1.58 (m, 3H); HPLC purity: 97% at 254 nm.

Example 21: N-(trans-3-(5-(1-methylazetidin-3-yl)-1,3,4-oxadiazol-2-yl)cyclobutyl)-3-phenylisoxazole-5-carboxamide trifluoroacetate Step 1: 3-phenyl-N-[trans-3-(hydrazinecarbonyl)cyclobutyl]isoxazole-5-carboxamide A solution of trans-3-(3-phenylisoxazole-5-amido)cyclobutane-1-carboxylic acid (1.706 g, 5.96 mmol, 1.00 eq.) and CDI (1.933 g, 11.92 mmol, 2.00 eq.) in tetrahydrofuran (30 mL) was stirred for 0.5 hour at room temperature. Hydrazine hydrate (1.118 g, 22.33 mmol, 3.75 eq.) was added to the reaction mixture and stirred for 2 hours at room temperature. The product was precipitated by the addition of water and collected by filtration to give 780 mg (44%) of 3-phenyl-N-[trans-3-(hydrazinecarbonyl)cyclobutyl]isoxazole-5-carboxamide as a white solid; LC-MS (ES, m/z): [M+H]⁺=301.2.

Step 2: 3-phenyl-N-[trans-3-[[(1-methylazetidin-3-yl)formohydrazido]carbonyl]cyclobutyl]-isoxazole-5-carboxamide 1-methylazetidine-3-carboxylic acid (172.5 mg, 1.50 mmol, 1.50 eq.), HATU (570 mg, 1.50 mmol, 1.50 eq.) and DIEA (387 mg, 2.99 mmol, 3.00 eq.) were added to a solution of 3-phenyl-N-[trans-3-(hydrazinecarbonyl)cyclobutyl]-isoxazole-5-carboxamide (300 mg, 1.00 mmol, 1.00 eq.) in DMF (10 mL) and then stirred for 2 hours at room temperature. The crude product was purified by Flash-Prep-HPLC with the following conditions (IntelFlash-1): Column, C18; mobile phase, MeCN/H₂O=5:95 increasing to MeCN/H₂O=95:5 within 30 min; Detector, UV 254 nm to give 200 mg (50%) of 3-phenyl-N-[trans-3-[[(1-methylazetidin-3-yl)formohydrazido]carbonyl]cyclobutyl]-isoxazole-5-carboxamide as an off-white solid; LC-MS (ES, m/z): [M+H]⁺=398.0.

Step 3: 3-phenyl-N-[trans-3-[5-(1-methylazetidin-3-yl)-1,3,4-oxadiazol-2-yl]cyclobutyl]-isoxazole-5-carboxamide I₂ (232 mg) and TEA (276 mg, 2.73 mmol, 5.99 eq.) were added to a cold (0° C.) solution of PPh₃ (239 mg, 0.91 mmol, 2.00 eq.) in DCM (20 mL). To the mixture was added 3-phenyl-N-[trans-3-[[(1-methylazetidin-3-yl)formohydrazido]carbonyl]cyclobutyl]-isoxazole-5-carboxamide (181 mg, 0.46 mmol, 1.00 eq.) at 0° C. The resulting solution was stirred for 3 hours at room temperature, diluted with 50 mL of DCM, washed with NaHSO₃ aqueous (2×50 mL) and concentrated under vacuum. The residue was applied onto a Prep-TLC with ethyl acetate/petroleum ether (1:1). The resulting crude product was purified by Prep-HPLC with the following conditions (HPLC-10): Column: XBridge C18 OBD Prep Column 100 Å, 10 m, 19 mm×250 mm; Mobile Phase A: water (10 mmol/L NH₄HCO₃), Mobile Phase B: ACN; Flow rate: 20 mL/min; Gradient: 20% B to 30% B in

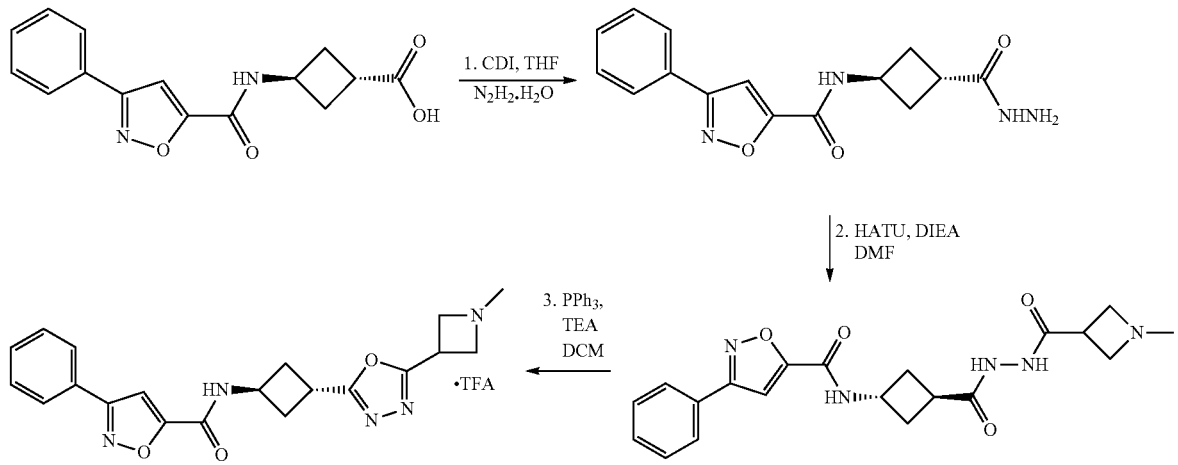

10 min; 254&220 nm to give 50 mg (29%) of 3-phenyl-N-[trans-3-[5-(1-methylazetidin-3-yl)-1,3,4-oxadiazol-2-yl]cyclobutyl]-isoxazole-5-carboxamide as a yellow solid; LC-MS (ES, m/z): [M-TFA+H]+=380.1; $^1$H NMR (300 MHz, DMSO-$d_6$, ppm): δ 10.19-10.12 (m, 1H), 9.49-9.47 (d, J=7.5 Hz, 1H), 7.95-7.92 (m, 2H), 7.66-7.64 (d, J=8.1 Hz, 1H), 7.56-7.54 (t, J=3.3 Hz, 3H), 4.75-4.62 (m, 6H), 3.78-3.69 (m, 1H), 2.94 (s, 3H), 2.44-2.72 (m, 4H); HPLC purity: 97.1% at 254 nm.

Example 22: N-trans-3-(5-(oxetan-3-yl)-1,3,4-oxadiazol-2-yl)cyclobutyl)-3-phenylisoxazole-5-carboxamide

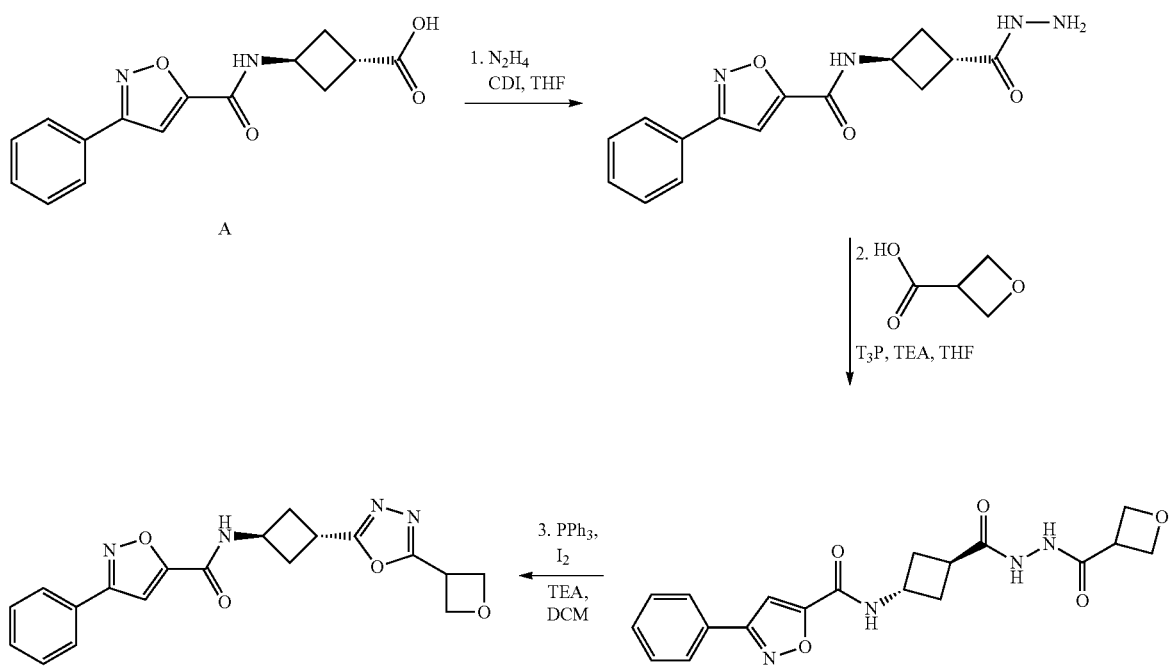

Step 1: 3-phenyl-N-[trans-3-(hydrazinecarbonyl)cyclobutyl]isoxazole-5-carboxamide CDI (2.26 g, 13.94 mmol, 2.00 eq.) was added to a solution of N-trans-3-(3-phenylisoxazole-5-amido)cyclobutane-1-carboxylic acid (prepared according to procedure shown in example 13, 2 g, 6.99 mmol 1.00 eq.) in THF (3 mL) and the solution was stirred for 1 hour at room temperature, followed by the addition of hydrazine hydrate (1.33 g, 21.25 mmol, 3.00 eq., 80%). The resulting solution was stirred for additional 1 hour at room temperature and then quenched with water. After removing the solids by filtration, the resulting mixture was concentrated under vacuum and the residue was washed with 10 mL of methanol to give 960 mg (46%) of 3-phenyl-N-[trans-3-(hydrazinecarbonyl)cyclobutyl]isoxazole-5-carboxamide as a white solid; LC-MS (ES, m/z): [M+H]+=301.1.

Step 2: 3-phenyl-N-[trans-3-[(oxetan-3-ylformohydrazido)carbonyl]cyclobutyl]isoxazole-5-carboxamide Oxetane-3-carboxylic acid (170 mg, 1.67 mmol, 1.00 eq.), $T_3P$ (5.3 g, 8.33 mmol, 5.00 eq., 50%) and TEA (838 mg, 8.3 mmol, 5.00 eq.) were added to a solution of 3-phenyl-N-[trans-3-(hydrazinecarbonyl)cyclobutyl]isoxazole-5-carboxamide (500 mg, 1.66 mmol, 1.00 eq.) in THF (50 mL). The resulting solution was stirred for 20 min at room temperature, then quenched by the addition of 200 mL of water. The resulting solution was extracted with dichloromethane (3×200 mL) and the organic layers combined. The resulting mixture was washed with brine, dried over anhydrous sodium sulfate and concentrated under vacuum. The residue solid was washed with 2 mL of methanol to afford 420 mg (66%) of 3-phenyl-N-[trans-3-[(oxetan-3-ylformohydrazido)carbonyl]cyclobutyl]isoxazole-5-carboxamide as an off-white solid; LC-MS (ES, m/z): [M+H]+= 385.0.

Step 3: 3-phenyl-N-[trans-3-[5-(oxetan-3-yl)-1,3,4-oxadiazol-2-yl]cyclobutyl]isoxazole-5-carboxamide $I_2$ (579 mg, 2.28 mmol, 2.50 eq.), TEA (598 mg, 5.91 mmol, 6.50 eq.) and 3-phenyl-N-[trans-3-[(oxetan-3-ylformohydrazido)carbonyl]cyclobutyl]isoxazole-5-carboxamide (350 mg, 0.91 mmol, 1.00 eq.) were added to a cold solution of $PPh_3$ (597 mg, 2.28 mmol, 2.50 eq.) in dichloromethane (30 mL) at 0° C. The resulting solution was stirred for 1 hour at room temperature, then quenched by the addition of water. The resulting solution was extracted with ethyl acetate and the organic layers combined. The resulting mixture was washed with brine, dried over anhydrous sodium sulfate and concentrated under vacuum. The residue was applied onto a silica gel column with dichloromethane/methanol (10:1) to afford 100.4 mg (30%) of 3-phenyl-N-[trans-3-[5-(oxetan-3-yl)-1,3,4-oxadiazol-2-yl]cyclobutyl]isoxazole-5-carboxamide as a white solid; LC-MS (ES, m/z): [M+H]+=367.1; $^1$H NMR (300 MHz, DMSO-$d_6$, ppm): δ 9.46-9.44 (d, 1H, J=7.5 Hz), 7.95-7.92 (m, 2H), 7.66 (s, 1H), 7.56-7.54 (m, 3H), 4.95-4.90 (m, 2H), 4.83-4.79 (m, 2H), 4.75-4.51 (m, 2H), 3.78-3.71 (m, 1H), 2.70-2.65 (m, 4H); HPLC purity: 96.5% at 254 nm.

Example 23: N-(trans-3-(5-(1,1-dioxidothietan-3-yl)-1,3,4-oxadiazol-2-yl)cyclobutyl)-3-phenylisoxazole-5-carboxamide

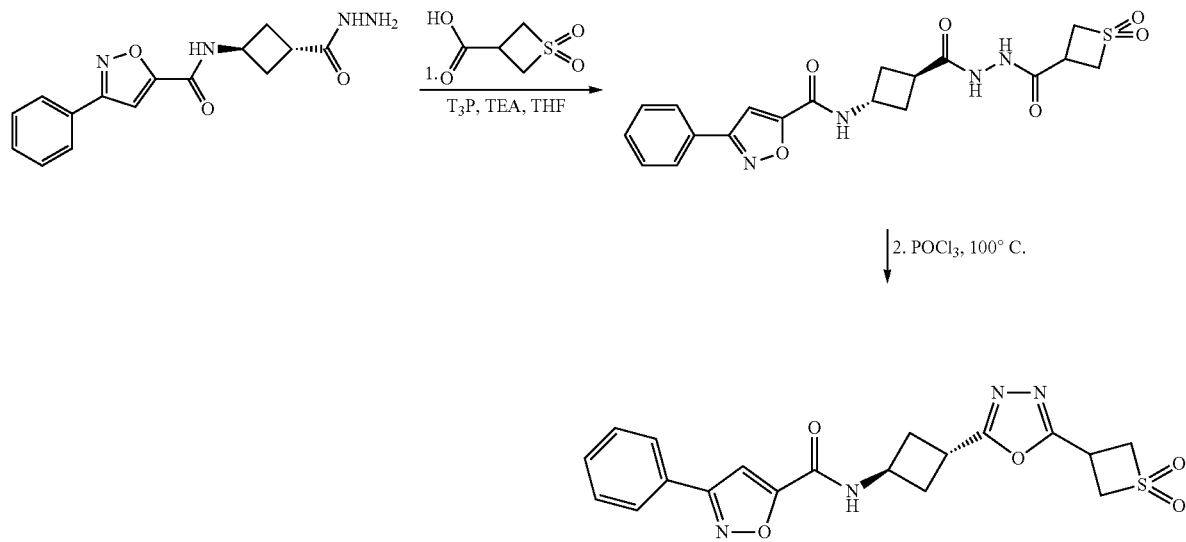

Step 1: N-(trans-3-(2-(1,1-dioxidothietane-3-carbonyl)hydrazine-1-carbonyl)cyclobutyl)-3-phenylisoxazole-5-carboxamide A solution of thietane-3-carboxylic acid 1,1-dioxide (500 mg, 3.4 mmol, 1.00 eq.), 3-phenyl-N-[trans-3-(hydrazinecarbonyl)cyclobutyl]-isoxazole-5-carboxamide (1.0 g, 3.4 mmol, 1.00 eq.), T$_3$P (10 mL) and TEA (4 mL) in tetrahydrofuran (20 mL) was stirred for 1 hour at room temperature. The reaction was then quenched by the addition of water and the solids were collected by filtration to afford 30 mg (42%) of N-(trans-3-(2-(1,1-dioxidothietane-3-carbonyl)hydrazine-1-carbonyl)cyclobutyl)-3-phenylisoxazole-5-carboxamide as a light yellow solid. LC-MS (ES, m/z): [M+H]$^+$=433.1.

Step 2: N-(trans-3-(5-(1,1-dioxidothietan-3-yl)-1,3,4-oxadiazol-2-yl)cyclobutyl)-3-phenylisoxazole-5-carboxamide A solution of N-(trans-3-(2-(1,1-dioxidothietane-3-carbonyl)hydrazine-1-carbonyl)cyclobutyl)-3-phenylisoxazole-5-carboxamide (400 mg, 0.92 mmol, 1.00 eq.) in POCl$_3$ (8 mL) was stirred for 3 hours at 100° C. in an oil bath. The reaction was then quenched by the addition of sodium bicarbonate aqueous/ice, extracted with ethyl acetate and the organic layers combined. The resulting mixture was washed with water, dried over anhydrous sodium sulfate and concentrated under vacuum to give 105.8 mg (28%) of N-(trans-3-(5-(1,1-dioxidothietan-3-yl)-1,3,4-oxadiazol-2-yl)cyclobutyl)-3-phenylisoxazole-5-carboxamide as a white solid; LC-MS (ES, m/z): [M+H]$^+$=415.2; $^1$H NMR (DMSO-d$_6$, 400 MHz): δ 9.46-9.42 (m, 1H), 7.95-7.91 (m, 2H), 7.66-7.65 (m, 1H), 7.55-7.54 (m, 3H), 4.75-4.57 (m, 5H), 4.23-4.14 (m, 1H), 3.73-3.52 (m, 1H), 2.70-2.66 (m, 4H); HPLC purity: 99.2% at 254 nm.

Example 24 and 25: N-cis-(3-(5-(1-(1-methylpiperidin-4-yl)azetidin-3-yl)-1,3,4-oxadiazol-2-yl)cyclobutyl)-3-phenylisoxazole-5-carboxamide and N-trans-(3-(5-(1-(1-methylpiperidin-4-yl)azetidin-3-yl)-1,3,4-oxadiazol-2-yl)cyclobutyl)-3-phenylisoxazole-5-carboxamide

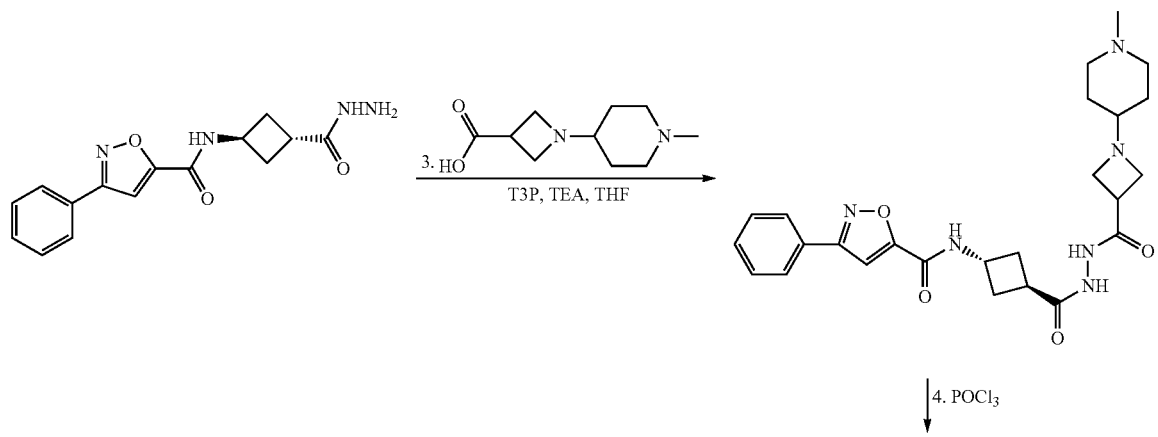

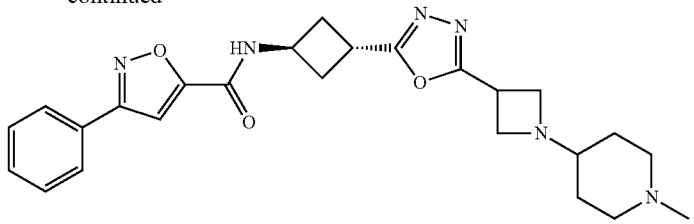

Step 1: benzyl 1-(1-methylpiperidin-4-yl)azetidine-3-carboxylate

A solution of trifluoroacetic acid benzyl azetidine-3-carboxylate (1.3 g, 4.26 mmol, 1.00 eq.), 1-methylpiperidin-4-one (482 mg, 4.26 mmol, 1.10 eq.) and acetic acid (255 mg, 4.25 mmol, 1.00 eq.) in DCE (20 mL) was stirred for 30 min, followed by the addition of NaBH(OAc)$_3$ (1.44 g, 6.79 mmol, 1.60 eq.). The resulting solution was stirred for 16 hours at room temperature. The reaction was then quenched by the addition of water, extracted with dichloromethane and the organic layers combined. The organic layer was washed with brine, dried over anhydrous sodium sulfate and concentrated under vacuum. The residue was applied onto a silica gel column with DCM/MeOH (10:1) to give 830 mg (68%) of benzyl 1-(1-methylpiperidin-4-yl)azetidine-3-carboxylate as yellow oil; LC-MS (ES, m/z): [M+H]$^+$=289.2.

Step 2: 1-(1-methylpiperidin-4-yl)azetidine-3-carboxylic acid

Palladium on carbon (100 mg) was added to a solution of benzyl 1-(1-methylpiperidin-4-yl)azetidine-3-carboxylate (830 mg, 2.88 mmol, 1.00 eq.) in methanol (20 mL), the solution was degassed and back filled with hydrogen. The resulting solution was stirred for 2 hours at room temperature, and the solids were filtered out. The resulting mixture was concentrated under vacuum to give 570 mg (crude) of 1-(1-methylpiperidin-4-yl)azetidine-3-carboxylic acid as light yellow oil; LC-MS (ES, m/z): [M+H]$^+$=199.1.

Step 3: 3-phenyl-N-[trans-3-([[1-(1-methylpiperidin-4-yl)azetidin-3-yl]formohydrazido]carbonyl)cyclobutyl]-isoxazole-5-carboxamide A solution of 3-phenyl-N-[trans-3-(hydrazinecarbonyl)cyclobutyl]-isoxazole-5-carboxamide (409 mg, 1.36 mmol, 1.00 eq.), 1-(1-methylpiperidin-4-yl)azetidine-3-carboxylic acid (270 mg, 1.36 mmol, 1.00 eq.), T$_3$P (4.3 g, 6.76 mmol, 5.00 eq., 50%) and TEA (688 mg, 6.80 mmol, 5.00 eq.) in tetrahydrofuran (10 mL) was stirred for 30 min at room temperature. The reaction was then quenched by the addition of water, extracted with ethyl acetate and the aqueous layers combined and concentrated under vacuum. The crude product was purified by Flash-Prep-HPLC with the following conditions (IntelFlash-1): Column, C18; mobile phase, methanol/H$_2$O=5:95 increasing to methanol/H$_2$O=95:5 within 30 min; Detector, UV 254 nm to give 220 mg (34%) of 3-phenyl-N-[trans-3-([[1-(1-methylpiperidin-4-yl)azetidin-3-yl]formohydrazido]carbonyl)cyclobutyl]-isoxazole-5-carboxamide as a light yellow solid; LC-MS (ES, m/z): [M+H]$^+$=481.2.

Step 4

A solution of 3-phenyl-N-[trans-3-([[1-(1-methylpiperidin-4-yl)azetidin-3-yl]formohydrazido]carbonyl)cyclobutyl]-isoxazole-5-carboxamide (160 mg, 0.33 mmol, 1.00 eq.) in POCl$_3$ (8 mL) was stirred for 1 hour at 100° C. The reaction was then quenched by the addition of water/ice, the pH value of the solution was adjusted to 8 with sodium bicarbonate aqueous. The resulting solution was extracted with dichloromethane and the organic layers combined, washed with brine, dried and concentrated under vacuum. The crude product was purified by Prep-HPLC with the following conditions (HPLC-10): Column, XBridge Shield RP18 OBD Column, 5 um, 19*150 mm; mobile phase, water (0.05% NH$_4$HCO$_3$) and ACN (27.0% ACN up to 37.0% in 8 min); Detector, UV 254/220 nm to give 19.6 mg (13%) of front peak as a white solid and 4.2 mg (3%) of second peak as an off-white solid.

Front Peak

LC-MS (ES, m/z): [M+H]$^+$=463.2; $^1$H NMR (300 MHz, DMSO-d$_6$, ppm): δ 9.45-9.43 (d, 1H, J=7.5 Hz), 7.95-7.92 (m, 2H), 7.66 (s, 1H), 7.56-7.53 (m, 3H), 4.67-4.64 (m, 1H), 3.85-3.80 (m, 1H), 3.73-3.69 (m, 1H), 3.60-3.55 (m, 2H), 3.29-3.24 (m, 3H), 2.68-2.62 (m, 5H), 2.12 (s, 3H), 2.04-1.98 (m, 1H), 1.91-1.84 (m, 2H), 1.62-1.58 (m, 2H), 1.21-1.11 (m, 2H); HPLC purity: 97.8% at 254 nm.

Second Peak

LC-MS (ES, m/z): [M+H]$^+$=463.2; $^1$H NMR (300 MHz, DMSO-d$_6$, ppm): δ 9.47-9.44 (d, 1H, J=7.8 Hz), 7.95-7.92 (m, 2H), 7.66 (s, 1H), 7.56-7.54 (m, 3H), 4.72-4.64 (m, 1H), 3.77-3.74 (m, 1H), 3.62 (s, 2H), 3.29 (s, 3H), 2.71-2.66 (m, 6H), 2.40-2.30 (m, 1H), 2.12 (s, 3H), 1.89-1.75 (m, 4H), 1.29-1.25 (m, 2H); HPLC purity: 95.1% at 254 nm.

Example 26: 3-phenyl-N-(trans-3-(5-(1-(2,2,2-trifluoroethyl)azetidin-3-yl)-1,3,4-oxadiazol-2-yl)cyclobutyl)isoxazole-5-carboxamide

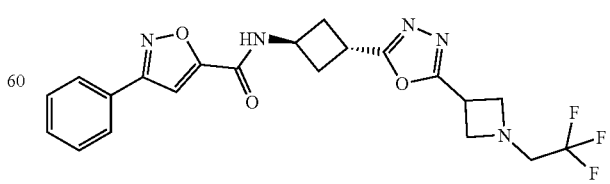

The title compound was prepared using a similar method as shown in example 20.

Example 27: N-(trans-3-(5-(1-(cyclobutylmethyl)azetidin-3-yl)-1,3,4-oxadiazol-2-yl)cyclobutyl)-3-phenylisoxazole-5-carboxamide

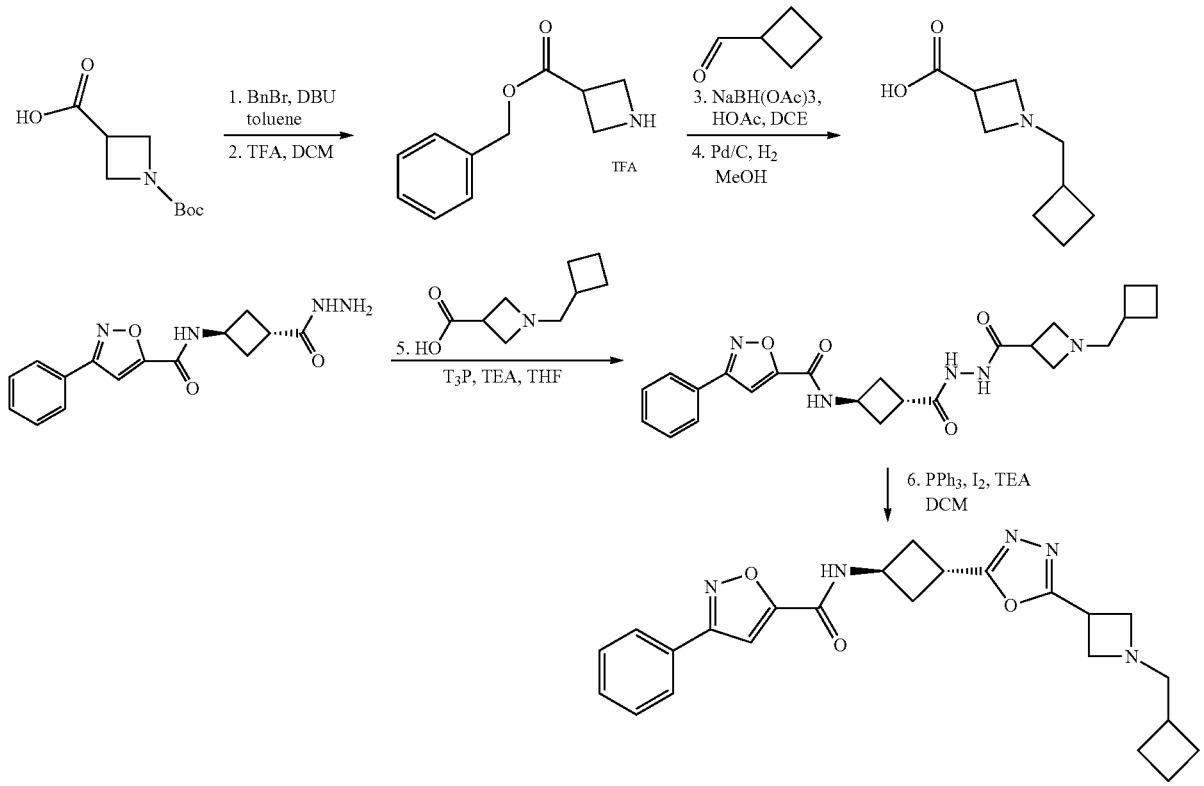

Step 1: 3-benzyl 1-tert-butyl azetidine-1,3-dicarboxylate

A solution of 1-[(tert-butoxy)carbonyl]azetidine-3-carboxylic acid (5 g, 24.85 mmol, 1.00 eq.), BnBr (4.65 g, 27.19 mmol, 1.10 eq.) and DBU (5.67 g, 37.24 mmol, 1.50 eq.) in toluene (80 mL) was stirred for 4 hours at room temperature. The reaction was then quenched by the addition of water, extracted with ethyl acetate and the organic layers combined. The resulting mixture was washed with brine, dried over anhydrous sodium sulfate and concentrated under vacuum. The residue was applied onto a silica gel column with ethyl acetate/petroleum ether (1:6) to give 5.4 g (75%) of 3-benzyl 1-tert-butyl azetidine-1,3-dicarboxylate as colorless oil; LC-MS (ES, m/z): [M+H-Boc]$^+$=192.0.

Step 2: 2,2,2-trifluoroacetic acid benzyl azetidine-3-carboxylate

A solution of 3-benzyl 1-tert-butyl azetidine-1,3-dicarboxylate (5.4 g, 18.53 mmol, 1.00 eq.)) and trifluoroacetic acid (7 mL). in dichloromethane (50 mL) was stirred overnight at room temperature. The resulting mixture was concentrated under vacuum to give 7 g (crude) of 2,2,2-trifluoroacetic acid benzyl azetidine-3-carboxylate as light yellow oil; LC-MS (ES, m/z): [M+H-TFA]$^+$=191.8.

Step 3: benzyl 1-(cyclobutylmethyl)azetidine-3-carboxylate

A solution of 2,2,2-trifluoroacetic acid cyclohexylmethyl azetidine-3-carboxylate (1.3 g, 4.18 mmol, 1.00 eq.), cyclobutanecarboxaldehyde (358 mg, 4.26 mmol, 1.00 eq.) and acetic acid (255 mg, 4.25 mmol, 1.00 eq.) in DCE (20 mL) was stirred for 30 min, and then NaBH(OAc)$_3$ (1.44 g, 6.79 mmol, 1.60 eq.) was added. The resulting solution was stirred for 2 hours at room temperature. The reaction was then quenched by the addition of water, extracted with dichloromethane and the organic layers combined. The resulting mixture was washed with brine, dried over anhydrous sodium sulfate and concentrated under vacuum. The residue was applied onto a silica gel column with dichloromethane/methanol (20:1) to give 650 mg (59%) of benzyl 1-(cyclobutylmethyl)azetidine-3-carboxylate as colorless oil; LC-MS (ES, m/z): [M+H]$^+$=260.1.

Step 4: 1-(cyclobutylmethyl)azetidine-3-carboxylic acid

To a solution of benzyl 1-(cyclobutylmethyl)azetidine-3-carboxylate (650 mg, 2.51 mmol, 1.00 eq.) in methanol (10 mL) was added Palladium on carbon (65 mg) and the solution was degassed and back filled with hydrogen. The resulting solution was stirred for 2 hours at room temperature. The solids were filtered out and concentrated under vacuum to afford 425 mg (99%) of 1-(cyclobutylmethyl)azetidine-3-carboxylic acid as a white solid; LC-MS (ES, m/z): [M+H]$^+$=170.1.

Step 5: 3-phenyl-N-[trans-3-([[1-(cyclobutylmethyl)azetidin-3-yl]formohydrazido]carbonyl)cyclobutyl]-isoxazole-5-carboxamide A solution of 3-phenyl-N-[(trans-3-(hydrazinecarbonyl)cyclobutyl]-isoxazole-5-carboxamide (300 mg, 1.00 mmol, 1.00 eq.), 1-(cyclobutylmethyl)azetidine-3-carboxylic acid (200 mg, 1.20 mmol, 1.20 eq.), T₃P (3.18 g, 5.00 mmol, 5.00 eq., 50%) and TEA (505 mg, 4.99 mmol, 5.00 eq.) in tetrahydrofuran (10 mL) was stirred for 30 min at room temperature. The reaction was then quenched by the addition of water, extracted with ethyl acetate and the aqueous layers combined and concentrated under vacuum. The crude product was purified by Flash-Prep-HPLC with the following conditions (IntelFlash-1): Column, C18; mobile phase, MeCN/H₂O=5:95 increasing to MeCN/H₂O=95:5 within 30 min; Detector, UV 254 nm to afford 210 mg (47%) of 3-phenyl-N-[trans-3-([[1-(cyclobutylmethyl)azetidin-3-yl]formohydrazido]carbonyl)cyclobutyl]-isoxazole-5-carboxamide as a light yellow solid; LC-MS (ES, m/z): [M+H]⁺= 452.1.

Step 6: 3-phenyl-N-[trans-3-[5-[1-(cyclobutylmethyl)azetidin-3-yl]-1,3,4-oxadiazol-2-yl]cyclobutyl]-isoxazole-5-carboxamide I₂ (401 mg, 1.58 mmol, 2.50 eq.), TEA (415 mg, 4.10 mmol, 6.50 eq.) and 3-phenyl-N-[trans-3-([[1-(cyclobutylmethyl)azetidin-3-yl]formohydrazido]carbonyl)cyclobutyl]-isoxazole-5-carboxamide (285 mg, 0.63 mmol, 1.00 eq.) were added to a solution of Ph₃P (414 mg, 1.58 mmol, 2.50 eq.) in dichloromethane (20 mL) under N₂. The reaction mixture was stirred for 1 hour at room temperature, quenched with water and then extracted with ethyl acetate and the organic layers combined. The organic layer was washed with brine, dried over anhydrous sodium sulfate and concentrated under vacuum. The residue was applied onto a silica gel column with DCM/MeOH (25:1). The resulting crude product was purified by Prep-HPLC with the following conditions (HPLC-10): Column, X Bridge Prep C18 OBD Column, 19*150 mm, 5 um; mobile phase, water (0.05% NH₄HCO₃) and ACN (30% ACN up to 80% within 8 min); Detector, UV 254 nm to give 125.6 mg (46%) of 3-phenyl-N-[trans-3-[5-[1-(cyclobutylmethyl)azetidin-3-yl]-1,3,4-oxadiazol-2-yl]cyclobutyl]-isoxazole-5-carboxamide as a white solid; LC-MS (ES, m/z): [M+H]⁺=434.3; ¹H NMR (400 MHz, DMSO-d₆, ppm): δ 9.45-9.43 (d, 1H, J=7.6 Hz), 7.95-7.93 (m, 2H), 7.65 (s, 1H), 7.55-7.54 (m, 2H), 4.71-4.63 (m, 1H), 3.88-3.81 (m, 1H), 3.74-3.67 (m, 1H), 3.59-3.55 (t, 2H, J=7.2 Hz), 3.31 (s, 1H), 3.29-3.26 (d, 1H, J=6.8 Hz), 2.70-2.63 (m, 4H), 2.45-2.43 (m, 2H), 2.32-2.24 (m, 1H), 1.99-1.95 (m, 2H), 1.88-1.73 (m, 2H), 1.67-1.59 (m, 2H); HPLC purity: 99.3% at 254 nm.

Examples 28 and 29: N-(cis-3-(5-(hydroxymethyl)-1H-1,2,3-triazol-1-yl)cyclobutyl)-3-phenylisoxazole-5-carboxamide and N-(cis-3-(4-(hydroxymethyl)-1H-1,2,3-triazol-1-yl)cyclobutyl)-3-phenylisoxazole-5-carboxamide

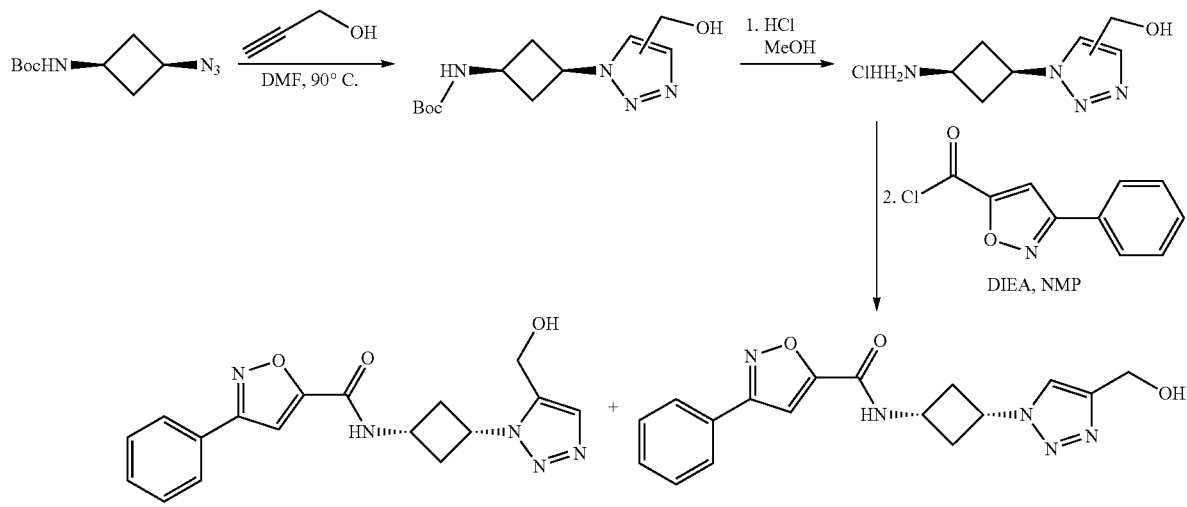

Step 1: 1-[cis-3-aminocyclobutyl]-1H-1,2,3-triazol-1-yl]methanol hydrochloride

A solution of tert-butyl N-[cis-3-[4/5-(hydroxymethyl)-1H-1,2,3-triazol-1-yl]cyclobutyl]carbamate (prepared using a procedure similar to example 36; 400 mg, 1.49 mmol, 1.00 eq.) in hydrogen chloride/MeOH (5 mL) was stirred for 18 hours at room temperature. The resulting mixture was concentrated under vacuum and diluted with 3 mL of dioxane. The solids were collected by filtration and dried in an oven under reduced pressure to give 301 mg (crude) of 1-[cis-3-aminocyclobutyl]-1H-1,2,3-triazol-5-yl]methanol hydrochloride as a white solid; LC-MS (ES, m/z): [M+1]=167.1.

Step 2: 3-phenyl-N-[cis-3-[4-(hydroxymethyl)-1H-1,2,3-triazol-1-yl]cyclobutyl]isoxazole-5-carboxamide and 3-phenyl-N-[cis-3-[5-(hydroxymethyl)-1H-1,2,3-triazol-1-yl]cyclobutyl]isoxazole-5-carboxamide DIEA (787 mg, 6.09 mmol, 3.00 eq.) was added dropwise to a cold solution (10° C.) of [1-[cis-3-aminocyclobutyl]-1H-1,2,3-triazol-4/5-yl]methanol hydrochloride (410 mg, 2.00 mmol, 1.00 eq.) in NMP (4 mL) and stirred for 30 min at 25° C., followed by the addition of a solution of 3-phenylisoxazole-5-carbonyl chloride (310 mg, 1.64 mmol, 1.00 eq.) in NMP (1 mL) dropwise with stirring at 0 to 10° C. The reaction was stirred for 30 min and then quenched by the addition of 0.5 mL of methanol. The mixture was stirred at 25° C. for 30 min then 40 mL of water was added. The crude solid was collected by filtration and purified by prep-HPLC: Column: XBridge BEH130 Prep C18 OBD Column 19*150 mm, 5 um, 13 nm; Mobile Phase A: water (10 mmol/L NH$_4$HCO$_3$), Mobile Phase B: ACN; Flow rate: 20 mL/min; Gradient: 22% B to 47% B in 8 min; 254 nm to give 152 mg (22%) of 3-phenyl-N-[cis-3-[5-(hydroxymethyl)-1H-1,2,3-triazol-1-yl]cyclobutyl]isoxazole-5-carboxamide as a white solid and 143.15 mg (28%) of 3-phenyl-N-[cis-3-[4-(hydroxymethyl)-1H-1,2,3-triazol-1-yl]cyclobutyl]isoxazole-5-carboxamide as a white solid.

3-phenyl-N-[cis-3-[5-(hydroxymethyl)-1H-1,2,3-triazol-1-yl]cyclobutyl]isoxazole-5-carboxamide LC-MS (ES, m/z): [M+1]$^+$=340.0; $^1$H NMR (300 MHz, DMSO-d$_6$, ppm): δ 9.48-9.45 (d, J=7.5 Hz, 1H), 7.94-7.91 (m, 2H), 7.66-7.62 (m, 2H), 7.56-7.54 (m, 3H), 5.46-5.42 (m, 1H), 4.89-4.80 (m, 1H), 4.58-4.57 (d, J=5.4 Hz, 2H), 4.45-4.35 (m, 1H), 2.92-2.80 (m, 4H); HPLC purity: 99.2% at 254 nm.

3-phenyl-N-[cis-3-[4-(hydroxymethyl)-1H-1,2,3-triazol-1-yl]cyclobutyl]isoxazole-5-carboxamide LC-MS (ES, m/z): [M+1]$^+$=340.0; $^1$H NMR (300 MHz, DMSO-d$_6$, ppm): δ 9.41-9.39 (d, J=8.4 Hz, 1H), 8.16 (s, 1H), 7.96-7.93 (m, 2H), 7.67 (s, 1H), 7.56-7.54 (m, 3H), 5.23-5.19 (t, J=5.6 Hz, 1H), 4.98-4.92 (m, 1H), 4.55-4.53 (d, J=5.4 Hz, 2H), 4.45-4.37 (m, 1H), 2.98-2.90 (m, 2H), 2.75-2.65 (m, 2H); HPLC purity: 99.3% at 254 nm.

Examples 30 and 31: N-(trans-3-(5-(oxetan-3-yl)-1H-1,2,3-triazol-1-yl)cyclobutyl)-5-phenylisoxazole-3-carboxamide and N-(trans-3-(4-(oxetan-3-yl)-1H-1,2,3-triazol-1-yl)cyclobutyl)-5-phenylisoxazole-3-carboxamide Step 1: oxetane-3-carbaldehyde A solution of oxetan-3-ylmethanol (2 g, 22.70 mmol, 1.00 eq.) in dichloromethane (20 mL) and 1,1,1-triacetoxy-1,1-dihydro-1,2-benziodoxol-3(1H)-one (11.7 g, 27.59 mmol, 1.00 eq.) was stirred for 2 hours at 25° C. The solids were filtered out and the mixture was concentrated under vacuum to give 2.1 g (crude) of oxetane-3-carbaldehyde as yellow oil.

Step 2: 3-ethynyloxetane

A solution of oxetane-3-carbaldehyde (2.1 g, 24.39 mmol, 1.00 eq.), potassium carbonate (6.6 g, 47.75 mmol, 2.00 eq.) and dimethyl (1-diazo-2-oxopropyl)phosphonate (7 g, 36.44 mmol, 1.50 eq.) in methanol (30 mL) was stirred for 3 hours at 25° C. The resulting solution was diluted with 150 mL of water, extracted with ethyl acetate (2×100 mL) and the organic layers combined. The resulting mixture was washed with brine (2×100 mL), dried over anhydrous sodium sulfate and concentrated under vacuum to give 820 mg (41%) of 3-ethynyloxetane as colorless oil.

Step 3: trans-3-azidocyclobutan-1-amine

A solution of tert-butyl N-[trans-3-azidocyclobutyl]carbamate (1 g, 4.71 mmol, 1.00 eq.) in tetrahydrofuran (20 mL)/conc. HCl aqueous (5 mL) was stirred for 2 hours at 25° C. The resulting mixture was concentrated under vacuum to give 800 mg (crude) of cis-3-azidocyclobutan-1-amine as yellow oil.

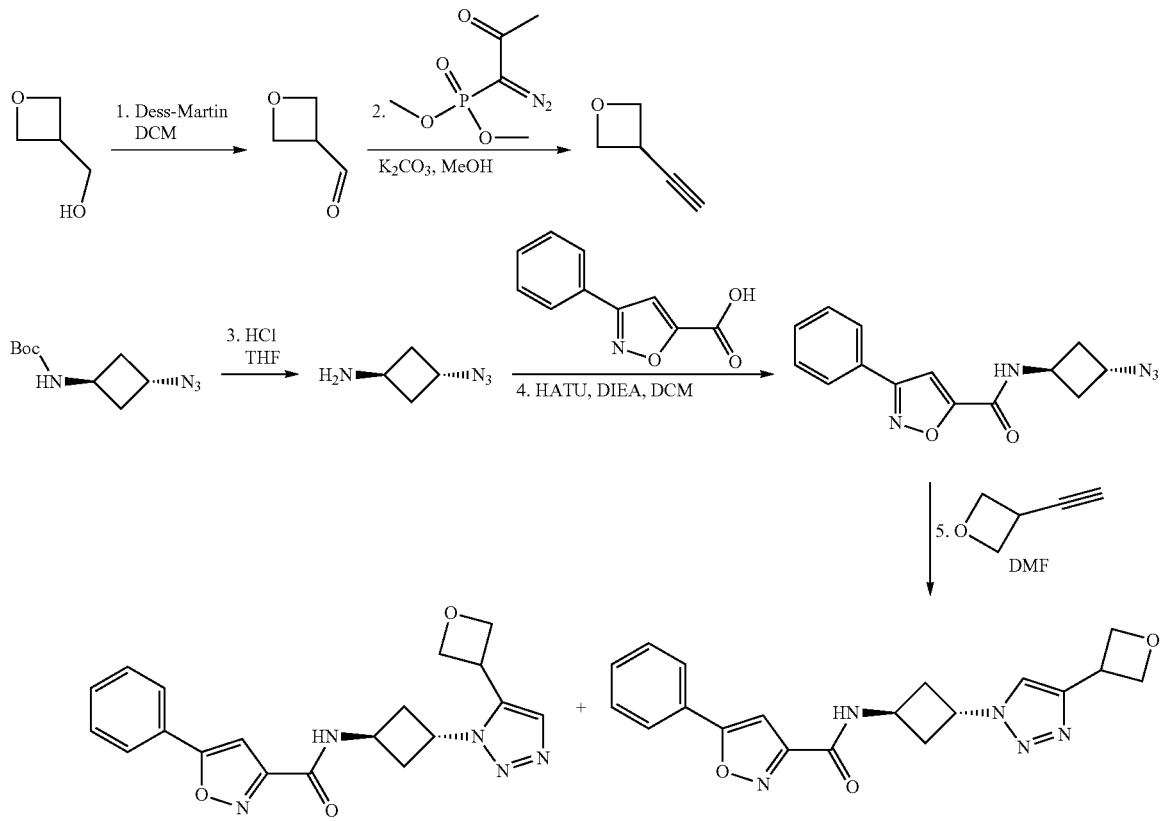

Step 4: 3-phenyl-N-[trans-3-azidocyclobutyl]-isoxazole-5-carboxamide

HATU (1.37 g, 3.60 mmol, 1.50 eq.), DIEA (928 mg, 7.18 mmol, 3.00 eq.) and 3-phenyl-isoxazole-5-carboxylic acid (453 mg, 2.39 mmol, 1.00 eq.) were added to a solution of trans-3-azidocyclobutan-1-amine (800 mg, 7.13 mmol, 1.00 eq.) in dichloromethane (15 mL) and the mixture was stirred for 2 hours at 25° C. The resulting solution was diluted with 150 mL of $H_2O$, extracted with ethyl acetate (2×100 mL) and the organic layers combined. The organic layer was washed with brine (2×100 mL), dried over anhydrous sodium sulfate and concentrated under vacuum. The residue was applied onto a silica gel column with petroleum ether: ethyl acetate (10:1) to afford 390 mg (19%) of 3-phenyl-N-[trans-3-azidocyclobutyl]-isoxazole-5-carboxamide as a yellow solid; LC-MS (ES, m/z): $[M+H]^+=284.1$.

Step 5: 5-phenyl-N-[trans-3-[4-(oxetan-3-yl)-1H-1,2,3-triazol-1-yl]cyclobutyl]isoxazole-3-carboxamide and 5-phenyl-N-[trans-3-[5-(oxetan-3-yl)-1H-1,2,3-triazol-1-yl]cyclobutyl]isoxazole-3-carboxamide A solution of 3-phenyl-N-[(trans-3-azidocyclobutyl]isoxazole-5-carboxamide (283 mg, 1.00 mmol, 1.00 eq.) and 3-ethynyloxetane (410 mg, 4.99 mmol, 5.00 eq.) in DMF (10 mL) was stirred for 16 hours at 100° C. The resulting solution was diluted with 100 mL of $H_2O$, extracted with ethyl acetate (2×100 mL) and the combined organic layers were dried over anhydrous sodium sulfate and concentrated under vacuum. The crude product was purified by Prep-TLC (petroleum ether:ethyl acetate=1:5). The resulting isomers was separated by Chiral-Prep-HPLC with the following conditions (Prep-HPLC-032): Column, Phenomenex Lux 5u Cellulose-4 AXIA Packed, 250*21.2 mm, 5 um; mobile phase, Hex and ethanol (hold 50.0% ethanol in 20 min); Detector, UV 254/220 nm to afford 16.8 mg (5%) of 5-phenyl-N-[trans-3-[5-(oxetan-3-yl)-1H-1,2,3-triazol-1-yl]cyclobutyl]isoxazole-3-carboxamide as a white solid and 29.1 mg (8%) of 3-phenyl-N-[trans-3-[4-(oxetan-3-yl)-1H-1,2,3-triazol-1-yl]cyclobutyl]isoxazole-5-carboxamide as a white solid.

5-phenyl-N-[trans-3-[5-(oxetan-3-yl)-1H-1,2,3-triazol-1-yl]cyclobutyl]isoxazole-3-carboxamide LC-MS (ES, m/z): $[M+H]^+=366.1$; $^1$H NMR (300 MHz, DMSO-$d_6$) δ 9.51-9.49 (d, J=7.2 Hz, 1H), 7.96-7.94 (m, 3H), 7.68 (s, 1H), 7.57-7.56 (m, 3H), 4.97-4.93 (m, 3H), 4.75-4.70 (m, 1H), 4.66-4.62 (m, 2H), 4.48-4.42 (m, 1H), 2.86-2.74 (m, 4H); HPLC purity: 99.5% at 254 nm.

5-phenyl-N-[trans-3-[4-(oxetan-3-yl)-1H-1,2,3-triazol-1-yl]cyclobutyl]isoxazole-3-carboxamide LC-MS (ES, m/z): $[M+H]^+=366.1$; $^1$H NMR (300 MHz, DMSO-$d_6$) δ 9.52-9.50 (d, J=6.9 Hz, 1H), 8.33 (s, 1H), 7.96-7.93 (m, 2H), 7.68 (s, 1H), 7.56-7.54 (m, 3H), 5.34-5.24 (m, 1H), 4.92-4.88 (m, 2H), 4.76-4.65 (m, 3H), 4.42-4.32 (m, 1H), 2.91-2.75 (m, 4H); HPLC purity: 98% at 254 nm.

Example 32 and 33: N-(trans-3-(4-(1-methylazetidin-3-yl)-1H-1,2,3-triazol-1-yl)cyclobutyl)-3-phenylisoxazole-5-carboxamide and N-(trans-3-(5-(1-methylazetidin-3-yl)-1H-1,2,3-triazol-1-yl)cyclobutyl)-3-phenylisoxazole-5-carboxamide

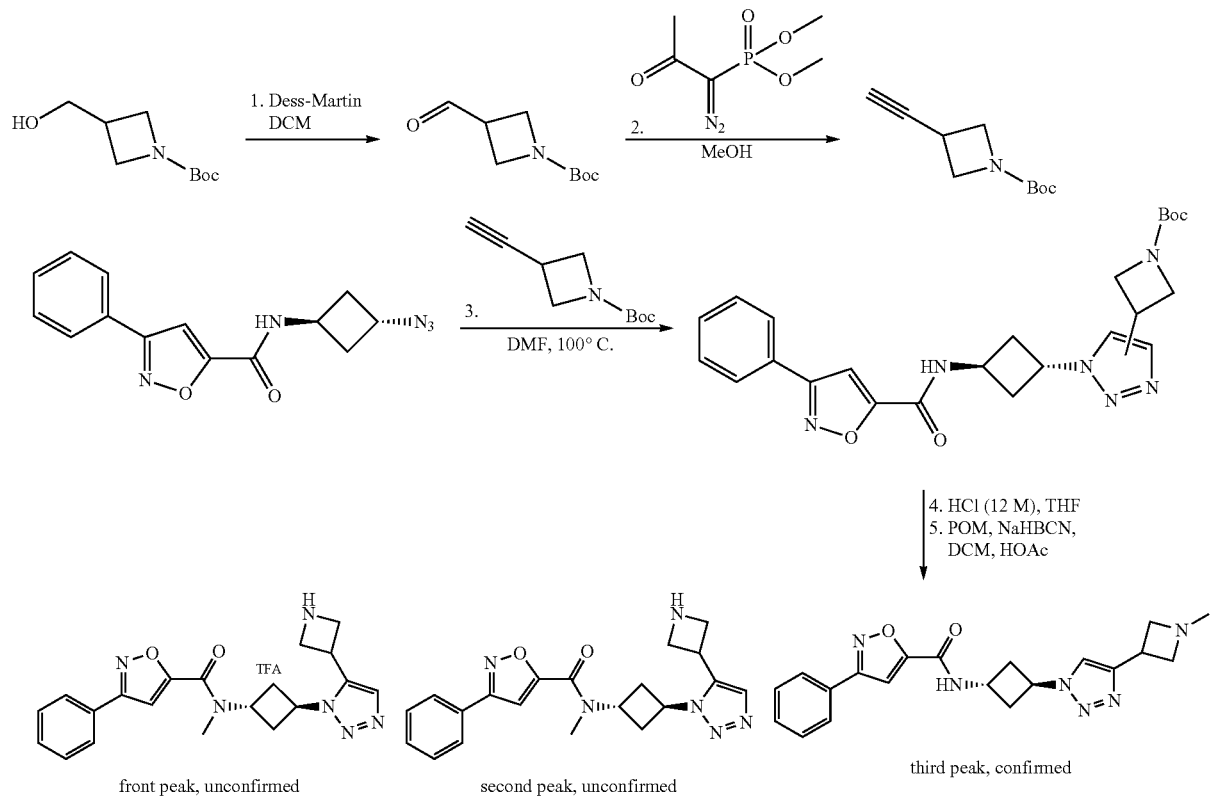

Step 1: tert-butyl 3-formylazetidine-1-carboxylate

A solution of tert-butyl 3-(hydroxymethyl)azetidine-1-carboxylate (3.74 g, 19.97 mmol, 1.00 equip), and Dess-Martin reagent (12.72 g, 30.00 mmol, 1.50 eq.) in dichloromethane (100 mL) was stirred for 2 hours at room temperature. The solids were filtered out, the resulting mixture was concentrated under vacuum to give 3.8 g (crude) of tert-butyl 3-formylazetidine-1-carboxylate as a white solid.

Step 2: tert-butyl 3-ethynylazetidine-1-carboxylate

A solution of tert-butyl 3-formylazetidine-1-carboxylate (3.7 g, 19.98 mmol, 1.00 eq.), potassium carbonate (8.28 g, 59.91 mmol, 3.00 eq.) and dimethyl (1-diazo-2-oxopropyl)phosphonate (5.76 g, 29.98 mmol, 1.50 eq.) in methanol (50 mL) was stirred for 3 hours at room temperature. The resulting solution was diluted with 200 mL of ether, washed with saturated sodium bicarbonate aqueous (2×200 mL), dried over anhydrous sodium sulfate and concentrated under vacuum to give 3.282 g (crude) of tert-butyl 3-ethynylazetidine-1-carboxylate as yellow oil.

Step 3: tert-butyl 3-[1-[trans-3-(3-phenylisoxazole-5-amido)cyclobutyl]-1H-1,2,3-triazol-4/5-yl]azetidine-1-carboxylate A solution of 3-phenyl-N-[trans-3-azidocyclobutyl]isoxazole-5-carboxamide (327 mg, 1.15 mmol, 1.00 eq.) and tert-butyl 3-ethynylazetidine-1-carboxylate (627 mg, 3.46 mmol, 3.00 eq.) in DMF (4 mL) was placed in a microwave reactor for 6 hours at 140° C. The resulting mixture was concentrated under vacuum and the residue was applied onto a silica gel column with ethyl acetate/petroleum ether (1:1) to give 553 mg (crude) mixture of tert-butyl 3-[1-[trans-3-(3-phenylisoxazole-5-amido)cyclobutyl]-1H-1,2,3-triazol-5-yl]azetidine-1-carboxylate and tert-butyl 3-[1-[trans-3-(3-phenylisoxazole-5-amido)cyclobutyl]-1H-1,2,3-triazol-4-yl]azetidine-1-carboxylate as a yellow solid; LC-MS (ES, m/z): [M+H]$^+$=465.3.

Step 4: 3-phenyl-N-[trans-3-[4/5-(azetidin-3-yl)-1H-1,2,3-triazol-1-yl]cyclobutyl]isoxazole-5-carboxamide hydrochloride A solution of the mixture of tert-butyl 3-[1-trans-3-(3-phenylisoxazole-5-amido)cyclobutyl]-1H-1,2,3-triazol-4/5-yl]azetidine-1-carboxylate (553 mg, 1.19 mmol, 1.00 eq.) in tetrahydrofuran (10 mL)/hydrogen chloride aqueous (6N, 6 mL) was stirred for 2 hours at room temperature. The resulting mixture was concentrated under vacuum to give 551 mg (crude) of a mixture of 3-phenyl-N-[trans-3-[4/5-(azetidin-3-yl)-1H-1,2,3-triazol-1-yl]cyclobutyl]isoxazole-5-carboxamide hydrochloride as a brown solid; LC-MS (ES, m/z): [M−HCl+H]$^+$=365.3.

Step 5: N-(trans-3-(4-(1-methylazetidin-3-yl)-1H-1,2,3-triazol-1-yl)cyclobutyl)-3-phenylisoxazole-5-carboxamide and N-(trans-3-(5-(1-methylazetidin-3-yl)-1H-1,2,3-triazol-1-yl)cyclobutyl)-3-phenylisoxazole-5-carboxamide A solution of the mixture of 3-phenyl-N-[trans-3-[4/5-(azetidin-3-yl)-1H-1,2,3-triazol-1-yl]cyclobutyl]isoxazole-5-carboxamide hydrochloride, POM (302 mg, 6.86 mmol, 4.99 eq.) and acetic acid (165 mg, 2.75 mmol, 2.00 eq.) in DCM (20 mL) was stirred for 30 min at room temperature. NaBHCN (346 mg, 5.49 mmol, 4.00 eq.) was added to the reaction mixture and it was stirred for 3 hours at room temperature. The mixture was concentrated under vacuum and the crude product was purified by Prep-HPLC with the following conditions (HPLC-10): Column, XBridge C18 OBD Prep Column, 19 mm×250 mm; mobile phase, water (10 mmol/L NH$_4$HCO$_3$) and ACN (40.0% ACN up to 90.0% in 8 min); Detector, UV 254/220 nm. This resulted in 50 mg crude first peak, 20 mg (4%) of second peak as a white solid and 75 mg (15%) of third peak) as a white solid. Then the crude first peak was purified by Prep-HPLC with the following conditions (HPLC-10): Column, XBridge C18 OBD Prep Column, 19 mm×250 mm; mobile phase, water (0.05% TFA) and ACN (20.0% ACN up to 50.0% in 10 min); Detector, UV 254/220 nm to give 30 mg of product as a yellow oil.

First Peak (Putative Structure)

Second Peak (Putative Structure)

LC-MS (ES, m/z): [M+H]$^+$=379.2; $^1$H NMR (400 MHz, CD$_3$OD, ppm): 8.05 (s, 1H), 7.89-7.88 (d, J=2.8 Hz, 2H), 7.52-7.51 (m, 3H), 7.43 (s, 1H), 5.11 (br, 1H), 4.90-4.88 (m, 1H), 4.74-7.54 (m, 1H), 4.54-4.46 (m, 2H), 4.36-4.25 (m, 2H), 3.10-2.91 (m, 5H), 2.89-2.88 (m, 2H); HPLC purity: 99.4% at 254 nm.

Third Peak: N-(trans-3-(4-(1-methylazetidin-3-yl)-1H-1,2,3-triazol-1-yl)cyclobutyl)-3-phenylisoxazole-5-carboxamide LC-MS [M+H]$^+$=379.3; $^1$H NMR (400 MHz, DMSO-d$_6$, ppm): δ 9.53-9.51 (d, J=6.8 Hz, 1H), 8.23 (s, 1H), 7.96-7.74 (m, 2H), 7.69 (s, 1H), 7.56-7.54 (m, 3H), 5.28-5.24 (m, 1H), 4.72-4.67 (m, 1H), 3.64-3.56 (m, 3H), 3.12-3.09 (m, 2H), 2.88-2.75 (m, 4H), 2.08 (s, 3H); HPLC purity; 98.7% at 254 nm.

Examples 34: N-(trans-3-(5-(1-(methylsulfonyl)ethyl)-1H-1,2,3-triazol-1-yl)cyclobutyl)-3-phenylisoxazole-5-carboxamide

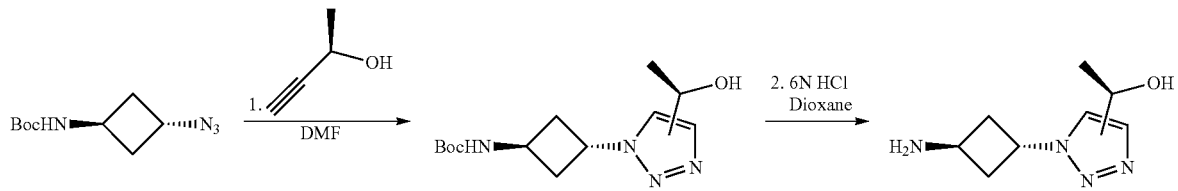

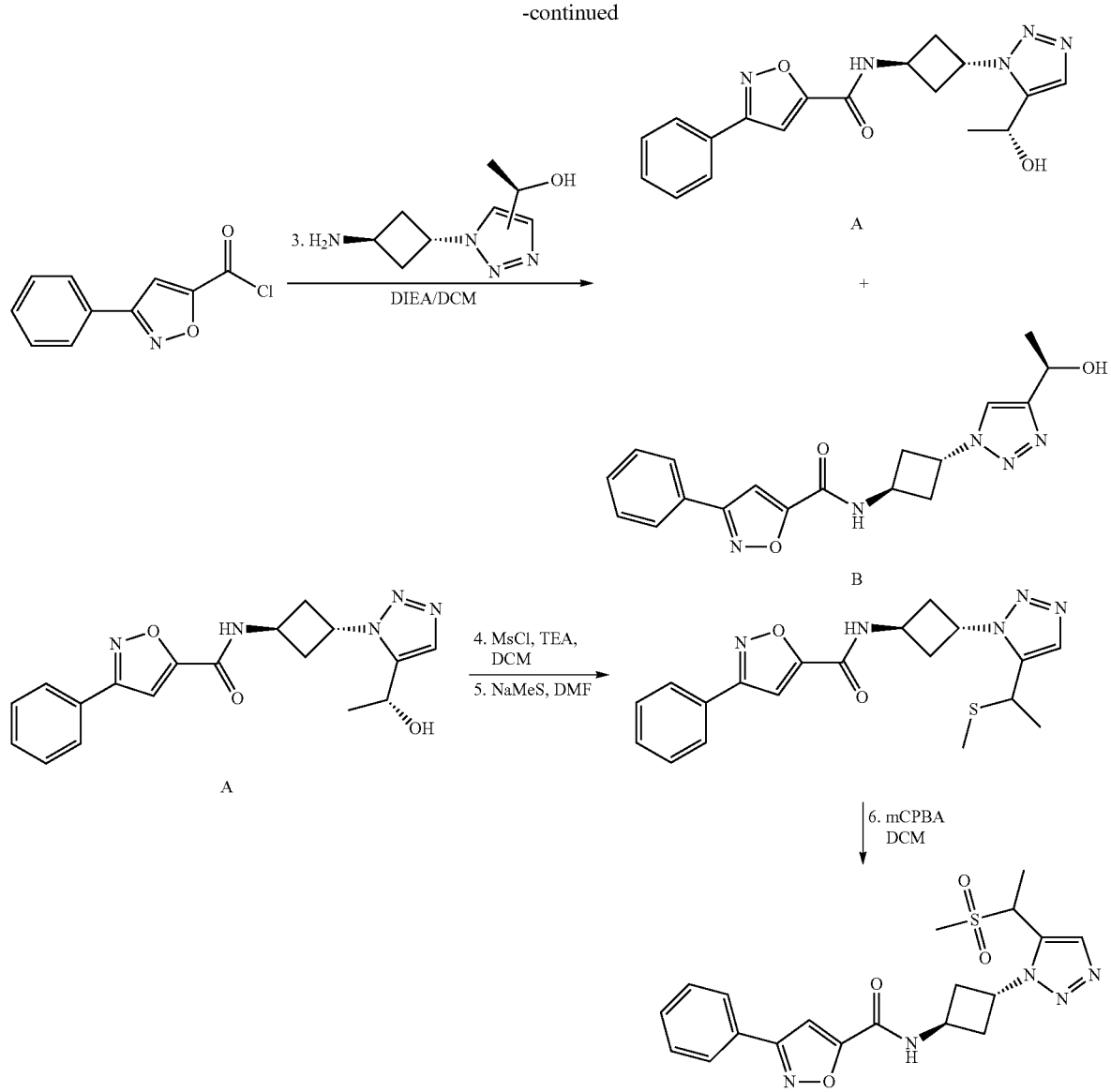

Preparation of Intermediates A and B

Step 1: N-[trans-3-[4/5-[(1R)-1-hydroxyethyl]-1H-1,2,3-triazol-1-yl]cyclobutyl]carbamate A solution of tert-butyl N-[trans-3-azidocyclobutyl]carbamate (2 g, 9.42 mmol, 1.00 eq.) and (2R)-but-3-yn-2-ol (3.3 g, 47.08 mmol, 5.00 eq.) in DMF (5 mL) was stirred for overnight at 100° C. in an oil bath. The resulting mixture was concentrated under vacuum. The residue was applied onto a silica gel column with ethyl acetate/petroleum ether (3:1) to give 2.1 g (79%) of a mixture of tert-butyl N-[trans-3-[4/5-[(1R)-1-hydroxyethyl]-1H-1,2,3-triazol-1-yl]cyclobutyl]carbamate as a light yellow solid; LC-MS (ES, m/z): [M+H]$^+$=283.2.

Step 2: (1R)-1-[1-[trans-3-aminocyclobutyl]-1H-1,2,3-triazol-4/5-yl]ethanol

A solution of the mixture of tert-butyl N-[trans-3-[4/5-[(1R)-1-hydroxyethyl]-1H-1,2,3-triazol-1-yl]cyclobutyl] carbamate in dioxane (10 mL)/hydrogen chloride aqueous (6N, 3 mL) was stirred for 2 hours at room temperature. The resulting mixture was concentrated under vacuum to give 1.45 g (crude) of a mixture of (1R)-1-[1-[trans-3-aminocyclobutyl]-1H-1,2,3-triazol-4/5-yl]ethanol as a light yellow solid; LC-MS-PH (ES, m/z): [M+H]$^+$=183.1.

Step 3: N-(trans-3-(5-((R)-1-hydroxyethyl)-1H-1,2,3-triazol-1-yl)cyclobutyl)-3-phenylisoxazole-5-carboxamide (A) and N-(trans-3-(4-((R)-1-hydroxyethyl)-1H-1,2,3-triazol-1-yl)cyclobutyl)-3-phenylisoxazole-5-carboxamide (B)

DIEA (2.55 g, 3.00 eq.) and 3-phenylisoxazole-5-carbonyl chloride (1.77 g, 8.53 mmol, 1.30 eq.) were added dropwise to a cold (0° C.) solution of a mixture of (1R)-1-[1-[trans-3-aminocyclobutyl]-1H-1,2,3-triazol-4/5-yl]ethanol in dichloromethane (20 mL) and the mixture was stirred for 2 hours at 0° C. The resulting mixture was washed with hydrogen chloride aqueous (2N) (1×50 mL) and potassium carbonate (5%) (1×100 mL), concentrated under vacuum, and the crude product was purified by prep-HPLC to give 0.236 g (10%) of N-(trans-3-(5-((R)-1-hydroxyethyl)-1H-1,2,3-triazol-1-yl)cyclobutyl)-3-phenylisoxazole-5-carboxamide and 0.333 g (14%) of N-(trans-3-(4-((R)-1-hydroxyethyl)-1H-1,2,3-triazol-1-yl)cyclobutyl)-3-phenylisoxazole-5-carboxamide as a white solid; LC-MS (ES, m/z): [M+H]$^+$= 354.2.

Preparation of N-(trans-3-(5-(1-(methylsulfonyl)ethyl)-1H-1,2,3-triazol-1-yl)cyclobutyl)-3-phenylisoxazole-5-carboxamide

Step 4: N-(trans-3-(5-((R)-1-chloroethyl)-1H-1,2,3-triazol-1-yl)cyclobutyl)-3-phenylisoxazole-5-carboxamide MsCl (81.3 mg, 2.00 eq.) was added dropwise to a 0° C. solution of 3-phenyl-N-[(trans-3-[5-[(1R)-1-hydroxyethyl]-1H-1,2,3-triazol-1-yl]cyclobutyl]isoxazole-5-carboxamide (126 mg, 0.36 mmol, 1.00 eq.) and TEA (108 mg, 3.00 eq.) in dichloromethane (20 mL) and the solution was stirred for 5 hours at room temperature. The mixture was diluted with 30 ml of dichloromethane, washed with CuSO$_4$ aqueous (2×30 mL) and concentrated under vacuum to give 151 mg (crude) of N-(trans-3-(5-((R)-1-chloroethyl)-1H-1,2,3-triazol-1-yl)cyclobutyl)-3-phenylisoxazole-5-carboxamide as a brown oil; LC-MS (ES, m/z): [M+H]$^+$=372.1.

Step 5

A solution of N-(trans-3-(5-((R)-1-chloroethyl)-1H-1,2,3-triazol-1-yl)cyclobutyl)-3-phenylisoxazole-5-carboxamide (151 mg, 0.41 mmol, 1.00 eq.) and NaSMe (50 mg, 2.00 eq.) in DMF (5 mL) was stirred for 5 hours at 100° C. in an oil bath. The reaction was then quenched by the addition of 20 mL of water, extracted with ethyl acetate (3×20 mL) and the organic layers combined. The resulting mixture was washed with brine (2×10 mL) and concentrated under vacuum to give 189 mg (crude) of 3-phenyl-N-[trans-3-[5-[1-(methylsulfanyl)ethyl]-1H-1,2,3-triazol-1-yl]cyclobutyl]-isoxazole-5-carboxamide as brown oil; LC-MS (ES, m/z): [M+H]$^+$= 384.4.

Step 6 mCPBA (338 mg, 1.96 mmol, 4.00 eq.) was added in several batches to a 0° C. solution of 3-phenyl-N-[trans-3-[5-[1-(methylsulfanyl)ethyl]-1H-1,2,3-triazol-1-yl]cyclobutyl]isoxazole-5-carboxamide (189 mg, 0.49 mmol, 1.00 eq.) in dichloromethane (10 mL) and the mixture was stirred for 5 hours at room temperature. The reaction mixture was diluted with 50 mL of dichloromethane, washed with Na$_2$S$_2$O$_3$ aqueous (1×50 mL) and concentrated under vacuum. The crude product was purified by Prep-HPLC with the following conditions (Water): Column, Xbridge Prep C18, 5 um, 19*150 mm; mobile phase, water with 0.08% NH$_4$HCO$_3$ and CH$_3$CN (30% CH$_3$CN up to 70% CH$_3$CN in 10 min, up to 95% in 2 min and down to 30% in 2 min); Detector, UV 254 nm and 220 nm to give 23.3 mg (11%) of 3-phenyl-N-[trans-3-[5-[1-methanesulfonylethyl]-1H-1,2,3-triazol-1-yl]cyclobutyl]-isoxazole-5-carboxamide as a white solid; LC-MS (ES, m/z): [M+H]$^+$=416.2; $^1$H NMR (DMSO-d$_6$, 400 MHz): δ 9.52-9.49 (d, J=12.0 Hz, 1H), 7.95-7.93 (m, 3H), 7.69 (s, 1H), 7.56-7.54 (m, 3H), 5.36-5.29 (m, 1H), 4.93-4.87 (m, 1H), 4.85-4.76 (m, 1H), 3.01 (s, 3H), 2.92-2.78 (m, 4H), 1.69-1.67 (d, J=7.2 Hz, 3H); HPLC purity: 99.2% at 254 nm.

Example 35: N-(trans-3-(4-(1-(methylsulfonyl)ethyl)-1H-1,2,3-triazol-1-yl)cyclobutyl)-3-phenylisoxazole-5-carboxamide The title compound was prepared by a similar procedure as shown in example 34 using intermediate B as the starting material. The crude product was purified by Prep-HPLC with the following conditions (Water): Column, Xbridge Prep C18, 5 um, 19*150 mm; mobile phase, water with 0.08% NH$_4$HCO$_3$ and CH$_3$CN (30% CH$_3$CN up to 75% CH$_3$CN in 10 min, up to 95% in 2 min and down to 30% in 2 min); Detector, UV 254 nm and 220 nm to give 54.5 mg (17.6%) of 3-phenyl-N-[trans-3-[5-[1-methanesulfonylethyl]-1H-1,2,3-triazol-1-yl]cyclobutyl]-isoxazole-5-carboxamide as a white solid; LC-MS (ES, m/z): [M+H]$^+$=416.2; $^1$H NMR (DMSO-d$_6$, 400 MHz): δ 9.54-9.52 (d, J=7.2 Hz, 1H), 8.43 (s, 1H), 7.96-7.94 (m, 2H), 7.68 (s, 1H), 7.56-7.54 (m, 3H), 5.37-5.29 (m, 1H), 4.72-4.68 (m, 2H), 2.95 (s, 3H), 2.88-2.81 (m, 4H), 1.68-1.66 (d, J=7.2 Hz, 3H); HPLC purity: 98.4% at 254 nm.

Example 36: 3-(4-fluorophenyl)-N-(trans-3-(5-((R)-1-hydroxyethyl)-1,3,4-oxadiazol-2-yl)cyclobutyl)isoxazole-5-carboxamide

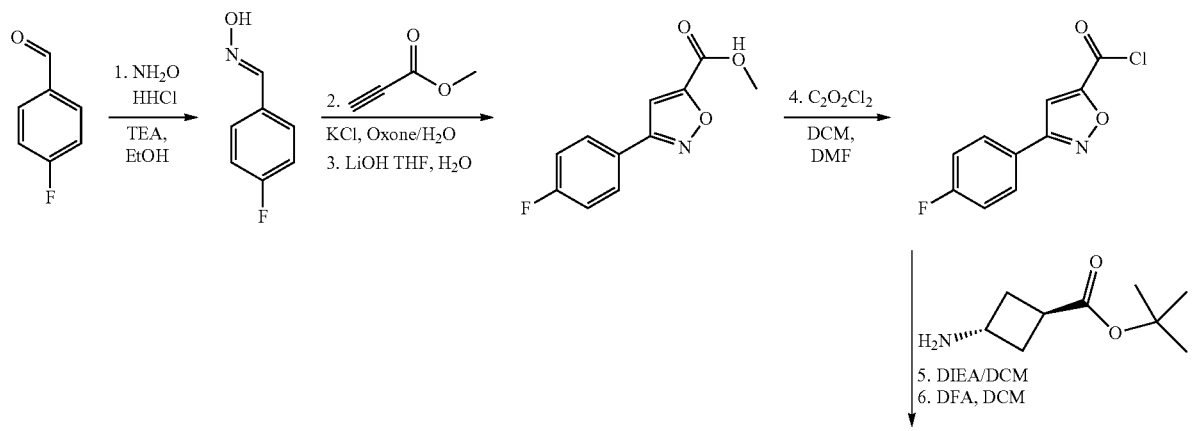

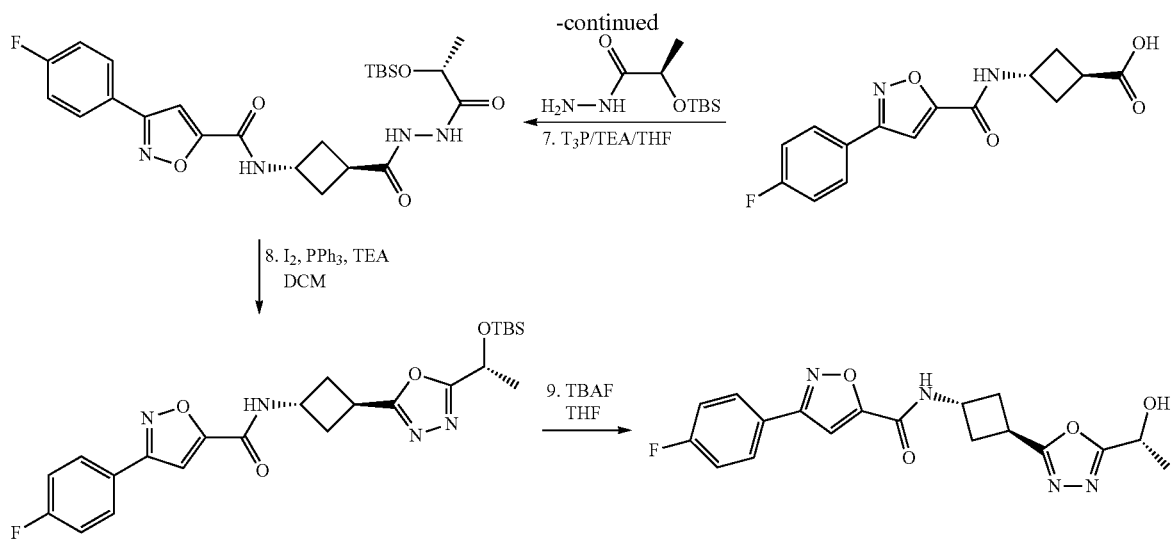

The title compound was prepared using a methodology similar to the one shown in example 13 and purified by Flash-Prep-HPLC with the following conditions (IntelFlash-1): Column, C18; mobile phase, $H_2O/CH_3CN=100:1$ increasing to $H_2O/CH_3CN=1:100$ within 30 min; Detector, UV 254 nm to give 37.7 mg (25%) as a white solid; LC-MS (ES, m/z): $[M+1]^+=373.0$; $^1H$ NMR (400 MHz, DMSO-$d_6$): δ9.49-9.47 (d, J=7.6 Hz, 1H), 8.03-7.98 (m, 2H), 7.68 (s, 1H), 7.42-7.37 (m, 2H), 5.97-5.95 (d, J=6 Hz, 1H), 7.96-4.89 (m, 1H), 4.71-4.65 (m, 1H), 3.76-3.72 (m, 1H), 2.73-2.60 (m, 4H), 1.50-1.48 (d, J=6.4 Hz, 3H); HPLC purity: 99.8% at 254 nm.

Examples 37 and 38: N-((1S,3s)-3-((5-((R)-1-hydroxyethyl)-1,3,4-oxadiazol-2-yl)methyl)cyclobutyl)-3-phenylisoxazole-5-carboxamide and N-((1R,3r)-3-((5-((R)-1-hydroxyethyl)-1,3,4-oxadiazol-2-yl)methyl)cyclobutyl)-3-phenylisoxazole-5-carboxamide

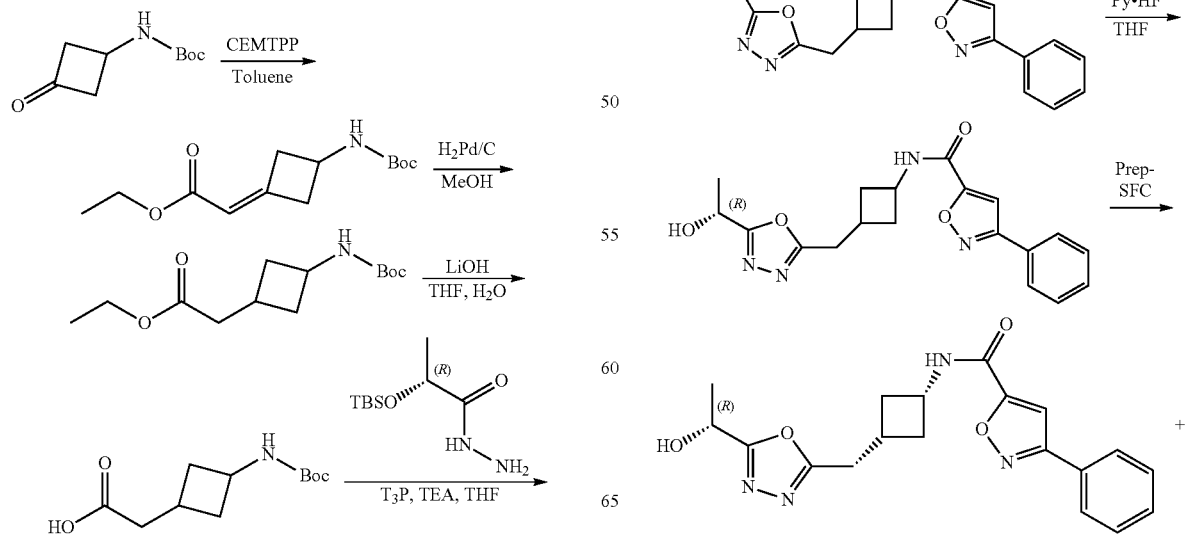

-continued

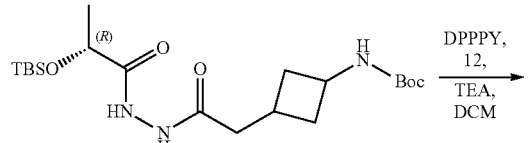
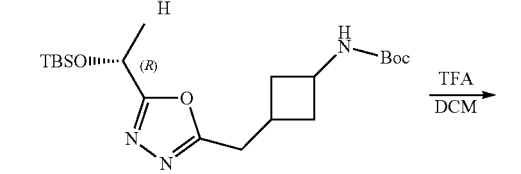
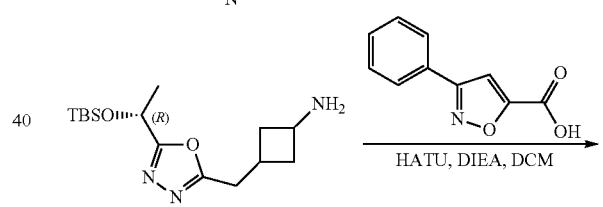
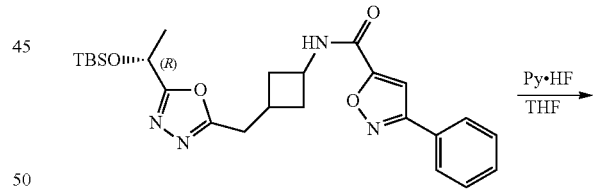
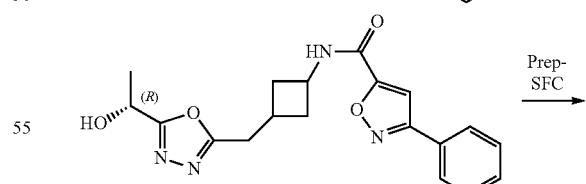
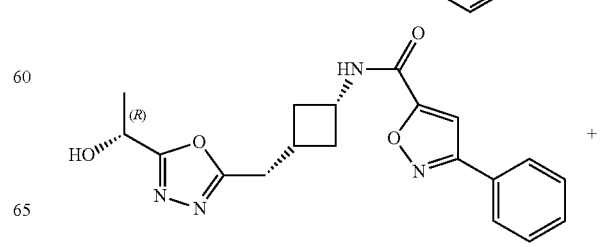

-continued

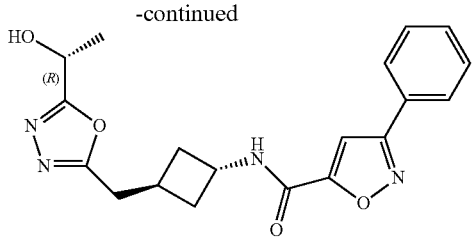

Step 1: Ethyl 2-(3-((tert-Butoxycarbonyl)amino) cyclobutylidene)acetate

To a 250-mL round-bottom flask was placed a solution of tert-butyl N-(3-oxocyclobutyl)carbamate (13 g, 70.19 mmol, 1.00 equiv) in toluene (100 mL), then (carbethoxymethylene)triphenylphosphorane (CEMTPP) (25.7 g, 73.77 mmol, 1.05 equiv) was added. The resulting solution was stirred for 2 h at 100° C. The resulting mixture was concentrated under vacuum then the residue was applied onto a silica gel column and eluted with EtOAc/petroleum ether (1:5) affording 16.7 g (93%) of ethyl 2-(3-[[(tert-butoxy) carbonyl]amino]cyclobutylidene) acetate as a white solid. LCMS (ES, m/z): [M+H]$^+$=256.2.

Step 2: Ethyl 2-(3-((tert-Butoxycarbonyl)amino) cyclobutyl)acetate

To a 250-mL round-bottom flask, was placed a solution of ethyl 2-(3-[[(tert-butoxy)carbonyl]amino]cyclobutylidene) acetate (16.7 g, 65.41 mmol, 1.00 equiv, as prepared above) in MeOH (100 mL), then Pd on carbon (1 g) was added. The solution was degassed and back filled with hydrogen. The resulting solution was stirred for 3 h at RT. The solids were removed by filtration, then the resulting solution was concentrated under reduced pressure affording 15.5 g (92%) of ethyl 2-(3-[[(tert-butoxy)carbonyl]amino]cyclobutyl) acetate as colorless oil. LCMS (ES, m/z): [M+H]$^+$=258.2.

Step 3: 2-(3-[[(tert-Butoxy)carbonyl]amino]cyclobutyl)acetic acid

To a 500-mL round-bottom flask was placed a solution of ethyl 2-(3-[[(tert-butoxy)carbonyl]amino]cyclobutyl)acetate (15.5 g, 60.23 mmol, 1.00 equiv) in THF/H$_2$O (150/50 mL) and LiOH (2.16 g, 90.20 mmol, 1.50 equiv). The resulting solution was stirred for 3 h at rt, then the resulting mixture was concentrated under reduced pressure. The resulting solution was diluted with 200 mL of aq.NaHSO$_4$, extracted with 3×150 mL of EtOAc, and then the organic extracts were combined. The solution was washed with 2×100 mL of brine, dried, and concentrated under reduced pressure, affording 13.8 g (crude) of 2-(3-[[(tert-butoxy)carbonyl] amino]cyclobutyl)acetic acid as colorless oil. LCMS (ES, m/z): [M+H]$^+$=230.1.

Step 4: tert-Butyl N-(3-[2-[(2R)-2-[(tert-Butyldimethylsilyl)oxy]propanehydrazido]-2-oxoethyl]cyclobutyl)carbamate To a 500-mL round-bottom flask was placed a solution of 2-(3-[[(tert-butoxy)carbonyl]amino]cyclobutyl)acetic acid (13 g, 56.70 mmol, 1.00 equiv) in THF (250 mL). To this solution were added (2R)-2-[(tert-butyldimethylsilyl)oxy] propanehydrazide (18.6 g, 85.18 mmol, 1.50 equiv), TEA (28.9 g, 285.60 mmol, 5.00 equiv) and T$_3$P (72 g, 113.21 mmol, 2.00 equiv). The reaction was stirred for 2 h at RT, then diluted with 400 mL of H$_2$O and extracted with EtOAc (3×300 mL). The organic extracts were combined, washed with brine (2×300 mL), dried over Na$_2$SO$_4$, and concentrated under reduced pressure. The residue was applied onto a silica gel column with petroleum ether/EtOAc (2:1) affording 14.5 g (60%) of tert-butyl N-(3-[2-[(2R)-2-[(tert-butyldimethyl silyl)oxy]propanehydrazido]-2-oxoethyl]cyclobutyl) carbamate as yellow oil. LCMS (ES, m/z): [M+H]$^+$=430.3.

Step 5: tert-butyl N-[3-([5-[(1R)-1-[(tert-butyldimethylsilyl)oxy]ethyl]-1,3,4-oxadiazol-2-yl]methyl) cyclobutyl]carbamate To a 250-mL 3-necked round-bottom flask purged and maintained with nitrogen was placed a solution of PPh$_3$ (2.84 g, 10.83 mmol, 2.00 equiv) in DCM (100 mL). To this solution were added I$_2$ (2.75 g, 10.83 mmol, 2.00 equiv), TEA (3.7 g, 36.56 mmol, 5.00 equiv) and tert-butyl N-[3-([N-[(2R)-2-[(tert-butyldimethylsilyl)oxy]propanoyl]hydrazinecarbonyl]methyl)cyclobutyl]carbamate (3.1 g, 7.22 mmol, 1.00 equiv). The resulting solution was stirred for 2 h at RT, then diluted with 150 mL of H$_2$O and extracted with EtOAc (2×150 mL). The organic extracts were combined, washed with brine (2×100 mL), dried over anhydrous Na$_2$SO$_4$, and concentrated under reduced pressure. The residue was applied onto a silica gel column and eluted with petroleum ether/EtOAc (5:1) affording 2 g (67%) of tert-butyl N-[3-([5-[(1R)-1-[(tert-butyldimethylsilyl)oxy]ethyl]-1,3,4-oxadiazol-2-yl]methyl)cyclobutyl]carbamate as yellow oil. LCMS (ES, m/z): [M+H]$^+$=412.3. $^1$H NMR (400 MHz, CDCl$_3$): δ 5.11-5.02 (m, 1H), 4.15-4.08 (m, 1H), 3.02-2.92 (m, 2H), 2.59-2.52 (m, 1H), 2.26-2.19 (m, 1H), 2.14-2.08 (m, 1H), 1.70-1.62 (m, 2H), 1.58-1.56 (d, J=7.6 Hz, 2H), 1.43 (s, 9H), 0.88 (s, 9H), 0.11 (s, 3H), 0.04 (s, 3H).

Step 6: 3-([5-[(1R)-1-[(tert-butyldimethylsilyl)oxy] ethyl]-1,3,4-oxadiazol-2-yl]methyl)cyclobutan-1-amine To a 100-mL round-bottom flask was placed a solution of tert-butyl N-[3-([5-[(1R)-1-[(tert-butyldimethylsilyl)oxy] ethyl]-1,3,4-oxadiazol-2-yl]methyl)cyclobutyl]carbamate (2 g, 4.86 mmol, 1.00 equiv) in DCM (50 mL), then TFA (3 mL, 8.00 equiv) was added. The resulting solution was stirred for 2 h at RT then concentrated under reduced pressure affording 2.5 g (crude) of 3-([5-[(1R)-1-[(tert-butyldimethylsilyl)oxy]ethyl]-1,3,4-oxadiazol-2-yl]methyl) cyclobutan-1-amine as yellow crude oil. LCMS (ES, m/z): [M+H]$^+$=312.2.

Step 7: N-[3-([5-[(1R)-1-[(tert-butyldimethylsilyl) oxy]ethyl]-1,3,4-oxadiazol-2-yl]methyl)cyclobutyl]-3-phenyl-1,2-oxazole-5-carboxamide To a 100-mL round-bottom flask was placed a solution of 3-([5-[(1R)-1-[(tert-butyldimethylsilyl)oxy]ethyl]-1,3,4-oxadiazol-2-yl]methyl)cyclobutan-1-amine (1 g, crude) in DCM (50 mL), then 3-phenyl-1,2-oxazole-5-carboxylic acid (468 mg, 2.47 mmol, 1.00 equiv), HATU (1.28 g, 3.37 mmol, 1.20 equiv) and DIEA (1.1 mL, 2.80 equiv) were added. The resulting solution was stirred for 2 h at RT, washed with water (3×50 mL), and then concentrated under reduced pressure affording 680 mg (crude) of N-[3-([5-[(1R)-1-[(tert-butyldimethylsilyl)oxy]ethyl]-1,3,4-oxadiazol-2-yl]methyl)cyclobutyl]-3-phenyl-1,2-oxazole-5-carboxamide as yellow oil. LCMS (ES, m/z): [M+H]⁺=483.2.

Step 8: N-[3-([5-[(1R)-1-hydroxyethyl]-1,3,4-oxadiazol-2-yl]methyl)cyclobutyl]-3-phenyl-1,2-oxazole-5-carboxamide To a 100-mL 3-necked round-bottom flask was placed a solution of N-[3-([5-[(1R)-1-[(tert-butyldimethylsilyl)oxy]ethyl]-1,3,4-oxadiazol-2-yl]methyl)cyclobutyl]-3-phenyl-1,2-oxazole-5-carboxamide (1 g, 2.07 mmol, 1.00 equiv) in THF (20 mL), then Py.HF (2.5 mL, 8.00 equiv) was added. The resulting solution was stirred for 2 h at 0° C. then quenched by the addition of 100 mL of brine. The resulting mixture was extracted with EtOAc (3×100 mL), then the organic extracts were combined, washed with NaHCO₃ (2×100 mL), brine (2×100 mL), and concentrated under reduced pressure. The residue was applied onto a silica gel column and eluted with petroleum ether/EtOAc (1:3) affording 460 mg of N-[3-([5-[(1R)-1-hydroxyethyl]-1,3,4-oxadiazol-2-yl]methyl)cyclobutyl]-3-phenyl-1,2-oxazole-5-carboxamide as light yellow oil. LCMS (ES, m/z): [M+H]⁺=369.2.

N-[3-([5-[(1R)-1-hydroxyethyl]-1,3,4-oxadiazol-2-yl]methyl)cyclobutyl]-3-phenyl-1,2-oxazole-5-carboxamide (520 mg, 1.41 mmol, 1.00 equiv) was purified by Prep-SFC with the following conditions: Column: Phenomenex Lux 5u Cellulose-4, 250*50 mm; Mobile Phase A: CO₂:50, Mobile Phase B: MeOH-Preparative:50; Flow rate: 150 mL/min; 220 nm; RT1:6.38; RT2:7.33 affording 98.6 mg (19%) of 3-phenyl-N-[(1s,3s)-3-([5-[(1R)-1-hydroxyethyl]-1,3,4-oxadiazol-2-yl]methyl)cyclobutyl]-1,2-oxazole-5-carboxamide as a white solid and 78.7 mg (15%) of 3-phenyl-N-[(1r,3r)-3-([5-[(1R)-1-hydroxyethyl]-1,3,4-oxadiazol-2-yl]methyl)cyclobutyl]-1,2-oxazole-5-carboxamide as a white solid.

3-Phenyl-N-[(1s,3s)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=369.0. ¹H NMR (300 MHz, DMSO-d₆): δ 9.23-9.20 (d, J=7.8 Hz, 1H), 7.94-7.91 (m, 2H), 7.62 (s, 1H), 7.55-7.53 (m, 3H), 5.92 (s, 1H), 4.92-4.85 (q, J=6.6 Hz, 1H), 4.35-4.27 (m, 1H), 2.99-2.97 (d, J=6.6 Hz, 2H), 2.45-2.35 (m, 3H), 1.98-1.92 (m, 2H), 1.47-1.44 (d, J=6.6 Hz, 3H). Purity (HPLC, 254 nm): 99.0%.

3-Phenyl-N-[(1r,3r)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=369.0. ¹H NMR (300 MHz, DMSO-d₆): δ 9.23-9.20 (d, J=8.4 Hz, 1H), 7.94-7.91 (m, 2H), 7.62 (s, 1H), 7.55-7.53 (m, 3H), 5.92 (s, 1H), 4.92-4.85 (q, J=6.6 Hz, 1H), 4.35-4.28 (m, 1H), 2.99-2.97 (d, J=6.6 Hz, 2H), 2.45-2.35 (m, 3H), 1.98-1.92 (m, 2H), 1.47-1.44 (d, J=6.6 Hz, 3H). Purity (HPLC, 254 nm): 98.3%.

Example 39 and 40: 3-(4-Fluorophenyl)-N-[(1s,3s)-3-([5-[(1R)-1-hydroxyethyl]-1,3,4-oxadiazol-2-yl]methyl)cyclobutyl]-1,2-oxazole-5-carboxamide and 3-(4-Fluorophenyl)-N-[(1r,3r)-3-([5-[(1R)-1-hydroxyethyl]-1,3,4-oxadiazol-2-yl]methyl)cyclobutyl]-1,2-oxazole-5-carboxamide The title compounds were prepared using a methodology similar to the one shown in Example 37. The mixture was separated by Chiral-Prep-HPLC with the following conditions: Column: Repaired IA, 21.2*150 mm, 5 um; Mobile Phase A:Hex-HPLC, Mobile Phase B: EtOH-HPLC; Flow rate: 20 mL/min; Gradient: 50 B to 50 B in 11.5 min; 254/220 nm; RT1:7.21; RT2:8.75. This resulted in 95 mg (34%) of 3-(4-fluorophenyl)-N-[(1s,3s)-3-([5-[(1R)-1-hydroxyethyl]-1,3,4-oxadiazol-2-yl]methyl)cyclobutyl]-1,2-oxazole-5-carboxamide as a white solid and 79.6 mg (28%) of 3-(4-fluorophenyl)-N-[(1r,3r)-3-([5-[(1R)-1-hydroxyethyl]-1,3,4-oxadiazol-2-yl]methyl)cyclobutyl]-1,2-oxazole-5-carboxamide as a white solid.

3-(4-fluorophenyl)-N-[(1s,3s)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=386.9. 1H NMR (300 MHz, DMSO-d₆): δ 9.23-9.20 (d, J=7.8 Hz, 1H), 8.02-7.97 (m, 2H), 7.63 (s, 1H), 7.42-7.36 (m, 2H), 5.92-5.90 (d, J=5.4 Hz 1H), 4.91-4.87 (m, 1H), 4.35-4.28 (m, 1H), 2.99-2.97 (d, J=6.9 Hz, 2H), 2.45-2.40 (m, 3H), 1.97-1.92 (m, 2H), 1.47-1.44 (d, J=6.9 Hz, 3H). Purity (HPLC, 254 nm): 99.3%.

3-(4-fluorophenyl)-N-[(1r,3r)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=386. ¹H NMR (300 MHz, DMSO-d₆): δ 9.31-9.29 (d, J=7.2 Hz, 1H), 8.01-7.96 (m, 2H), 7.64 (s, 1H), 7.41-7.35 (m, 2H), 5.92-5.90 (d, J=5.7 Hz 1H), 4.93-4.84 (m, 1H), 4.58-4.51 (q, J=7.5 Hz, 1H), 3.10-3.07 (d, J=7.8 Hz, 2H), 2.70-2.64 (s, 1H), 2.38-2.29 (m, 2H), 2.18-2.09 (m, 2H), 1.46-1.44 (d, J=6.6 Hz, 3H). Purity (HPLC, 254 nm): 98.0%.

Examples 41 and 42: 3-Phenyl-N-[(1s,3s)-3-([5-[(1R)-1-hydroxyethyl]-1,3,4-thiadiazol-2-yl]methyl)cyclobutyl]-1,2-oxazole-5-carboxamide and 3-Phenyl-N-[(1r,3r)-3-([5-[(1R)-1-hydroxyethyl]-1,3,4-thiadiazol-2-yl]methyl)cyclobutyl]-1,2-oxazole-5-carboxamide

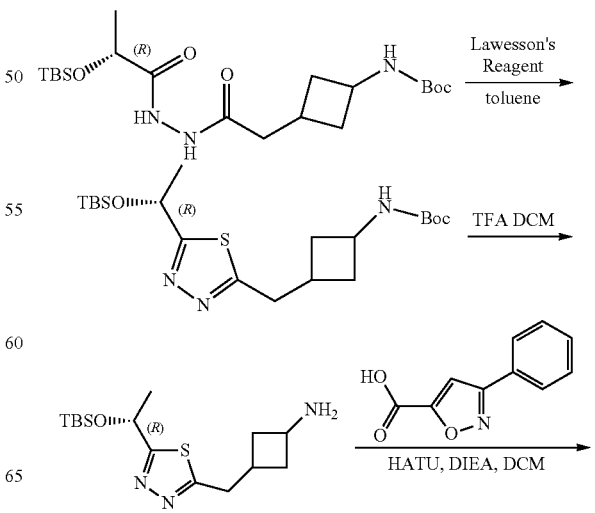

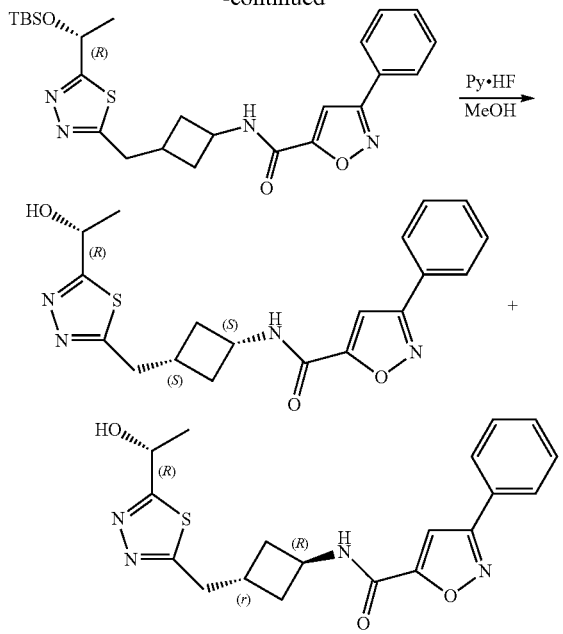

Step 1: tert-Butyl N-[3-([5-[(1R)-1-[(tert-Butyldimethylsilyl)oxy]ethyl]-1,3,4-thiadiazol-2-yl]methyl)cyclobutyl]carbamate To a 250-mL round-bottom flask was placed a solution of tert-butyl N-(3-[2-[(2R)-2-[(tert-butyldimethylsilyl)oxy]propanehydrazido]-2-oxoethyl]cyclobutyl)carbamate (6 g, 13.97 mmol, 1.00 equiv) in toluene (100 mL) then Lawesson's reagent (8.5 g, 21.02 mmol, 1.50 equiv) was added. The resulting solution was stirred for 1.5 h at 80° C. then concentrated under reduced pressure. The resulting solution was diluted with 200 mL of H$_2$O and then extracted with EtOAc (3×200 mL). The organic extracts were combined, washed with brine (2×200 mL), dried over anhydrous Na$_2$SO$_4$, and concentrated under reduced pressure. The crude product was purified by Flash-Prep-HPLC (Combi-Flash-1: Column, C18; mobile phase, X:H$_2$O (0.5% NH$_4$HCO$_3$), Y:CAN, X/Y=80/20 increasing to X/Y=5/95 within 40 min; Detector, UV 254 nm) affording 2.2 g (37%) of tert-butyl N-[3-([5-[(1R)-1-[(tert-butyldimethylsilyl)oxy]ethyl]-1,3,4-thiadiazol-2-yl]methyl)cyclobutyl]carbamate as yellow oil. LCMS (ES, m/z): [M+H-BOC]$^+$=328.0.

Step 2: 3-([5-[(1R)-1-[(tert-butyldimethylsilyl)oxy]ethyl]-1,3,4-thiadiazol-2-yl]methyl)cyclobutan-1-amine To a 50-mL round-bottom flask was placed a solution of tert-butyl N-[3-([5-[(1R)-1-[(tert-butyldimethylsilyl)oxy]ethyl]-1,3,4-thiadiazol-2-yl]methyl)cyclobutyl]carbamate (2.2 g, 5.14 mmol, 1.00 equiv) in DCM (20 mL) and TFA (4 mL). The resulting solution was stirred for 1 h at RT then concentrated under reduced pressure affording 3 g (crude) of 3-([5-[(1R)-1-[(tert-butyldimethylsilyl)oxy]ethyl]-1,3,4-thiadiazol-2-yl]methyl)cyclobutan-1-amine as yellow oil.

Step 3: N-[3-([5-[(1R)-1-[(tert-butyldimethylsilyl)oxy]ethyl]-1,3,4-thiadiazol-2-yl]methyl)cyclobutyl]-3-phenyl-1,2-oxazole-5-carboxamide To a 50-mL round-bottom flask was placed a solution of 3-([5-[(1R)-1-[(tert-butyldimethylsilyl)oxy]ethyl]-1,3,4-thiadiazol-2-yl]methyl)cyclobutan-1-amine (500 mg, 1.53 mmol, 1.00 equiv) in DCM (20 mL), then HATU (753 mg, 1.98 mmol, 1.30 equiv), 3-phenyl-1,2-oxazole-5-carboxylic acid (317 mg, 1.68 mmol, 1.10 equiv) and DIEA (589 mg, 4.56 mmol, 3.00 equiv) were added. The resulting mixture was stirred for 2 h at RT then diluted with 100 mL of H$_2$O and extracted with EtOAc (2×50 mL). The organic extracts were combined, washed with brine (2×50 mL), dried over anhydrous Na$_2$SO$_4$, and concentrated under reduced pressure. The residue was applied onto a silica gel column and eluted with EtOAc/petroleum ether (1:5) affording 320 mg (42%) of N-[3-([5-[(1R)-1-[(tert-butyldimethylsilyl)oxy]ethyl]-1,3,4-thiadiazol-2-yl]methyl)cyclobutyl]-3-phenyl-1,2-oxazole-5-carboxamide as yellow oil. LCMS (ES, m/z): [M+H]$^+$=499.1.

Step 4: 3-Phenyl-N-[(1s,3s)-3-([5-[(1R)-1-hydroxyethyl]-1,3,4-thiadiazol-2-yl]methyl)cyclobutyl]-1,2-oxazole-5-carboxamide and 3-Phenyl-N-[(1r,3r)-3-([5-[(1R)-1-hydroxyethyl]-1,3,4-thiadiazol-2-yl]methyl)cyclobutyl]-1,2-oxazole-5-carboxamide To a 10-mL round-bottom flask was placed a solution of N-[3-([5-[(1R)-1-[(tert-butyldimethylsilyl)oxy]ethyl]-1,3,4-thiadiazol-2-yl]methyl)cyclobutyl]-3-phenyl-1,2-oxazole-5-carboxamide (320 mg, 0.64 mmol, 1.00 equiv) in MeOH (3 mL), then Py.HF (1 mL) was added. The resulting solution was stirred for 2 h at rt, diluted with 50 mL of H$_2$O, and extracted with EtOAc (2×50 mL). The organic extracts were combined, washed with brine (2×50 mL), dried over anhydrous Na$_2$SO$_4$, and concentrated under reduced pressure. The residue was applied onto a silica gel column and eluted with EtOAc/petroleum ether (1:1). The resulting isomers were separated by Chiral-Prep-HPLC (Prep-HPLC-004: Column, Phenomenex Lux 5u Cellulose-4AXIA Packed, 250*21.2 mm, 5 um; mobile phase, Hex and IPA (hold 50.0% IPA in 18 min); Detector, UV 254/220 nm) affording 88.7 mg (36%) of 3-phenyl-N-[(1s,3s)-3-([5-[(1R)-1-hydroxyethyl]-1,3,4-thiadiazol-2-yl]methyl)cyclobutyl]-1,2-oxazole-5-carboxamide as a white solid and 57.8 mg (23%) of 3-phenyl-N-[(1r,3r)-3-([5-[(1R)-1-hydroxyethyl]-1,3,4-thiadiazol-2-yl]methyl)cyclobutyl]-1,2-oxazole-5-carboxamide as a white solid.

3-Phenyl-N-[(1s,3s)-3-([5-[(1R)-1-hydroxyethyl]-1,3,4-thiadiazol-2-yl]methyl)cyclobutyl]-1,2-oxazole-5-carboxamide LCMS (ES, m/z): [M+H]$^+$=385.0. $^1$H NMR (300 MHz, DMSO-d$_6$) δ 9.23-9.20 (d, J=7.5 Hz, 1H), 7.94-7.91 (m, 2H), 7.62 (s, 1H), 7.55-7.53 (m, 3H), 6.26-6.24 (d, J=5.1 Hz, 1H), 5.09-5.03 (m, 1H), 4.35-4.28 (m, 1H), 3.19-3.16 (d, J=7.2 Hz, 2H), 2.43-2.34 (m, 3H), 1.98-1.92 (m, 2H), 1.49-1.47 (d, J=6.3 Hz, 3H). Purity (HPLC, 254 nm): 97.9%.

3-Phenyl-N-[(1r,3r)-3-([5-[(1R)-1-hydroxyethyl]-1,3,4-thiadiazol-2-yl]methyl)cyclobutyl]-1,2-oxazole-5-carboxamide LCMS (ES, m/z): [M+H]$^+$=385. $^1$H NMR (300 MHz, DMSO-d$_6$): δ 9.31-9.29 (d, J=7.2 Hz, 1H), 7.94-7.91 (m, 2H), 7.64 (s, 1H), 7.55-7.53 (m, 3H), 6.25-6.24 (d, J=5.1 Hz, 1H), 5.09-5.01 (m, 1H), 4.60-4.52 (m, 1H), 3.29-3.26 (m, 2H), 2.66-2.62 (m, 1H), 2.37-2.27 (m, 2H), 2.18-2.12 (m, 2H), 1.49-1.47 (d, J=6.6 Hz, 3H). Purity (HPLC, 254 nm): 98.4%.

Examples 43 and 44: 3-(4-Fluorophenyl)-N-[(1s,3s)-3-([5-[(1R)-1-hydroxyethyl]-1,3,4-thiadiazol-2-yl]methyl)cyclobutyl]-1,2-oxazole-5-carboxamide and 3-(4-Fluorophenyl)-N-[(1r,3r)-3-([5-[(1R)-1-hydroxyethyl]-1,3,4-thiadiazol-2-yl]methyl)cyclobutyl]-1,2-oxazole-5-carboxamide The title compounds were prepared using a methodology similar to the one shown in Example 41. The resulting isomers were separated by Prep-SFC (Prep SFC100: Column, Phenomenex Lux 5u Cellulose-4AXIA Packed, 250*21.2 mm, 5 um; mobile phase, CO2 (60%), ETOH (0.2% DEA)-(40%); Detector, uv 220 nm) affording 125 mg (22%) of 3-(4-fluorophenyl)-N-[(1 s,3 s)-3-([5-[(1R)-1-hydroxyethyl]-1,3,4-thiadiazol-2-yl]methyl)cyclobutyl]-1,2-oxazole-5-carboxamide as a white solid and 110.8 mg (20%) of 3-(4-fluorophenyl)-N-[(1 r,3r)-3-([5-[(1R)-1-hydroxyethyl]-1,3,4-thiadiazol-2-yl]methyl)cyclobutyl]-1,2-oxazole-5-carboxamide as a white solid.

3-(4-Fluorophenyl)-N-[(1s,3s)-3-([5-[(1R)-1-hydroxyethyl]-1,3,4-thiadiazol-2-yl]methyl)cyclobutyl]-1,2-oxazole-5-carboxamide LCMS (ES, m/z): [M+H]$^+$=403. $^1$H NMR (400 MHz, DMSO-$d_6$) δ 9.24-9.22 (d, J=8.0 Hz, 1H), 8.01-7.98 (m, 2H), 7.63 (s, 1H), 7.41-7.37 (m, 2H), 6.25 (s, 1H), 5.05-5.04 (m, 1H), 4.34-4.28 (m, 1H), 3.18-3.16 (d, J=6.8 Hz, 2H), 2.45-2.36 (m, 3H), 1.94-1.92 (m, 2H), 1.48-1.47 (d, J=6.4 Hz, 3H). Purity (HPLC, 254 nm): 99.4%.

3-(4-Fluorophenyl)-N-[(1r,3r)-3-([5-[(1R)-1-hydroxyethyl]-1,3,4-thiadiazol-2-yl]methyl)cyclobutyl]-1,2-oxazole-5-carboxamide LCMS (ES, m/z): [M+H]$^+$=403.0. $^1$H NMR (300 MHz, DMSO-$d_6$) δ 9.32-9.29 (d, J=7.5 Hz, 1H), 8.02-7.97 (m, 2H), 7.65 (s, 1H), 7.42-7.36 (m, 2H), 6.25-6.24 (d, J=5.1 Hz, 1H), 5.09-5.01 (m, 1H), 4.62-4.50 (m, 1H), 3.29-3.26 (d, J=8.1 Hz, 2H), 2.69-2.60 (m, 1H), 2.37-2.27 (m, 2H), 2.19-2.10 (m, 2H), 1.49-1.47 (d, J=6.6 Hz, 3H). Purity (HPLC, 254 nm): 96.3%.

Examples 45 and 46: N-[(1s,3s)-3-([5-[(1R)-1-Hydroxyethyl]-1,3,4-oxadiazol-2-yl]methyl)cyclobutyl]-3-(thiophen-2-yl)-1,2-oxazole-5-carboxamide and N-[(1r,3r)-3-([5-[(1R)-1-Hydroxyethyl]-1,3,4-oxadiazol-2-yl]methyl)cyclobutyl]-3-(thiophen-2-yl)-1,2-oxazole-5-carboxamide

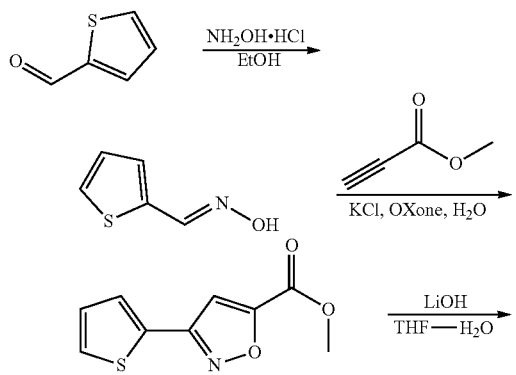

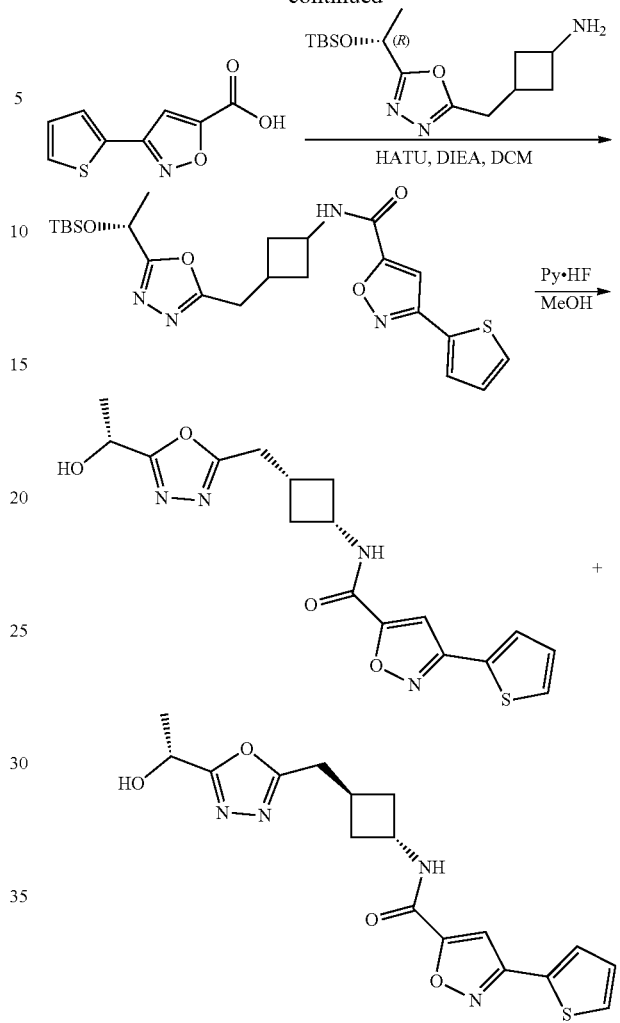

Step 1: N-(thiophen-2-ylmethylidene)hydroxylamine

To a 100-mL round-bottom flask was placed a solution of thiophene-2-carbaldehyde (5 g, 44.58 mmol, 1.00 equiv) in EtOH (50 mL) then NH$_2$OH.HCl (3.7 g, 1.20 equiv) was added. The resulting solution was stirred for 2 h at RT then the reaction was extracted with EtOAc. The organic extracts were combined, dried, and concentrated under reduced pressure affording 4.5 g (79%) of N-(thiophen-2-ylmethylidene)hydroxylamine as yellow oil. LCMS (ES, m/z): [M+H]$^+$=128.0.

Step 2: Methyl 3-(Thiophen-2-yl)-1,2-oxazole-5-carboxylate

To a 100-mL round-bottom flask was placed a solution of N-(thiophen-2-ylmethylidene)hydroxylamine (4.5 g, 35.39 mmol, 1.00 equiv) in H$_2$O (50 mL), then methyl prop-2-ynoate (8 mL, 2.50 equiv), KCl (2.6 g, 1.00 equiv) and Oxone (14.4 g, 1.50 equiv) were added. The resulting solution was stirred for 2 h at RT then the reaction was extracted with EtOAc (3×100 mL). The organic extracts were combined, dried, and concentrated under reduced pressure affording 5.4 g (73%) of methyl 3-(thiophen-2-yl)-1,2-oxazole-5-carboxylate as a yellow solid. LCMS (ES, m/z): [M+H]⁺=210.0.

Step 3: 3-(thiophen-2-yl)-1,2-oxazole-5-carboxylic acid

To a 250-mL round-bottom flask was placed a solution of methyl 3-(thiophen-2-yl)-1,2-oxazole-5-carboxylate (5.4 g, 25.81 mmol, 1.00 equiv) in THF and H₂O (30 mL/10 mL), then LiOH (1.33 g, 55.53 mmol, 2.00 equiv) was added. The resulting solution was stirred for 1 h at RT. After concentrating under reduced pressure, the residue was diluted with 100 mL of H₂O then the resulting solution was washed with EtOAc (2×30 mL). The pH value of the aqueous layer was adjusted to 3 with HCl, then the solution was extracted with EtOAc (3×100 mL). The organic extracts were combined, dried over anhydrous Na₂SO₄, and concentrated under reduced pressure affording 3.2 g (64%) of 3-(thiophen-2-yl)-1,2-oxazole-5-carboxylic acid as a white solid. LCMS (ES, m/z): [M+H]⁺=196.1.

Step 4: N-[3-([5-[(1R)-1-[(tert-butyldimethylsilyl)oxy]ethyl]-1,3,4-oxadiazol-2-yl]methyl)cyclobutyl]-3-(thiophen-2-yl)-1,2-oxazole-5-carboxamide To a 100-mL 3-necked round-bottom flask was placed a solution of 3-([5-[(1R)-1-[(tert-butyldimethylsilyl)oxy]ethyl]-1,3,4-oxadiazol-2-yl]methyl)cyclobutan-1-amine (1.25 g, 4.02 mmol, 1.00 equiv) in DCM (30 mL) then 3-(thiophen-2-yl)-1,2-oxazole-5-carboxylic acid (800 mg, 4.10 mmol, 1.02 equiv), HATU (2.3 g, 6.05 mmol, 1.50 equiv) and DIEA (3.1 g, 24.01 mmol, 6.00 equiv) were added. The resulting solution was stirred for 3 h at RT then washed with brine (2×60 mL), dried over anhydrous Na₂SO₄, and concentrated under reduced pressure. The residue was applied onto a silica gel column and eluted with EtOAc/petroleum ether (1:8 affording 2.3 g (crude) of N-[3-([5-[(1R)-1-[(tert-butyldimethylsilyl)oxy]ethyl]-1,3,4-oxadiazol-2-yl]methyl)cyclobutyl]-3-(thiophen-2-yl)-1,2-oxazole-5-carboxamide as yellow oil. LCMS (ES, m/z): [M+H]⁺=489.2.

Step 5: N-[(1s,3s)-3-([5-[(1R)-1-Hydroxyethyl]-1,3,4-oxadiazol-2-yl]methyl)cyclobutyl]-3-(thiophen-2-yl)-1,2-oxazole-5-carboxamide and N-[(1r,3r)-3-([5-[(1R)-1-Hydroxyethyl]-1,3,4-oxadiazol-2-yl]methyl)cyclobutyl]-3-(thiophen-2-yl)-1,2-oxazole-5-carboxamide To a 100-mL 3-necked round-bottom flask was placed a solution of N-[3-([5-[(1R)-1-[(tert-butyldimethylsilyl)oxy]ethyl]-1,3,4-oxadiazol-2-yl]methyl)cyclobutyl]-3-(thiophen-2-yl)-1,2-oxazole-5-carboxamide (1.1 g, 2.25 mmol, 1.00 equiv) in MeOH (50 mL) then Py.HF (6 mL) was added. The resulting solution was stirred for 1 h at RT then concentrated under reduced pressure. The residue was dissolved in EtOAc (60 mL), washed with NaHCO₃ solution (2×50 mL) and brine (2×50 mL), then dried over anhydrous Na₂SO₄, and concentrated under reduced pressure. The residue was applied onto a silica gel column and eluted with EtOAc/petroleum ether (1:3) affording 150 mg of a mixture of PH-PTS-005-0005 and PH-PTS-005-0017. The mixture was separated by Chiral-Prep-HPLC (Column: Phenomenex Lux 5u Cellulose-4, AXIA Packed, 250*21.2 mm, 5 um; Mobile Phase A:Hex, Mobile Phase B: EtOH; Flow rate: 20 mL/min; Gradient: 30 B to 30 B in 27 min; 254/220 nm; RT1:19.83; RT2:23.28) affording 52.6 mg of N-[(1s,3s)-3-([5-[(1R)-1-hydroxyethyl]-1,3,4-oxadiazol-2-yl]methyl)cyclobutyl]-3-(thiophen-2-yl)-1,2-oxazole-5-carboxamide as a white solid and 51.3 mg of N-[(1r,3r)-3-([5-[(1R)-1-hydroxyethyl]-1,3,4-oxadiazol-2-yl]methyl)cyclobutyl]-3-(thiophen-2-yl)-1,2-oxazole-5-carboxamide as a white solid.

N-[(1s,3s)-3-([5-[(1R)-1-hydroxyethyl]-1,3,4-oxadiazol-2-yl]methyl)cyclobutyl]-3-(thiophen-2-yl)-1,2-oxazole-5-carboxamide LC-MS-PH-PTS-005-0005-0: (ES, m/z): [M+H]⁺=375.0. ¹H NMR (300 MHz, DMSO-d₆): δ 9.24-9.20 (d, J=7.5 Hz, 1H), 7.80-7.78 (m, 2H), 7.59 (s, 1H), 7.26-7.23 (m, 1H), 5.92-5.90 (d, J=5.7 Hz, 1H), 4.93-4.84 (m, 1H), 4.35-4.27 (m, 1H), 2.99-2.96 (d, J=6.6 Hz, 2H), 2.47-2.37 (m, 3H), 1.97-1.91 (m, 2H), 1.46-1.44 (d, J=6.6 Hz, 3H). Purity (HPLC, 254 nm): 95.9%.

N-[(1r,3r)-3-([5-[(1R)-1-hydroxyethyl]-1,3,4-oxadiazol-2-yl]methyl)cyclobutyl]-3-(thiophen-2-yl)-1,2-oxazole-5-carboxamide LCMS (ES, m/z): [M+H]⁺=375.0. ¹H NMR (300 MHz, DMSO-d₆): δ 9.32-9.30 (d, J=7.2 Hz, 1H), 7.80-7.78 (d, J=4.5 Hz, 2H), 7.60 (s, 1H), 7.26-7.23 (m, 1H), 5.93-5.91 (d, J=5.4 Hz, 1H), 4.93-4.85 (m, 1H), 4.58-4.51 (m, 1H), 3.10-3.08 (d, J=7.8 Hz, 2H), 2.72-2.65 (m, 1H), 2.83-2.29 (m, 2H), 2.18-2.11 (m, 2H), 1.47-1.44 (d, J=6.9 Hz, 3H). Purity (HPLC, 254 nm): 99.7%.

Examples 47 and 48: N-((1r,3r)-3-((5-(Hydroxymethyl)-1H-1,2,3-triazol-1-yl)methyl)cyclobutyl)-3-phenylisoxazole-5-carboxamide and N-((1r,3r)-3-((4-(Hydroxymethyl)-1H-1,2,3-triazol-1-yl)methyl)cyclobutyl)-3-phenylisoxazole-5-carboxamide

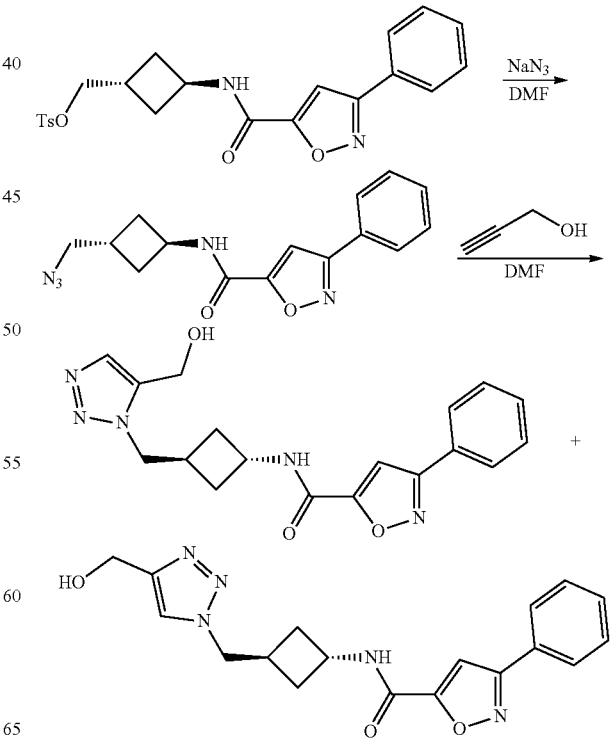

Step 1: N-((1r,3r)-3-(Azidomethyl)cyclobutyl)-3-phenylisoxazole-5-carboxamide To a 50-mL round-bottom flask was placed a solution of ((1r,3r)-3-(3-phenylisoxazole-5-carboxamido)cyclobutyl) methyl 4-methylbenzenesulfonate (1.5 g, 3.52 mmol, 1.00 equiv) in DMF (15 mL) then $NaN_3$ (390 mg, 6.00 mmol, 1.50 equiv) was added. The resulting solution was stirred for 5 h at 80° C., quenched by the addition of 20 mL of ice/water, and extracted with DCM (2×30 mL). The organic extracts were combined, dried over anhydrous $Na_2SO_4$, and concentrated under reduced pressure. The residue was applied onto a silica gel column and eluted with EtOAc/petroleum ether (1:20) affording 0.9 g (86%) of N-((1r,3r)-3-(azidomethyl)cyclobutyl)-3-phenylisoxazole-5-carboxamide as a white solid. LCMS: (ES, m/z): [M+H]$^+$=298.1.

Step 2: N-((1r,3r)-3-((5-(Hydroxymethyl)-1H-1,2,3-triazol-1-yl)methyl)cyclobutyl)-3-phenylisoxazole-5-carboxamide and N-((1r,3r)-3-((4-(Hydroxymethyl)-1H-1,2,3-triazol-1-yl)methyl)cyclobutyl)-3-phenylisoxazole-5-carboxamide To a 25-mL round-bottom flask was placed a solution of N-((1r,3r)-3-(azidomethyl)cyclobutyl)-3-phenylisoxazole-5-carboxamide (700 mg, 2.35 mmol, 1.00 equiv) in DMF (5 mL) then prop-2-yn-1-ol (660 mg, 11.77 mmol, 5.00 equiv) was added. The resulting solution was stirred for 24 h at 80° C., then the solvent was removed under reduced pressure. The residue was applied onto a silica gel column and eluted with EtOAc/petroleum ether (1:5). The resulting mixture was separated by Prep-SFC (Column: Lux 5u Celluloes-3, AXIA Packed, 250*21.2 mm; Mobile Phase A: $CO_2$:70, Mobile Phase B: MeOH:30; Flow rate: 40 mL/min; 220 nm; RT1:4.47; RT2:5.32) affording 120 mg (27%) of N-((1r,3r)-3-((5-(hydroxymethyl)-1H-1,2,3-triazol-1-yl)methyl)cyclobutyl)-3-phenylisoxazole-5-carboxamide as a white solid and 119.8 mg (27%) of N-((1r,3r)-3-((4-(hydroxymethyl)-1H-1,2,3-triazol-1-yl)methyl)cyclobutyl)-3-phenylisoxazole-5-carboxamide as a white solid.

N-((1r,3r)-3-((5-(Hydroxymethyl)-1H-1,2,3-triazol-1-yl)methyl)cyclobutyl)-3-phenylisoxazole-5-carboxamide LCMS (ES, m/z): [M+H]$^+$=354.1. $^1$H NMR (300 MHz, DMSO-$d_6$): δ 9.29-9.27 (d, J=7.2 Hz, 1H), 8.00 (s, 1H), 7.93-7.90 (m, 2H), 7.63 (s, 1H), 7.55-7.52 (m, 3H), 5.17-5.13 (t, J=5.7 Hz, 1H), 4.60-4.49 (m, 5H), 2.74-2.70 (m, 1H), 2.31-2.12 (m, 4H). Purity (HPLC, 254 nm): 98.8%.

N-((1r,3r)-3-((4-(Hydroxymethyl)-1H-1,2,3-triazol-1-yl)methyl)cyclobutyl)-3-phenylisoxazole-5-carboxamide LCMS (ES, m/z): [M+H]$^+$=354. $^1$H NMR (300 MHz, DMSO-$d_6$): δ 9.30-9.27 (d, J=7.5 Hz, 1H), 7.93-7.90 (m, 2H), 7.63-7.60 (m, 2H), 7.57-7.52 (m, 5H), 5.51-5.47 (t, J=5.7 Hz, 1H), 4.66-4.60 (m, 3H), 4.53-4.47 (m, 2H), 2.86-2.78 (m, 1H), 2.30-2.15 (m, 4H). Purity (HPLC, 254 nm): 96.9%.

Example 49: 3-Phenyl-N-[(1r,3r)-3-[5-(oxetan-2-yl)-1,3,4-oxadiazol-2-yl]cyclobutyl]-1,2-oxazole-5-carboxamide

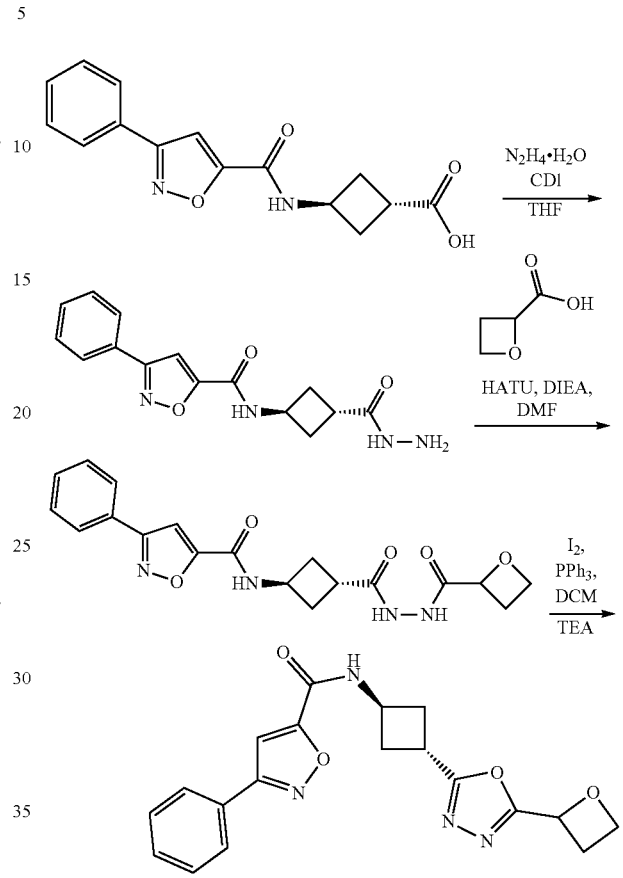

Step 1: 3-Phenyl-N-[(1r,3r)-3-(hydrazinecarbonyl)cyclobutyl]-1,2-oxazole-5-carboxamide To a 100-mL round-bottom flask was placed a solution of (1r,3r)-3-(3-phenyl-1,2-oxazole-5-amido)cyclobutane-1-carboxylic acid (2.87 g, 10.03 mmol, 1.00 equiv) in THF (50 mL), then CDI (3.24 g, 20.00 mmol, 2.00 equiv) was added. The resulting solution was stirred for 1 h at 25° C. and then $N_2H_4 \cdot H_2O$ (2.1 g, 30.00 mmol, 3.00 equiv) was added. The resulting solution was stirred for 16 h at RT then diluted with 300 mL of $H_2O$. The solids were collected by filtration and dried in an oven under reduced pressure affording 487 mg (16%) of 3-phenyl-N-[(1r,3r)-3-(hydrazinecarbonyl)cyclobutyl]-1,2-oxazole-5-carboxamide as a light yellow solid. LCMS (ES, m/z): [M+H]$^+$=301.1.

Step 2: 3-Phenyl-N-[(1r,3r)-3-[(oxetan-2-ylformohydrazido)carbonyl]cyclobutyl]-1,2-oxazole-5-carboxamide To a 25-mL round-bottom flask was placed a solution of 3-phenyl-N-[(1r,3r)-3-(hydrazinecarbonyl)cyclobutyl]-1,2-oxazole-5-carboxamide (280 mg, 0.93 mmol, 1.00 equiv) in DMF (5 mL) then HATU (570 mg, 1.50 mmol, 1.50 equiv), DIEA (361 mg, 2.79 mmol, 3.00 equiv) and oxetane-2-carboxylic acid (143 mg, 1.40 mmol, 1.50 equiv) were added. The resulting solution was stirred for 2 h at RT then diluted with 50 mL of H₂O and extracted with EtOAc (2×50 mL). The organic extracts were combined, washed with brine (2×50 mL), dried over anhydrous Na₂SO₄, and concentrated under reduced pressure. The crude product was purified by Prep-TLC (petroleum ether/ethyl acetate=1:2) affording 220 mg (61%) of 3-phenyl-N-[(1r,3r)-3-[(oxetan-2-ylformohydrazido)carbonyl]cyclobutyl]-1,2-oxazole-5-carboxamide as a yellow solid. LCMS (ES, m/z): [M+H]⁺=385.1.

Step 3: 3-Phenyl-N-[(1r,3r)-3-[5-(oxetan-2-yl)-1,3,4-oxadiazol-2-yl]cyclobutyl]-1,2-oxazole-5-carboxamide To a 100-mL 3-necked round-bottom flask was placed a solution of PPh₃ (299 mg, 1.14 mmol, 2.00 equiv) in DCM (20 mL), then I₂ (290 mg, 1.14 mmol, 2.00 equiv) and TEA (230 mg, 2.27 mmol, 4.00 equiv) were added. The resulting solution was stirred for 10 min at RT then 3-phenyl-N-[(1r,3r)-3-[(oxetan-2-ylformohydrazido)carbonyl]cyclobutyl]-1,2-oxazole-5-carboxamide (220 mg, 0.57 mmol, 1.00 equiv) was added and stirred for 1 h at rt. The reaction was diluted with 100 mL of H₂O and extracted with EtOAc (2×100 mL). The organic extracts were combined, washed with brine (2×100 mL), dried over anhydrous Na₂SO₄, and concentrated under reduced pressure. The residue was applied onto a silica gel column and eluted with EtOAc/petroleum ether (2:1) affording 174.8 mg (83%) of 3-phenyl-N-[(1 r,3r)-3-[5-(oxetan-2-yl)-1,3,4-oxadiazol-2-yl]cyclobutyl]-1,2-oxazole-5-carboxamide as an off-white solid. LCMS (ES, m/z): [M+H]⁺=367.3. ¹H NMR (400 MHz, DMSO-d₆) δ 9.45 (d, J=7.2 Hz, 1H), 7.93-7.91 (m, 2H), 7.65 (s, 1H), 7.54-7.52 (m, 3H), 5.88-5.84 (t, J=7.6 Hz, 1H), 4.72-4.62 (m, 3H), 3.81-3.74 (m, 1H), 3.12-2.96 (m, 2H), 2.73-2.66 (m, 4H). Purity (HPLC, 254 nm): 99.5%.

Example 50: 4-Fluoro-3-phenyl-N-[(1r,3r)-3-[5-[(1R)-1-hydroxyethyl]-1,3,4-oxadiazol-2-yl]cyclobutyl]-1,2-oxazole-5-carboxamide

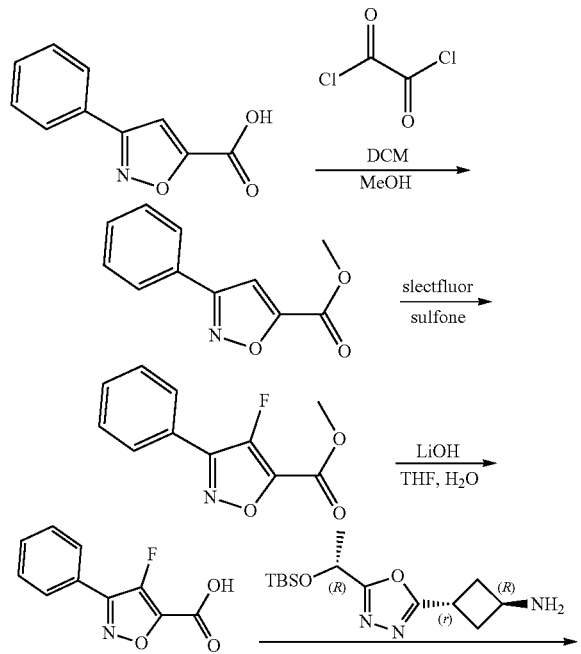

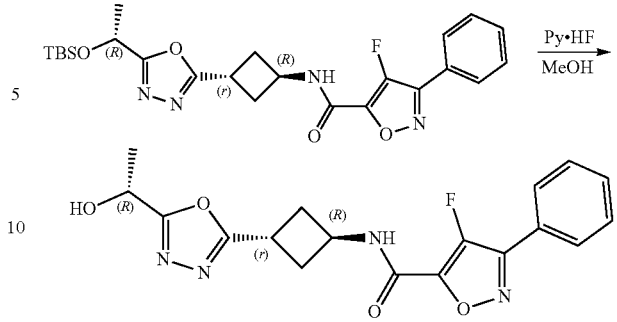

Step 1: Methyl 3-Phenyl-1,2-oxazole-5-carboxylate

To a 50-mL round-bottom flask was placed a solution of 3-phenyl-1,2-oxazole-5-carboxylic acid (1.89 g, 9.99 mmol, 1.00 equiv) in DCM (20 mL) then oxalyl chloride (1.9 g, 14.97 mmol, 1.50 equiv) and a drop of DMF were added. The resulting solution was stirred for 1 h at RT then MeOH (5 mL) was added. The reaction was stirred for 1 h at RT then concentrated under reduced pressure affording 1.9 g (94%) of methyl 3-phenyl-1,2-oxazole-5-carboxylate as a yellow solid.

Step 2: Methyl 4-Fluoro-3-phenyl-1,2-oxazole-5-carboxylate

To a 25-mL round-bottom flask was placed a solution of methyl 3-phenyl-1,2-oxazole-5-carboxylate (1 g, 4.92 mmol, 1.00 equiv) in sulfone (10 mL) then Selectfluor (3.54 g, 10.00 mmol, 2.00 equiv) was added. The resulting solution was stirred for 16 h at 120° C., diluted with 100 mL of H₂O, and extracted with EtOAc (2×100 mL). The organic extracts were combined, washed with brine (2×100 mL), dried over anhydrous Na₂SO₄, and concentrated under reduced pressure. The crude product was purified by Prep-TLC (petroleum ether/ethyl acetate=10:1) affording 250 mg (25%) of methyl 4-fluoro-3-phenyl-1,2-oxazole-5-carboxylate as a white solid. LCMS (ES, m/z): [M+H]⁺=222.0.

Step 3: 4-Fluoro-3-phenyl-1,2-oxazole-5-carboxylic acid

To a 25-mL round-bottom flask was placed a solution of methyl 4-fluoro-3-phenyl-1,2-oxazole-5-carboxylate (250 mg, 1.13 mmol, 1.00 equiv) in THF/H₂O (10/3 mL) then LiOH (82 mg, 3.42 mmol, 3.00 equiv) was added. The resulting solution was stirred for 2 h at RT and then diluted with 50 mL of H₂O. The pH of the solution was adjusted to 4-5 using concentrated 12M HCl, then extracted with EtOAc (2×50 mL). The organic extracts were combined, washed with brine (2×50 mL), dried over anhydrous Na₂SO₄, and concentrated under reduced pressure affording 210 mg (90%) of 4-fluoro-3-phenyl-1,2-oxazole-5-carboxylic acid as a white solid.

Step 3: 4-Fluoro-3-phenyl-N-[(1r,3r)-3-[5-[(1S)-1-[(tert-butyldimethylsilyl)oxy]ethyl]-1,3,4-oxadiazol-2-yl]cyclobutyl]-1,2-oxazole-5-carboxamide To a 50-mL round-bottom flask was placed a solution of 4-fluoro-3-phenyl-1,2-oxazole-5-carboxylic acid (210 mg, 1.01 mmol, 1.00 equiv) in DCM (10 mL), then HATU (570 mg, 1.50 mmol, 1.50 equiv), (1r,3r)-3-5-[(1S)-1-[(tert-butyldimethylsilyl)oxy]ethyl]-1,3,4-oxadiazol-2-ylcyclobutan-1-amine (300 mg, 1.01 mmol, 1.00 equiv) and DIEA (387 mg, 2.99 mmol, 3.00 equiv) were added. The resulting solution was stirred for 1 h at RT, diluted with 100 mL of H₂O, and extracted with EtOAc (2×100 mL). The organic extracts were combined, washed with brine (2×100 mL), dried over anhydrous Na₂SO₄, and concentrated under reduced pressure. The residue was applied onto a silica gel column and eluted with EtOAc/petroleum ether (1:5) affording 360 mg (73%) of 4-fluoro-3-phenyl-N-[(1r,3r)-3-[5-[(1S)-1-[(tert-butyldimethylsilyl)oxy]ethyl]-1,3,4-oxadiazol-2-yl]cyclobutyl]-1,2-oxazole-5-carboxamide as a white solid. LCMS (ES, m/z): [M+H]⁺=487.3.

Step 4: 4-Fluoro-3-phenyl-N-[(1r,3r)-3-[5-[(1R)-1-hydroxyethyl]-1,3,4-oxadiazol-2-yl]cyclobutyl]-1,2-oxazole-5-carboxamide To a 25-mL round-bottom flask was placed a solution of 4-fluoro-3-phenyl-N-[(1r,3r)-3-[5-[(1R)-1-[(tert-butyldimethylsilyl)oxy]ethyl]-1,3,4-oxadiazol-2-yl]cyclobutyl]-1,2-oxazole-5-carboxamide (360 mg, 0.74 mmol, 1.00 equiv) in methanol (6 mL) then Py.HF (2 mL) was added. The resulting solution was stirred for 1 h at RT then diluted with 50 mL of H₂O, and extracted with EtOAc (2×50 mL). The organic extracts were combined, washed with brine (3×50 mL), dried over anhydrous Na₂SO₄, and concentrated under reduced pressure. The crude product was purified by Prep-HPLC (HPLC-10: Column, X Bridge C18 OBD Prep Column, 19 mm×250 mm; mobile phase, Water (0.5% NH₄HCO₃) and ACN (30.0% ACN up to 50.0% in 8 min); Detector, UV 254/220 nm) affording 133.3 mg (48%) of 4-fluoro-3-phenyl-N-[(1r,3r)-3-[5-[(1R)-1-hydroxyethyl]-1,3,4-oxadiazol-2-yl]cyclobutyl]-1,2-oxazole-5-carboxamide as a white solid. LCMS (ES, m/z): [M+H]⁺=372.9. $^1$H NMR (400 MHz, DMSO-d₆) δ 9.49-9.47 (d, J=7.2 Hz, 1H), 7.99-7.94 (m, 1H), 7.65-7.60 (m, 1H), 7.52 (s, 1H), 7.48-7.37 (m, 2H), 5.96-5.95 (d, J=6.4 Hz, 1H), 4.95-4.89 (m, 1H), 4.70-4.64 (m, 1H), 3.78-3.72 (m, 1H), 2.72-2.63 (m, 4H), 1.49-1.48 (d, J=6.8 Hz, 3H). Purity (HPLC, 254 nm): 99.7%.

Examples 51 and 52: 3-Phenyl-N-[(1s,3s)-3-[5-[(1R)-1-hydroxyethyl]-1H-1,2,3-triazol-1-yl]cyclobutyl]-1,2-oxazole-5-carboxamide and 3-Phenyl-N-[(1s,3s)-3-[4-[(1R)-1-hydroxyethyl]-1H-1,2,3-triazol-1-yl]cyclobutyl]-1,2-oxazole-5-carboxamide

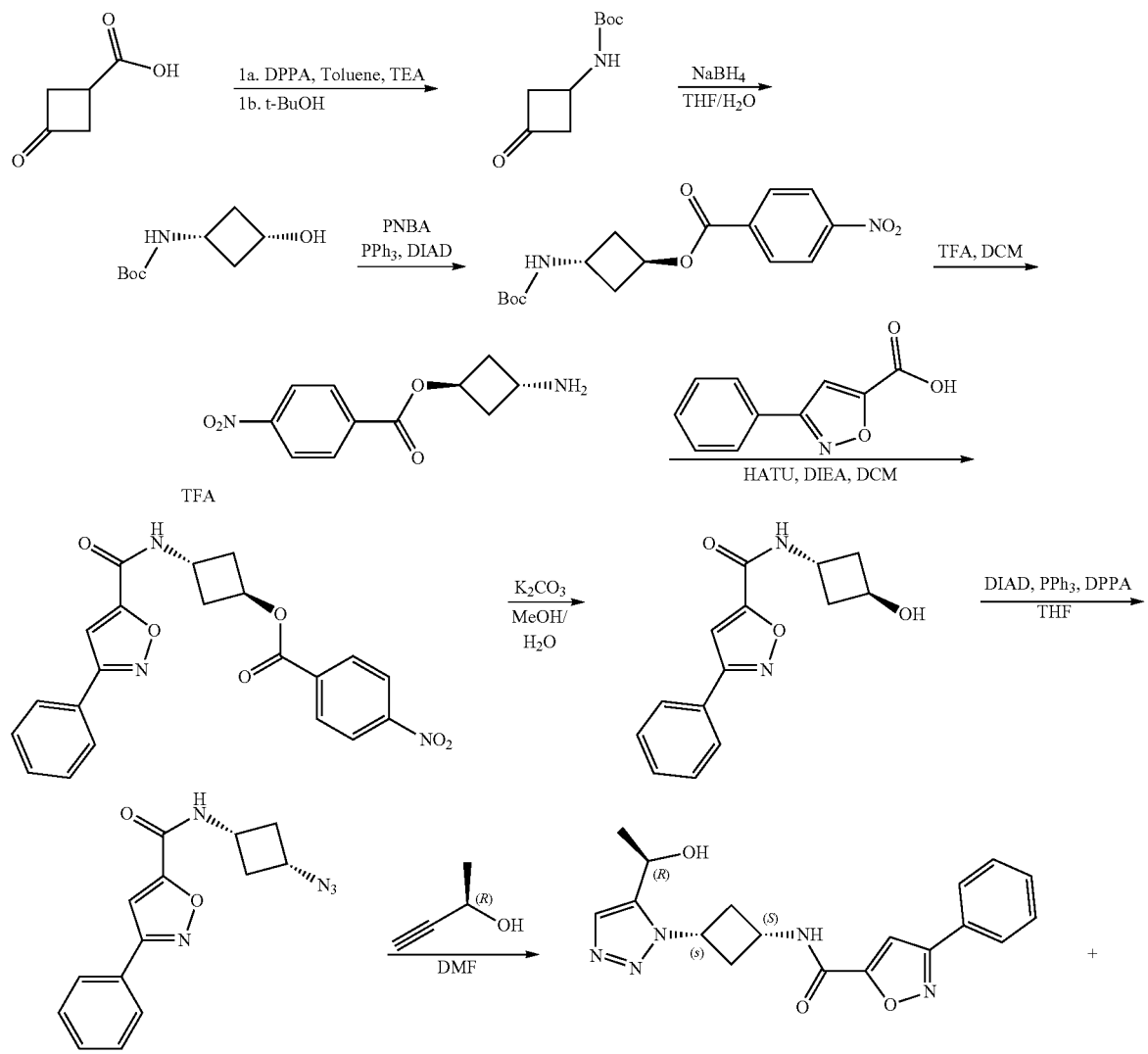

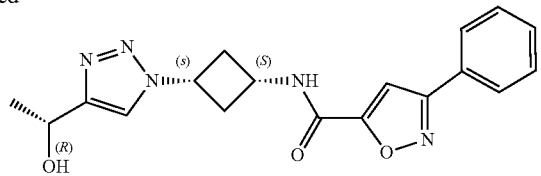

Step 1: tert-Butyl N-(3-Oxocyclobutyl)carbamate

To a 1000-mL 3-necked round-bottom flask was placed a solution of 3-oxocyclobutane-1-carboxylic acid (20 g, 175.29 mmol, 1.00 equiv) in toluene (400 mL), then TEA (19.5 g, 192.71 mmol, 1.10 equiv) and DPPA (53 g, 192.73 mmol, 1.10 equiv) were added. The resulting solution was stirred overnight at 0° C., then washed with saturated sodium bicarbonate aqueous (2×120 mL), $H_2O$ (1×120 mL), and brine (1×60 mL) at 0~10° C. The solution was dried over anhydrous $Na_2SO_4$ and filtered. To this solution was added t-BuOH (100 mL) and then the reaction was stirred for 16 h at 100° C. The solvent was removed under reduced pressure then the residue was washed with TBME (60 mL) affording 8.3 g (26%) of tert-butyl N-(3-oxocyclobutyl) carbamate as a light white solid. $^1$H NMR (400 MHz, $CDCl_3$) δ 4.94 (brs, 1H), 4.29 (brs, 1H), 3.48-3.36 (m, 2H), 3.13-3.01 (m, 2H), 1.48 (s, 9H).

Step 2: tert-Butyl N-[(1s,3s)-3-Hydroxycyclobutyl]carbamate

To a 250-mL round-bottom flask was placed a solution of tert-butyl N-(3-oxocyclobutyl)carbamate (8.3 g, 44.81 mmol, 1.00 equiv) in $THF/H_2O$=9:1 (100 mL) then $NaBH_4$ (830 mg, 22.54 mmol, 0.50 equiv) was added in portions at −70° C. The resulting solution was stirred for 1 h at −50° C. then the reaction was quenched by the addition of water. The mixture was extracted with EtOAc, the organic extracts were combined and the solvent was removed under reduced pressure. The residue was dissolved in 20 mL of toluene at 80° C., then the solution was cooled to RT and stirred for 1 h. The solids were collected by filtration affording 7.56 g (90%) of tert-butyl N-[(1s,3s)-3-hydroxycyclobutyl]carbamate as a white solid. $^1$H NMR (400 MHz, $CDCl_3$) δ 4.67 (brs, 1H), 4.08-4.01 (m, 1H), 3.69-3.66 (m, 1H), 2.82-2.76 (m, 2H), 2.00 (brs, 1H), 1.88-1.75 (m, 2H), 1.46 (s, 9H).

Step 3: (1r,3r)-3-[[(tert-Butoxy)carbonyl]amino]cyclobutyl-4-nitrobenzoate

To a 250-mL 3-necked round-bottom flask purged and maintained with an inert atmosphere of nitrogen was placed a solution of tert-butyl N-[(1s,3s)-3-hydroxycyclobutyl]carbamate (7.56 g, 40.38 mmol, 1.00 equiv) in THF (100 mL), then $PPh_3$ (15.89 g, 60.58 mmol, 1.50 equiv) and PNBA (7.43 g, 1.10 equiv) were added. This was followed by the addition of DIAD (12.25 g, 60.58 mmol, 1.50 equiv) dropwise with stirring at 0° C. The resulting solution was stirred overnight at RT, then the reaction was quenched by the addition of water and extracted with EtOAc. The organic extracts were combined and then concentrated under reduced pressure. The residue was dissolved in 10 mL of EtOH and stirred for 2 h at RT. The solids were collected by filtration affording 10.8 g (80%) of (1r,3r)-3-[[(tert-butoxy)carbonyl]amino]cyclobutyl 4-nitrobenzoate as a white solid. $^1$H NMR (300 MHz, $CDCl_3$) δ 8.28-8.17 (m, 4H), 5.36-5.32 (m, 1H), 4.77 (brs, 1H), 4.36 (brs, 1H), 2.65-2.56 (m, 2H), 2.47-2.38 (m, 2H), 1.43 (s, 9H).

Step 4: (1r,3r)-3-Aminocyclobutyl 4-nitrobenzoate trifluoroacetic acid salt

To a 100-mL round-bottom flask was placed a solution of (1r,3r)-3-[[(tert-butoxy)carbonyl]amino]cyclobutyl 4-nitrobenzoate (10.8 g, 32.11 mmol, 1.00 equiv) in DCM (25 mL) and TFA (7 mL). The resulting solution was stirred overnight at RT, then the solvent was removed under reduced pressure affording 10.3 g (92%) of (1r,3r)-3-aminocyclobutyl 4-nitrobenzoate trifluoroacetic acid salt as a white solid. $^1$H NMR (300 MHz, $CD_3OD$) δ 8.28-8.25 (m, 4H), 5.52-5.44 (m, 1H), 4.09-4.00 (m, 1H), 2.85-2.62 (m, 4H).

Step 5: (1r,3r)-3-(3-Phenyl-1,2-oxazole-5-amido) cyclobutyl 4-nitrobenzoate

To a 250-mL round-bottom flask was placed a solution of (1r,3r)-3-aminocyclobutyl 4-nitrobenzoate trifluoroacetic acid salt (4 g, 11.42 mmol, 1.00 equiv), DIEA (7.4 g, 57.26 mmol, 5.00 equiv) and 3-phenyl-1,2-oxazole-5-carboxylic acid (2.6 g, 13.74 mmol, 1.20 equiv) in DCM (100 mL). To this solution was added HATU (6.5 g, 17.09 mmol, 1.50 equiv), then the reaction was stirred for 30 min at RT. The reaction was quenched with $H_2O$ and extracted with EtOAc. The organic extracts were combined, washed with brine, dried over anhydrous $Na_2SO_4$, and concentrated under reduced pressure. The residue was applied onto a silica gel column and eluted with EtOAc/petroleum ether (1:5) affording 4.57 g (98%) of (1r,3r)-3-(3-phenyl-1,2-oxazole-5-amido)cyclobutyl 4-nitrobenzoate as a white solid. LCMS (ES, m/z): [M+H]$^+$=408.1.

Step 6: 3-Phenyl-N-[(1r,3r)-3-hydroxycyclobutyl]-1,2-oxazole-5-carboxamide

To a 100-mL round-bottom flask was placed a solution of (1r,3r)-3-(3-phenyl-1,2-oxazole-5-amido)cyclobutyl 4-nitrobenzoate (4.4 g, 10.80 mmol, 1.00 equiv) in $MeOH/H_2O$=2:1 (30 mL), then $K_2CO_3$ (4.4 g, 31.83 mmol, 3.00 equiv) was added. The resulting mixture was stirred overnight at 40° C. The reaction was quenched with $H_2O$ and then extracted with EtOAc. The organic extracts were combined, washed with brine, dried over $Na_2SO_4$, and then concentrated under reduced pressure affording 2.2 g (79%) of 3-phenyl-N-[(1r,3r)-3-hydroxycyclobutyl]-1,2-oxazole-5-carboxamide as a white solid. LCMS (ES, m/z): [M+H]$^+$=259.1.

Step 7: 3-Phenyl-N-[(1s,3s)-3-azidocyclobutyl]-1,2-oxazole-5-carboxamide

To a 100-mL round-bottom flask was placed a solution of 3-phenyl-N-[(1r,3r)-3-hydroxycyclobutyl]-1,2-oxazole-5- carboxamide (2.2 g, 8.52 mmol, 1.00 equiv), DPPA (2.8 g, 10.17 mmol, 1.20 equiv) and PPh₃ (3.3 g, 12.58 mmol, 1.50 equiv) in THF (40 mL), then DIAD (2.6 g, 12.86 mmol, 1.50 equiv) was added dropwise. The reaction was stirred for 1 h at 30° C., quenched by the addition of brine, and extracted with EtOAc. The organic extracts were combined, dried over anhydrous Na₂SO₄, and concentrated under reduced pressure. The residue was applied onto a silica gel column and eluted with ethyl acetate/petroleum ether (1:10) affording 860 mg (36%) of 3-phenyl-N-[(1s,3s)-3-azidocyclobutyl]-1,2-oxazole-5-carboxamide as a white solid.

Step 8: 3-Phenyl-N-[(1s,3s)-3-[5-[(1R)-1-hydroxyethyl]-1H-1,2,3-triazol-1-yl]cyclobutyl]-1,2-oxazole-5-carboxamide and 3-Phenyl-N-[(1s,3s)-3-[4-[(1R)-1-hydroxyethyl]-1H-1,2,3-triazol-1-yl]cyclobutyl]-1,2-oxazole-5-carboxamide To a 10-mL sealed tube was placed a solution of 3-phenyl-N-[(1s,3 s)-3-azidocyclobutyl]-1,2-oxazole-5-carboxamide (550 mg, 1.94 mmol, 1.00 equiv) in DMF (2.5 mL), then (2R)-but-3-yn-2-ol (680 mg, 9.70 mmol, 5.00 equiv) was added. The resulting solution was stirred overnight at 100° C. After removing the solvent under reduced pressure, the residue was applied onto a silica gel column with ethyl acetate/petroleum ether (1:3). The resulting mixture was separated by Prep-SFC (Prep SFC80-1: Column, Chiralpak AD-H, 2*25 cm; mobile phase, CO₂ (50%) and ethanol (50%); Detector, UV 220 nm) affording 170.0 mg (25%) of 3-phenyl-N-[(1s,3s)-3-[5-[(1R)-1-hydroxyethyl]-1H-1,2,3-triazol-1-yl]cyclobutyl]-1,2-oxazole-5-carboxamide as a white solid and 222 mg (32%) of 3-phenyl-N-[(1 s,3 s)-3-[4-[(1R)-1-hydroxyethyl]-1H-1,2,3-triazol-1-yl]cyclobutyl]-1,2-oxazole-5-carboxamide as a white solid.

3-Phenyl-N-[(1s,3s)-3-[5-[(1R)-1-hydroxyethyl]-1H-1,2,3-triazol-1-yl]cyclobutyl]-1,2-oxazole-5-carboxamide LCMS (ES, m/z): [M+H]+=354. ¹H NMR (300 MHz, DMSO-d₆) δ 9.50-9.47 (d, J=7.2 Hz, 1H), 7.94-7.90 (m, 2H), 7.66 (s, 1H), 7.61 (s, 1H), 7.56-7.54 (m, 3H), 5.52-5.50 (d, J=6.0 Hz, 1H), 4.95-4.85 (m, 2H), 4.45-4.31 (m, 1H), 2.94-2.80 (m, 4H), 1.45-1.43 (d, J=6.6 Hz, 3H). Purity (HPLC, 254 nm): 99.4%.

3-Phenyl-N-[(1s,3s)-3-[4-[(1R)-1-hydroxyethyl]-1H-1,2,3-triazol-1-yl]cyclobutyl]-1,2-oxazole-5-carboxamide LCMS (ES, m/z): [M+H]+=354. ¹H NMR (300 MHz, DMSO-d₆) δ 9.41-9.39 (d, J=8.4 Hz, 1H), 8.13 (s, 1H), 7.96-7.93 (m, 2H), 7.68 (s, 1H), 7.56-7.54 (m, 3H), 5.30-5.28 (d, J=4.8 Hz, 1H), 5.00-4.80 (m, 2H), 4.48-4.35 (m, 1H), 2.98-2.89 (m, 2H), 2.74-2.64 (m, 2H), 1.43-1.41 (d, J=6.6 Hz, 3H).

Examples 53 and 54: 3-Phenyl-N-[(1s,3s)-3-[5-[(1S)-1-hydroxyethyl]-1H-1,2,3-triazol-1-yl]cyclobutyl]-1,2-oxazole-5-carboxamide and 3-Phenyl-N-[(1s,3s)-3-[4-[(1S)-1-hydroxyethyl]-1H-1,2,3-triazol-1-yl]cyclobutyl]-1,2-oxazole-5-carboxamide Step 1: 3-Phenyl-N-[(1s,3s)-3-[5-[(1S)-1-hydroxyethyl]-1H-1,2,3-triazol-1-yl]cyclobutyl]-1,2-oxazole-5-carboxamide and 3-Phenyl-N-[(1s,3s)-3-[4-[(1S)-1-hydroxyethyl]-1H-1,2,3-triazol-1-yl]cyclobutyl]-1,2-oxazole-5-carboxamide To a 10-mL sealed tube, was placed a solution of 3-phenyl-N-[(1 s,3s)-3-azidocyclobutyl]-1,2-oxazole-5-carboxamide (500 mg, 1.77 mmol, 1.00 equiv) in DMF (2.5 mL), then (2S)-but-3-yn-2-ol (618 mg, 8.82 mmol, 5.00 equiv) was added. The reaction was stirred overnight at 100° C. then concentrated under reduced pressure. The residue was applied onto a silica gel column with EtOAc/petroleum ether (1:3). The resulting mixture was separated by Prep-SFC (Prep SFC80-1: Column, Chiralpak AD-H, 2*25 cm; mobile phase, CO2 (55%) and methanol (45%); Detector, UV 220 nm) affording 106.1 mg (17%) of 3-phenyl-N-[(1s,3s)-3-[5-[(1S)-1-hydroxyethyl]-1H-1,2,3-triazol-1-yl]cyclobutyl]-1,2-oxazole-5-carboxamide as a white solid and 192.2 mg (31%) of 3-phenyl-N-[(1 s,3s)-3-[4-[(1 S)-1-hydroxyethyl]-1H-1,2,3-triazol-1-yl]cyclobutyl]-1,2-oxazole-5-carboxamide as a white solid.

3-Phenyl-N-[(1s,3s)-3-[5-[(1S)-1-hydroxyethyl]-1H-1,2,3-triazol-1-yl]cyclobutyl]-1,2-oxazole-5-carboxamide LCMS (ES, m/z): [M+H]+=354. ¹H NMR (300 MHz, DMSO-d₆) δ 9.50-9.47 (d, J=7.5 Hz, 1H), 7.94-7.90 (m, 2H), 7.66 (s, 1H), 7.61 (s, 1H), 7.56-7.54 (m, 3H), 5.52-5.50 (d, J=6.0 Hz, 1H), 4.95-4.85 (m, 2H), 4.45-4.31 (m, 1H), 2.94-2.80 (m, 4H), 1.45-1.43 (d, J=6.3 Hz, 3H). Purity (HPLC, 254 nm): 96.0%.

3-Phenyl-N-[(1s,3s)-3-[4-[(1S)-1-hydroxyethyl]-1H-1,2,3-triazol-1-yl]cyclobutyl]-1,2-oxazole-5-carboxamide LCMS (ES, m/z): [M+H]+=354. ¹H NMR (300 MHz, DMSO-d₆) δ 9.41-9.39 (d, J=8.1 Hz, 1H), 8.13 (s, 1H), 7.96-7.93 (m, 2H), 7.68 (s, 1H), 7.56-7.54 (m, 3H), 5.30-5.28 (d, J=4.5 Hz, 1H), 5.00-4.92 (m, 1H), 4.88-4.80 (m, 1H), 4.48-4.35 (m, 1H), 2.98-2.89 (m, 2H), 2.74-2.50 (m, 2H), 1.43-1.41 (d, J=6.6 Hz, 3H). Purity (HPLC, 254 nm): 97.7%.

Examples 55 and 56: 3-Phenyl-N-[(1s,3s)-3-([5-[(1R)-1-hydroxyethyl]-1H-1,2,3-triazol-1-yl]methyl)cyclobutyl]-1,2-oxazole-5-carboxamide and 3-Phenyl-N-[(1s,3s)-3-([4-[(1R)-1-hydroxyethyl]-1H-1,2,3-triazol-1-yl]methyl)cyclobutyl]-1,2-oxazole-5-carboxamide

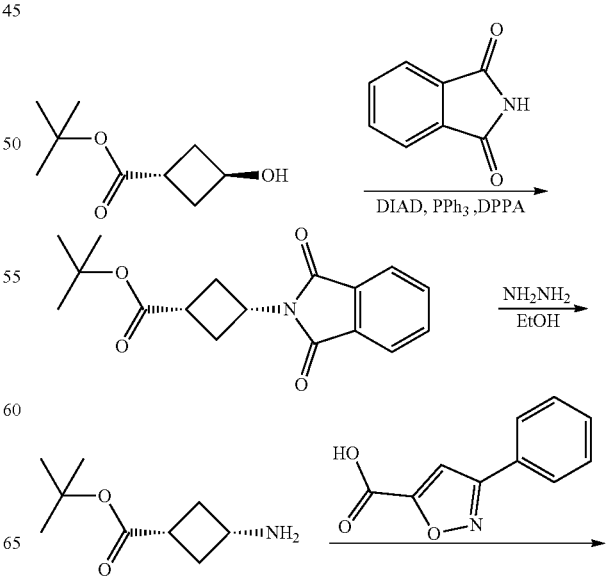

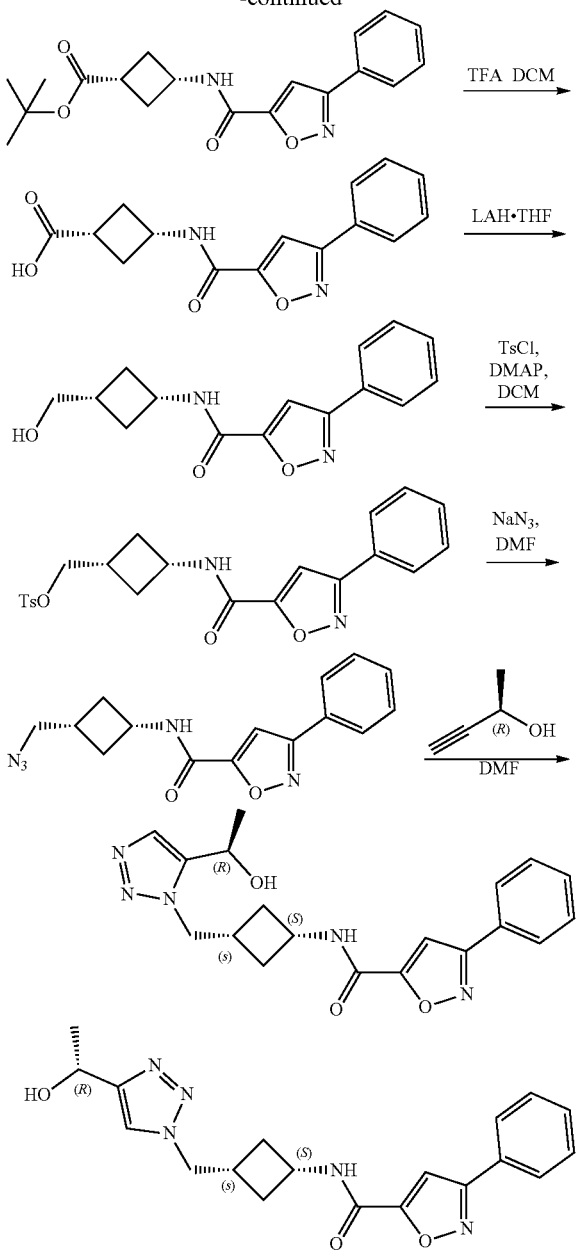

EtOAc/petroleum ether (1:40) affording 810 mg of tert-butyl (1s,3s)-3-(1,3-dioxo-2,3-dihydro-1H-isoindol-2-yl)cyclobutane-1-carboxylate as a white solid. LCMS (ES, m/z): [M+H]$^+$=302.2.

Step 2: tert-Butyl (1s,3s)-3-Aminocyclobutane-1-carboxylate

To a 2000-mL round-bottom flask was placed a solution of tert-butyl (1s,3s)-3-(1,3-dioxo-2,3-dihydro-1H-isoindol-2-yl)cyclobutane-1-carboxylate (810 mg, 2.64 mmol, 1.00 equiv) in EtOH (50 mL) and then N$_2$H$_4$.H$_2$O (400 mg, 3.00 equiv) was added. The resulting solution was stirred for 4 h at RT, then the solids were removed by filtration. The filtrate was concentrated under reduced pressure affording 500 mg of crude tert-butyl (1s,3 s)-3-aminocyclobutane-1-carboxylate as light yellow oil. LCMS [M+H]$^+$=172.1

Step 3: tert-Butyl (1s,3s)-3-(3-Phenyl-1,2-oxazole-5-amido)cyclobutane-1-carboxylate To a 100-mL round-bottom flask was placed a solution of tert-butyl (1s,3s)-3-aminocyclobutane-1-carboxylate (1.7 g, 9.93 mmol, 1.00 equiv) in DCM (50 mL), then 3-phenyl-1,2-oxazole-5-carboxylic acid (1.9 g, 10.04 mmol, 1.00 equiv), HATU (5.7 g, 14.99 mmol, 1.50 equiv) and DIEA (3.9 g, 30.18 mmol, 3.00 equiv) were added. The resulting solution was stirred for 1 h at RT, then quenched by the addition of water and extracted with EtOAc. The organic extracts were combined, washed with brine, dried over anhydrous Na$_2$SO$_4$, and concentrated under reduced pressure. The residue was applied onto a silica gel column and eluted with EtOAc/petroleum ether (1:7) affording 2 g (59%) of tert-butyl (1s,3s)-3-(3-phenyl-1,2-oxazole-5-amido)cyclobutane-1-carboxylate as a white solid. LCMS (ES, m/z): [M+H]$^+$=343.2.

Step 4: (1s,3s)-3-(3-Phenyl-1,2-oxazole-5-amido)cyclobutane-1-carboxylic acid

To a 25-mL round-bottom flask was placed a solution of tert-butyl (1s,3s)-3-(3-phenyl-1,2-oxazole-5-amido)cyclobutane-1-carboxylate (830 mg, 2.42 mmol, 1.00 equiv) in DCM (10 mL) and TFA (3 mL). The resulting solution was stirred for 2 h at rt, then the reaction was concentrated under reduced pressure affording 680 mg (98%) of (1s,3s)-3-(3-phenyl-1,2-oxazole-5-amido)cyclobutane-1-carboxylic acid as a light yellow solid.

Step 5: 3-Phenyl-N-[(1s,3s)-3-(hydroxymethyl)cyclobutyl]-1,2-oxazole-5-carboxamide To a 100-mL 3-necked round-bottom flask was placed a solution of (1s,3s)-3-(3-phenyl-1,2-oxazole-5-amido)cyclobutane-1-carboxylic acid (1.2 g, 4.19 mmol, 1.00 equiv) in THF (50 mL) followed by the addition of LiAlH$_4$ (319 mg, 8.41 mmol, 2.00 equiv) in portions at 0° C. over 5 min. The resulting solution was stirred for 2 h at RT, then quenched by the addition of 100 mL of 2N HCl, and extracted with EtOAc (2×100 mL). The organic extracts were combined, washed with brine (2×100 mL), dried over anhydrous Na$_2$SO$_4$, and concentrated under reduced pressure affording 860 mg (75%) of 3-phenyl-N-[(1s,3s)-3-(hydroxymethyl)cyclobutyl]-1,2-oxazole-5-carboxamide as a light yellow solid. LCMS (ES, m/z): [M+H]$^+$=273.1.

Step 1: tert-Butyl (1s,3s)-3-(1,3-Dioxo-2,3-dihydro-1H-isoindol-2-yl)cyclobutane-1-carboxylate To a 250-mL 3-necked round-bottom flask was placed a solution of tert-butyl (1r,3r)-3-hydroxycyclobutane-1-carboxylate (1.1 g, 5.87 mmol, 1.00 equiv), 2,3-dihydro-1H-isoindole-1,3-dione (1.04 g, 7.07 mmol, 1.19 equiv), and PPh$_3$ (2.5 g) in THF (60 mL). This was followed by the addition of DIAD (300 mg) dropwise with stirring at 0° C. The resulting solution was stirred for 1 h at RT then the reaction was quenched by the addition of 50 mL of water. The resulting solution was extracted with EtOAc (3×50 mL) and the organic layers combined. The resulting mixture was washed with brine (2×50 mL), dried over anhydrous Na$_2$SO$_4$, and concentrated under reduced pressure. The residue was applied onto a silica gel column and eluted with Step 6: [(1s,3s)-3-(3-Phenyl-1,2-oxazole-5-amido)cyclobutyl]methyl 4-methylbenzene-1-sulfonate To a 50-mL round-bottom flask was placed a solution of 3-phenyl-N-[(s,3 s)-3-(hydroxymethyl)cyclobutyl]-1,2-oxazole-5-carboxamide (860 mg, 3.16 mmol, 1.00 equiv) in DCM (20 mL) then DMAP (781 mg, 6.39 mmol, 2.00 equiv) and TsCl (779 mg, 4.09 mmol, 1.30 equiv) were added. The resulting solution was stirred for 16 h at RT, diluted with 100 mL of $H_2O$, and extracted with EtOAc (2×100 mL). The organic extracts were combined, washed with brine (2×100 mL), dried over anhydrous $Na_2SO_4$, and concentrated under reduced pressure affording 1.1 g (82%) of [(1s,3s)-3-(3-phenyl-1,2-oxazole-5-amido)cyclobutyl]methyl 4-methylbenzene-1-sulfonate as a yellow solid. LCMS (ES, m/z): $[M+H]^+$=427.2.

Step 7: 3-Phenyl-N-[(1s,3s)-3-(azidomethyl)cyclobutyl]-1,2-oxazole-5-carboxamide To a 25-mL round-bottom flask was placed a solution of [(1s,3s)-3-(3-phenyl-1,2-oxazole-5-amido)cyclobutyl]methyl 4-methylbenzene-1-sulfonate (1.1 g, 2.58 mmol, 1.00 equiv) in DMF (10 mL), then $NaN_3$ (254 mg, 3.91 mmol, 1.50 equiv) was added. The resulting solution was stirred for 1 h at 80° C., diluted with 100 mL of $H_2O$, and extracted with EtOAc (2×100 mL). The organic extracts were combined, washed with brine (5×100 mL), dried over anhydrous $Na_2SO_4$, and concentrated under reduced pressure affording 750 mg (98%) of 3-phenyl-N-[(1s,3s)-3-(azidomethyl)cyclobutyl]-1,2-oxazole-5-carboxamide as a yellow solid.

Step 8: 3-Phenyl-N-[(1s,3s)-3-([5-[(1R)-1-hydroxyethyl]-1H-1,2,3-triazol-1-yl]methyl)cyclobutyl]-1,2-oxazole-5-carboxamide and 3-Phenyl-N-[(1s,3s)-3-([4-[(1R)-1-hydroxyethyl]-1H-1,2,3-triazol-1-yl]methyl)cyclobutyl]-1,2-oxazole-5-carboxamide To a 25-mL round-bottom flask was placed a solution of 3-phenyl-N-[(1s,3s)-3-(azidomethyl)cyclobutyl]-1,2-oxazole-5-carboxamide (350 mg, 1.18 mmol, 1.00 equiv) in DMF (5 mL), then (2R)-but-3-yn-2-ol (420 mg, 5.99 mmol, 5.00 equiv) was added. The resulting solution was stirred for 16 h at 80° C., then diluted with 50 mL of $H_2O$, and extracted with EtOAc (3×50 mL). The organic extracts were combined, washed with brine (3×50 mL), dried over anhydrous $Na_2SO_4$, and concentrated under reduced pressure. The residue was applied onto a silica gel column and eluted with EtOAc/petroleum ether (5:1). The pure isomers were separated by Chiral-Prep-HPLC (Prep-HPLC-009: Column, Chiralpak IB, 2*25 cm, 5 um; mobile phase, Hex and ethanol (hold 15.0% ethanol in 29 min); Detector, UV 254/220 nm) affording 29.4 mg (7%) of 3-phenyl-N-[(1 s,3s)-3-([5-[(1R)-1-hydroxyethyl]-1H-1,2,3-triazol-1-yl]methyl)cyclobutyl]-1,2-oxazole-5-carboxamide as a light yellow solid and 31.6 mg (7%) of 3-phenyl-N-[(1 s,3s)-3-([4-[(1R)-1-hydroxyethyl]-1H-1,2,3-triazol-1-yl]methyl)cyclobutyl]-1,2-oxazole-5-carboxamide as a white solid.

3-Phenyl-N-[(1s,3s)-3-([5-[(1R)-1-hydroxyethyl]-1H-1,2,3-triazol-1-yl]methyl)cyclobutyl]-1,2-oxazole-5-carboxamide LCMS (ES, m/z): $[M+H]^+$=368.1. $^1$H NMR (300 MHz, DMSO-$d_6$) δ 9.25-9.22 (d, J=7.8 Hz, 1H), 7.94-7.91 (m, 2H), 7.63-7.60 (d, J=6.9 Hz, 2H), 7.55-7.53 (m, 3H), 5.53-7.51 (d, J=6.0 Hz, 1H), 4.93-4.85 (m, 1H), 4.43-4.40 (d, J=7.2 Hz, 2H), 4.35-4.27 (m, 1H), 2.64-2.55 (m, 1H), 2.39-2.30 (m, 2H), 2.03-1.94 (m, 2H), 1.48-1.46 (d, J=6.3 Hz, 3H). Purity (HPLC, 254 nm): 95.2%.

3-Phenyl-N-[(1s,3s)-3-([4-[(1R)-1-hydroxyethyl]-1H-1,2,3-triazol-1-yl]methyl)cyclobutyl]-1,2-oxazole-5-carboxamide LCMS (ES, m/z): $[M+H]^+$=368.1. $^1$H NMR (300 MHz, DMSO-$d_6$) δ 9.22-9.19 (d, J=7.8 Hz, 1H), 7.90-7.76 (m, 2H), 7.84 (s, 1H), 7.59 (s, 1H), 7.55-7.46 (m, 3H), 5.19-5.18 (d, J=4.5 Hz, 1H), 4.80-4.76 (m, 1H), 4.35-4.24 (m, 3H), 2.60-2.50 (m, 1H), 2.33-2.25 (m, 2H), 1.95-1.88 (m, 2H), 1.37-1.35 (d, J=6.3 Hz, 3H). Purity (HPLC, 254 nm): 95.0%.

Examples 57 and 58: 3-Phenyl-N-[(1s,3s)-3-([5-[(1S)-1-hydroxyethyl]-11H-1,2,3-triazol-1-yl]methyl)cyclobutyl]-1,2-oxazole-5-carboxamide and 3-Phenyl-N-[(1s,3s)-3-([4-[(1S)-1-hydroxyethyl]-1H-1,2,3-triazol-1-yl]methyl)cyclobutyl]-1,2-oxazole-5-carboxamide Into a 25-mL round-bottom flask, was placed a solution of 3-phenyl-N-[(1s,3s)-3-(azidomethyl)cyclobutyl]-1,2-oxazole-5-carboxamide (270 mg, 0.91 mmol, 1.00 equiv) in toluene (5 mL), then (2S)-but-3-yn-2-ol (315 mg, 4.49 mmol, 5.00 equiv) was added. The resulting solution was stirred for 16 h at 100° C. and then concentrated under reduced pressure. The crude product was purified by Prep-TLC (petroleum ether/EtOAc=1:5). The resulting mixture was separated by Chiral-Prep-HPLC (2#-Gilson Gx 281 (HPLC-09): Column: Chiralpak IB, 2*25 cm, 5 um; Mobile Phase A: hexane, Mobile Phase B: EtOH; Flow rate: 20 mL/min; Gradient: 30 B to 30 B in 15 min; 254/220 nm; RT1:7.642; RT2:10.588) affording 32.8 mg (10%) of 3-phenyl-N-[(1 s,3s)-3-([5-[(1 S)-1-hydroxyethyl]-1H-1,2,3-triazol-1-yl]methyl)cyclobutyl]-1,2-oxazole-5-carboxamide as a white solid and 68.5 mg (21%) of 3-phenyl-N-[(1 s,3 s)-3-([4-[(1 S)-1-hydroxyethyl]-1H-1,2,3-triazol-1-yl]methyl)cyclobutyl]-1,2-oxazole-5-carboxamide as a white solid.

3-Phenyl-N-[(1s,3s)-3-([5-[(1S)-1-hydroxyethyl]-1H-1,2,3-triazol-1-yl]methyl)cyclobutyl]-1,2-oxazole-5-carboxamide LCMS (ES, m/z): $[M+H]^+$=368.2. $^1$H NMR (400 MHz, DMSO-$d_6$) δ 9.24-9.22 (d, J=7.6 Hz, 1H), 7.94-7.92 (m, 2H), 7.62-7.60 (d, J=8.4 Hz, 1H), 7.55-7.53 (m, 3H), 5.52-5.50 (d, J=6.0 Hz, 1H), 4.95-4.83 (m, 1H), 4.43-4.40 (m, 2H), 4.35-4.31 (m, 3H), 2.54-2.52 (m, 1H), 2.36-2.33 (m, 2H), 2.05-1.98 (m, 2H), 1.48-1.46 (d, J=6.4 Hz, 3H). Purity (HPLC, 254 nm): 93.1%.

3-Phenyl-N-[(1s,3s)-3-([4-[(1S)-1-hydroxyethyl]-1H-1,2,3-triazol-1-yl]methyl)cyclobutyl]-1,2-oxazole-5-carboxamide LCMS (ES, m/z): $[M+H]^+$=368.2. $^1$H NMR (400 MHz, DMSO-$d_6$) δ 9.24-9.22 (d, J=7.6 Hz, 1H), 7.94-7.92 (m, 2H), 7.87 (s, 1H), 7.62 (s, 1H), 7.55-7.53 (m, 3H), 5.22-5.21 (d, J=4.8 Hz, 1H), 4.85-4.79 (m, 1H), 4.38-4.37 (d, J=7.2 Hz, 2H), 4.34-4.28 (m, 1H), 2.54-2.46 (m, 1H), 2.39-2.32 (m, 2H), 2.01-1.93 (m, 2H), 1.41-1.39 (d, J=6.4 Hz, 3H). Purity (HPLC, 254 nm): 98.6%.

Examples 59 and 60: 3-Phenyl-N-[(1r,3r)-3-([5-[(1R)-1-hydroxyethyl]-1H-1,2,3-triazol-1-yl]methyl)cyclobutyl]-1,2-oxazole-5-carboxamide and 3-Phenyl-N-[(1r,3r)-3-([4-[(1R)-1-hydroxyethyl]-1H-1,2,3-triazol-1-yl]methyl)cyclobutyl]-1,2-oxazole-5-carboxamide Step 1: 3-Phenyl-N-[(1r,3r)-3-(azidomethyl)cyclobutyl]-1,2-oxazole-5-carboxamide To a 25-mL round-bottom flask was placed a solution of [(1r,3r)-3-(3-phenyl-1,2-oxazole-5-amido)cyclobutyl]methyl 4-methylbenzene-1-sulfonate (920 mg, 2.16 mmol, 1.00 equiv) in DMF (10 mL), then NaN₃ (169 mg, 2.60 mmol, 1.20 equiv) was added. The resulting solution was stirred for 2 h at 80° C., then diluted with 100 mL of H₂O, and extracted with EtOAc (2×50 mL). The organic extracts were combined, washed with brine (2×50 mL), dried over anhydrous Na₂SO₄, and concentrated under reduced pressure affording 600 mg (94%) of 3-phenyl-N-[(1r,3r)-3-(azidomethyl)cyclobutyl]-1,2-oxazole-5-carboxamide as a light yellow solid.

Step 2: 3-Phenyl-N-[(1r,3r)-3-([5-[(1R)-1-hydroxyethyl]-1H-1,2,3-triazol-1-yl]methyl)cyclobutyl]-1,2-oxazole-5-carboxamide and 3-phenyl-N-[(1r,3r)-3-([4-[(1R)-1-hydroxyethyl]-1H-1,2,3-triazol-1-yl]methyl)cyclobutyl]-1,2-oxazole-5-carboxamide To a 5-mL round-bottom flask was placed a solution of 3-phenyl-N-[(1r,3r)-3-(azidomethyl)cyclobutyl]-1,2-oxazole-5-carboxamide (300 mg, 1.01 mmol, 1.00 equiv) in DMF (5 mL), then (2R)-but-3-yn-2-ol (210 mg, 3.00 mmol, 3.00 equiv) was added. The resulting solution was stirred for 16 h at 100° C., then diluted with 50 mL of H₂O, and extracted with EtOAc (2×50 mL). The organic extracts were combined, washed with brine (2×50 mL), dried over anhydrous Na₂SO₄, and concentrated under reduced pressure. The crude product was purified by Prep-TLC (petroleum ether/ethyl acetate=1:5). The resulting mixture was separated by Chiral-Prep-HPLC (Prep-HPLC-004: Column, Chiralpak IA, 2*25 cm, 5 um; mobile phase, Hex and IPA (hold 30.0% IPA in 15 min); Detector, UV 254/220 nm) affording 103.5 mg (28%) of 3-phenyl-N-[(1r,3r)-3-([5-[(1R)-1-hydroxyethyl]-1H-1,2,3-triazol-1-yl]methyl)cyclobutyl]-1,2-oxazole-5-carboxamide as a white solid and 127.1 mg (38%) of 3-phenyl-N-[(1r,3r)-3-([4-[(1R)-1-hydroxyethyl]-1H-1,2,3-triazol-1-yl]methyl)cyclobutyl]-1,2-oxazole-5-carboxamide as a light yellow solid.

3-Phenyl-N-[(1r,3r)-3-([5-[(1R)-1-hydroxyethyl]-1H-1,2,3-triazol-1-yl]methyl)cyclobutyl]-1,2-oxazole-5-carboxamide LCMS (ES, m/z): [M+H]⁺=368.2. ¹H NMR (400 MHz, DMSO-d₆) δ 9.29-9.27 (d, J=7.2 Hz, 1H), 7.92-7.90 (m, 2H), 7.62-7.59 (m, 2H), 7.53-7.52 (m, 3H), 5.53-5.52 (d, J=6.0 Hz, 1H), 4.92-4.89 (m, 1H), 4.62-4.58 (m, 1H), 4.56-4.48 (m, 2H), 2.85-2.81 (m, 1H), 2.27-2.17 (m, 4H), 1.46-1.44 (d, J=6.4 Hz, 3H). Purity (HPLC, 254 nm): 95.0%.

3-Phenyl-N-[(1r,3r)-3-([4-[(1R)-1-hydroxyethyl]-1H-1,2,3-triazol-1-yl]methyl)cyclobutyl]-1,2-oxazole-5-carboxamide LCMS (ES, m/z): [M+H]⁺=368.2. ¹H NMR (400 MHz, DMSO-d₆) δ 9.27-9.25 (d, J=7.2 Hz, 1H), 7.94 (s, 1H), 7.93-7.89 (m, 2H), 7.62 (s, 1H), 7.53-7.51 (m, 3H), 5.21-5.20 (d, J=4.8 Hz, 1H), 4.83-4.80 (m, 1H), 4.59-4.51 (m, 1H), 4.48-4.46 (d, J=7.6 Hz, 2H), 2.74-2.66 (m, 1H), 2.28-2.21 (m, 2H), 2.17-2.11 (m, 2H), 1.39-1.37 (d, J=6.8 Hz, 3H). Purity (HPLC, 254 nm): 96.9%.

Examples 61 and 62: 3-Phenyl-N-[(1r,3r)-3-([5-[(1S)-1-hydroxyethyl]-1H-1,2,3-triazol-1-yl]methyl)cyclobutyl]-1,2-oxazole-5-carboxamide and 3-Phenyl-N-[(1r,3r)-3-([4-[(1S)-1-hydroxyethyl]-1H-1,2,3-triazol-1-yl]methyl)cyclobutyl]-1,2-oxazole-5-carboxamide To a 25-mL round-bottom flask was placed a solution of 3-phenyl-N-[(1r,3r)-3-(azidomethyl)cyclobutyl]-1,2-oxazole-5-carboxamide (210 mg, 0.71 mmol, 1.00 equiv) in toluene (5 mL), then (2S)-but-3-yn-2-ol (245 mg, 3.50 mmol, 5.00 equiv) was added. The resulting solution was stirred for 16 h at 100° C., then concentrated under reduced pressure. The crude product was purified by Prep-TLC (petroleum ether/EtOAc=1:5). The resulting mixture was separated by Chiral-Prep-HPLC (Prep-HPLC-004: Column, Chiralpak IC, 2*25 cm, 5 um; mobile phase, Hex and ethanol (hold 50.0% ethanol in 15 min); Detector, UV 254/220 nm) affording 44.2 mg (17%) of 3-phenyl-N-[(1r,3r)-3-([5-[(1S)-1-hydroxyethyl]-1H-1,2,3-triazol-1-yl]methyl)cyclobutyl]-1,2-oxazole-5-carboxamide as a white solid and 78.5 mg (30%) of 3-phenyl-N-[(1r,3r)-3-([4-[(1S)-1-hydroxyethyl]-1H-1,2,3-triazol-1-yl]methyl)cyclobutyl]-1,2-oxazole-5-carboxamide as a white solid.

3-Phenyl-N-[(1r,3r)-3-([5-[(1S)-1-hydroxyethyl]-1H-1,2,3-triazol-1-yl]methyl)cyclobutyl]-1,2-oxazole-5-carboxamide LCMS (ES, m/z): [M+H]⁺=368.2. ¹H NMR (400 MHz, DMSO-d₆) δ 9.31-9.29 (d, J=7.2 Hz, 1H), 7.94-7.91 (m, 2H), 7.64-7.60 (m, 2H), 7.55-7.52 (m, 3H), 5.55-5.53 (d, J=6.0 Hz, 1H), 4.95-4.89 (m, 1H), 4.64-4.47 (m, 3H), 2.88-2.82 (m, 1H), 2.30-2.19 (m, 4H), 1.48-1.46 (d, J=6.4 Hz, 3H). Purity (HPLC, 254 nm): 97.5%.

3-Phenyl-N-[(1r,3r)-3-([4-[(1S)-1-hydroxyethyl]-1H-1,2,3-triazol-1-yl]methyl)cyclobutyl]-1,2-oxazole-5-carboxamide LCMS (ES, m/z): [M+H]⁺=368.2. ¹H NMR (400 MHz, DMSO-d₆) δ 9.30-9.28 (d, J=7.6 Hz, 1H), 7.96 (s, 1H), 7.94-7.91 (m, 2H), 7.64 (s, 1H), 7.55-7.53 (m, 3H), 5.23-5.21 (d, J=4.8 Hz, 1H), 4.85-4.79 (m, 1H), 4.58-4.53 (m, 1H), 4.50-4.48 (d, J=7.6 Hz, 2H), 2.75-2.71 (m, 1H), 2.30-2.23 (m, 2H), 2.18-2.12 (m, 2H), 1.41-1.39 (d, J=6.4 Hz, 3H). Purity (HPLC, 254 nm): 99.2%.

Examples 63 and 64: 3-Phenyl-N-[(1r,3r)-3-([3-[(1R)-1-hydroxyethyl]-1H-pyrazol-1-yl]methyl)cyclobutyl]-1,2-oxazole-5-carboxamide and 3-Phenyl-N-[(1r,3r)-3-([3-[(1S)-1-hydroxyethyl]-1H-pyrazol-1-yl]methyl)cyclobutyl]-1,2-oxazole-5-carboxamide

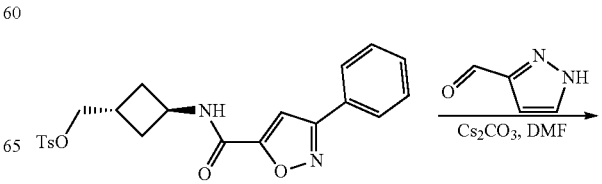

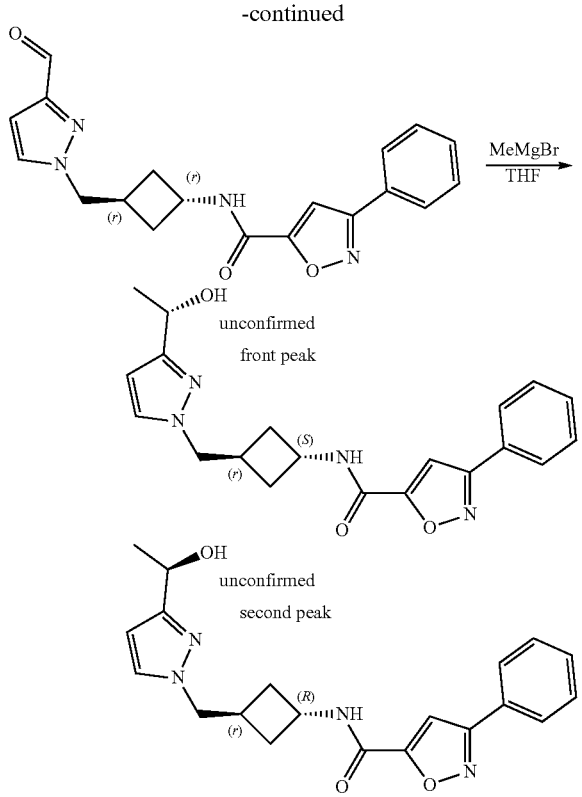

Step 1: 3-Phenyl-N-[(1r,3r)-3-[(3-formyl-1H-pyrazol-1-yl)methyl]cyclobutyl]-1,2-oxazole-5-carboxamide To a 50-mL round-bottom flask was placed a solution of [(1r,3r)-3-(3-phenyl-1,2-oxazole-5-amido)cyclobutyl]methyl 4-methylbenzene-1-sulfonate (1.28 g, 3.00 mmol, 1.00 equiv) in DMF (20 mL), then $Cs_2CO_3$ (1.95 g, 5.98 mmol, 2.00 equiv) and 1H-pyrazole-3-carbaldehyde (432 mg, 4.50 mmol, 1.50 equiv) were added. The resulting solution was stirred for 3 h at 100° C., then the solids were removed by filtration. The filtrate was purified by Flash-Prep-HPLC (CombiFlash-1: Column, C18; mobile phase, X: $H_2O$ (0.5% $NH_4HCO_3$), Y: CAN, X/Y=90/10 increasing to X/Y=5/95 within 40 min; Detector, UV 254 nm) affording 450 mg (43%) of 3-phenyl-N-[(1r,3r)-3-[(3-formyl-1H-pyrazol-1-yl)methyl]cyclobutyl]-1,2-oxazole-5-carboxamide as a yellow solid. LCMS (ES, m/z): [M+H]$^+$=351.2.

Step 2: 3-Phenyl-N-[(1r,3r)-3-([3-[(1R)-1-hydroxyethyl]-1H-pyrazol-1-yl]methyl)cyclobutyl]-1,2-oxazole-5-carboxamide (Front Peak) and 3-phenyl-N-[(1r,3r)-3-([3-[(1S)-1-hydroxyethyl]-1H-pyrazol-1-yl]methyl)cyclobutyl]-1,2-oxazole-5-carboxamide (Second Peak)

To a 50-mL 3-necked round-bottom flask was placed a solution of 3-phenyl-N-[(1r,3r)-3-[(3-formyl-1H-pyrazol-1-yl)methyl]cyclobutyl]-1,2-oxazole-5-carboxamide (450 mg, 1.28 mmol, 1.00 equiv) in THF (20 mL). The solution was cooled to 0° C., then MeMgBr (1.3 mL, 3.00 equiv, 3 mol/L) was added dropwise with stirring at 0° C. over 10 min. The reaction was stirred for 2 h at RT, then quenched by the addition of 10 mL of 2N HCl and 50 mL of $H_2O$, and extracted with EtOAc (3×50 mL). The organic extracts were combined, washed with brine (3×50 mL), dried over anhydrous $Na_2SO_4$, and concentrated under reduced pressure. The residue was applied onto a silica gel column and eluted with EtOAc/petroleum ether (2:1). The resulting mixture was separated by Chiral-Prep-HPLC (Prep-HPLC-004: Column, Chiralpak IC, 2*25 cm, 5 um; mobile phase, Hex and ethanol (hold 50.0% ethanol in 13 min); Detector, UV 254/220 nm) affording 126.1 mg (27%) of 3-phenyl-N-[(1r,3r)-3-([3-[(1R)-1-hydroxyethyl]-1H-pyrazol-1-yl]methyl)cyclobutyl]-1,2-oxazole-5-carboxamide (front peak) as a light yellow solid and 136.9 mg (29%) of 3-phenyl-N-[(1r,3r)-3-([3-[(1 S)-1-hydroxyethyl]-1H-pyrazol-1-yl]methyl)cyclobutyl]-1,2-oxazole-5-carboxamide (second peak) as a white solid.

3-Phenyl-N-[(1r,3r)-3-([3-[(1R)-1-hydroxyethyl]-1H-pyrazol-1-yl]methyl)cyclobutyl]-1,2-oxazole-5-carboxamide LCMS (ES, m/z): [M+H]$^+$=367.0. $^1$H NMR (300 MHz, DMSO-$d_6$) δ 9.28-9.25 (d, J=7.2 Hz, 1H), 7.94-7.91 (m, 2H), 7.65-7.63 (m, 2H), 7.55-7.53 (m, 3H), 6.15-6.14 (d, J=1.8 Hz, 1H), 4.95-4.93 (d, J=4.8 Hz, 1H), 4.72-4.64 (m, 1H), 4.58-4.45 (m, 1H), 4.19-4.16 (d, J=7.8 Hz, 2H), 2.72-2.64 (m, 1H), 2.27-2.12 (m, 4H), 1.34-1.32 (d, J=6.3 Hz, 3H). Purity (HPLC, 254 nm): 98.9%.

3-Phenyl-N-[(1r,3r)-3-([3-[(1S)-1-hydroxyethyl]-1H-pyrazol-1-yl]methyl)cyclobutyl]-1,2-oxazole-5-carboxamide LCMS (ES, m/z): [M+H]$^+$=367.0. $^1$H NMR (300 MHz, DMSO-$d_6$) δ 9.28-9.25 (d, J=7.5 Hz, 1H), 7.94-7.91 (m, 2H), 7.65-7.63 (m, 2H), 7.55-7.53 (m, 3H), 6.15-6.14 (d, J=2.1 Hz, 1H), 4.95-4.93 (d, J=5.1 Hz, 1H), 4.72-4.63 (m, 1H), 4.55-4.48 (m, 1H), 4.19-4.16 (d, J=7.5 Hz, 2H), 2.69-2.64 (m, 1H), 2.27-2.11 (m, 4H), 1.34-1.32 (d, J=6.3 Hz, 3H). Purity (HPLC, 254 nm): 98.3%.

Examples 65 and 66: 3-Phenyl-N-[(1s,3s)-3-([3-[(1S)-1-hydroxyethyl]-1H-pyrazol-1-yl]methyl)cyclobutyl]-1,2-oxazole-5-carboxamide (Front Peak) and 3-Phenyl-N-[(1s,3s)-3-([3-[(1R)-1-hydroxyethyl]-1H-pyrazol-1-yl]methyl)cyclobutyl]-1,2-oxazole-5-carboxamide (Second Peak)

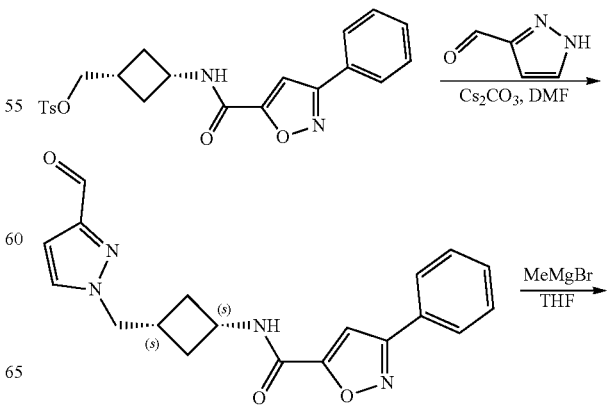

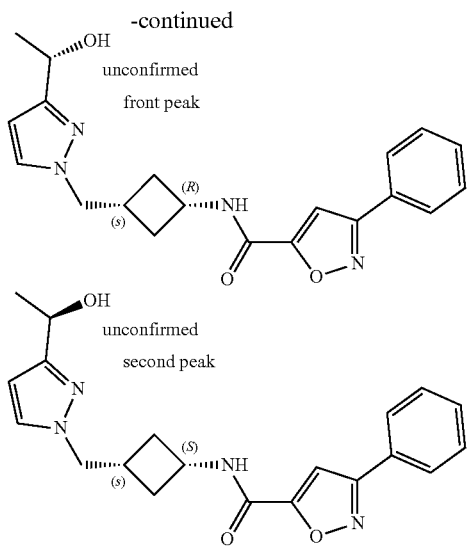

Step 1: 3-Phenyl-N-[(1s,3s)-3-[(3-formyl-1H-pyrazol-1-yl)methyl]cyclobutyl]-1,2-oxazole-5-carboxamide To a 50-mL round-bottom flask was placed a solution of [(1s,3 s)-3-(3-phenyl-1,2-oxazole-5-amido)cyclobutyl] methyl 4-methylbenzene-1-sulfonate (1.3 g, 3.05 mmol, 1.00 equiv) in DMF (15 mL), then $Cs_2CO_3$ (1.96 g, 6.02 mmol, 2.00 equiv) and 1H-pyrazole-3-carbaldehyde (432 mg, 4.50 mmol, 1.50 equiv) were added. The resulting solution was stirred for 3 h at 100° C., then the solids were removed by filtration. The filtrate was purified by Flash-Prep-HPLC (CombiFlash-1: Column, C18; mobile phase, X: $H_2O$ (0.5% $NH_4HCO_3$), Y: ACN, X/Y=90/10 increasing to X/ACN=5/95 within 40 min; Detector, UV 254 nm) affording 430 mg (40%) of 3-phenyl-N-[(1 s,3 s)-3-[(3-formyl-1H-pyrazol-1-yl)methyl]cyclobutyl]-1,2-oxazole-5-carboxamide as a yellow solid. LCMS (ES, m/z): [M+H]$^+$=351.2.

Step 2: 3-Phenyl-N-[(1s,3s)-3-([3-[(1S)-1-hydroxyethyl]-1H-pyrazol-1-yl]methyl)cyclobutyl]-1,2-oxazole-5-carboxamide (Front Peak) and 3-phenyl-N-[(1s,3s)-3-([3-[(1R)-1-hydroxyethyl]-1H-pyrazol-1-yl]methyl)cyclobutyl]-1,2-oxazole-5-carboxamide (Second Peak)

To a 100-mL 3-necked round-bottom flask was placed a solution of 3-phenyl-N-[(1s,3 s)-3-[(3-formyl-1H-pyrazol-1-yl)methyl]cyclobutyl]-1,2-oxazole-5-carboxamide (430 mg, 1.23 mmol, 1.00 equiv) in THF (30 mL), then the solution was cooled to 0° C. and MeMgBr (1.2 mL, 3 mol/L, 3.00 equiv) was added dropwise with stirring at 0° C. over 5 min. The reaction was stirred for 3 h at RT, then quenched by the addition of 2N HCl (10 mL) and 50 mL of $H_2O$, and extracted with EtOAc (3×50 mL). The organic extracts were combined, washed with brine (3×50 mL), dried over anhydrous $Na_2SO_4$, and concentrated under reduced pressure. The residue was applied onto a silica gel column and eluted with EtOAc/petroleum ether (2:1). The pure isomers were separated by Chiral-Prep-HPLC (Prep-HPLC-009: Column, Phenomenex Lux 5u Cellulose-3, 5*25 cm, 5 um; mobile phase, Hex and IPA (hold 50.0% IPA-in 17 min); Detector, UV 220/254 nm) affording 89.5 mg (20%) of 3-phenyl-N-[(1s,3s)-3-([3-[(1S)-1-hydroxyethyl]-1H-pyrazol-1-yl]methyl)cyclobutyl]-1,2-oxazole-5-carboxamide (front peak) as a white solid and 65.5 mg (15%) of 3-phenyl-N-[(1s,3s)-3-([3-[(1R)-1-hydroxyethyl]-1H-pyrazol-1-yl]methyl)cyclobutyl]-1,2-oxazole-5-carboxamide (second peak) as a white solid.

3-Phenyl-N-[(1s,3s)-3-([3-[(1S)-1-hydroxyethyl]-1H-pyrazol-1-yl]methyl)cyclobutyl]-1,2-oxazole-5-carboxamide (Front Peak)

LCMS (ES, m/z): [M+H]$^+$=367.1. $^1$H NMR (300 MHz, DMSO-$d_6$) δ 9.21-9.18 (d, J=7.5 Hz, 1H), 7.94-7.92 (m, 2H), 7.62 (s, 1H), 7.55-7.53 (m, 4H), 6.15 (d, J=2.1 Hz, 1H), 4.94-4.92 (d, J=4.8 Hz, 1H), 4.71-4.63 (m, 1H), 4.34-4.26 (m, 1H), 4.09-4.06 (d, J=6.9 Hz, 2H), 2.48-2.29 (m, 3H), 1.98-1.89 (m, 2H), 1.34-1.32 (d, J=6.3 Hz, 3H). Purity (HPLC, 254 nm): 98.2%.

3-Phenyl-N-[(1s,3s)-3-([3-[(1R)-1-hydroxyethyl]-1H-pyrazol-1-yl]methyl)cyclobutyl]-1,2-oxazole-5-carboxamide (Second Peak)

LCMS (ES, m/z): [M+H]$^+$=367.2. $^1$H NMR (300 MHz, DMSO-$d_6$) δ 9.21-9.18 (d, J=7.5 Hz, 1H), 7.93-7.90 (m, 2H), 7.61 (s, 1H), 7.54-7.52 (m, 4H), 6.14 (d, J=2.1 Hz, 1H), 4.94-4.93 (d, J=4.8 Hz, 1H), 4.70-4.62 (m, 1H), 4.35-4.22 (m, 1H), 4.08-4.05 (d, J=6.9 Hz, 2H), 2.46-2.28 (m, 3H), 1.97-1.88 (m, 2H), 1.33-1.31 (d, J=6.6 Hz, 3H). Purity (HPLC, 254 nm): 97.9%.

Examples 67 and 68: 3-Phenyl-N-[(1r,3r)-3-([4-[(1S)-1-hydroxyethyl]-1H-pyrazol-1-yl]methyl)cyclobutyl]-1,2-oxazole-5-carboxamide (Front Peak) and 3-Phenyl-N-[(1r,3r)-3-([4-[(1R)-1-hydroxyethyl]-1H-pyrazol-1-yl]methyl)cyclobutyl]-1,2-oxazole-5-carboxamide (Second Peak)

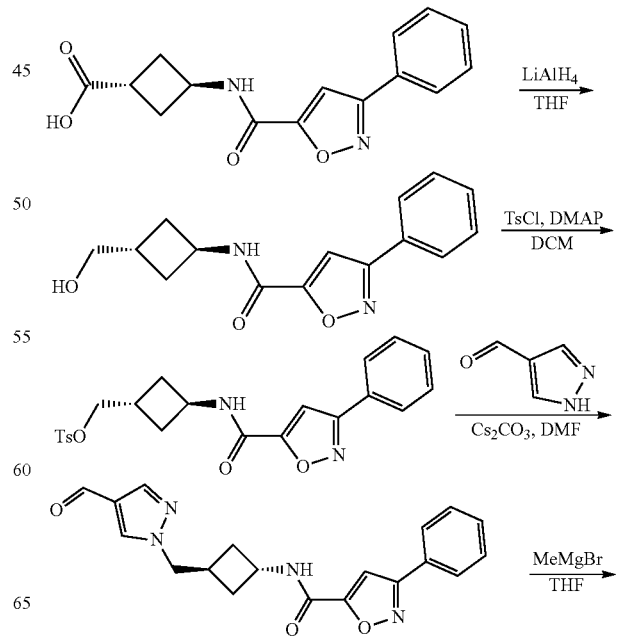

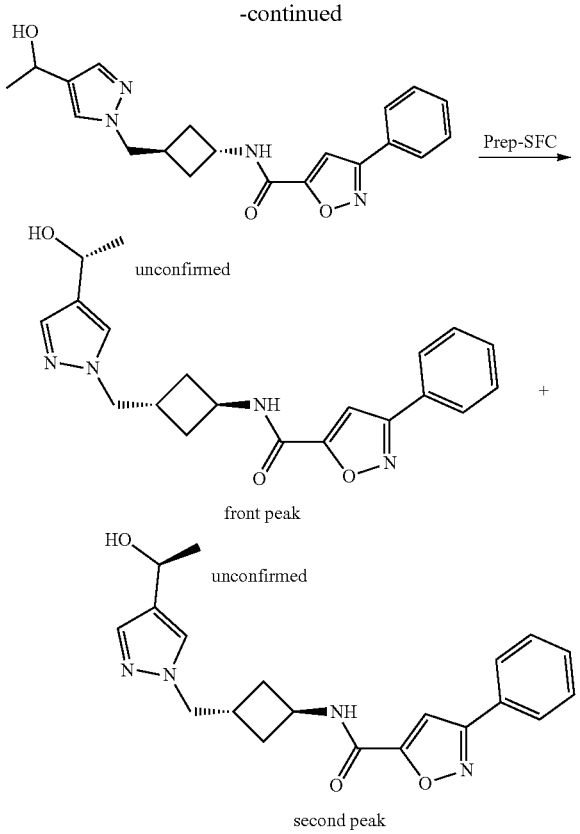

front peak second peak

Step 1: 3-Phenyl-N-[(1r,3r)-3-(hydroxymethyl)cyclobutyl]-1,2-oxazole-5-carboxamide To a 250-mL 3-necked round-bottom flask was placed a solution of (1r,3r)-3-(3-phenyl-1,2-oxazole-5-amido)cyclobutane-1-carboxylic acid (2 g, 6.99 mmol, 1.00 equiv) in THF (40 mL), then the solution was cooled to 0° C. and LiAlH$_4$ (800 mg, 21.08 mmol, 3.00 equiv) was added. The resulting solution was stirred for 2 h at 5° C., then quenched by the addition of Na$_2$SO$_4$.10H$_2$O. The solids were removed by filtration, then the filtrate was concentrated under reduced pressure affording 850 mg (45%) of 3-phenyl-N-[(1r,3r)-3-(hydroxymethyl)cyclobutyl]-1,2-oxazole-5-carboxamide as a yellow oil. LCMS (ES, m/z): [M+H]$^+$=273.1.

Step 2: [(1r,3r)-3-(3-Phenyl-1,2-oxazole-5-amido)cyclobutyl]methyl 4-methylbenzene-1-sulfonate To a 50-mL round-bottom flask was placed a solution of 3-phenyl-N-[(1r,3r)-3-(hydroxymethyl)cyclobutyl]-1,2-oxazole-5-carboxamide (850 mg, 3.12 mmol, 1.00 equiv) and DMAP (762 mg, 6.24 mmol, 1.20 equiv) in DCM (20 mL). To this solution was added TsCl (712 mg, 3.73 mmol, 1.20 equiv) then the mixture was stirred for 24 h at RT. The reaction was diluted with 50 mL of water/ice and extracted with DCM. The organic extracts were combined, dried over anhydrous Na$_2$SO$_4$, and concentrated under reduced pressure affording 980 mg (crude) of [(1r,3r)-3-(3-phenyl-1,2-oxazole-5-amido)cyclobutyl]methyl 4-methylbenzene-1-sulfonate as a light yellow solid. LCMS (ES, m/z): [M+H]$^+$=427.1.

Step 3: 3-Phenyl-N-[(1r,3r)-3-[(4-formyl-1H-pyrazol-1-yl)methyl]cyclobutyl]-1,2-oxazole-5-carboxamide To a 50-mL round-bottom flask was placed a solution of [(1r,3r)-3-(3-phenyl-1,2-oxazole-5-amido)cyclobutyl]methyl 4-methylbenzene-1-sulfonate (980 mg, 2.30 mmol, 1.00 equiv) in DMF (20 mL), then 1H-pyrazole-4-carbaldehyde (331 mg, 3.44 mmol, 1.50 equiv) and Cs$_2$CO$_3$ (1.1 g, 3.37 mmol, 1.50 equiv) were added. The resulting solution was stirred for 3 h at 70° C., diluted with 50 mL of H$_2$O, filtered, and then extracted with EtOAc. The organic extracts were combined, dried over anhydrous Na$_2$SO$_4$, and concentrated under reduced pressure. The residue was applied onto a silica gel column and eluted with EtOAc/petroleum ether (1:3) affording 400 mg (50%) of 3-phenyl-N-[(1r,3r)-3-[(4-formyl-1H-pyrazol-1-yl)methyl]cyclobutyl]-1,2-oxazole-5-carboxamide as a white solid. LCMS (ES, m/z): [M+H]$^+$=351.1.

Step 4: 3-Phenyl-N-[(1r,3r)-3-[[4-(1-hydroxyethyl)-1H-pyrazol-1-yl]methyl]cyclobutyl]-1,2-oxazole-5-carboxamide To a 150-mL round-bottom flask was placed a solution of 3-phenyl-N-[(1r,3r)-3-[(4-formyl-1H-pyrazol-1-yl)methyl]cyclobutyl]-1,2-oxazole-5-carboxamide (600 mg, 1.71 mmol, 1.00 equiv) in THF (20 mL) then the solution was cooled to 5° C. To this solution was added MeMgBr (1M in hexane, 1.79 mL, 1.79 mmol, 4.00 equiv) at 5° C. under nitrogen. The resulting solution was stirred for 3 h at 5° C. The pH value of the solution was adjusted to 3 with 1M HCl, then the resulting solution was extracted with EtOAc. The organic extracts were combined, dried over anhydrous Na$_2$SO$_4$, and concentrated under reduced pressure. The residue was applied onto a silica gel column and eluted with EtOAc/petroleum ether (1:3) affording 440 mg (70%) of 3-phenyl-N-[(1r,3r)-3-[[4-(1-hydroxyethyl)-1H-pyrazol-1-yl]methyl]cyclobutyl]-1,2-oxazole-5-carboxamide as a yellow solid. LCMS (ES, m/z): [M+H]$^+$=367.2.

Step 5: 3-Phenyl-N-[(1r,3r)-3-([4-[(1S)-1-hydroxyethyl]-1H-pyrazol-1-yl]methyl)cyclobutyl]-1,2-oxazole-5-carboxamide (Front Peak) and 3-phenyl-N-[(1r,3r)-3-([4-[(1R)-1-hydroxyethyl]-1H-pyrazol-1-yl]methyl)cyclobutyl]-1,2-oxazole-5-carboxamide (Second Peak)

The crude N-(3-[[4-(1-hydroxyethyl)-1H-pyrazol-1-yl]methyl]cyclobutyl)-3-phenyl-1,2-oxazole-5-carboxamide (440 mg, 1.20 mmol, 1.00 equiv) was separated by Prep-SFC (Column: Phenomenex Lux 5u Cellulose-4£¬AXIA Packed, 250*21.2 mm, 5 um; Mobile Phase A: CO2: 60, Mobile Phase B: Hex: 40; Flow rate: 40 mL/min; 220 nm; RT1:5.12; RT2:6.06) affording 141.7 mg (32%) of 3-phenyl-N-[(1r,3r)-3-([4-[(1S)-1-hydroxyethyl]-1H-pyrazol-1-yl]methyl)cyclobutyl]-1,2-oxazole-5-carboxamide (front peak) as a white solid and 146.5 mg (33%) of 3-phenyl-N-[(1r,3r)-3-([4-[(1R)-1-hydroxyethyl]-1H-pyrazol-1-yl]methyl)cyclobutyl]-1,2-oxazole-5-carboxamide (second peak) as a red solid.

3-Phenyl-N-[(1r,3r)-3-([4-[(1S)-1-hydroxyethyl]-1H-pyrazol-1-yl]methyl)cyclobutyl]-1,2-oxazole-5-carboxamide (Front Peak)

LCMS (ES, m/z): [M+H−H$_2$O]$^+$=349.1. $^1$H NMR (300 MHz, DMSO-d$_6$): δ 9.26-9.23 (d, J=7.5 Hz, 1H), 7.93-7.90

(m, 2H), 7.62-7.60 (m, 2H), 7.54-7.52 (m, 3H), 7.32 (s, 1H), 4.85-4.83 (d, J=4.8 Hz, 1H), 4.71-4.63 (m, 1H), 4.55-4.47 (m, 1H), 4.20-4.17 (d, J=7.8 Hz, 2H), 2.68-2.64 (m, 1H), 2.27-2.10 (m, 4H), 1.33-1.31 (d, J=6.3 Hz, 3H). Purity (HPLC, 254 nm): 98.2%.

3-Phenyl-N-[(1r,3r)-3-([4-[(1R)-1-hydroxyethyl]-1H-pyrazol-1-yl]methyl)cyclobutyl]-1,2-oxazole-5-carboxamide (Second Peak)

LCMS (ES, m/z): [M+H–H$_2$O]$^+$=349.1. $^1$H NMR (300 MHz, DMSO-d$_6$): δ 9.26-9.24 (d, J=7.2 Hz, 1H), 7.93-7.90 (m, 2H), 7.64-7.60 (m, 2H), 7.54-7.52 (m, 3H), 7.32 (s, 1H), 4.85-4.84 (d, J=4.8 Hz, 1H), 4.71-4.63 (m, 1H), 4.58-4.45 (m, 1H), 4.20-4.17 (d, J=7.8 Hz, 2H), 2.68-2.64 (m, 1H), 2.27-2.10 (m, 4H), 1.33-1.31 (d, J=6.3 Hz, 3H). Purity (HPLC, 254 nm): 97.0%.

Examples 69 and 70: 3-Phenyl-N-[(1s,3s)-3-([4-[(1R)-1-hydroxyethyl]-1H-pyrazol-1-yl]methyl)cyclobutyl]-1,2-oxazole-5-carboxamide (Front Peak) and 3-phenyl-N-[(1s,3s)-3-([4-[(1S)-1-hydroxyethyl]-1H-pyrazol-1-yl]methyl)cyclobutyl]-1,2-oxazole-5-carboxamide (Second Peak)

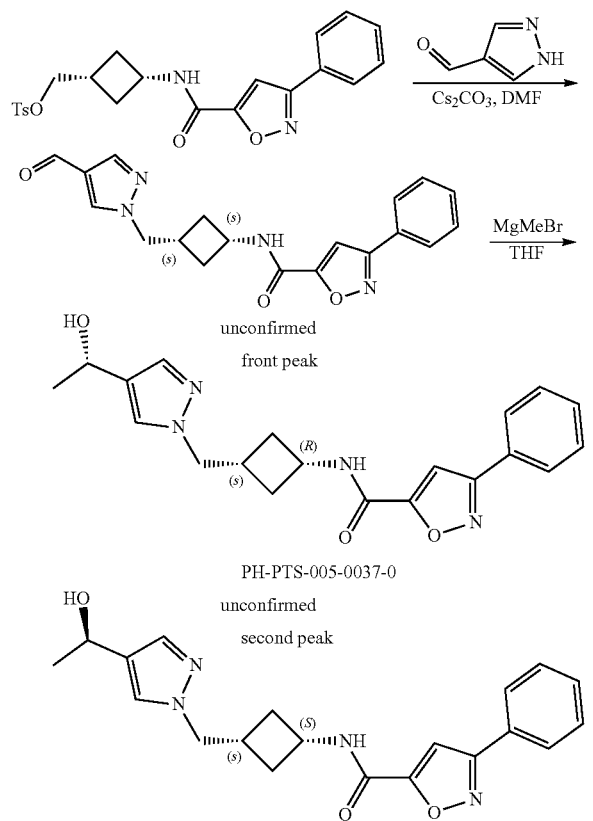

Step 1: 3-Phenyl-N-[(1s,3s)-3-[(4-formyl-1H-pyrazol-1-yl)methyl]cyclobutyl]-1,2-oxazole-5-carboxamide To a 50-mL round-bottom flask was placed a solution of [(1s,3s)-3-(3-phenyl-1,2-oxazole-5-amido)cyclobutyl]methyl 4-methylbenzene-1-sulfonate (1 g, 2.34 mmol, 1.00 equiv) in DMF (15 mL) then Cs$_2$CO$_3$ (1.5 g, 4.60 mmol, 2.00 equiv) and 1H-pyrazole-4-carbaldehyde (338 mg, 3.52 mmol, 1.50 equiv) were added. The resulting solution was stirred for 3 h at 100° C. then the solids were removed by filtration. The crude product was purified by Flash-Prep-HPLC (CombiFlash-1: Column, C18 silica gel; mobile phase, X: H$_2$O (0.5% NH$_4$HCO$_3$), Y: ACN, X/Y=90/10 increasing to X/Y=5/95 within 40 min; Detector, UV 254 nm) affording 460 mg (56%) of 3-phenyl-N-[(1s,3s)-3-[(4-formyl-1H-pyrazol-1-yl)methyl]cyclobutyl]-1,2-oxazole-5-carboxamide as a yellow solid. LCMS (ES, m/z): [M+H]$^+$=351.1.

Step 2: 3-Phenyl-N-[(1s,3s)-3-([4-[(1R)-1-hydroxyethyl]-1H-pyrazol-1-yl]methyl)cyclobutyl]-1,2-oxazole-5-carboxamide (Front Peak) and 3-phenyl-N-[(1s,3s)-3-([4-[(1S)-1-hydroxyethyl]-1H-pyrazol-1-yl]methyl)cyclobutyl]-1,2-oxazole-5-carboxamide (Second Peak)

To a 100-mL 3-necked round-bottom flask was placed a solution of 3-phenyl-N-[(1s,3 s)-3-[(4-formyl-1H-pyrazol-1-yl)methyl]cyclobutyl]-1,2-oxazole-5-carboxamide (460 mg, 1.31 mmol, 1.00 equiv) in THF (30 mL) then the solution was cooled to 0° C. To this solution was added MeMgBr (1.3 mL, 3.00 equiv) dropwise with stirring at 0° C. over 10 min. The resulting solution was stirred for 3 h at RT, quenched with 2N HCl (10 mL) and 50 mL of H$_2$O, and extracted with EtOAc (3×50 mL). The organic extracts were combined, washed with brine (3×50 mL), dried over anhydrous Na$_2$SO$_4$, and concentrated under reduced pressure. The residue was applied onto a silica gel column and eluted with EtOAc/petroleum ether (2:1). The product was purified by Chiral-Prep-HPLC (Prep-HPLC-004: Column, Chiralpak IB, 2*25 cm, 5 um; mobile phase, Hex and ethanol (hold 10.0% ethanol in 41 min); Detector, uv 254/220 nm) affording 132.3 mg (28%) of 3-phenyl-N-[(1 s,3 s)-3-([4-[(1R)-1-hydroxyethyl]-1H-pyrazol-1-yl]methyl)cyclobutyl]-1,2-oxazole-5-carboxamide front peak) as an off-white solid and 139.4 mg (29%) of 3-phenyl-N-[(1 s,3 s)-3-([4-[(1 S)-1-hydroxyethyl]-1H-pyrazol-1-yl]methyl)cyclobutyl]-1,2-oxazole-5-carboxamide (second peak) as an off-white solid.

3-Phenyl-N-[(1s,3s)-3-([4-[(1R)-1-hydroxyethyl]-1H-pyrazol-1-yl]methyl)cyclobutyl]-1,2-oxazole-5-carboxamide (Front Peak)

LCMS (ES, m/z): [M+H]$^+$=367.1. $^1$H NMR (300 MHz, DMSO-d$_6$) δ 9.21-9.18 (d, J=7.5 Hz, 1H), 7.94-7.91 (m, 2H), 7.62 (s, 1H), 7.55-7.51 (m, 3H), 7.48 (s, 1H), 7.32 (s, 1H), 4.85 (brs, 1H), 4.70-4.64 (q, J=6.6 Hz, 1H), 4.36-4.23 (m, 1H), 4.10-4.07 (d, J=6.9 Hz, 2H), 2.46-2.29 (m, 3H), 1.99-1.89 (m, 2H), 1.33-1.31 (d, J=6.3 Hz, 3H). Purity (HPLC, 254 nm): 96.4%.

3-Phenyl-N-[(1s,3s)-3-([4-[(1S)-1-hydroxyethyl]-1H-pyrazol-1-yl]methyl)cyclobutyl]-1,2-oxazole-5-carboxamide (Second Peak)

LCMS (ES, m/z): [M+H]$^+$=367.1. $^1$H NMR (300 MHz, DMSO-d$_6$) δ 9.21-9.18 (d, J=7.5 Hz, 1H), 7.92-7.87 (m, 2H), 7.68 (s, 1H), 7.61-7.48 (m, 4H), 7.31 (s, 1H), 4.85 (brs, 1H), 4.73-4.65 (m, 1H), 4.36-4.28 (m, 1H), 4.09-4.07 (d, J=6.6 Hz, 2H), 2.43-2.32 (m, 3H), 1.95-1.85 (m, 2H), 1.32-1.31 (d, J=5.1 Hz, 3H). Purity (HPLC, 254 nm): 96.0%.

Example 71: 3-Phenyl-N-[(1r,3r)-3-(4-fluorophenoxymethyl)cyclobutyl]-1,2-oxazole-5-carboxamide

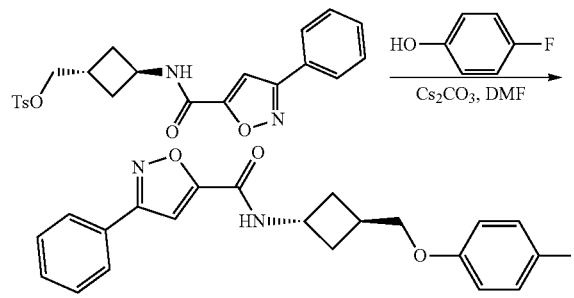

To a 50-mL round-bottom flask was placed a solution of [(1r,3r)-3-(3-phenyl-1,2-oxazole-5-amido)cyclobutyl] methyl 4-methylbenzene-1-sulfonate (550 mg, 1.29 mmol, 1.00 equiv) in DMF (10 mL), then 4-fluorophenol (217 mg, 1.94 mmol, 1.50 equiv) and Cs₂CO₃ (631 mg, 1.93 mmol, 1.50 equiv) were added. The resulting solution was stirred for 3 h at 70° C., then diluted with H₂O, and extracted with EtOAc. The organic extracts were combined, dried over anhydrous Na₂SO₄, and concentrated under reduced pressure. The residue was applied onto a silica gel column and eluted with EtOAc/petroleum ether (1:4). The resulting crude product was further purified by Prep-HPLC (Waters: Column, X Bridge Shield RP18 OBD Column, 5 um, 19*150 mm; mobile phase, water with 0.03% TFA and CH₃CN (10.0% CH₃CN up to 30% CH₃CN in 8 min, up to 100% in 4 min and down to 10% in 3 min); Detector, uv 254 nm and 220 nm) affording 152.3 mg (53%) of 3-phenyl-N-[(1r,3r)-3-(4-fluorophenoxymethyl)cyclobutyl]-1,2-oxazole-5-carboxamide as a white solid. LCMS (ES, m/z): [M+H]⁺=367.1. ¹H NMR (300 MHz, DMSO-d₆): δ 9.31-9.29 (d, J=7.2 Hz, 1H), 7.92-7.91 (m, 2H), 7.63 (s, 1H), 7.55-7.54 (m, 3H), 7.15-7.09 (m, 2H), 6.99-6.95 (m, 2H), 4.61-4.53 (m, 1H), 4.05-4.03 (d, J=6.9 Hz, 2H), 2.69-2.63 (m, 1H), 2.38-2.29 (m, 2H), 2.23-2.17 (m, 2H). Purity (HPLC, 254 nm): 97.4%.

Example 72: 3-phenyl-N-[(1s,3s)-3-(4-fluorophenoxymethyl)cyclobutyl]-1,2-oxazole-5-carboxamide

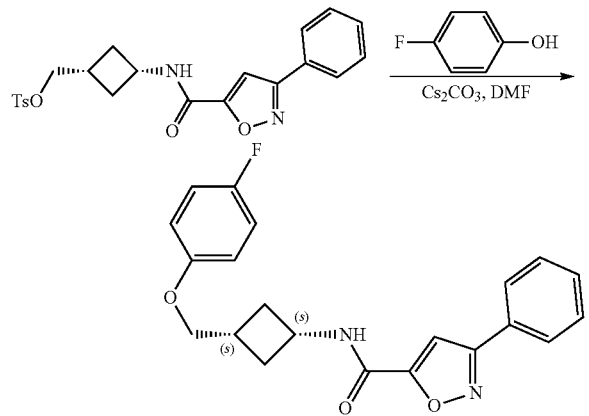

To a 25-mL round-bottom flask was placed a solution of [(1s,3s)-3-(3-phenyl-1,2-oxazole-5-amido)cyclobutyl] methyl 4-methylbenzene-1-sulfonate (213 mg, 0.50 mmol, 1.00 equiv) in DMF (5 mL), then Cs₂CO₃ (326 mg, 1.00 mmol, 2.00 equiv) and 4-fluorophenol (84 mg, 0.75 mmol, 1.50 equiv) were added. The resulting solution was stirred for 3 h at 100° C., then diluted with 50 mL of H₂O, and extracted with EtOAc (2×50 mL). The organic extracts were combined, washed with brine (2×50 mL), dried over anhydrous Na₂SO₄, and concentrated under reduced pressure. The crude product was purified by Prep-TLC (petroleum ether/ethyl acetate=1:2) affording 56.9 mg (31%) of 3-phenyl-N-[(1s,3 s)-3-(4-fluorophenoxymethyl)cyclobutyl]-1,2-oxazole-5-carboxamide as a white solid. LCMS (ES, m/z): [M+H]⁺=367.1. ¹H NMR (300 MHz, DMSO-d₆) δ 9.23-9.21 (d, J=7.5 Hz, 1H), 7.94-7.90 (m, 2H), 7.62 (s, 1H), 7.55-7.48 (m, 3H), 7.14-7.07 (m, 2H), 6.97-6.93 (m, 2H), 4.40-4.32 (m, 1H), 3.94-3.92 (d, J=5.1 Hz, 2H), 2.43-2.39 (m, 3H), 2.00-1.94 (m, 2H). Purity (HPLC, 254 nm): 99.5%.

Example 73: 3-phenyl-N-[(1r,3r)-3-(4-cyanophenoxymethyl)cyclobutyl]-1,2-oxazole-5-carboxamide

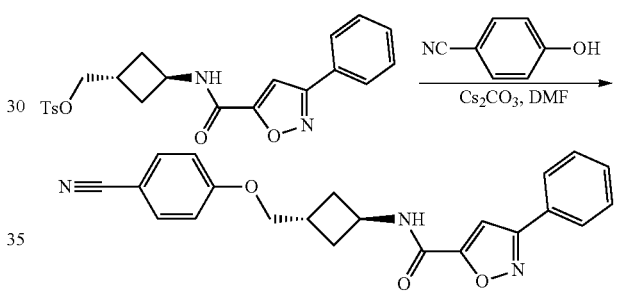

To a 50-mL round-bottom flask was placed a solution of [(1r,3r)-3-(3-phenyl-1,2-oxazole-5-amido)cyclobutyl] methyl 4-methylbenzene-1-sulfonate (560 mg, 1.31 mmol, 1.00 equiv) in DMF (10 mL), then 4-hydroxybenzonitrile (235 mg, 1.97 mmol, 1.50 equiv) and Cs₂CO₃ (643 mg, 1.97 mmol, 1.50 equiv) were added. The resulting solution was stirred for 2 h at 110° C., then diluted by the addition of water, and extracted with EtOAc. The organic extracts were combined, was washed with H₂O, dried over anhydrous Na₂SO₄, and concentrated under reduced pressure. This residue was purified by Prep-HPLC (Waters: Column, X Bridge Prep C18 5 um, 19*150 mm; mobile phase, water with 0.03% TFA and CH₃CN (10.0% CH₃CN up to 30% CH₃CN in 6 min, up to 100% in 5 min and down to 10% in 2 min); Detector, uv 254 nm and 220 nm) affording 129.9 mg (87%) of 3-phenyl-N-[(1r,3r)-3-(4-cyanophenoxymethyl)cyclobutyl]-1,2-oxazole-5-carboxamide as a white solid. LCMS-PH-PTS (ES, m/z): [M+H]⁺=374.1. ¹H NMR (300 MHz, DMSO-d₆): δ 9.32-9.30 (d, J=7.5 Hz, 1H), 7.94-7.91 (m, 2H), 7.78-7.76 (d, J=8.7 Hz, 2H), 7.63 (s, 1H), 7.55-7.54 (m, 3H), 7.15-7.12 (m, J=8.7 Hz, 2H), 4.63-4.55 (m, 1H), 4.19-4.17 (d, J=6.9 Hz, 2H), 2.72-2.66 (m, 1H), 2.40-2.30 (m, 2H), 2.24-2.18 (m, 2H). Purity (HPLC, 254 nm): 97.3%.

Example 74: 3-Phenyl-N-[(1s,3s)-3-(4-cyanophenoxymethyl)cyclobutyl]-1,2-oxazole-5-carboxamide

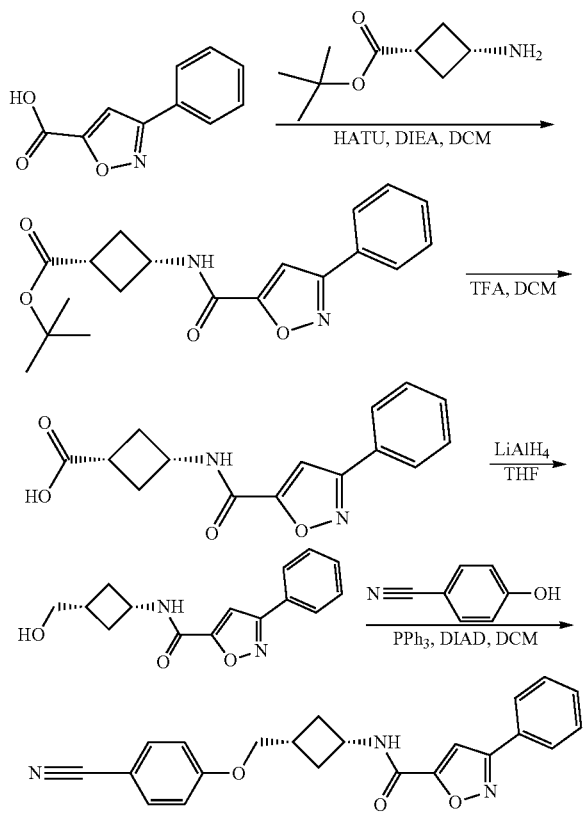

Step 1: tert-Butyl (1s,3s)-3-(3-Phenyl-1,2-oxazole-5-amido)cyclobutane-1-carboxylate To a 100-mL round-bottom flask was placed a solution of tert-butyl (1s,3s)-3-aminocyclobutane-1-carboxylate (1.7 g, 9.93 mmol, 1.00 equiv) in DCM (50 mL), then 3-phenyl-1,2-oxazole-5-carboxylic acid (1.9 g, 10.04 mmol, 1.00 equiv), HATU (5.7 g, 14.99 mmol, 1.50 equiv) and DIEA (3.9 g, 30.18 mmol, 3.00 equiv) were added. The resulting solution was stirred for 1 h at RT, then quenched by the addition of water, and extracted with EtOAc. The organic extracts were combined, washed with brine, dried over anhydrous Na$_2$SO$_4$, and concentrated under reduced pressure. The residue was applied onto a silica gel column and eluted with EtOAc/petroleum ether (1:7) affording 2 g (59%) of tert-butyl (1s,3s)-3-(3-phenyl-1,2-oxazole-5-amido)cyclobutane-1-carboxylate as a white solid. LCMS (ES, m/z): [M+Na]$^+$=365.1.

Step 2: (1s,3s)-3-(3-Phenyl-1,2-oxazole-5-amido)cyclobutane-1-carboxylic acid To a 100-mL round-bottom flask was placed a solution of tert-butyl (1s,3s)-3-(3-phenyl-1,2-oxazole-5-amido)cyclobutane-1-carboxylate (2 g, 5.84 mmol, 1.00 equiv) in DCM (20 mL) and TFA (7 mL). The resulting solution was stirred for 4 h at RT, then the solvent was removed under reduced pressure affording 1.8 g (crude) of (1s,3s)-3-(3-phenyl-1,2-oxazole-5-amido)cyclobutane-1-carboxylic acid as an off-white solid. LCMS (ES, m/z): [M+H]$^+$=286.8.

Step 3: 3-Phenyl-N-[(1s,3s)-3-(hydroxymethyl)cyclobutyl]-1,2-oxazole-5-carboxamide To a 100-mL round-bottom flask was placed a solution of (1s,3s)-3-(3-phenyl-1,2-oxazole-5-amido)cyclobutane-1-carboxylic acid (1 g, 2.79 mmol, 1.00 equiv, 80%) in THF (25 mL), then the solution was cooled to 0° C. To this solution was added LiAlH$_4$ (425 mg, 11.18 mmol, 4.00 equiv) in portions at 0° C., then the resulting solution was stirred for 1 h at 10° C. The reaction was quenched by the addition of Na$_2$SO$_4$.10H$_2$O, then the solids were removed by filtration, and the filtrate was concentrated under reduced pressure. The residue was applied onto a silica gel column and eluted with EtOAc/petroleum ether (1:2) affording 420 mg (55%) of 3-phenyl-N-[(1s,3s)-3-(hydroxymethyl)cyclobutyl]-1,2-oxazole-5-carboxamide as a white solid. LCMS (ES, m/z): [M+H]$^+$=273.1.

Step 4: 3-Phenyl-N-[(1s,3s)-3-(4-cyanophenoxymethyl)cyclobutyl]-1,2-oxazole-5-carboxamide To a 100-mL 3-necked round-bottom flask purged and maintained with an inert atmosphere of nitrogen, was placed a solution of 3-phenyl-N-[(1s,3s)-3-(hydroxymethyl)cyclobutyl]-1,2-oxazole-5-carboxamide (420 mg, 1.31 mmol, 1.00 equiv, 85%), 4-hydroxybenzonitrile (320 mg, 2.69 mmol, 2.00 equiv) and PPh$_3$ (1.08 g, 4.12 mmol, 3.00 equiv) in THF (10 mL). This was followed by the addition of DIAD (840 mg, 4.15 mmol, 3.00 equiv) dropwise with stirring at 0° C. The resulting solution was stirred for 2 h at RT. The reaction was quenched by the addition of water, then extracted with EtOAc. The organic extracts were combined, washed with brine, dried over anhydrous Na$_2$SO$_4$, and concentrated under reduced pressure. The crude product was purified by Flash-Prep-HPLC (IntelFlash-1: Column, C18; mobile phase, MeCN/H$_2$O=5:95 increasing to MeCN/H$_2$O=50:50 within 20 min; Detector, UV 254 nm) affording 148.5 mg (30%) of 3-phenyl-N-[(1s,3s)-3-(4-cyanophenoxymethyl)cyclobutyl]-1,2-oxazole-5-carboxamide as a white solid. LCMS (ES, m/z): [M+H]$^+$=374.2. $^1$H NMR (400 MHz, DMSO-d$_6$): δ 9.25-9.24 (d, J=7.6 Hz, 1H), 7.94-7.92 (m, 2H), 7.79-7.76 (m, 2H), 7.64 (s, 1H), 7.55-7.53 (m, 3H), 7.16-7.12 (m, 2H), 4.43-4.35 (p, J=8.0 Hz, 1H), 4.08-4.06 (d, J=6.0 Hz, 2H), 2.45-2.40 (m, 3H), 2.02-1.97 (m, 2H). Purity (HPLC, 254 nm): 98.2%.

Example 75 and 76: 3-(5-Fluorothiophen-2-yl)-N-[(1s,3s)-3-([5-[(1R)-1-hydroxyethyl]-1,3,4-oxadiazol-2-yl]methyl)cyclobutyl]-1,2-oxazole-5-carboxamide and 3-(5-Fluorothiophen-2-yl)-N-[(1r,3r)-3-([5-[(1R)-1-hydroxyethyl]-1,3,4-oxadiazol-2-yl]methyl)cyclobutyl]-1,2-oxazole-5-carboxamide

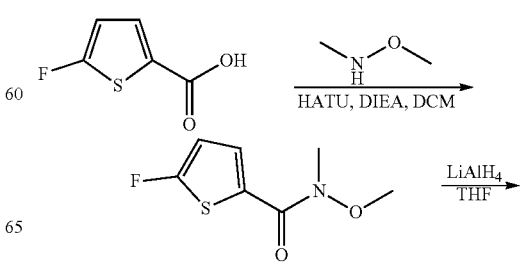

143

-continued

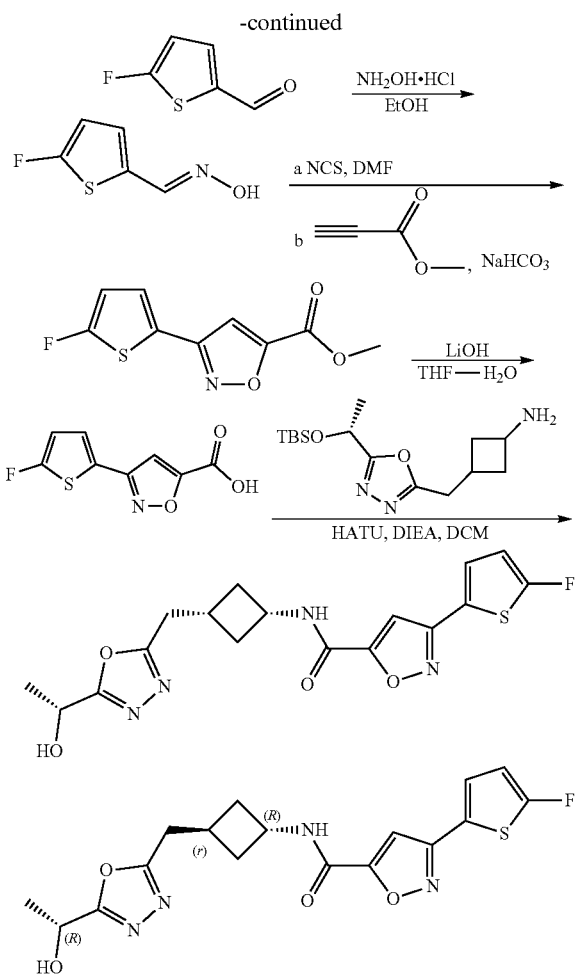

Step 1: 5-Fluoro-N-methoxy-N-methylthiophene-2-carboxamide

To a 100-mL round-bottom flask was placed a solution of 5-fluorothiophene-2-carboxylic acid (1 g, 6.84 mmol, 1.00 equiv) in DCM (50 mL), then methoxy(methyl)amine hydrochloride (730 mg, 7.53 mmol, 1.10 equiv), HATU (3.9 g, 10.26 mmol, 1.50 equiv), and DIEA (2.82 mL, 3.00 equiv) were added. The reaction was stirred for 3 h at room temperature, diluted with $H_2O$, and extracted with DCM (2×100 mL). The organic extracts were combined, washed with brine (2×50 mL), dried over anhydrous $Na_2SO_4$, and concentrated under reduced pressure. The residue was applied onto a silica gel column and eluted with EtOAc/petroleum ether (1:4) affording 1.14 g (88%) of 5-fluoro-N-methoxy-N-methylthiophene-2-carboxamide as a yellow liquid. LCMS (ES, m/z): $[M+H]^+$=190.0.

Step 2: (E)-N-[(5-Fluorothiophen-2-yl)methylidene]hydroxylamine

To a 50-mL round-bottom flask was placed a solution of 5-fluoro-N-methoxy-N-methylthiophene-2-carboxamide (1.14 g, 6.03 mmol, 1.00 equiv) in THF (20 mL), then $LiAlH_4$ (342 mg, 9.01 mmol, 1.20 equiv) was added. The action was stirred for 1 h at room temperature, then quenched by the addition of 20 mL of $H_2O$/ice, and extracted with EtOAc (2×20 mL). The organic extracts were dried and used directly in the next step.

To a 250-mL round-bottom flask was placed a solution of 5-fluorothiophene-2-carbaldehyde (780 mg, 5.99 mmol, 1.00 equiv) in EtOH/EtOAc (120 mL), then $NH_2OH \cdot HCl$ (0.5 g, 1.20 equiv) was added. The resulting solution was stirred for 3 h at room temperature then the solvent was removed under reduced pressure. The residue was dissolved in $H_2O$ (50 mL), then the resulting solution was extracted with EtOAc (3×100 mL). The organic extracts were combined, washed with brine (2×100 mL), dried over anhydrous $Na_2SO_4$, and concentrated under reduced pressure affording 650 mg (75%) of (E)-N-[(5-fluorothiophen-2-yl)methylidene]hydroxylamine as a yellow solid. LCMS (ES, m/z): $[M+H]^+$=146.0.

Step 3: Methyl 3-(5-Fluorothiophen-2-yl)-1,2-oxazole-5-carboxylate

To a 25-mL round-bottom flask was placed a solution of (E)-N-[(5-fluorothiophen-2-yl)methylidene]hydroxylamine (300 mg, 2.07 mmol, 1.00 equiv) DMF (5 mL), then NCS (414 mg, 3.11 mmol, 1.50 equiv) was added in small portions. The resulting solution was stirred for 1 h at room temperature, then methyl prop-2-ynoate (0.27 mL, 2.00 equiv) was added followed by $Na_2CO_3$ (260 mg, 3.09 mmol, 1.50 equiv) in small portions. The reaction was stirred for 2 h at room temperature, diluted with 50 mL of $H_2O$, and extracted with EtOAc (3×100 mL). The organic extracts were combined, washed with brine (2×50 mL), dried over anhydrous $Na_2SO_4$, and concentrated under vacuum. The residue was purified by prep TLC (ethyl acetate/petroleum ether=1/3) affording 200 mg (43%) of methyl 3-(5-fluorothiophen-2-yl)-1,2-oxazole-5-carboxylate as a yellow solid.

Step 4: 3-(5-fluorothiophen-2-yl)-1,2-oxazole-5-carboxylic acid

To a 50-mL round-bottom flask was placed a solution of methyl 3-(5-fluorothiophen-2-yl)-1,2-oxazole-5-carboxylate (254 mg, 1.12 mmol, 1.00 equiv) in THF-$H_2O$ (3:1, 10 mL), then LiOH (52 mg, 2.17 mmol, 2.00 equiv) was added. The reaction was stirred for 1 h at room temperature, diluted with $H_2O$ (20 mL), and washed with ethyl acetate (2×50 mL). The pH of the aqueous layer was adjusted to 3 with 1M HCl, then the resulting solution was extracted with EtOAc (3×50 mL). The organic extracts were combined, was washed with brine (2×50 mL), dried over anhydrous $Na_2SO_4$, and concentrated under reduced pressure affording 170 mg (71%) of 3-(5-fluorothiophen-2-yl)-1,2-oxazole-5-carboxylic acid as a yellow solid. LCMS (ES, m/z): $[M+H]^+$=214.1.

Step 5: 3-(5-Fluorothiophen-2-yl)-N-[(1s,3s)-3-([5-[(1R)-1-hydroxyethyl]-1,3,4-oxadiazol-2-yl]methyl)cyclobutyl]-1,2-oxazole-5-carboxamide and 3-(5-Fluorothiophen-2-yl)-N-[(1r,3r)-3-([5-[(1R)-1-hydroxyethyl]-1,3,4-oxadiazol-2-yl]methyl)cyclobutyl]-1,2-oxazole-5-carboxamide To a 50-mL round-bottom flask was placed a solution of 3-(5-fluorothiophen-2-yl)-1,2-oxazole-5-carboxylic acid (170 mg, 0.80 mmol, 1.00 equiv) in DCM (20 mL), then 3-([5-[(1R)-1-[(tert-butyldimethylsilyl)oxy]ethyl]-1,3,4-oxadiazol-2-yl]methyl)cyclobutan-1-amine (273 mg, 0.88 mmol, 1.10 equiv), HATU (455 mg, 1.20 mmol, 1.50 equiv), and DIEA (0.33 mL, 3.00 equiv) were added. The reaction was stirred for 3 h at room temperature, diluted with H₂O, and extracted with DCM. The organic extracts were combined, washed with brine (2×30 mL), dried over anhydrous Na₂SO₄, and concentrated under reduced pressure. The residue was purified by Prep-TLC (EtOAc/petroleum ether=1/4), then the resulting pure isomers were separated by Chiral-Prep-HPLC (Prep-HPLC-032: Column, Lux 5u Cellulose-4, AXIA Packed, 250*21.2 mm; mobile phase, Hex and IPA (hold 30.0% IPA in 21 min); Detector, UV 254/220 nm) affording 37.2 mg (19%) of 3-(5-fluorothiophen-2-yl)-N-[(1 s,3 s)-3-([5-[(1R)-1-hydroxyethyl]-1,3,4-oxadiazol-2-yl]methyl)cyclobutyl]-1,2-oxazole-5-carboxamide as a white solid and 9.4 mg (5%) of 3-(5-fluorothiophen-2-yl)-N-[(1r,3r)-3-([5-[(1R)-1-hydroxyethyl]-1,3,4-oxadiazol-2-yl]methyl)cyclobutyl]-1,2-oxazole-5-carboxamide as a white solid.

3-(5-Fluorothiophen-2-yl)-N-[(1s,3s)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=393.1. ¹H NMR (300 MHz, DMSO-d₆): δ 9.23-9.20 (d, J=7.8 Hz, 1H), 7.61 (s, 1H), 7.57-7.55 (t, J=3.9 Hz, 2H), 6.94-6.92 (m, 1H), 5.91-5.89 (d, J=5.7 Hz, 1H), 4.92-4.83 (m, 1H), 4.33-4.23 (m, 1H), 2.97-2.95 (d, J=6.3 Hz, 2H), 2.46-2.33 (m, 3H), 1.96-1.90 (m, 2H), 1.45-1.43 (d, J=6.6 Hz, 3H). Purity (HPLC, 254 nm): 98.8%.

3-(5-Fluorothiophen-2-yl)-N-[(1r,3r)-3-([5-[(1R)-1-hydroxyethyl]-1,3,4-oxadiazol-2-yl]methyl)cyclobutyl]-1,2-oxazole-5-carboxamide LCMS (ES, m/z): [M+H]⁺=393.1. ¹H NMR (300 MHz, DMSO-d₆): δ 9.33-9.31 (d, J=7.2 Hz, 1H), 7.62 (s, 1H), 7.57-7.54 (t, J=4.2 Hz, 1H), 6.94-6.92 (m, 1H), 5.92-5.90 (d, J=5.7 Hz, 1H), 4.92-4.84 (m, 1H), 4.57-4.49 (m, 1H), 3.09-3.06 (d, J=7.8 Hz, 2H), 2.72-2.64 (m, 1H), 2.37-2.27 (m, 2H), 2.17-2.12 (m, 2H), 1.46-1.43 (d, J=6.6 Hz, 3H). Purity (HPLC, 254 nm): 99.3%.

Example 77: CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% CO₂ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilized, the chambers are clamped, and data is recorded by pulse readings every 5 seconds. Following baseline current stabilization, the following additions can be applied and the changes in current and resistance of the cells can be monitored:

1. Benzamil to the apical chamber to inhibit ENaC sodium channel.
2. Forskolin to both chambers to activate ΔF508-CFTR by phosphorylation.
3. Genistein to both chambers to potentiate ΔF508-CFTR channel opening.
4. CFTRinh-172 to the apical chamber to inhibit ΔF508-CFTR Cl— conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% CO₂ for 24 hours. At the end of the treatment period, the media was changed to the Ieq experimental solution for 30 minutes before the experiment and plates are maintained in a CO₂-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:

1. The baseline $V_T$ and $G_T$ values were measured for approximately 20 minutes.
2. Benzamil was added to block ENaC for 15 minutes.
3. Forskolin plus VX-770 were added to maximally activate ΔF508-CFTR for 27 minutes.
4. Bumetanide was added to inhibit the NaK₂Cl cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples.

The results are shown below in Table 2. ++ indicates activity ≥25% run at 10 uM of VX-809 at 1 uM, + indicates activity 10 to <25% run at 10 uM of VX-809 at 1 uM, **indicates activity ≥200% of VX-809 (1 uM) with compound at 10 uM and VX-809 at 1 uM; * indicates activity 100-200% of VX-809 (1 uM) with compound at 10 uM and VX-809 at 1 uM. ## indicates activity ≥200% of VX-809 (3 uM) with compound at 10 uM and VX-809 at 3 uM; # indicates activity 100-200% of VX-809 (3 uM) with compound at 10 uM and VX-809 at 3 uM.

TABLE 2

| # | Structure | Ieq | Ussing |
|---|---|---|---|
| 1 | 3-phenyl-N-(2-methoxyethyl)isoxazole-5-carboxamide | ++ | |
| 2 | 3-phenyl-N-((tetrahydrofuran-2-yl)methyl)isoxazole-5-carboxamide | ++ | |
| 3 | 3-phenyl-N-(2-morpholinoethyl)isoxazole-5-carboxamide | ++ | |
| 4 | 3-phenyl-N-(3-(1H-imidazol-1-yl)propyl)isoxazole-5-carboxamide | + | |
| 5 | 3-phenyl-N-(trans-3-(5-(hydroxymethyl)-1H-1,2,3-triazol-1-yl)cyclobutyl)isoxazole-5-carboxamide | | ## |
| 6 | 3-phenyl-N-(trans-3-(5-((S)-1-hydroxyethyl)-1,3,4-oxadiazol-2-yl)cyclobutyl)isoxazole-5-carboxamide | * | ## |
| 7 | 3-phenyl-N-(3-(1-methyl-1H-pyrazol-5-yl)propyl)isoxazole-5-carboxamide | ++, * | |
| 8 | 4-phenyl-N-(2-methoxyethyl)furan-2-carboxamide | + | |

TABLE 2-continued

| # | Structure | Ieq | Ussing |
|---|-----------|-----|--------|
| 9 | 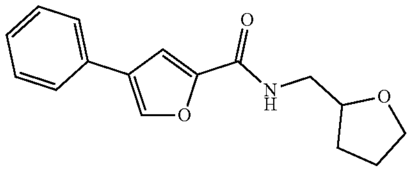 [SMILES: O=C(NCC1CCCO1)c1cc(-c2ccccc2)co1] | ++ | |
| 10 | 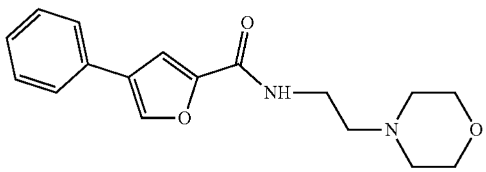 [SMILES: O=C(NCCN1CCOCC1)c1cc(-c2ccccc2)co1] | + | |
| 11 | 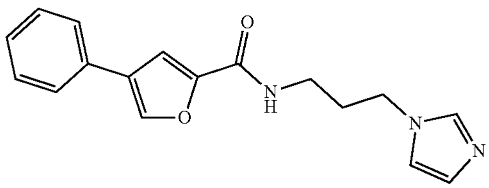 [SMILES: O=C(NCCCn1ccnc1)c1cc(-c2ccccc2)co1] | ++ | |
| 12 | 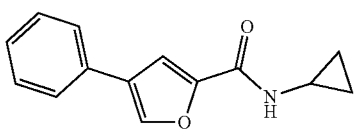 [SMILES: O=C(NC1CC1)c1cc(-c2ccccc2)co1] | ++, * | |
| 13 | 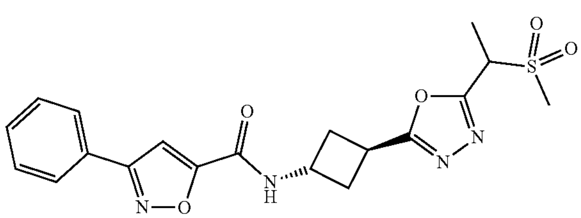 | | |
| 14 | 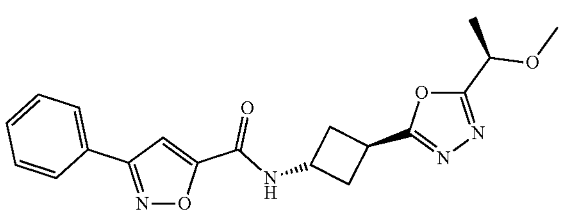 | * | |
| 15 | 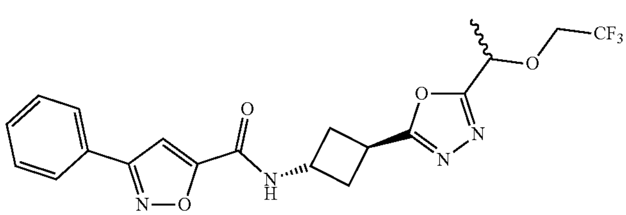 | * | |
| 16 | 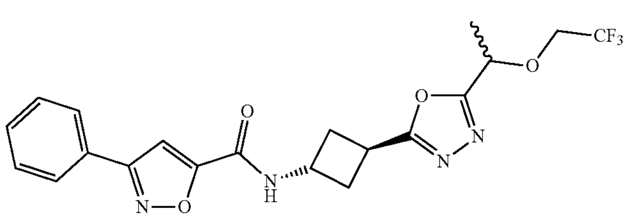 | | |

TABLE 2-continued
| # | Structure | Ieq | Ussing |
|---|---|---|---|
| 17 | 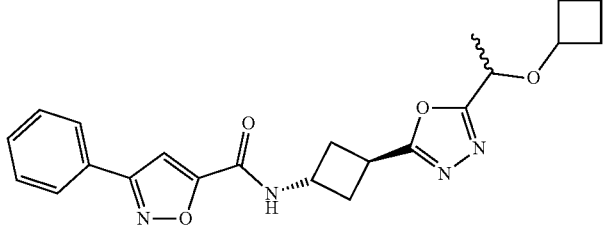 | * | |
| 18 | 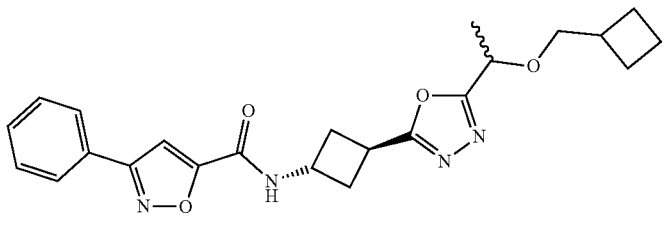 | | |
| 19 | 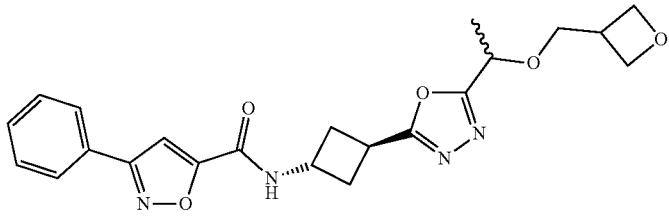 | | |
| 20 | 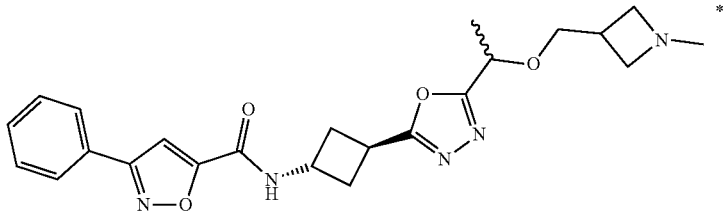 | * | |
| 21 | 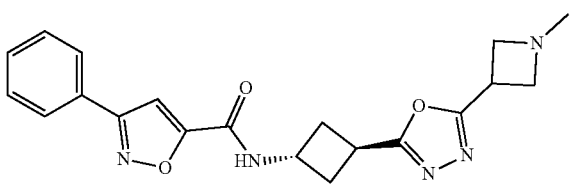 [SMILES: CN1CC(c2nnc([C@H]3C[C@H](NC(=O)c4cc(-c5ccccc5)no4)C3)o2)C1] | * | |
| 22 | 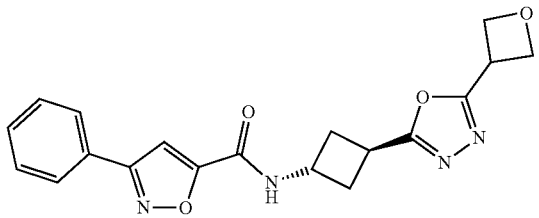 | * | |
| 23 | 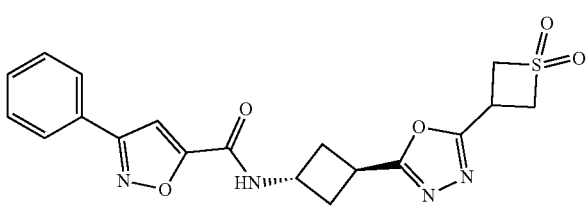 [SMILES: O=C(N[C@H]1C[C@H](c2nnc(C3CS(=O)(=O)C3)o2)C1)c1cc(-c2ccccc2)no1] | * | |

TABLE 2-continued

| # | Structure | Ieq | Ussing |
|---|-----------|-----|--------|
| 24 | 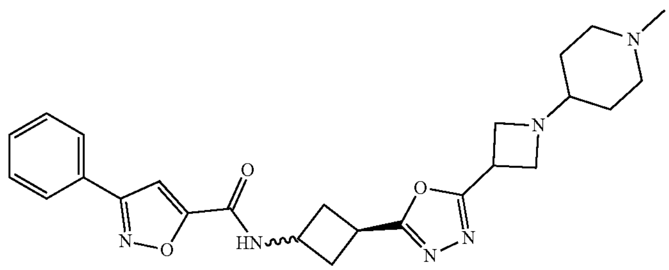 | * | |
| 25 | 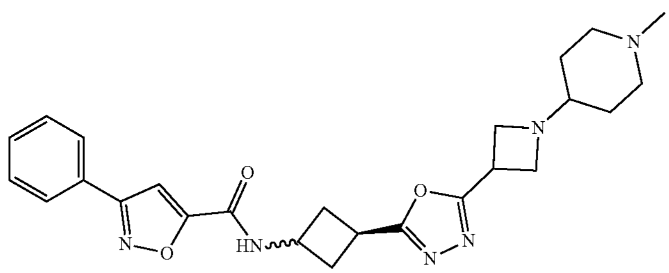 | * | |
| 26 | 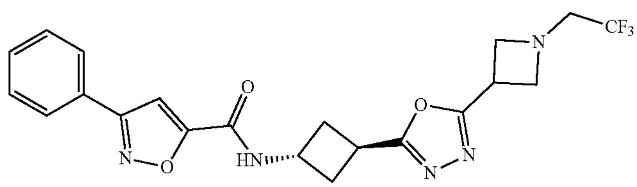 [SMILES: O=C(N[C@H]1C[C@H](c2nnc(C3CN(CC(F)(F)F)C3)o2)C1)c1cc(-c2ccccc2)no1] | | |
| 27 | 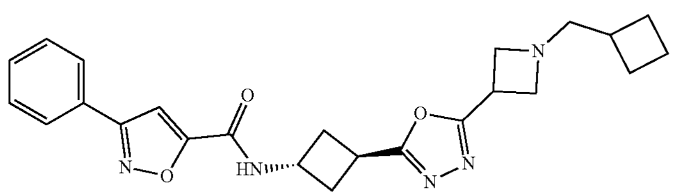 [SMILES: O=C(N[C@H]1C[C@H](c2nnc(C3CN(CC4CCC4)C3)o2)C1)c1cc(-c2ccccc2)no1] | * | |
| 28 | 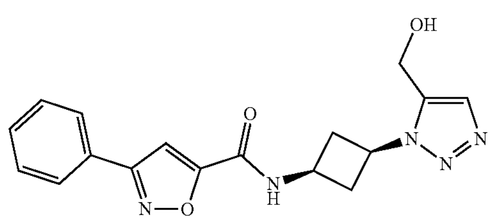 [SMILES: O=C(N[C@H]1C[C@@H](n2nncc2CO)C1)c1cc(-c2ccccc2)no1] | ** | |
| 29 | 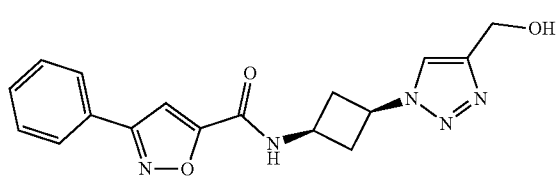 [SMILES: O=C(N[C@H]1C[C@@H](n2cc(CO)nn2)C1)c1cc(-c2ccccc2)no1] | ** | |
| 30 | 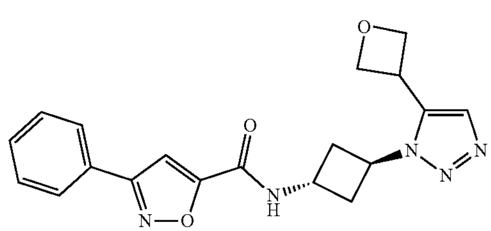 [SMILES: O=C(N[C@H]1C[C@H](n2nncc2C2COC2)C1)c1cc(-c2ccccc2)no1] | * | |

TABLE 2-continued

| # | Structure | Ieq | Ussing |
|---|---|---|---|
| 31 | 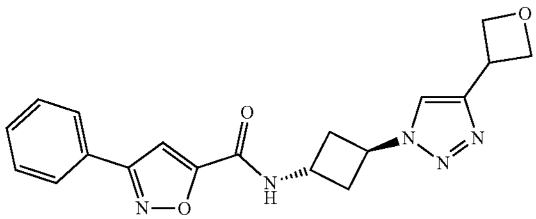 | | |
| 32 | 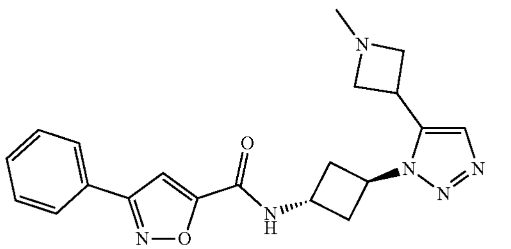 [SMILES: CN1CC(c2cnnn2[C@H]2C[C@H](NC(=O)c3cc(-c4ccccc4)no3)C2)C1] | | |
| 33 | 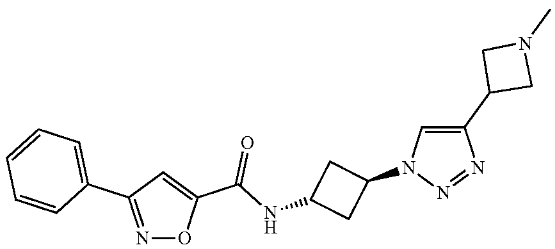 | | |
| 34 | 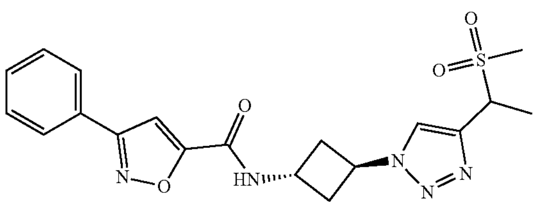 [SMILES: CC(c1cn([C@H]2C[C@H](NC(=O)c3cc(-c4ccccc4)no3)C2)nn1)S(C)(=O)=O] | | |
| 35 | 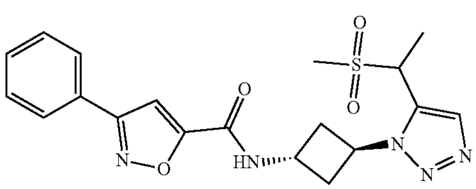 [SMILES: CC(c1cnnn1[C@H]1C[C@H](NC(=O)c2cc(-c3ccccc3)no2)C1)S(C)(=O)=O] | | * |
| 36 | 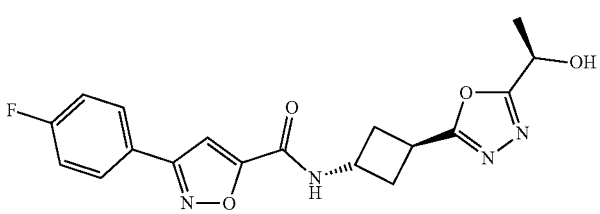 | | * |
| 37 | 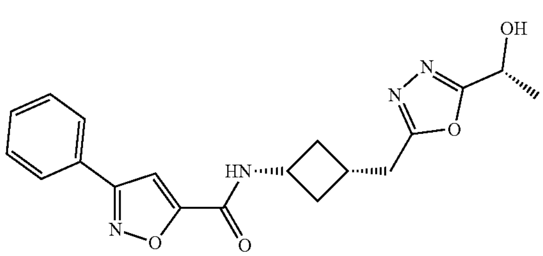 | | ** |

TABLE 2-continued
| # | Structure | Ieq | Ussing |
|---|---|---|---|
| 38 | 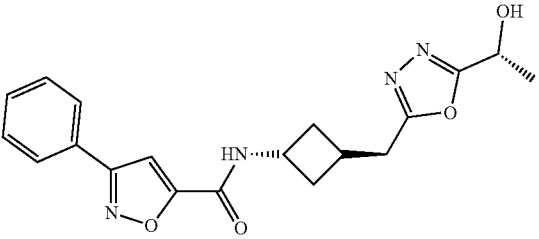 | ** | |
| 39 | 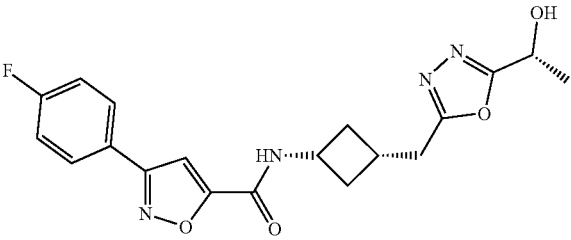 | | |
| 40 | 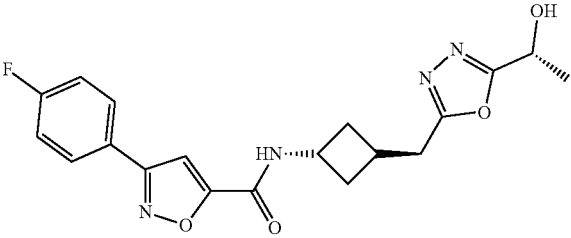 | ** | |
| 41 | 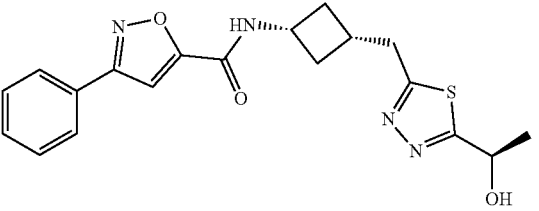 [SMILES: C[C@@H](O)c1nnc(C[C@H]2C[C@@H](NC(=O)c3cc(-c4ccccc4)no3)C2)s1] | ** | |
| 42 | 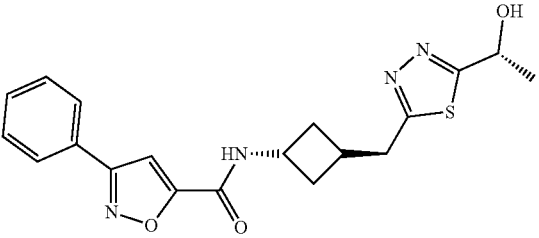 | * | |
| 43 | 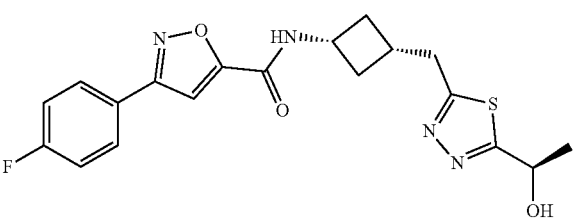 [SMILES: C[C@@H](O)c1nnc(C[C@H]2C[C@@H](NC(=O)c3cc(-c4ccc(F)cc4)no3)C2)s1] | ** | |

TABLE 2-continued

| # | Structure | Ieq | Ussing |
|---|---|---|---|
| 44 | 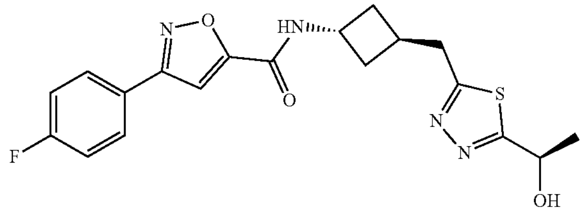 [SMILES: C[C@@H](O)c1nnc(C[C@H]2C[C@H](NC(=O)c3cc(-c4ccc(F)cc4)no3)C2)s1] | ** | |
| 45 | 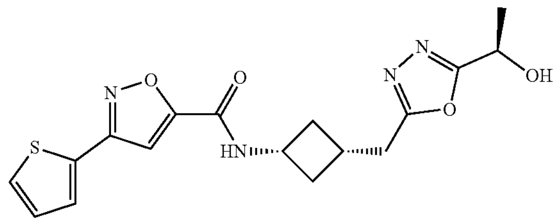 [SMILES: C[C@@H](O)c1nnc(C[C@H]2C[C@@H](NC(=O)c3cc(-c4cccs4)no3)C2)o1] | * | |
| 46 | 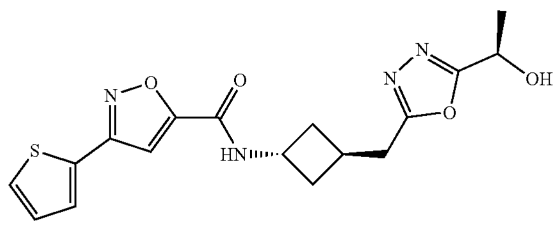 [SMILES: C[C@@H](O)c1nnc(C[C@H]2C[C@H](NC(=O)c3cc(-c4cccs4)no3)C2)o1] | * | |
| 47 | 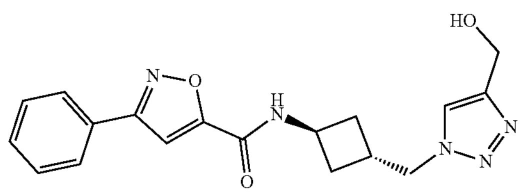 [SMILES: O=C(N[C@H]1C[C@H](Cn2cc(CO)nn2)C1)c1cc(-c2ccccc2)no1] | * | |
| 48 | 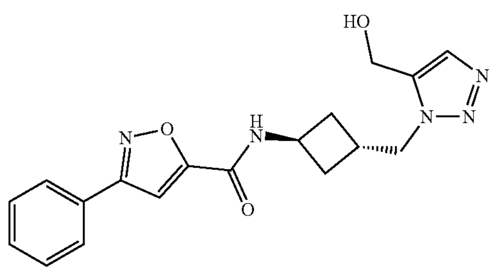 [SMILES: O=C(N[C@H]1C[C@H](Cn2nncc2CO)C1)c1cc(-c2ccccc2)no1] | | |
| 49 | 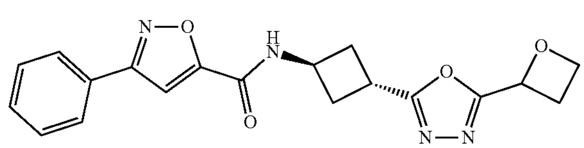 [SMILES: O=C(N[C@H]1C[C@H](c2nnc(C3CCO3)o2)C1)c1cc(-c2ccccc2)no1] | | |
| 50 | 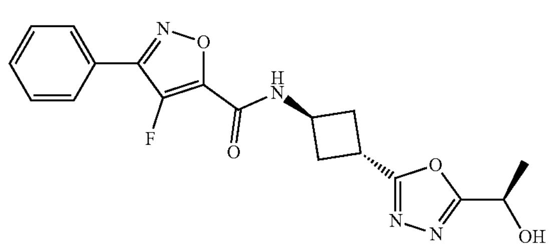 [SMILES: C[C@@H](O)c1nnc([C@H]2C[C@H](NC(=O)c3onc(-c4ccccc4)c3F)C2)o1] | * | |

TABLE 2-continued

| # | Structure | Ieq | Ussing |
|---|-----------|-----|--------|
| 51 | 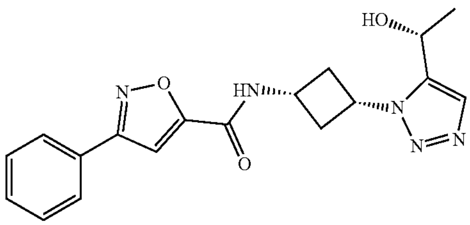 [SMILES: C[C@@H](O)c1cnnn1[C@H]1C[C@@H](NC(=O)c2cc(-c3ccccc3)no2)C1] | | |
| 52 | 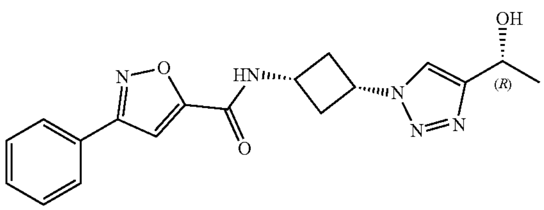 | | |
| 53 | 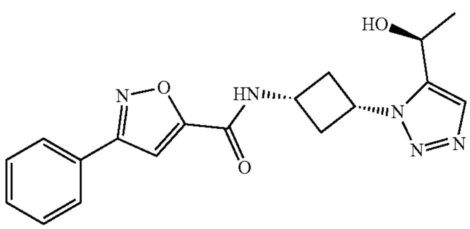 [SMILES: C[C@H](O)c1cnnn1[C@H]1C[C@@H](NC(=O)c2cc(-c3ccccc3)no2)C1] | | |
| 54 | 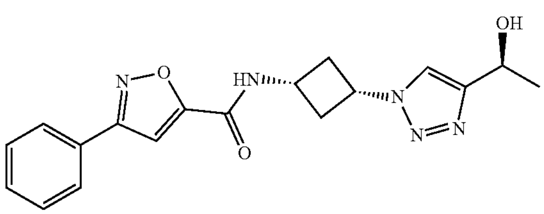 [SMILES: C[C@H](O)c1cn([C@H]2C[C@@H](NC(=O)c3cc(-c4ccccc4)no3)C2)nn1] | | |
| 55 | 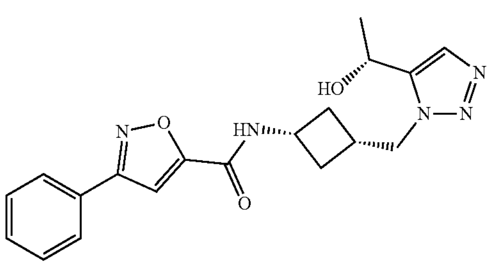 [SMILES: C[C@@H](O)c1cnnn1C[C@H]1C[C@@H](NC(=O)c2cc(-c3ccccc3)no2)C1] | | |
| 56 | 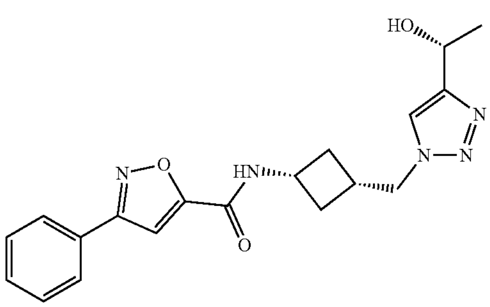 [SMILES: C[C@@H](O)c1cn(C[C@H]2C[C@@H](NC(=O)c3cc(-c4ccccc4)no3)C2)nn1] | | |

TABLE 2-continued

| # | Structure | Ieq | Ussing |
|---|-----------|-----|--------|
| 57 | 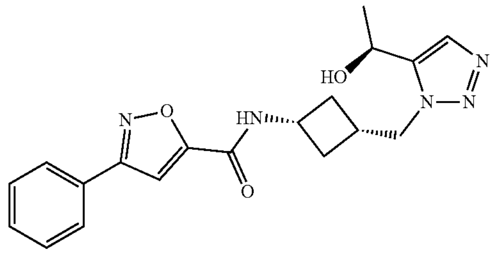 [SMILES: C[C@H](O)c1cnnn1C[C@H]1C[C@@H](NC(=O)c2cc(-c3ccccc3)no2)C1] | | ** |
| 58 | 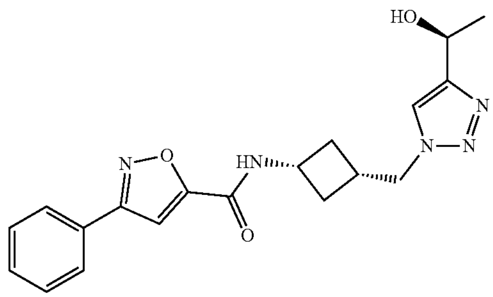 [SMILES: C[C@H](O)c1cn(C[C@H]2C[C@@H](NC(=O)c3cc(-c4ccccc4)no3)C2)nn1] | | * |
| 59 | 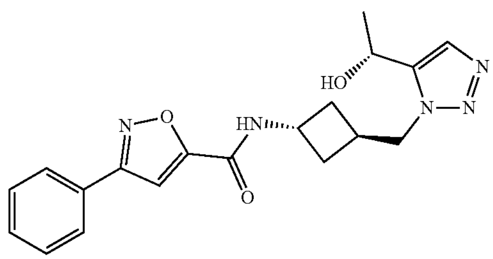 [SMILES: C[C@@H](O)c1cnnn1C[C@H]1C[C@H](NC(=O)c2cc(-c3ccccc3)no2)C1] | | |
| 60 | 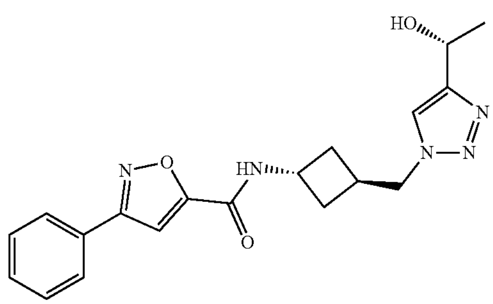 [SMILES: C[C@@H](O)c1cn(C[C@H]2C[C@H](NC(=O)c3cc(-c4ccccc4)no3)C2)nn1] | | |
| 61 | 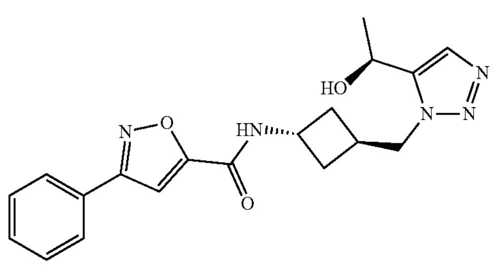 [SMILES: C[C@H](O)c1cnnn1C[C@H]1C[C@H](NC(=O)c2cc(-c3ccccc3)no2)C1] | | |

TABLE 2-continued

| # | Structure | Ieq | Ussing |
|---|-----------|-----|--------|
| 62 | 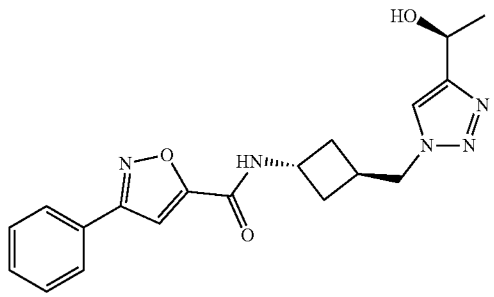 [SMILES: C[C@H](O)c1cn(C[C@H]2C[C@H](NC(=O)c3cc(-c4ccccc4)no3)C2)nn1] | | |
| 63 | 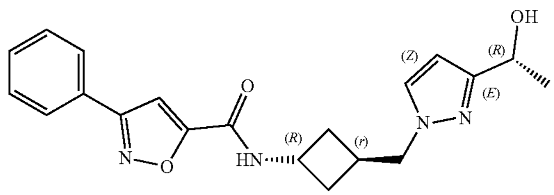 | | |
| 64 | 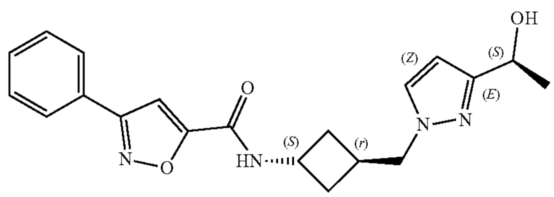 | | |
| 65 | 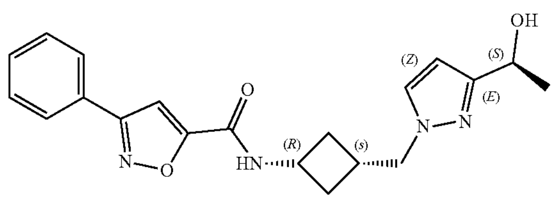 | | |
| 66 | 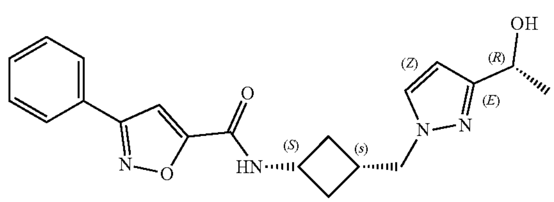 | | |
| 67 | 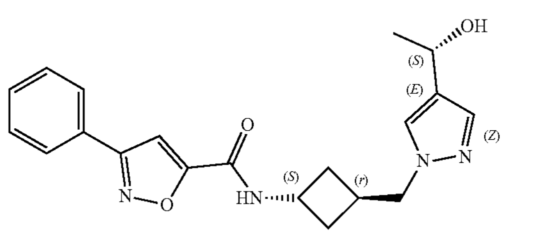 | | |
| 68 | 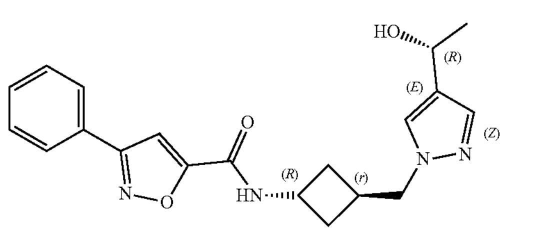 | | |

TABLE 2-continued

| # | Structure | Ieq | Ussing |
|---|-----------|-----|--------|
| 69 | 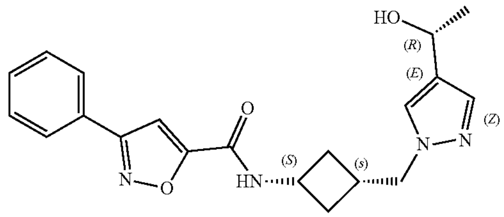 | | |
| 70 | 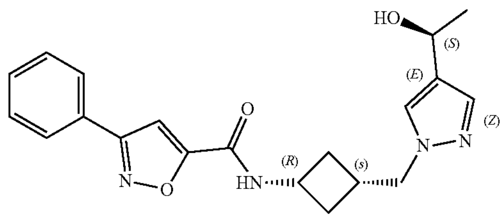 | | |
| 71 | 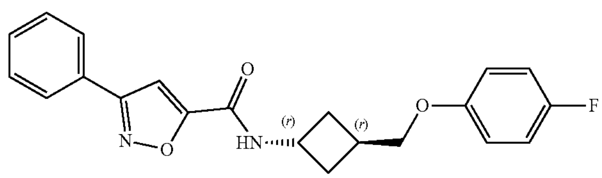 | | |
| 72 | 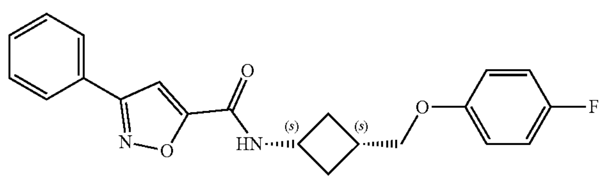 | | |
| 73 | 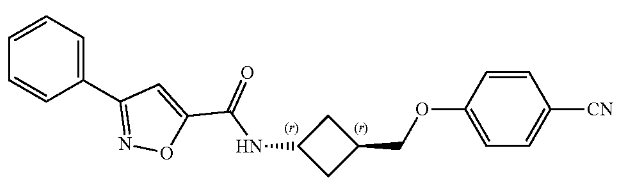 | | |
| 74 | 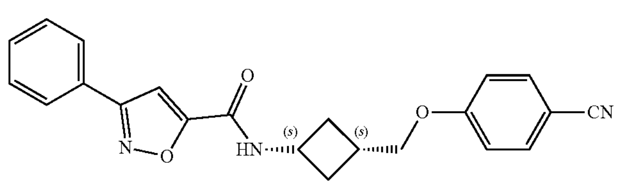 | | |
| 75 | 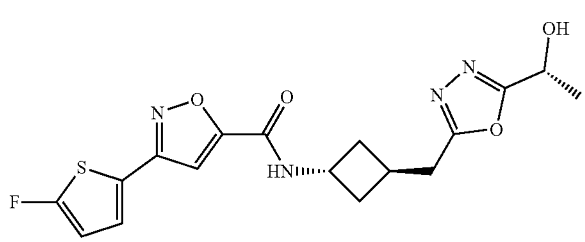 [SMILES: C[C@@H](O)c1nnc(C[C@H]2C[C@H](NC(=O)c3cc(-c4ccc(F)s4)no3)C2)o1] | | |

TABLE 2-continued

| # | Structure | Ieq | Ussing |
|---|-----------|-----|--------|
| 76 | (structure shown) | | |

Example 78 i. Ussing Measurements

As discussed above, Ussing measurements can be used to measure CFTR activity. In this method, primary lung epithelial cells (hBEs) with a Cystic fibrosis causing class I mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO or aqueous stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data are recorded by pulse readings every 5 seconds. Following baseline current stabilization, the following additions are applied and the changes in current and resistance of the cells are monitored:
1. Benzamil to the apical chamber to inhibit ENaC sodium channel.
2. Forskolin to both chambers to activate ΔF508-CFTR by phosphorylation.
3. Ivacaftor or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 79 i. Ussing Measurements

As discussed above, Ussing measurements can be used to measure CFTR activity. In this method, primary lung epithelial cells (hBEs) with a Cystic Fibrosis-causing class III mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 80 i. Ussing Measurements

As discussed above, Ussing measurements can be used to measure CFTR activity. In this method, primary lung epithelial cells (hBEs) with a Cystic Fibrosis-causing class V mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
1. Benzamil to the apical chamber to inhibit ENaC sodium channel.

2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements are made following additions with standardized time periods:

1. The baseline $V_T$ and $G_T$ values are measured for approximately 20 minutes.
2. Benzamil is added to block ENaC for 15 minutes.
3. Forskolin plus VX-770 (ivacaftor) are added to maximally activate ΔF508-CFTR for 27 minutes.
4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

While this invention has been particularly shown and described with references to preferred embodiments thereof, it will be understood by those skilled in the art that various changes in form and details may be made therein without departing from the scope of the invention encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed:

1. A compound represented by:

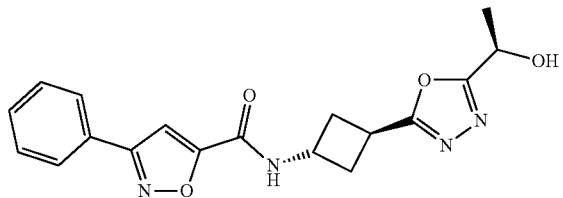

or a pharmaceutically acceptable salt thereof.

2. A pharmaceutically acceptable composition comprising the compound of claim 1 and a pharmaceutically acceptable excipient.

* * * * *